United States Patent
Koehler et al.

(10) Patent No.: US 10,017,520 B2
(45) Date of Patent: Jul. 10, 2018

(54) MYC MODULATORS AND USES THEREOF

(71) Applicant: Massachusetts Institute of Technology, Cambridge, MA (US)

(72) Inventors: Angela N. Koehler, Belmont, MA (US); Eric Stefan, Boston, MA (US); Francisco Caballero, Brookline, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 14/965,549

(22) Filed: Dec. 10, 2015

(65) Prior Publication Data
US 2016/0168165 A1    Jun. 16, 2016

Related U.S. Application Data

(60) Provisional application No. 62/090,290, filed on Dec. 10, 2014.

(51) Int. Cl.
| | | |
|---|---|---|
| *C07D 417/14* | (2006.01) | |
| *C07D 405/12* | (2006.01) | |
| *C07D 495/04* | (2006.01) | |
| *C07D 405/14* | (2006.01) | |
| *C07D 417/12* | (2006.01) | |
| *C07D 471/04* | (2006.01) | |

(52) U.S. Cl.
CPC ......... *C07D 495/04* (2013.01); *C07D 405/12* (2013.01); *C07D 405/14* (2013.01); *C07D 417/12* (2013.01); *C07D 417/14* (2013.01); *C07D 471/04* (2013.01)

(58) Field of Classification Search
CPC ... C07D 417/14; C07D 405/12; C07D 495/04
See application file for complete search history.

(56) References Cited

U.S. PATENT DOCUMENTS

| | | | |
|---|---|---|---|
| 5,965,574 A | 10/1999 | Chen | |
| 6,452,014 B1* | 9/2002 | Akama | C07D 417/14 546/260 |
| 8,642,660 B2 | 2/2014 | Goldfarb | |
| 2006/0074124 A1 | 4/2006 | Napper et al. | |
| 2011/0152240 A1* | 6/2011 | Haddach | C07D 487/04 514/210.18 |
| 2013/0184240 A1* | 7/2013 | Tonogaki | C07D 471/04 514/81 |
| 2014/0296307 A1 | 10/2014 | Fletcher et al. | |

FOREIGN PATENT DOCUMENTS

| | | |
|---|---|---|
| EP | 1 746 097 A1 | 1/2007 |
| EP | 1746097 | 1/2007 |
| JP | H02191695 A | 7/1990 |
| JP | H02194085 A | 7/1990 |
| JP | H02196887 A | 8/1990 |
| JP | H02208392 A | 8/1990 |
| JP | H02222488 A | 9/1990 |
| JP | H02227489 A | 9/1990 |
| JP | H02227490 A | 9/1990 |

(Continued)

OTHER PUBLICATIONS

Chemical Abstracts Registry No. 444693-02-1, indexed in the Registry file on STN CAS Online Aug. 22, 2002.*
Chemical Abstracts Registry No. 444714-90-3, indexed in the Registry file on STN CAS Online Aug. 22, 2002.*
Chemical Abstracts Registry No. 444653-79-6, indexed in the Registry file on STN CAS Online Aug. 22, 2002.*
Chemical Abstracts Registry No. 497836-62-1, indexed in the Registry file on STN CAS Online Mar. 11, 2003.*
Chemical Abstracts Registry No. 675830-23-6, indexed in the Registry file on STN CAS Online Apr. 16, 2004.*
Chemical Abstracts Registry No. 1458427-65-0, indexed in the Registry file on STN CAS Online Oct. 15, 2013.*
Chemical Abstracts Registry No. 439814-35-4, indexed in the Registry file on STN CAS Online Jul. 23, 2002.*

(Continued)

*Primary Examiner* — Laura L. Stockton
(74) *Attorney, Agent, or Firm* — Wolf, Greenfield & Sacks, P.C.

(57) ABSTRACT

The present disclosure provides compounds of Formula (I-a), Formula (I), and Formula (II). The compounds described herein may be Myc modulators (e.g., Myc inhibitors) and may be useful in treating in a subject in need thereof diseases associated with Myc and proliferative diseases (e.g., cancer). Also provided in the present disclosure are pharmaceutical compositions, kits, methods, and uses including a compound described herein.

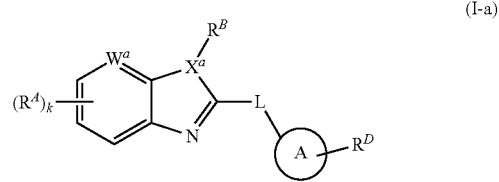

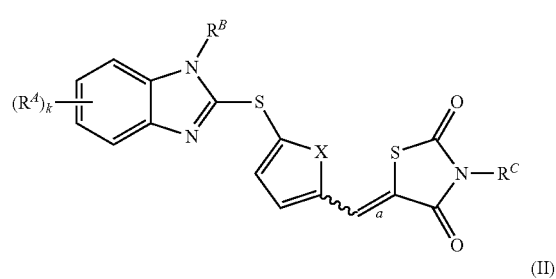

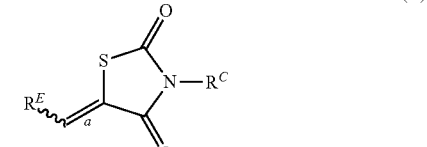

27 Claims, 8 Drawing Sheets

(56) References Cited

FOREIGN PATENT DOCUMENTS

| | | |
|---|---|---|
| JP | H02227491 A | 9/1990 |
| JP | H02242882 A | 9/1990 |
| JP | H02247280 A | 10/1990 |
| JP | H02247282 A | 10/1990 |
| JP | H02255793 A | 10/1990 |
| JP | H02255794 A | 10/1990 |
| JP | H08231541 A | 9/1996 |
| JP | 2003-057783 A | 2/2003 |
| JP | 2003-075955 A | 3/2003 |
| JP | 2003-075957 A | 3/2003 |
| JP | 2004-131463 A | 4/2004 |
| JP | 2006-084592 A | 3/2006 |
| JP | 2007-217298 A | 8/2007 |
| JP | 2010-207767 A | 9/2010 |
| WO | WO 00/023451 A1 | 4/2000 |
| WO | WO 2004/080989 A1 | 9/2004 |
| WO | WO 2005/002503 A2 | 1/2005 |
| WO | WO 2005/026112 A2 | 3/2005 |
| WO | WO 2005/033090 A1 | 4/2005 |
| WO | WO 2006/031894 A2 | 3/2006 |
| WO | WO 2007/047604 A2 | 4/2007 |
| WO | WO 2007/146712 A2 | 12/2007 |
| WO | WO 2008/012010 A1 | 1/2008 |
| WO | WO 2009/092764 A1 | 7/2009 |
| WO | WO 2009/108905 A2 | 9/2009 |
| WO | WO 2010/054398 A1 | 5/2010 |
| WO | WO 2010/075282 | 7/2010 |
| WO | WO 2012/153780 A1 | 11/2012 |
| WO | WO 2013/038650 A1 | 3/2013 |
| WO | WO 2013/177241 A1 | 11/2013 |
| WO | WO 2014/132971 | 9/2014 |
| WO | WO 2015/089180 | 6/2015 |

OTHER PUBLICATIONS

Chemical Abstracts Registry No. 83490-12-4, indexed in the Registry file on STN CAS Online Nov. 16, 1984.*
Chemical Abstracts Registry No. 920536-51-2, indexed in the Registry file on STN CAS Online Feb. 12, 2007.*
Chemical Abstracts Registry No. 641607-16-1, indexed in the Registry file on STN CAS Online on Jan. 26, 2004.*
Chemical Abstracts Registry No. 1024883-05-3, indexed in the Registry file on STN CAS Online on Jun. 3, 2008.*
Verma et al., Synthetic Communications, Jul. 2013, 43(14), pp. 1882-1895.*
Boxer et al., Translocations involving c-myc and c-myc function. Oncogene. Sep. 10, 2001;20(40):5595-610.
Dang et al., c-Myc target genes involved in cell growth, apoptosis, and metabolism. Mol Cell Biol. Jan. 1999;19(1):1-11.
Dang et al., The c-Myc target gene network.Semin Cancer Biol. Aug. 2006;16(4):253-64. Epub Jul. 25, 2006.
Duffner et al., A pipeline for ligand discovery using small-molecule microarrays. Curr Opin Chem Biol. Feb. 2007;11(1):74-82. Epub Dec. 13, 2006.
Eilers et al., Myc's broad reach. Genes Dev. Oct. 15, 2008;22(20):2755-66. doi: 10.1101/gad.1712408.
Felsher et al., Reversible tumorigenesis by MYC in hematopoietic lineages.Mol Cell. Aug. 1999;4(2):199-207.
Frost et al., Comparative immunohistochemical analysis of pediatric Burkitt lymphoma and diffuse large B-cell lymphoma. Am J Clin Pathol. Mar. 2004;121(3):384-92.
Frye et al., The art of the chemical probe. Nat Chem Biol. Mar. 2010;6(3):159-161.
Leskov et al., Rapid generation of human B-cell lymphomas via combined expression of Myc and Bcl2 and their use as a preclinical model for biological therapies. Oncogene. Feb. 21, 2013;32(8):1066-72. doi: 10.1038/onc.2012.117. Epub Apr. 9, 2012.
Mitchell et al., a structurally diverse library of polycyclic lactams resulting from systematic placement of proximal functional groups. Angew Chem Int Ed Engl. Mar. 3, 2006;45(11):1722-6.
Nitsche et al., Thiazolidinone-peptide hybrids as dengue virus protease inhibitors with antiviral activity in cell culture. J Med Chem. Nov. 14, 2013;56(21):8389-403. doi: 10.1021/jm400828u.
Norgren et al., On-Resin Click-Glycoconjugation of Peptoids. Synthesis. 2009; 3: 488-94.
Pajic et al., Cell cycle activation by c-myc in a burkitt lymphoma model cell line. Int J Cancer. Sep. 15, 2000;87(6):787-93.
Seiler et al., ChemBank: a small-molecule screening and cheminformatics resource database. Nucleic Acids Res. Jan. 2008;36(Database issue):D351-9. Epub Oct. 18, 2007.
Sekar et al., S-arylation of mercaptobenzimidazoles using Cu(I) catalysts-experimental and theoretical observations. Tetrahedron Letters. 2011;52:3347-52.
Soucek et al., Inhibition of Myc family proteins eradicates KRas-driven lung cancer in mice. Genes Dev. Mar. 1, 2013;27(5):504-13. doi: 10.1101/gad.205542.112.
vanRiggelen et al., MYC as a regulator of ribosome biogenesis and protein synthesis. Nat Rev Cancer. Apr. 2010;10(4):301-9. doi: 10.1038/nrc2819.
Vita et al., The Myc oncoprotein as a therapeutic target for human cancer. Semin Cancer Biol. Aug. 2006;16(4):318-30. Epub Aug. 3, 2006.
International Search Report and Written Opinion for PCT/US2015/065044, dated Feb. 22, 2016.
International Search Report and Written Opinion for PCT/US2017/018162, dated Apr. 20, 2017.
International Preliminary Report on Patentability for PCT/US2015/065044, dated Jun. 22, 2017.
Huang et al., Photocycloadditions of substituted oxazoles with isoquinoline-1,3,4-trione--chemo-, regio-, diastereoselectivities and transformation of the photocycloadducts. Org Biomol Chem. Aug. 14, 2013;11(30):5023-33. doi: 10.1039/c3ob40645h. Epub Jun. 26, 2013.
Wang et al., Small-molecule reagents for cellular pull-down experiments. Bioconjug Chem. Mar. 2008;19(3):585-7. doi: 10.1021/bc700297j. Epub Jan. 15, 2008.

* cited by examiner

Compound 1

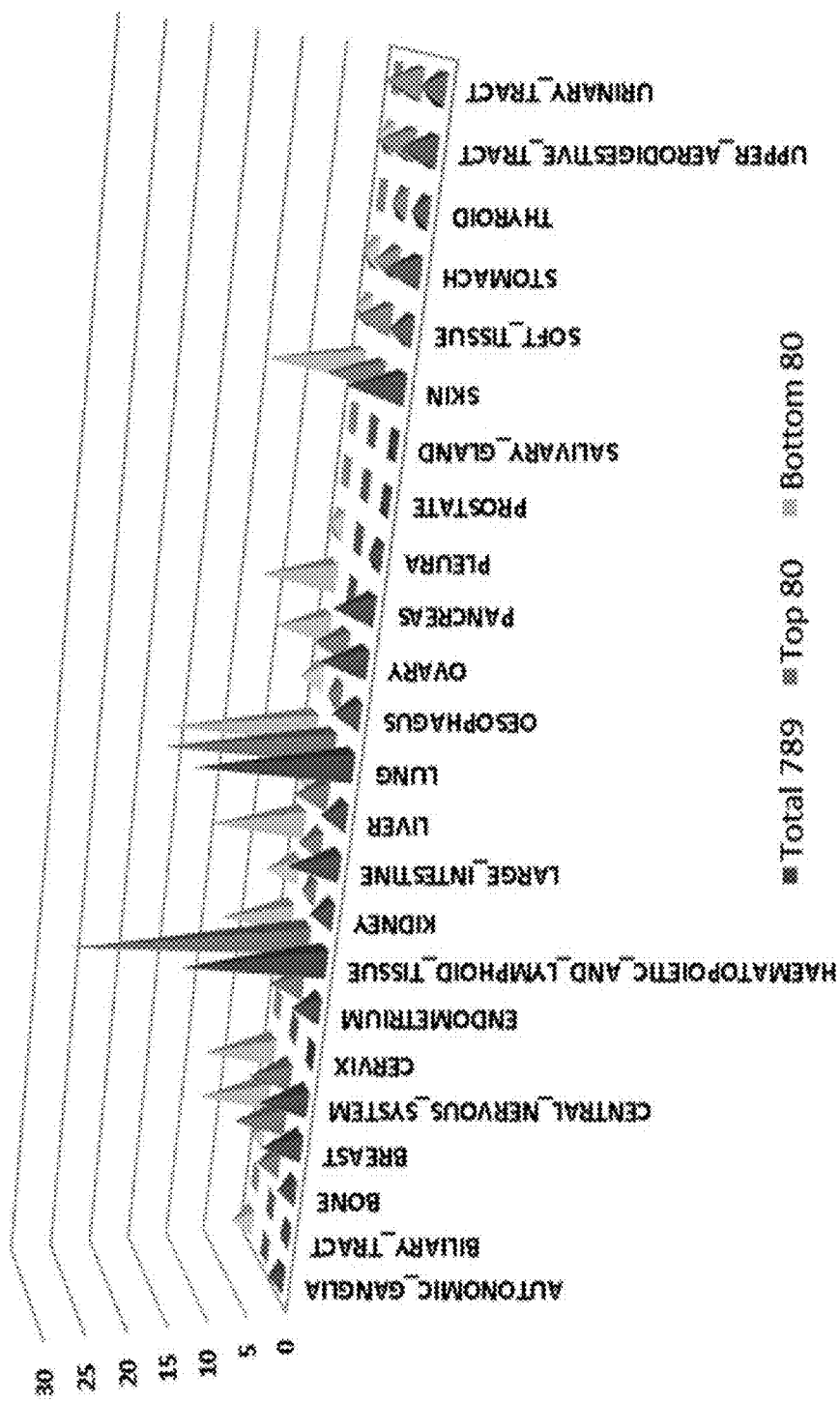

MYC MODULATORS AND USES THEREOF

RELATED APPLICATIONS

This application claims priority under 35 U.S.C. § 119(e) to U.S. Provisional Application, U.S. Ser. No. 62/090,290, filed Dec. 10, 2014, which is incorporated herein by reference.

GOVERNMENT SUPPORT

This invention was made with government support under grant number CA 160860 awarded by the National Institutes of Health. The government has certain rights in the invention.

BACKGROUND OF THE INVENTION

Activation of c-Myc is one of the most common oncogenic events in human malignancies [1, 2]. In normal cells, the Myc family of transcription factors (c-Myc, L-Myc, and N-Myc) regulates a diverse set of biological processes including DNA replication, gene transcription, and protein translation. Consequently, numerous cellular processes are regulated by Myc, including growth, proliferation, apoptosis, metabolism, differentiation, self-renewal, and angiogenesis [3, 4, 5]. It has been estimated that c-Myc regulates expression of more than 15% of all genes and therefore is considered to be a master regulator [6]. In malignant cells, Myc activation can occur through several mechanisms such as point mutation, somatic gene amplification, chromosomal translocation, overexpression, enhanced translation, and increased protein stability [2]. One estimate attributes 100,000 cancer deaths annually in the United States to deregulation of Myc [6]. Burkitt's lymphoma provides a paradigm for Myc deregulation in malignancy as nearly all cases involve balanced translocation of the MYC gene and overexpression of the oncoprotein [7, 8]. c-Myc deregulation may result in uncontrolled cell proliferation, alterations in the apoptotic pathway, genomic instability, escape from immune surveillance, growth factor independence, and immortalization [2]. The report that the inhibition of Myc in vivo eradicated lung cancer in mice [9] shows the potential of Myc as a target in cancer treatment.

SUMMARY OF THE INVENTION

In one aspect, described herein are compounds of Formula (I), and pharmaceutically acceptable salts, solvates, hydrates, polymorphs, co-crystals, tautomers, stereoisomers, isotopically labeled derivatives, and prodrugs thereof. The compounds described herein may be modulators (e.g., inhibitors) of Myc (e.g., c-Myc, L-Myc, N-Myc). The compounds may be useful in modulating (e.g., inhibiting) the activity of Myc in a subject in need thereof, treating diseases associated with Myc (e.g., diseases associated with aberrant activity (e.g., increased activity) of Myc) in a subject in need thereof, treating proliferative diseases in a subject in need thereof, preventing diseases associated with Myc (e.g., diseases associated with aberrant activity (e.g., increased activity) of Myc) in a subject in need thereof, preventing proliferative diseases in a subject in need thereof, inducing apoptosis of a cell in a subject, biological sample, or tissue, and/or as research tools (e.g., for studying Myc (e.g., studying the activity of Myc) in a subject, biological sample, tissue, or cell). Also provided are pharmaceutical compositions, kits, methods, and uses including a compound described herein.

In one aspect, the present disclosure provides compounds of Formula (I-a):

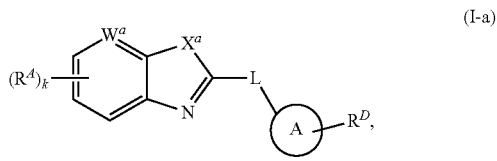

and pharmaceutically acceptable salts, solvates, hydrates, polymorphs, co-crystals, tautomers, stereoisomers, isotopically labeled derivatives, and prodrugs thereof, wherein $R^A$, k, $R^B$, $W^a$, $X^a$ L, Ring A, and $R^D$ are as defined herein. Exemplary compounds of Formula (I-a) include, but are not limited to:

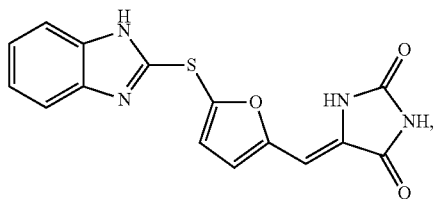

2

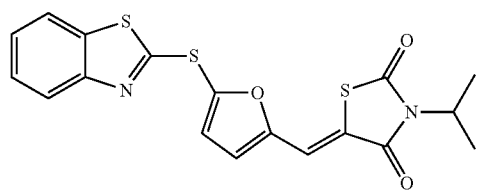

3

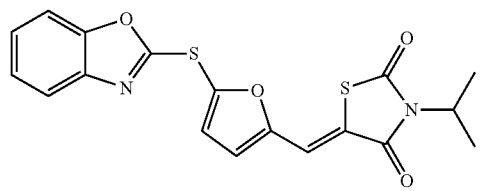

6

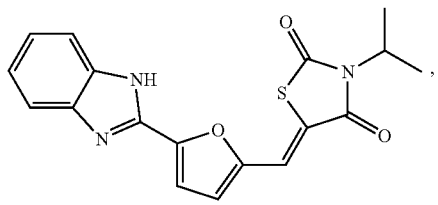

7

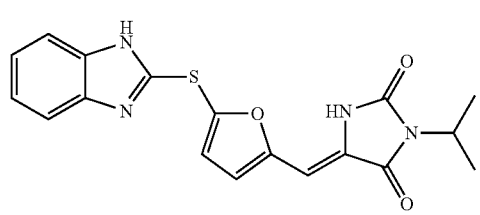

8

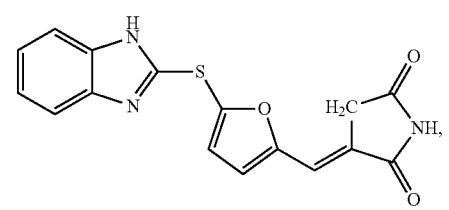
9
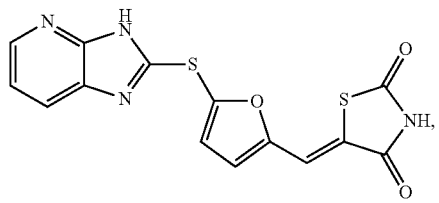
10
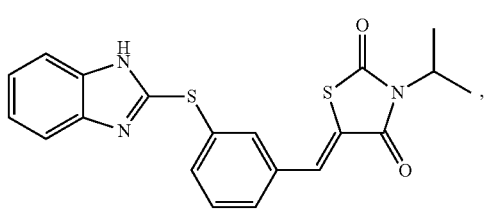
12
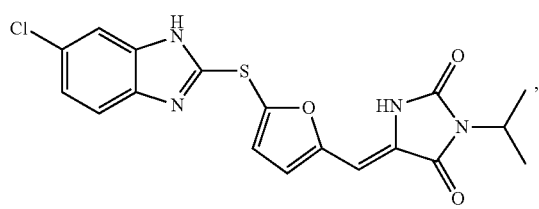
22
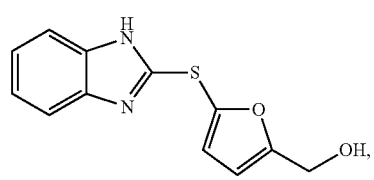
40
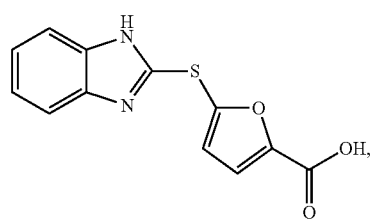
41
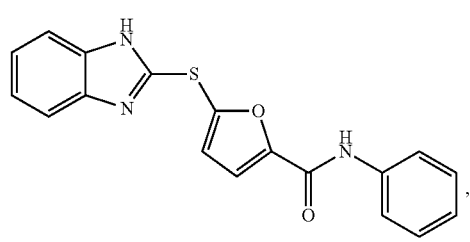
42
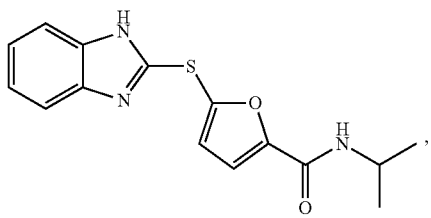
43
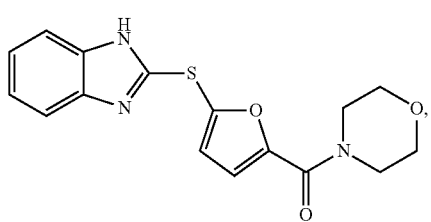
44
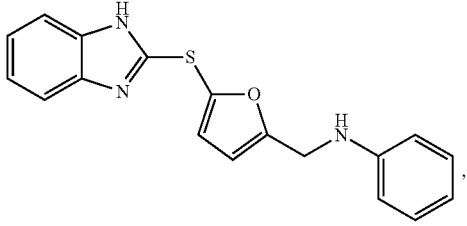
45
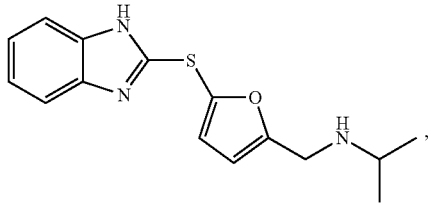
46
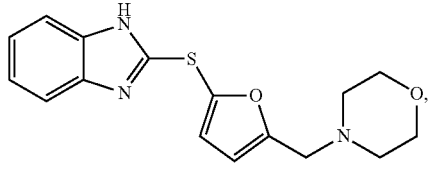
47
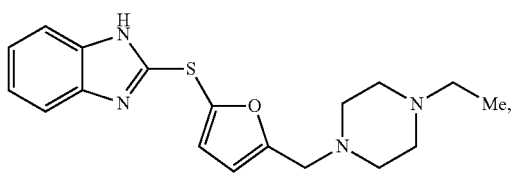
48
49
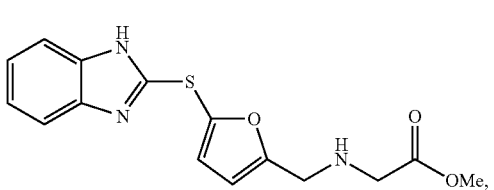
50

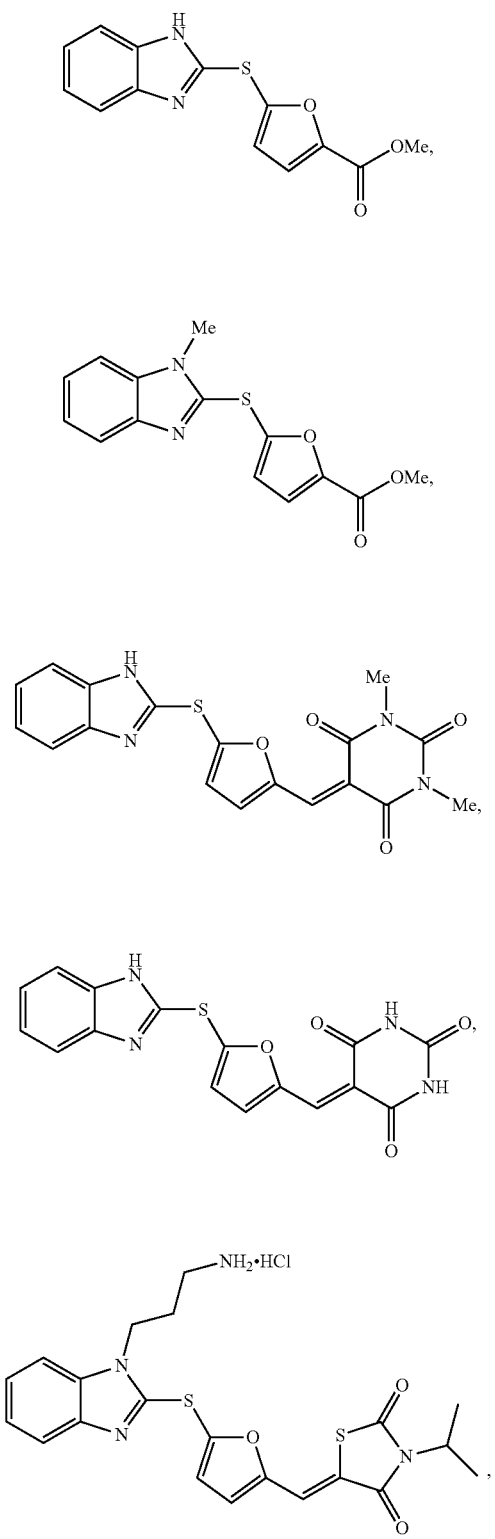
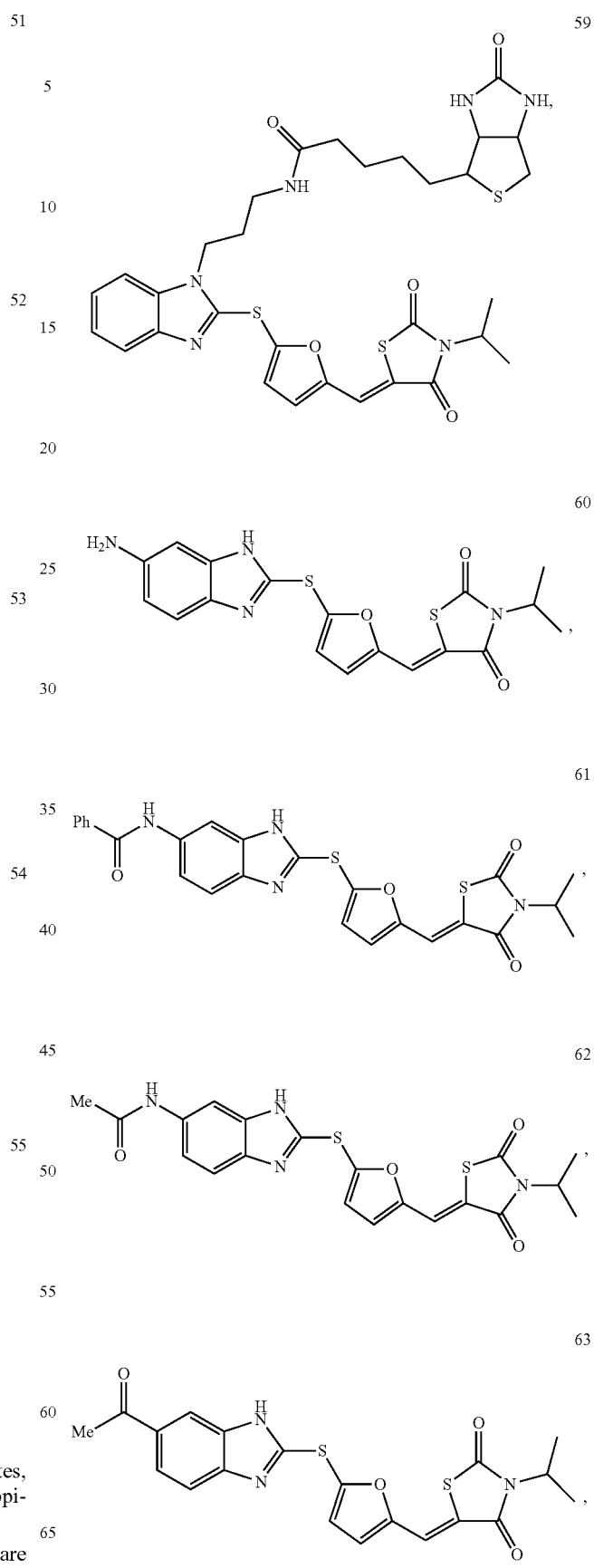
and pharmaceutically acceptable salts, solvates, hydrates, polymorphs, co-crystals, tautomers, stereoisomers, isotopically labeled derivatives, and prodrugs thereof.
Exemplary compounds of Formula (I-a) include, but are not limited to:

64
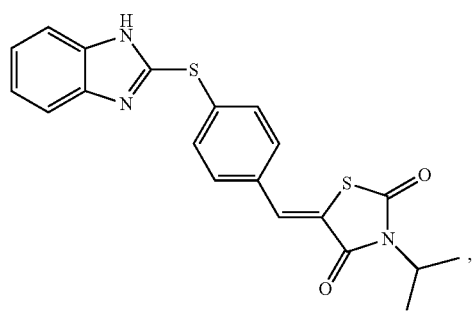
65
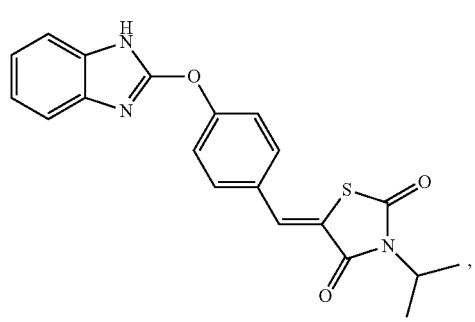
66
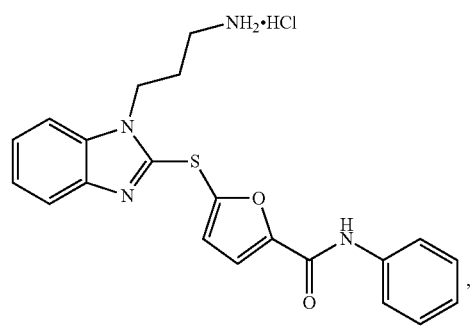
67
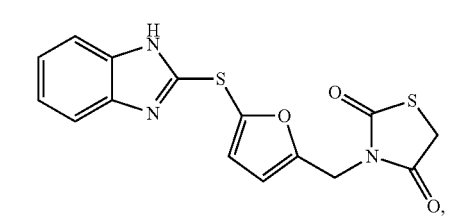
68
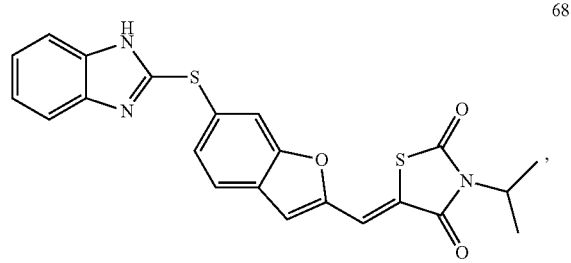
69
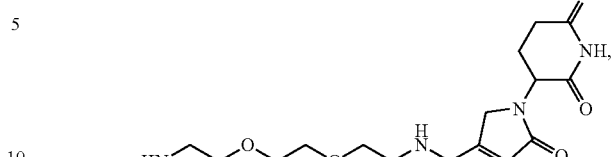
70
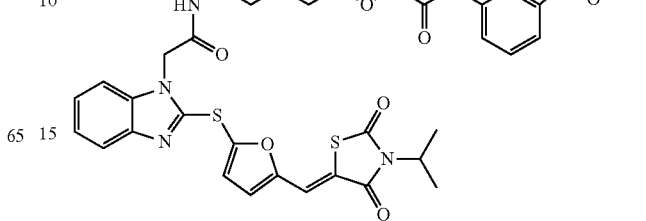
71
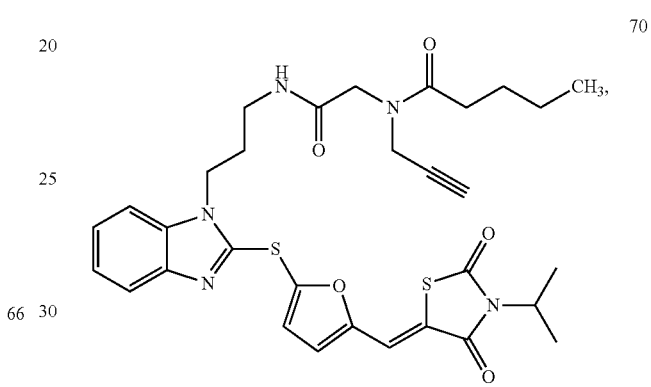
72
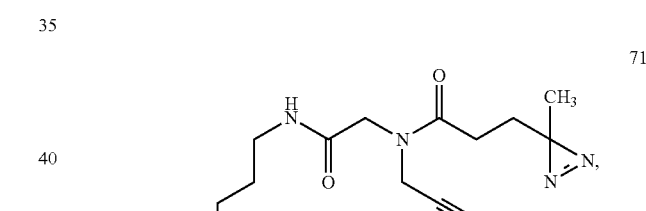
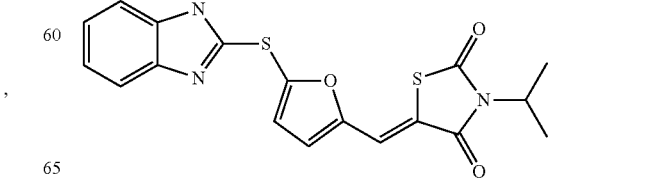

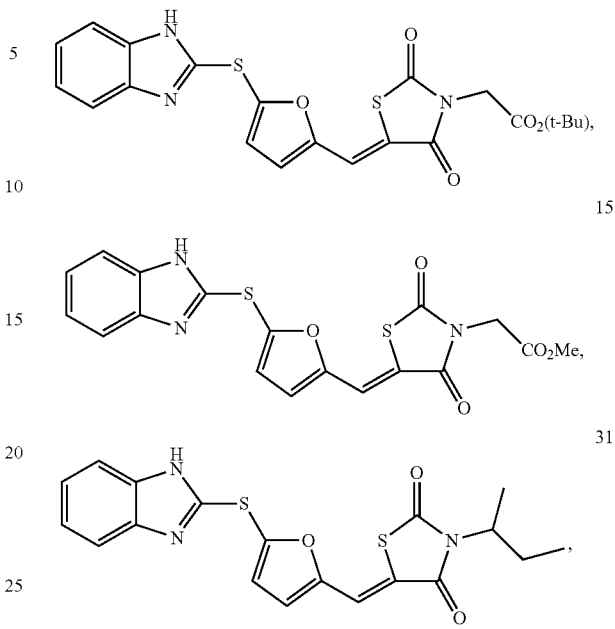

and pharmaceutically acceptable salts, solvates, hydrates, polymorphs, co-crystals, tautomers, stereoisomers, isotopically labeled derivatives, and prodrugs thereof.

In one aspect, the present disclosure provides compounds of Formula (I):

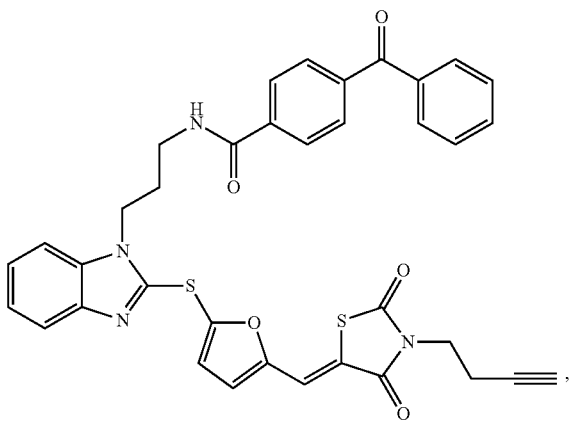

and pharmaceutically acceptable salts, solvates, hydrates, polymorphs, co-crystals, tautomers, stereoisomers, isotopically labeled derivatives, and prodrugs thereof, wherein $R^A$, k, $R^B$, X, and $R^C$ are as defined herein.

Exemplary compounds of Formula (I) include, but are not limited to:

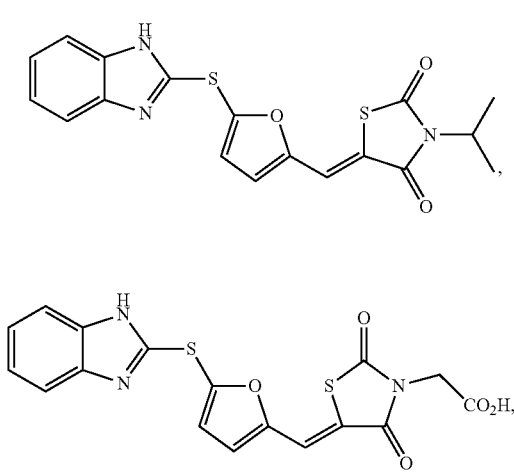

and pharmaceutically acceptable salts, solvates, hydrates, polymorphs, co-crystals, tautomers, stereoisomers, isotopically labeled derivatives, and prodrugs thereof.

Additional exemplary compounds of Formula (I) include, but are not limited to:

4
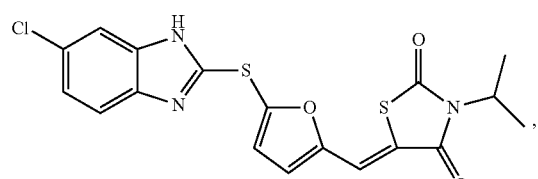
5
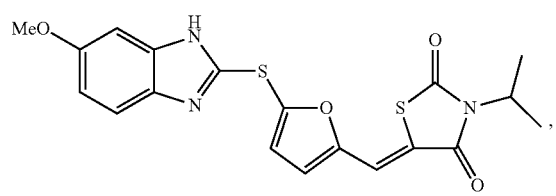
18
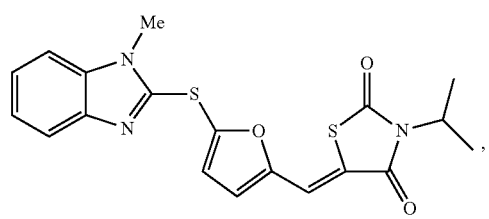
19
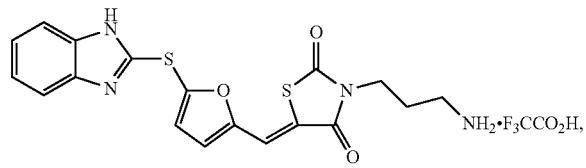
20
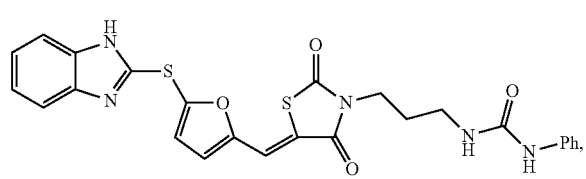
21
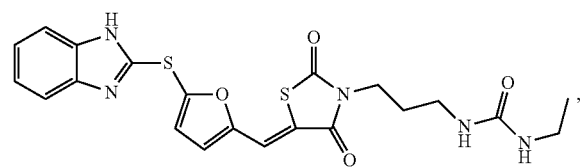
23
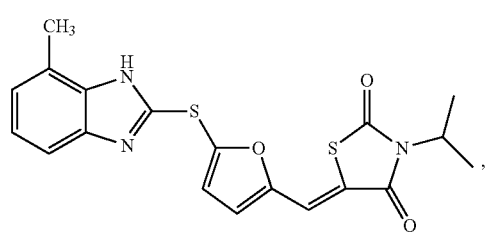
24
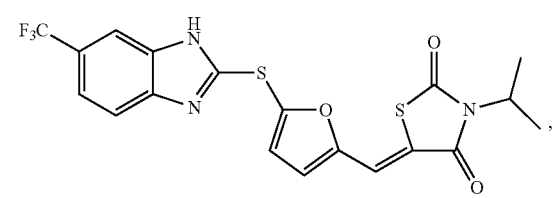
25
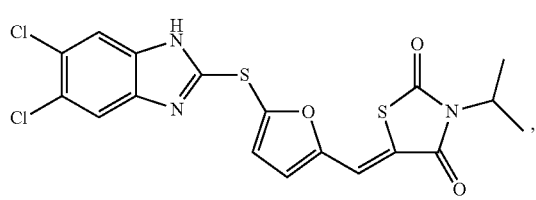
26
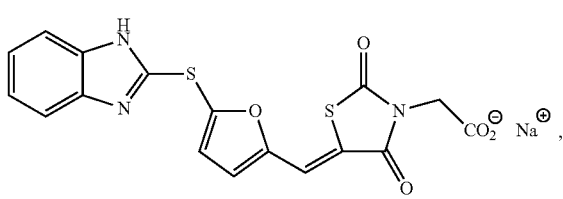
27
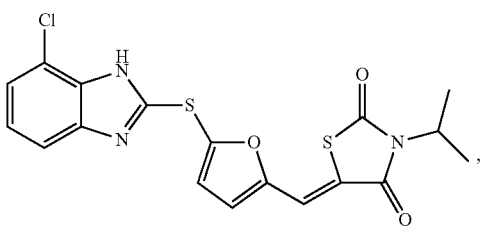
28
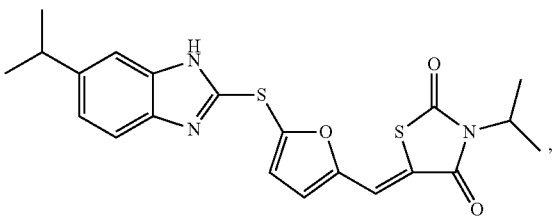
29
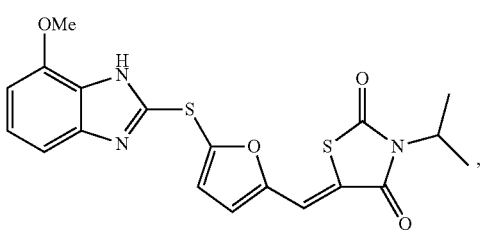
30 and pharmaceutically acceptable salts, solvates, hydrates, polymorphs, co-crystals, tautomers, stereoisomers, isotopically labeled derivatives, and prodrugs thereof.

In another aspect, the present disclosure provides compounds of Formula (II):

(II)

and pharmaceutically acceptable salts, solvates, hydrates, polymorphs, co-crystals, tautomers, stereoisomers, isotopically labeled derivatives, and prodrugs thereof, wherein $R^E$, a, and $R^C$ are as defined herein.

Exemplary compounds of Formula (II) include, but are not limited to:

and pharmaceutically acceptable salts, solvates, hydrates, polymorphs, co-crystals, tautomers, stereoisomers, isotopically labeled derivatives, and prodrugs thereof.

In another aspect, described herein are pharmaceutical compositions including a compound described herein, and optionally a pharmaceutically acceptable excipient. In certain embodiments, a pharmaceutical composition described herein includes an effective amount (e.g., therapeutically effective amount or prophylactically effective amount) of a compound described herein. In certain embodiments, a pharmaceutical composition described herein further comprises an additional pharmaceutical agent. The pharmaceutical compositions may be useful in modulating (e.g., inhibiting) the activity of Myc in a subject in need thereof, treating diseases associated with Myc (e.g., diseases associated with aberrant activity (e.g., increased activity) of Myc) in a subject in need thereof, treating proliferative diseases in a subject in need thereof, preventing diseases associated with Myc (e.g., diseases associated with aberrant activity (e.g., increased activity) of Myc) in a subject in need thereof, preventing proliferative diseases in a subject in need thereof, inducing apoptosis of a cell in a subject, biological sample, or tissue, and/or as research tools (e.g., for studying Myc (e.g., studying the activity of Myc) in a subject, biological sample, tissue, or cell).

In certain embodiments, the proliferative disease is associated with aberrant activity (e.g., increased or decreased activity) of Myc. In certain embodiments, the proliferative disease is associated with increased activity of Myc. In certain embodiments, the proliferative disease is cancer, benign neoplasm, or pathological angiogenesis.

In certain embodiments, the subject is a human. In certain embodiments, the subject is a non-human animal. In certain embodiments, the cell is in vitro. In certain embodiments, the cell is in vivo.

In still another aspect, described herein are kits including a container with a compound or pharmaceutical composition described herein. A kit described herein may include a single dose or multiple doses of the compound or pharmaceutical composition. The described kits may be useful in modulating (e.g., inhibiting) the activity of Myc in a subject in need thereof, treating diseases associated with Myc (e.g., diseases associated with aberrant activity (e.g., increased activity) of Myc) in a subject in need thereof, treating proliferative diseases in a subject in need thereof, preventing diseases associated with Myc (e.g., diseases associated with aberrant activity (e.g., increased activity) of Myc) in a subject in need thereof, preventing proliferative diseases in a subject in need thereof, inducing apoptosis of a cell in a subject, biological sample, or tissue, and/or as research tools (e.g., for studying Myc (e.g., studying the activity of Myc) in a subject, biological sample, tissue, or cell). In certain embodiments, a kit described herein further includes instructions for using the compound or pharmaceutical composition included in the kit.

In another aspect, the present disclosure provides methods of modulating (e.g., inhibiting) the activity of Myc in a subject in need thereof, the methods comprising administering to the subject an effective amount of a compound or pharmaceutical composition described herein.

In another aspect, the present disclosure provides methods of modulating (e.g., inhibiting) the activity of Myc in a biological sample, tissue, or cell, the methods comprising contacting the biological sample, tissue, or cell with an effective amount of a compound or pharmaceutical composition described herein.

In certain embodiments, the compound being administered or used selectively modulates (e.g., inhibits) the activity of a particular Myc (e.g., c-Myc, L-Myc, and/or N-Myc), compared to a different Myc and/or a different transcription factor.

Another aspect of the present disclosure relates to methods of treating a proliferative disease in a subject in need thereof, the methods comprising administering to the subject an effective amount of a compound or pharmaceutical composition described herein.

In another aspect, the present disclosure provides methods of preventing a proliferative disease in a subject in need thereof, the methods comprising administering to the subject an effective amount of a compound or pharmaceutical composition described herein.

In another aspect, the present disclosure provides methods of inducing apoptosis of a cell in a subject, the methods comprising administering to the subject an effective amount of a compound or pharmaceutical composition described herein.

In another aspect, the present disclosure provides methods of inducing apoptosis of a cell in a biological sample, tissue, or cell, the methods comprising contacting the biological sample, tissue, or cell with an effective amount of a compound or pharmaceutical composition described herein.

Another aspect of the disclosure relates to methods of screening a library of compounds to identify a compound that is useful in a method described herein.

In yet another aspect, the present disclosure provides compounds and pharmaceutical compositions described herein for use in a method of the disclosure (e.g., a method of modulating (e.g., inhibiting) the activity of Myc, a method of treating a proliferative disease, a method of preventing a proliferative disease, a method of inducing apoptosis, and/or a method of screening a library of compounds).

Definitions

Definitions of specific functional groups and chemical terms are described in more detail below. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987. The disclosure is not intended to be limited in any manner by the exemplary listing of substituents described herein.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, N Y, 1962); and Wilen, *Tables of Resolving Agents and Optical Resolutions* p. 268 (E. L. Eliel, Ed., Univ. of Notre Dame Press, Notre Dame, Ind. 1972). The disclosure additionally encompasses compounds described herein as individual isomers substantially free of other isomers, and alternatively, as mixtures of various isomers.

When a range of values is listed, it is intended to encompass each value and sub-range within the range. For example "$C_{1-6}$" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$ $C_{4-5}$, and $C_{5-6}$.

The term "aliphatic" includes both saturated and unsaturated, straight chain (i.e., unbranched), branched, acyclic, cyclic, or polycyclic aliphatic hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, the term "alkyl" includes straight, branched and cyclic alkyl groups. An analogous convention applies to other generic terms such as "alkenyl", "alkynyl", and the like. Furthermore, the terms "alkyl", "alkenyl", "alkynyl", and the like encompass both substituted and unsubstituted groups. In certain embodiments, "lower alkyl" is used to indicate those alkyl groups (cyclic, acyclic, substituted, unsubstituted, branched or unbranched) having 1-6 carbon atoms.

In certain embodiments, the alkyl, alkenyl, and alkynyl groups employed in the disclosure contain 1-20 aliphatic carbon atoms. In certain other embodiments, the alkyl, alkenyl, and alkynyl groups employed in the disclosure contain 1-10 aliphatic carbon atoms. In yet other embodiments, the alkyl, alkenyl, and alkynyl groups employed in the disclosure contain 1-8 aliphatic carbon atoms. In still other embodiments, the alkyl, alkenyl, and alkynyl groups employed in the disclosure contain 1-6 aliphatic carbon atoms. In yet other embodiments, the alkyl, alkenyl, and alkynyl groups employed in the disclosure contain 1-4 carbon atoms. Illustrative aliphatic groups thus include, but are not limited to, for example, methyl, ethyl, n-propyl, isopropyl, cyclopropyl, —CH$_2$-cyclopropyl, vinyl, allyl, n-butyl, sec-butyl, isobutyl, tert-butyl, cyclobutyl, —CH$_2$-cyclobutyl, n-pentyl, sec-pentyl, isopentyl, tert-pentyl, cyclopentyl, —CH$_2$-cyclopentyl, n-hexyl, sec-hexyl, cyclohexyl, —CH$_2$-cyclohexyl moieties and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl, and the like.

The term "alkyl" refers to a radical of a straight-chain or branched saturated hydrocarbon group having from 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), propyl ($C_3$) (e.g., n-propyl, isopropyl), butyl ($C_4$) (e.g., n-butyl, tert-butyl, sec-butyl, iso-butyl), pentyl ($C_5$) (e.g., n-pentyl, 3-pentanyl, amyl, neopentyl, 3-methyl-2-butanyl, tertiary amyl), and hexyl ($C_6$) (e.g., n-hexyl). Additional examples of alkyl groups include n-heptyl ($C_7$), n-octyl ($C_8$), and the like. Unless otherwise specified, each instance of an alkyl group is independently unsubstituted (an "unsubstituted alkyl") or substituted (a "substituted alkyl") with one or more substituents (e.g., halogen, such as F). In certain embodiments, the alkyl group is an unsubstituted $C_{1-10}$ alkyl (such as unsubstituted $C_{1-6}$alkyl, e.g., —CH$_3$ (Me), unsubstituted ethyl (Et), unsubstituted propyl (Pr, e.g., unsubstituted n-propyl (n-Pr), unsubstituted isopropyl (i-Pr)), unsubstituted butyl (Bu, e.g., unsubstituted n-butyl (n-Bu), unsubstituted tert-butyl (tert-Bu or t-Bu), unsubstituted sec-butyl (sec-Bu), unsubstituted isobutyl (i-Bu)). In certain embodiments, the alkyl group is a substituted $C_{1-10}$ alkyl (such as substituted $C_{1-6}$ alkyl, e.g., —CF$_3$, Bn).

"Alkenyl" refers to a radical of a straight-chain or branched hydrocarbon group having from 2 to 20 carbon atoms, one or more carbon-carbon double bonds, and no triple bonds ("$C_{2-20}$ alkenyl"). In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently optionally substituted, i.e., unsubstituted (an "unsubstituted alkenyl") or substituted (a "substituted alkenyl") with one or more substituents. In certain embodiments, the alkenyl group is unsubstituted $C_{2-10}$ alkenyl. In certain embodiments, the alkenyl group is substituted $C_{2-10}$ alkenyl. In an alkenyl group, a C=C double bond for which the stereochemistry is not specified (e.g., —CH=CHCH$_3$ or

)

may be an (E)- or (Z)-double bond.

"Alkynyl" refers to a radical of a straight-chain or branched hydrocarbon group having from 2 to 20 carbon atoms, one or more carbon-carbon triple bonds, and optionally one or more double bonds ("$C_{2-20}$ alkynyl"). In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$alkynyl"). In some embodiments, an alkynyl group has 2 to 3 carbon atoms ("C$_{2-3}$ alkynyl"). In some embodiments, an alkynyl group has 2 carbon atoms ("C$_2$ alkynyl"). The one or more carbon-carbon triple bonds can be internal (such as in 2-butynyl) or terminal (such as in 1-butynyl). Examples of C$_{2-4}$ alkynyl groups include, without limitation, ethynyl (C$_2$), 1-propynyl (C$_3$), 2-propynyl (C$_3$), 1-butynyl (C$_4$), 2-butynyl (C$_4$), and the like. Examples of C$_{2-6}$ alkenyl groups include the aforementioned C$_{2-4}$ alkynyl groups as well as pentynyl (C$_5$), hexynyl (C$_6$), and the like. Additional examples of alkynyl include heptynyl (C$_7$), octynyl (C$_8$), and the like. Unless otherwise specified, each instance of an alkynyl group is independently optionally substituted, i.e., unsubstituted (an "unsubstituted alkynyl") or substituted (a "substituted alkynyl") with one or more substituents. In certain embodiments, the alkynyl group is unsubstituted C$_{2-10}$ alkynyl. In certain embodiments, the alkynyl group is substituted C$_{2-10}$ alkynyl.

"Carbocyclyl" or "carbocyclic" refers to a radical of a non-aromatic cyclic hydrocarbon group having from 3 to 10 ring carbon atoms ("C$_{3-10}$ carbocyclyl") and zero heteroatoms in the non-aromatic ring system. In some embodiments, a carbocyclyl group has 3 to 8 ring carbon atoms ("C$_{3-8}$ carbocyclyl"). In some embodiments, a carbocyclyl group has 3 to 6 ring carbon atoms ("C$_{3-6}$ carbocyclyl"). In some embodiments, a carbocyclyl group has 3 to 6 ring carbon atoms ("C$_{3-6}$ carbocyclyl"). In some embodiments, a carbocyclyl group has 5 to 10 ring carbon atoms ("C$_{5-10}$ carbocyclyl"). Exemplary C$_{3-6}$ carbocyclyl groups include, without limitation, cyclopropyl (C$_3$), cyclopropenyl (C$_3$), cyclobutyl (C$_4$), cyclobutenyl (C$_4$), cyclopentyl (C$_5$), cyclopentenyl (C$_5$), cyclohexyl (C$_6$), cyclohexenyl (C$_6$), cyclohexadienyl (C$_6$), and the like. Exemplary C$_{3-8}$ carbocyclyl groups include, without limitation, the aforementioned C$_{3-6}$ carbocyclyl groups as well as cycloheptyl (C$_7$), cycloheptenyl (C$_7$), cycloheptadienyl (C$_7$), cycloheptatrienyl (C$_7$), cyclooctyl (C$_8$), cyclooctenyl (C$_8$), bicyclo[2.2.1]heptanyl (C$_7$), bicyclo[2.2.2]octanyl (C$_8$), and the like. Exemplary C$_{3-10}$ carbocyclyl groups include, without limitation, the aforementioned C$_{3-8}$ carbocyclyl groups as well as cyclononyl (C$_9$), cyclononenyl (C$_9$), cyclodecyl (C$_{10}$), cyclodecenyl (C$_{10}$), octahydro-1H-indenyl (C$_9$), decahydronaphthalenyl (C$_{10}$), spiro[4.5]decanyl (C$_{10}$), and the like. As the foregoing examples illustrate, in certain embodiments, the carbocyclyl group is either monocyclic ("monocyclic carbocyclyl") or contain a fused, bridged or spiro ring system such as a bicyclic system ("bicyclic carbocyclyl") and can be saturated or can be partially unsaturated. "Carbocyclyl" also includes ring systems wherein the carbocyclic ring, as defined above, is fused with one or more aryl or heteroaryl groups wherein the point of attachment is on the carbocyclic ring, and in such instances, the number of carbons continue to designate the number of carbons in the carbocyclic ring system. Unless otherwise specified, each instance of a carbocyclyl group is independently optionally substituted, i.e., unsubstituted (an "unsubstituted carbocyclyl") or substituted (a "substituted carbocyclyl") with one or more substituents. In certain embodiments, the carbocyclyl group is unsubstituted C$_{3-10}$ carbocyclyl. In certain embodiments, the carbocyclyl group is substituted C$_{3-10}$ carbocyclyl.

In some embodiments, "carbocyclyl" is a monocyclic, saturated carbocyclyl group having from 3 to 10 ring carbon atoms ("C$_{3-10}$ cycloalkyl"). In some embodiments, a cycloalkyl group has 3 to 8 ring carbon atoms ("C$_{3-8}$ cycloalkyl"). In some embodiments, a cycloalkyl group has 3 to 6 ring carbon atoms ("C$_{3-6}$ cycloalkyl"). In some embodiments, a cycloalkyl group has 5 to 6 ring carbon atoms ("C$_{5-6}$ cycloalkyl"). In some embodiments, a cycloalkyl group has 5 to 10 ring carbon atoms ("C$_{5-10}$ cycloalkyl"). Examples of C$_{5-6}$ cycloalkyl groups include cyclopentyl (C$_5$) and cyclohexyl (C$_5$). Examples of C$_{3-6}$ cycloalkyl groups include the aforementioned C$_{5-6}$ cycloalkyl groups as well as cyclopropyl (C$_3$) and cyclobutyl (C$_4$). Examples of C$_{3-8}$ cycloalkyl groups include the aforementioned C$_{3-6}$ cycloalkyl groups as well as cycloheptyl (C$_7$) and cyclooctyl (C$_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted C$_{3-10}$ cycloalkyl. In certain embodiments, the cycloalkyl group is substituted C$_{3-10}$ cycloalkyl.

"Heterocyclyl" or "heterocyclic" refers to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged, or spiro ring system, such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclic ring, as defined above, is fused with one or more carbocyclyl groups wherein the point of attachment is either on the carbocyclyl or heterocyclic ring, or ring systems wherein the heterocyclic ring, as defined above, is fused with one or more aryl or heteroaryl groups, wherein the point of attachment is on the heterocyclic ring, and in such instances, the number of ring members continue to designate the number of ring members in the heterocyclic ring system. Unless otherwise specified, each instance of heterocyclyl is independently optionally substituted, i.e., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, sulfur, boron, phosphorus, and silicon ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, thiiranyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, and dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

"Aryl" refers to a radical of a monocyclic or polycyclic (e.g., bicyclic or tricyclic) 4n+2 aromatic ring system (e.g., having 6, 10, or 14 pi electrons shared in a cyclic array) having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently optionally substituted, i.e., unsubstituted (an "unsubstituted aryl") or substituted (a "substituted aryl") with one or more substituents. In certain embodiments, the aryl group is unsubstituted $C_{6-14}$ aryl. In certain embodiments, the aryl group is substituted $C_{6-14}$ aryl.

"Aralkyl" is a subset of alkyl and aryl and refers to an optionally substituted alkyl group substituted by an optionally substituted aryl group. In certain embodiments, the aralkyl is optionally substituted benzyl. In certain embodiments, the aralkyl is benzyl. In certain embodiments, the aralkyl is optionally substituted phenethyl. In certain embodiments, the aralkyl is phenethyl.

"Heteroaryl" refers to a radical of a 5-10 membered monocyclic or bicyclic 4n+2 aromatic ring system (e.g., having 6 or 10 pi electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently optionally substituted, i.e., unsubstituted (an "unsubstituted heteroaryl") or substituted (a "substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl, and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benziisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

"Heteroaralkyl" is a subset of alkyl and heteroaryl and refers to an optionally substituted alkyl group substituted by an optionally substituted heteroaryl group.

"Unsaturated" or "partially unsaturated" refers to a group that includes at least one double or triple bond. A "partially unsaturated" ring system is further intended to encompass rings having multiple sites of unsaturation, but is not intended to include aromatic groups (e.g., aryl or heteroaryl groups). Likewise, "saturated" refers to a group that does not contain a double or triple bond, i.e., contains all single bonds.

Alkyl, alkenyl, alkynyl, carbocyclyl, heterocyclyl, aryl, and heteroaryl groups, which are divalent bridging groups, are further referred to using the suffix -ene, e.g., alkylene, alkenylene, alkynylene, carbocyclylene, heterocyclylene, arylene, and heteroarylene.

An atom, moiety, or group described herein may be unsubstituted or substituted, as valency permits, unless otherwise provided expressly. The term "optionally substituted" refers to substituted or unsubstituted.

A group is optionally substituted unless expressly provided otherwise. The term "optionally substituted" refers to being substituted or unsubstituted. In certain embodiments, alkyl, alkenyl, alkynyl, carbocyclyl, heterocyclyl, aryl, and heteroaryl groups are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present disclosure contemplates any and all such combinations in order to arrive at a stable compound. For purposes of this disclosure, heteroatoms such as nitrogen may have hydrogen substituents and/or any suitable substituent as described herein which satisfy the valencies of the heteroatoms and results in the formation of a stable moiety. In certain embodiments, the substituent is a carbon atom substituent. In certain embodiments, the substituent is a nitrogen atom substituent. In certain embodiments, the substituent is an oxygen atom substituent. In certain embodiments, the substituent is a sulfur atom substituent.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR N(R$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$ —C(=S)N(R$^{bb}$)$_2$, —C(=O)SR$^{aa}$, —C(=S) SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)(R$^{aa}$)$_2$, —P(=O)(OR$^{cc}$)$_2$, —OP(=O)(R$^{aa}$)$_2$, —OP(=O)(OR$^{cc}$)$_2$, —P(=O)(N(R$^{bb}$)$_2$)$_2$, —OP(=)(N(R$^{bb}$)$_2$)$_2$, —NR$^{bb}$P(=O) (R$^{aa}$)$_2$, —NR$^{bb}$P(=O)(OR$^{cc}$)$_2$, —NR$^{bb}$P(=O)(N(R$^{bb}$)$_2$)$_2$, —P(R$^{cc}$)$_2$, —P(OR$^{cc}$)$_2$, —P(R$^{cc}$)$_3^+$X$^-$, —P(OR$^{cc}$)$_3^+$X$^-$, —P(R$^{cc}$)$_4$, —P(OR$^{cc}$)$_4$, —OP(R$^{cc}$)$_2$, —OP(R$^{cc}$)$_3^+$X$^-$, —OP (OR$^{cc}$)$_2$, —OP(OR$^{cc}$)$_3^+$X$^-$, —OP(R$^{cc}$)$_4$, —OP(OR$^{cc}$)$_4$, —B(R$^{cc}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 R$^{dd}$ groups; wherein X$^-$ is a counterion;

or two geminal hydrogens on a carbon atom are replaced with the group =O, =S, =NN(R$^{bb}$)$_2$, =NNR$^{bb}$C(=O) R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$) OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)(R$^{aa}$)$_2$, —P(=O)(OR$^{cc}$)$_2$, —P(=O)(N(R$^{cc}$)$_2$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups; wherein X$^-$ is a counterion;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3^+$X$^-$, —N(OR$^{ee}$) R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)(OR$^{ee}$)$_2$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S; wherein X$^-$ is a counterion;

each instance of R$^{ee}$ is, independently, selected from C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from hydrogen, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl and 5-10 membered heteroaryl, or two R$^{ff}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{gg}$ groups; and each instance of R$^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3^+$X$^-$, —NH(C$_{1-6}$ alkyl)$_2^+$X$^-$, —NH$_2$(C$_{1-6}$ alkyl)$^+$X$^-$, —NH$_3^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$-C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$alkyl, —SC(=S)SC$_{1-6}$ alkyl, —P(=O)(OC$_{1-6}$alkyl)$_2$, —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, 5-10 membered heteroaryl; or two geminal R$^{gg}$ substituents can be joined to form =O or =S; wherein X$^-$ is a counterion.

A "counterion" or "anionic counterion" is a negatively charged group associated with a positively charged group in order to maintain electronic neutrality. An anionic counterion may be monovalent (i.e., including one formal negative charge). An anionic counterion may also be multivalent (i.e., including more than one formal negative charge), such as divalent or trivalent. Exemplary counterions include halide ions (e.g., F$^-$, Cl$^-$, Br$^-$, I$^-$), NO$_3^-$, ClO$_4^-$, OH$^-$, H$_2$PO$_4^-$, HSO$_4^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), carboxylate ions (e.g., acetate, propanoate, benzoate, glycerate, lactate, tartrate, glycolate, gluconate, and the like), BF$_4^-$, PF$_4^-$, PF$_6^-$, AsF$_6^-$, SbF$_6^-$, B[3,5-(CF$_3$)$_2$C$_6$H$_3$]$_4^-$, BPh$_4^-$, Al(OC(CF$_3$)$_3$)$_4^-$, and a carborane anion (e.g., CB$_{11}$H$_{12}^-$ or (HCB$_{11}$Me$_5$Br$_6$)$^-$). Exemplary counterions which may be multivalent include CO$_3^{2-}$, HPO$_4^{2-}$, PO$_4^{3-}$, B$_4$O$_7^{2-}$, SO$_4^{2-}$, S$_2$O$_3^{2-}$, carboxylate anions (e.g., tartrate, citrate, fumarate, maleate, malate, malonate, gluconate, succinate, glutarate, adipate, pimelate, suberate, azelate, sebacate, salicylate, phthalates, aspartate, glutamate, and the like), and carboranes.

"Halo" or "halogen" refers to fluorine (fluoro, —F), chlorine (chloro, —Cl), bromine (bromo, —Br), or iodine (iodo, —I).

"Acyl" refers to a moiety selected from the group consisting of —C(=O)R$^{aa}$, —CHO, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$)N(R$^{bb}$)$_2$, —C(=O)NR$^{bb}$SO$_2$R$^{aa}$, —C(=S)N(R$^{bb}$)$_2$, —C(=O)SR$^{aa}$, or —C(=S)SR$^{aa}$, wherein R$^{aa}$ and R$^{bb}$ are as defined herein.

Nitrogen atoms can be substituted or unsubstituted as valency permits, and include primary, secondary, tertiary, and quaternary nitrogen atoms. Exemplary nitrogen atom substituents include, but are not limited to, hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)(OR$^{cc}$)$_2$, —P(=O)(R$^{aa}$)$_2$, —P(=O)(N(R$^{cc}$)$_2$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups attached to a nitrogen atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups, and wherein R$^{aa}$, R$^{bb}$, R$^{cc}$, and R$^{dd}$ are as defined above.

In certain embodiments, the substituent present on a nitrogen atom is a nitrogen protecting group (also referred to as an amino protecting group). Nitrogen protecting groups include, but are not limited to, —OH, —OR$^{aa}$, —N(R$^{cc}$)$_2$, —C(=O)R$^{aa}$, —C(=O)N(R$^{cc}$)$_2$, —CO$_2$R$^{aa}$, —SO$_2$R$^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, C$_{1-10}$ alkyl (e.g., aralkyl, heteroaralkyl), C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl groups, wherein each alkyl, alkenyl, alkynyl, carbocyclyl, heterocyclyl, aralkyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined herein. Nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

For example, nitrogen protecting groups such as amide groups (e.g., —C(=O)R$^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, and o-(benzoyloxymethyl)benzamide.

Nitrogen protecting groups such as carbamate groups (e.g., —C(=O)OR$^{aa}$) include, but are not limited to, methyl carbamate, ethyl carbamate, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl) ethyl carbamate (Pyoc), 2-(N,N-dicyclohexylcarboxamido) ethyl carbamate, t-butyl carbamate (BOC or Boc), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo) benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., —S(=O)$_2$R$^{aa}$) include, but are not limited to, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene) amine, N,N'-isopropylidenediamine, N-p-nitrobenzylideneamine, N-salicylideneamine, N-5-chlorosalicylideneamine, N-(5-chloro-2-hydroxyphenyl) phenylmethyleneamine, N-cyclohexylideneamine, N-(5,5-dimethyl-3-oxo-1-cyclohexenyl)amine, N-borane derivative, N-diphenylborinic acid derivative, N-[phenyl (pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

Exemplary oxygen atom substituents include, but are not limited to, —R$^{aa}$, —C(=O)SR$^{aa}$, —C(=O)R$^{aa}$, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$)N(R$^{bb}$)$_2$, —S(=O)R$^{aa}$, —SO$_2$R$^{aa}$, —Si(R$^{aa}$)$_3$, —P(R$^{cc}$)$_2$, —P(R$^{cc}$)$_3$$^+$X$^-$, —P(OR$^{cc}$)$_2$, —P(OR$^{cc}$)$_3$$^+$X$^-$, —P(=O)(R$^{aa}$)$_2$, —P(=O)(OR$^{cc}$)$_2$, and —P(=O)(N(R$^{bb}$)$_2$)$_2$, wherein X$^-$, R$^{aa}$, R$^{bb}$, and R$^{cc}$ are as defined herein. In certain embodiments, the oxygen atom substituent present on an oxygen atom is an oxygen protecting group (also referred to as a hydroxyl protecting group). Oxygen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference. Exemplary oxygen protecting groups include, but are not limited to, methyl, t-butyloxycarbonyl (BOC or Boc), methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, I-ethoxyethyl, 1-(2-chloroethoxy)ethyl, 1-methyl-1-methoxyethyl, i-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodisulfuran-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1, 1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

Exemplary sulfur atom substituents include, but are not limited to, —$R^{aa}$, —$C(=O)SR^{aa}$, —$C(=O)R^{aa}$, —$CO_2R^{aa}$, —$C(=O)N(R^{bb})_2$, —$C(=NR^{bb})R^{aa}$, —$C(=NR^{bb})OR^{aa}$, —$C(=NR^{bb})N(R^{bb})_2$, —$S(=O)R^{aa}$, —$SO_2R^{aa}$, —$Si(R^{aa})_3$, —$P(R^{cc})_2$, —$P(R^{cc})_3^+X^-$, —$P(OR^{cc})_2$, —$P(OR^{cc})_3^+X^-$, —$P(=O)(R^{aa})_2$, —$P(=O)(OR^{cc})_2$, and —$P(=O)(N(R^{bb})_2)_2$, wherein $R^{aa}$, $R^{bb}$, and $R^{cc}$ are as defined herein. In certain embodiments, the sulfur atom substituent present on a sulfur atom is a sulfur protecting group (also referred to as a thiol protecting group). Sulfur protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

The term "leaving group" is given its ordinary meaning in the art of synthetic organic chemistry and refers to an atom or a group capable of being displaced by a nucleophile. See, for example, Smith, *March Advanced Organic Chemistry* 6th ed. (501-502). Examples of suitable leaving groups include, but are not limited to, halogen (such as F, Cl, Br, or I (iodine)), alkoxycarbonyloxy, aryloxycarbonyloxy, alkanesulfonyloxy, arenesulfonyloxy, alkyl-carbonyloxy (e.g., acetoxy), arylcarbonyloxy, aryloxy, methoxy, N,O-dimethylhydroxylamino, pixyl, and haloformates. In some cases, the leaving group is an activated substituted hydroxyl group (e.g., —$OC(=O)SR^{aa}$, —$OC(=O)R^{aa}$, —$OCO_2R^{aa}$, —$OC(=O)N(R^{bb})_2$, —$OC(=NR^{bb})R^{aa}$, —$OC(=NR^{bb})OR^{aa}$, —$OC(=NR^{bb})N(R^{bb})_2$, —$OS(=O)R^{aa}$, —$OSO_2R^{aa}$, —$OP(R^{cc})_2$, —$OP(R^{cc})_3$, —$OP(=O)_2R^{aa}$, —$OP(=O)(R^{aa})_2$, —$OP(=O)(OR^{cc})_2$, —$OP(=O)_2N(R^{bb})_2$, and —$OP(=O)(NR^{bb})_2$, wherein $R^{aa}$, $R^{bb}$, and $R^{cc}$ are as defined herein). In some cases, the leaving group is a sulfonic acid ester, such as toluenesulfonate (tosylate, —OTs), methanesulfonate (mesylate, —OMs), p-bromobenzenesulfonyloxy (brosylate, —OBs), —$OS(=O)_2(CF_2)_3CF_3$ (nonaflate, —ONf), or trifluoromethanesulfonate (triflate, —OTf). In some cases, the leaving group is a brosylate, such as p-bromobenzenesulfonyloxy. In some cases, the leaving group is a nosylate, such as 2-nitrobenzenesulfonyloxy. In some embodiments, the leaving group is a sulfonate-containing group. In some embodiments, the leaving group is a tosylate group. The leaving group may also be a phosphineoxide (e.g., formed during a Mitsunobu reaction) or an internal leaving group such as an epoxide or cyclic sulfate. Other non-limiting examples of leaving groups are water, ammonia, alcohols, ether moieties, thioether moieties, zinc halides, magnesium moieties, diazonium salts, and copper moieties.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art. For example, Berge et al., describe pharmaceutically acceptable salts in detail in *J. Pharmaceutical Sciences*, 1977, 66, 1-19, incorporated herein by reference. Pharmaceutically acceptable salts of the compounds described herein include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid, and perchloric acid or with organic acids such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}$ alkyl$)_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

The term "solvate" refers to forms of the compound, or a salt thereof, that are associated with a solvent, usually by a solvolysis reaction. This physical association may include hydrogen bonding. Conventional solvents include water, methanol, ethanol, acetic acid, DMSO, THF, diethyl ether, and the like. The compounds described herein may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolatable solvates. Representative solvates include hydrates, ethanolates, and methanolates.

The term "hydrate" refers to a compound that is associated with water. Typically, the number of the water molecules contained in a hydrate of a compound is in a definite ratio to the number of the compound molecules in the hydrate. Therefore, a hydrate of a compound may be represented, for example, by the general formula R.x $H_2O$, wherein R is the compound, and x is a number greater than 0. A given compound may form more than one type of hydrate, including, e.g., monohydrates (x is 1), lower hydrates (x is a number greater than 0 and smaller than 1, e.g., hemihydrates (R.0.5 $H_2O$)), and polyhydrates (x is a number greater than 1, e.g., dihydrates (R.$2H_2O$) and hexahydrates (R.$6H_2O$)).

The term "tautomers" or "tautomeric" refers to two or more interconvertible compounds resulting from at least one formal migration of a hydrogen atom and at least one change in valency (e.g., a single bond to a double bond, a triple bond to a single bond, or vice versa). The exact ratio of the tautomers depends on several factors, including temperature, solvent, and pH. Tautomerizations (i.e., the reaction providing a tautomeric pair) may catalyzed by acid or base. Exemplary tautomerizations include keto-to-enol, amide-to-imide, lactam-to-lactim, enamine-to-imine, and enamine-to-(a different enamine) tautomerizations.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The term "polymorphs" refers to a crystalline form of a compound (or a salt, hydrate, or solvate thereof). All polymorphs have the same elemental composition. Different crystalline forms usually have different X-ray diffraction patterns, infrared spectra, melting points, density, hardness, crystal shape, optical and electrical properties, stability, and solubility. Recrystallization solvent, rate of crystallization, storage temperature, and other factors may cause one crystal form to dominate. Various polymorphs of a compound can be prepared by crystallization under different conditions.

The term "prodrugs" refers to compounds that have cleavable groups and become by solvolysis or under physiological conditions the compounds described herein, which are pharmaceutically active in vivo. Such examples include, but are not limited to, choline ester derivatives and the like, N-alkylmorpholine esters and the like. Other derivatives of the compounds described herein have activity in both their acid and acid derivative forms, but in the acid sensitive form often offer advantages of solubility, tissue compatibility, or delayed release in the mammalian organism (see, Bundgard, H., *Design of Prodrugs*, pp. 7-9, 21-24, Elsevier, Amsterdam 1985). Prodrugs include acid derivatives well known to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides, and anhydrides derived from acidic groups pendant on the compounds described herein are particular prodrugs. In some cases it is desirable to prepare double ester type prodrugs such as (acyloxy)alkyl esters or ((alkoxycarbonyl)oxy)alkylesters. $C_1$-$C_8$ alkyl, $C_2$-$C_8$ alkenyl, $C_2$-$C_8$ alkynyl, aryl, $C_7$-$C_{12}$ substituted aryl, and $C_7$-$C_{12}$ arylalkyl esters of the compounds described herein may be preferred.

The term "small molecule" refers to molecules, whether naturally-occurring or artificially created (e.g., via chemical synthesis) that have a relatively low molecular weight. Typically, a small molecule is an organic compound (i.e., it contains carbon). The small molecule may contain multiple carbon-carbon bonds, stereocenters, and other functional groups (e.g., amines, hydroxyl, carbonyls, and heterocyclic rings, etc.). In certain embodiments, the molecular weight of a small molecule is not more than about 1,000 g/mol, not more than about 900 g/mol, not more than about 800 g/mol, not more than about 700 g/mol, not more than about 600 g/mol, not more than about 500 g/mol, not more than about 400 g/mol, not more than about 300 g/mol, not more than about 200 g/mol, or not more than about 100 g/mol. In certain embodiments, the molecular weight of a small molecule is at least about 100 g/mol, at least about 200 g/mol, at least about 300 g/mol, at least about 400 g/mol, at least about 500 g/mol, at least about 600 g/mol, at least about 700 g/mol, at least about 800 g/mol, or at least about 900 g/mol, or at least about 1,000 g/mol. Combinations of the above ranges (e.g., at least about 200 g/mol and not more than about 500 g/mol) are also possible. In certain embodiments, the small molecule is a therapeutically active agent such as a drug (e.g., a molecule approved by the U.S. Food and Drug Administration as provided in the Code of Federal Regulations (C.F.R.)). The small molecule may also be complexed with one or more metal atoms and/or metal ions. Preferred small molecules are biologically active in that they produce a biological effect in animals, preferably mammals, more preferably humans. Small molecules include, but are not limited to, radionuclides and imaging agents. In certain embodiments, the small molecule is a drug. Preferably, though not necessarily, the drug is one that has already been deemed safe and effective for use in humans or animals by the appropriate governmental agency or regulatory body. For example, drugs approved for human use are listed by the FDA under 21 C.F.R. §§ 330.5, 331 through 361, and 440 through 460, incorporated herein by reference; drugs for veterinary use are listed by the FDA under 21 C.F.R. §§ 500 through 589, incorporated herein by reference. All listed drugs are considered acceptable for use in accordance with the present invention.

The term "small molecule label" refers to a small molecule that is capable of being detected, or a radical of such a small molecule. Exemplary small molecule labels include, but are not limited to, biotin, radioactive isotopes, enzymes, luminescent agents, precipitating agents, fluorophores, and dyes.

The term "small molecule fluorophore" refers to a small molecule that is fluorescent, e.g., being able to re-emit light upon light excitation. Exemplary small molecule fluorophores include, but are not limited to, fluorescein, rhodamine, coumarin, cyanine, and derivatives thereof.

The term "inhibition", "inhibiting", "inhibit," or "inhibitor" refer to the ability of a compound to reduce, slow, halt or prevent activity of a particular biological process (e.g., activity of Myc) in a cell relative to vehicle.

When a compound, pharmaceutical composition, method, use, or kit is referred to as "selectively," "specifically," or "competitively" inhibiting a Myc, the compound, pharmaceutical composition, method, use, or kit inhibits the Myc to a greater extent (e.g., not less than 2-fold, not less than 5-fold, not less than 10-fold, not less than 30-fold, not less than 100-fold, not less than 1,000-fold, or not less than 10,000-fold; and/or not more than 2-fold, not more than 5-fold, not more than 10-fold, not more than 30-fold, not more than 100-fold, not more than 1,000-fold, or not more than 10,000-fold) than inhibiting a different Myc and/or a different transcription factor.

The term "aberrant activity" refers to activity deviating from normal activity. In certain embodiments, the aberrant activity is increased activity. In certain embodiments, the aberrant activity is decreased activity. The term "increased activity" refers to activity higher than normal activity. The term "decreased activity" refers to activity lower than normal activity.

The terms "composition" and "formulation" are used interchangeably.

A "subject" to which administration is contemplated refers to a human (i.e., male or female of any age group, e.g., pediatric subject (e.g., infant, child, or adolescent) or adult subject (e.g., young adult, middle-aged adult, or senior adult)) or non-human animal. In certain embodiments, the non-human animal is a mammal (e.g., primate (e.g., cynomolgus monkey or rhesus monkey), commercially relevant mammal (e.g., cattle, pig, horse, sheep, goat, cat, or dog), or bird (e.g., commercially relevant bird, such as chicken, duck, goose, or turkey)). In certain embodiments, the non-human animal is a fish, reptile, or amphibian. The non-human animal may be a male or female at any stage of development. The non-human animal may be a transgenic animal or genetically engineered animal. A "patient" refers to a human subject in need of treatment of a proliferative disease.

The term "biological sample" refers to any sample including tissue samples (such as tissue sections and needle biopsies of a tissue); cell samples (e.g., cytological smears (such as Pap or blood smears) or samples of cells obtained by microdissection); samples of whole organisms (such as samples of yeasts or bacteria); or cell fractions, fragments or organelles (such as obtained by lysing cells and separating the components thereof by centrifugation or otherwise). Other examples of biological samples include blood, serum, urine, semen, fecal matter, cerebrospinal fluid, interstitial fluid, mucous, tears, sweat, pus, biopsied tissue (e.g., obtained by a surgical biopsy or needle biopsy), nipple aspirates, milk, vaginal fluid, saliva, swabs (such as buccal swabs), or any material containing biomolecules that is derived from a first biological sample.

The terms "administer," "administering," or "administration" refers to implanting, absorbing, ingesting, injecting, inhaling, or otherwise introducing a compound described herein, or a composition thereof, in or on a subject.

The terms "treatment," "treat," and "treating" refer to reversing, alleviating, delaying the onset of, or inhibiting the progress of a proliferative disease described herein. In some embodiments, treatment may be administered after one or more signs or symptoms of the proliferative disease have developed or have been observed. In other embodiments, treatment may be administered in the absence of signs or symptoms of the proliferative disease. For example, treatment may be administered to a susceptible subject prior to the onset of symptoms (e.g., in light of a history of symptoms and/or in light of exposure to a pathogen). Treatment may also be continued after symptoms have resolved, for example, to delay or prevent recurrence.

The term "prevent," "preventing," or "prevention" refers to a prophylactic treatment of a subject who is not and was not with a proliferative disease but is at risk of developing the proliferative disease or who was with a proliferative disease, is not with the proliferative disease, but is at risk of regression of the proliferative disease. In certain embodiments, the subject is at a higher risk of developing the proliferative disease or at a higher risk of regression of the proliferative disease than an average healthy member of a population.

The terms "condition," "disease," and "disorder" are used interchangeably.

An "effective amount" of a compound described herein refers to an amount sufficient to elicit the desired biological response. An effective amount of a compound described herein may vary depending on such factors as the desired biological endpoint, the pharmacokinetics of the compound, the condition being treated, the mode of administration, and the age and health of the subject. In certain embodiments, an effective amount is a therapeutically effective amount. In certain embodiments, an effective amount is a prophylactic treatment. In certain embodiments, an effective amount is the amount of a compound described herein in a single dose. In certain embodiments, an effective amount is the combined amounts of a compound described herein in multiple doses.

A "therapeutically effective amount" of a compound described herein is an amount sufficient to provide a therapeutic benefit in the treatment of a condition or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms, signs, or causes of the condition, and/or enhances the therapeutic efficacy of another therapeutic agent. In certain embodiments, a therapeutically effective amount is effective for modulating (e.g., inhibiting) the activity of Myc. In certain embodiments, a therapeutically effective amount is effective for treating a proliferative disease. In certain embodiments, a therapeutically effective amount is effective for modulating (e.g., inhibiting) the activity of Myc and effective for treating a proliferative disease. In certain embodiments, a therapeutically effective amount is effective for inducing apoptosis.

A "prophylactically effective amount" of a compound described herein is an amount sufficient to prevent a condition, or one or more symptoms associated with the condition or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent. In certain embodiments, a prophylactically effective amount is effective for modulating (e.g., inhibiting) the activity of Myc. In certain embodiments, a prophylactically effective amount is effective for preventing a proliferative disease. In certain embodiments, a prophylactically effective amount is effective for modulating (e.g., inhibiting) the activity of Myc and effective for preventing a proliferative disease. In certain embodiments, a prophylactically effective amount is effective for inducing apoptosis.

The term "transcription factor" refers to is a protein that binds to specific DNA sequences, thereby controlling the rate of transcription of genetic information from DNA to messenger RNA. Transcription factors perform their functions alone or with other proteins in a complex, by promoting (as an activator), or blocking (as a repressor) the recruitment of RNA polymerase to specific genes. A feature of transcription factors is that they contain one or more DNA-binding domains (DBDs), which attach to specific sequences of DNA adjacent to the genes that they regulate. Additional proteins such as coactivators, chromatin remodelers, histone acetylases, deacetylases, kinases, and methylases, while also playing crucial roles in gene regulation, lack DNA-binding domains, and, therefore, are not classified as transcription factors. In certain embodiments, a transcription factor described herein is Myc. In certain embodiments, a transcription factor described herein is c-Myc. In certain embodiments, a transcription factor described herein is SP1, AP-1, C/EBP, heat shock factor, ATF/CREB, Oct-1, or NF-1.

The term "Myc" refers to the Myc family of transcription factors and the genes encoding the Myc family of transcription factors. In certain embodiments, the Myc is c-Myc (encoded by the MYC gene (HomoloGene: 31092; ChEMBL: 1250348; GeneCards: MYC Gene)). In certain embodiments, the Myc is L-Myc (encoded by the MYCL gene (HomoloGene: 3921; GeneCards: MYCL Gene)) or N-Myc (encoded by the MYCN gene (HomoloGene: 3922; GeneCards: MYCN Gene)). In certain embodiments, the Myc is MYC. In certain embodiments, the Myc is MYCL or MYCN.

A "proliferative disease" refers to a disease that occurs due to abnormal growth or extension by the multiplication of cells (Walker, *Cambridge Dictionary of Biology*; Cambridge University Press: Cambridge, UK, 1990). A proliferative disease may be associated with: 1) the pathological proliferation of normally quiescent cells; 2) the pathological migration of cells from their normal location (e.g., metastasis of neoplastic cells); 3) the pathological expression of proteolytic enzymes such as the matrix metalloproteinases (e.g., collagenases, gelatinases, and elastases); or 4) the pathological angiogenesis as in proliferative retinopathy and tumor metastasis. Exemplary proliferative diseases include cancers (i.e., "malignant neoplasms"), benign neoplasms, angiogenesis, inflammatory diseases, and autoimmune diseases.

The term "angiogenesis" refers to the physiological process through which new blood vessels form from pre-existing vessels. Angiogenesis is distinct from vasculogenesis, which is the de novo formation of endothelial cells from mesoderm cell precursors. The first vessels in a developing embryo form through vasculogenesis, after which angiogenesis is responsible for most blood vessel growth during normal or abnormal development. Angiogenesis is a vital process in growth and development, as well as in wound healing and in the formation of granulation tissue. However, angiogenesis is also a fundamental step in the transition of tumors from a benign state to a malignant one, leading to the use of angiogenesis inhibitors in the treatment of cancer. Angiogenesis may be chemically stimulated by angiogenic proteins, such as growth factors (e.g., VEGF). "Pathological angiogenesis" refers to abnormal (e.g., excessive or insufficient) angiogenesis that amounts to and/or is associated with a disease.

The terms "neoplasm" and "tumor" are used herein interchangeably and refer to an abnormal mass of tissue wherein the growth of the mass surpasses and is not coordinated with the growth of a normal tissue. A neoplasm or tumor may be "benign" or "malignant," depending on the following characteristics: degree of cellular differentiation (including morphology and functionality), rate of growth, local invasion, and metastasis. A "benign neoplasm" is generally well differentiated, has characteristically slower growth than a malignant neoplasm, and remains localized to the site of origin. In addition, a benign neoplasm does not have the capacity to infiltrate, invade, or metastasize to distant sites. Exemplary benign neoplasms include, but are not limited to, lipoma, chondroma, adenomas, acrochordon, senile angiomas, seborrheic keratoses, lentigos, and sebaceous hyperplasias. In some cases, certain "benign" tumors may later give rise to malignant neoplasms, which may result from additional genetic changes in a subpopulation of the tumor's neoplastic cells, and these tumors are referred to as "pre-malignant neoplasms." An exemplary pre-malignant neoplasm is a teratoma. In contrast, a "malignant neoplasm" is generally poorly differentiated (anaplasia) and has characteristically rapid growth accompanied by progressive infiltration, invasion, and destruction of the surrounding tissue. Furthermore, a malignant neoplasm generally has the capacity to metastasize to distant sites. The term "metastasis," "metastatic," or "metastasize" refers to the spread or migration of cancerous cells from a primary or original tumor to another organ or tissue and is typically identifiable by the presence of a "secondary tumor" or "secondary cell mass" of the tissue type of the primary or original tumor and not of that of the organ or tissue in which the secondary (metastatic) tumor is located. For example, a prostate cancer that has migrated to bone is said to be metastasized prostate cancer and includes cancerous prostate cancer cells growing in bone tissue.

The term "cancer" refers to a class of diseases characterized by the development of abnormal cells that proliferate uncontrollably and have the ability to infiltrate and destroy normal body tissues. See, e.g., Stedman's Medical Dictionary, 25th ed.; Hensyl ed.; Williams & Wilkins: Philadelphia, 1990. Exemplary cancers include, but are not limited to, hematological malignancies. Additional exemplary cancers include, but are not limited to, lung cancer (e.g., bronchogenic carcinoma, small cell lung cancer (SCLC), non-small cell lung cancer (NSCLC), adenocarcinoma of the lung); kidney cancer (e.g., nephroblastoma, a.k.a. Wilms' tumor, renal cell carcinoma); acoustic neuroma; adenocarcinoma; adrenal gland cancer, anal cancer, angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer, breast cancer (e.g., adenocarcinoma of the breast, papillary carcinoma of the breast, mammary cancer, medullary carcinoma of the breast); brain cancer (e.g., meningioma, glioblastomas, glioma (e.g., astrocytoma, oligodendroglioma), medulloblastoma); bronchus cancer, carcinoid tumor, cervical cancer (e.g., cervical adenocarcinoma); choriocarcinoma; chordoma; craniopharyngioma; colorectal cancer (e.g., colon cancer, rectal cancer, colorectal adenocarcinoma); connective tissue cancer, epithelial carcinoma; ependymoma; endotheliosarcoma (e.g., Kaposi's sarcoma, multiple idiopathic hemorrhagic sarcoma); endometrial cancer (e.g., uterine cancer, uterine sarcoma); esophageal cancer (e.g., adenocarcinoma of the esophagus, Barrett's adenocarcinoma); Ewing's sarcoma; ocular cancer (e.g., intraocular melanoma, retinoblastoma); familiar hypereosinophilia; gall bladder cancer, gastric cancer (e.g., stomach adenocarcinoma); gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); heavy chain disease (e.g., alpha chain disease, gamma chain disease, mu chain disease; hemangioblastoma; hypopharynx cancer, inflammatory myofibroblastic tumors; immunocytic amyloidosis; liver cancer (e.g., hepatocellular cancer (HCC), malignant hepatoma); leiomyosarcoma (LMS); mastocytosis (e.g., systemic mastocytosis); muscle cancer; myelodysplastic syndrome (MDS); mesothelioma; myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendoctrine tumor (GEP-NET), carcinoid tumor); osteosarcoma (e.g., bone cancer); ovarian cancer (e.g., cystadenocarcinoma, ovarian embryonal carcinoma, ovarian adenocarcinoma); papillary adenocarcinoma; pancreatic cancer (e.g., pancreatic andenocarcinoma, intraductal papillary mucinous neoplasm (IPMN), Islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasms; prostate cancer (e.g., prostate adenocarcinoma); rectal cancer; rhabdomyosarcoma; salivary gland cancer; skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; small intestine cancer, sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer, vaginal cancer; and vulvar cancer (e.g., Paget's disease of the vulva). The term "hematological malignancy" refers to tumors that affect blood, bone marrow, and/or lymph nodes. Exemplary hematological malignancies include, but are not limited to, leukemia, such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL)); lymphoma, such as Hodgkin lymphoma (HL) (e.g., B-cell HL, T-cell HL) and non-Hodgkin lymphoma (NHL) (e.g., B-cell NHL, such as diffuse large cell lymphoma (DLCL) (e.g., diffuse large B-cell lymphoma (DLBCL, e.g., activated B-cell (ABC) DLBCL (ABC-DLBCL))), follicular lymphoma, chronic lymphocytic leukemia/small lymphocytic lymphoma (CLL/SLL), mantle cell lymphoma (MCL), marginal zone B-cell lymphoma (e.g., mucosa-associated lymphoid tissue (MALT) lymphoma, nodal marginal zone B-cell lymphoma, splenic marginal zone B-cell lymphoma), primary mediastinal B-cell lymphoma, Burkitt's lymphoma, Waldenström's macroglobulinemia (WM, lymphoplasmacytic lymphoma), hairy cell leukemia (HCL), immunoblastic large cell lymphoma, precursor B-lymphoblastic lymphoma, central nervous system (CNS) lymphoma (e.g., primary CNS lymphoma and secondary CNS lymphoma); and T-cell NHL, such as precursor T-lymphoblastic lymphoma/leukemia, peripheral T-cell lymphoma (PTCL) (e.g., cutaneous T-cell lymphoma (CTCL) (e.g., mycosis fungoides, Sezary syndrome), angioimmunoblastic T-cell lymphoma, extranodal natural killer T-cell lymphoma, enteropathy type T-cell lymphoma, subcutaneous panniculitis-like T-cell lymphoma, and anaplastic large cell lymphoma); lymphoma of an immune privileged site (e.g., cerebral lymphoma, ocular lymphoma, lymphoma of the placenta, lymphoma of the fetus, testicular lymphoma); a mixture of one or more leukemia/lymphoma as described above; myelodysplasia; and multiple myeloma (MM).

BRIEF DESCRIPTION OF THE DRAWINGS

FIG. 2A), SNUC5 (colon; FIG. 2B), Namalwa (Burkitt's lymphoma; FIG. 2C), KLP1 (breast; FIG. 2D), and Hela (cervix; FIG. 2E). Results were expressed as a mean+/−SEM (n=3). RLU: Relative Luminescence Units.

FIGS. 3A to 3B show CTD$^2$ viability data profile of cancer cell lines treated with compound 1. FIG. 3A: dose response curves of 789 cell lines treated with compound 1 for 72 hours. FIG. 3B: relative percent composition of cell lineages and enrichment analysis after treatment with compound 1.

DETAILED DESCRIPTION OF CERTAIN EMBODIMENTS OF THE INVENTION

Figure 1A:
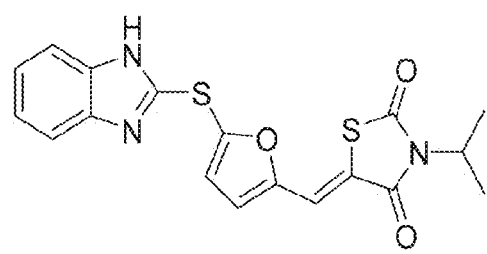
FIG. 1A shows the chemical structure of compound 1.

The present disclosure provides, in one aspect, compounds of Formula (I), and pharmaceutically acceptable salts, solvates, hydrates, polymorphs, co-crystals, tautomers, stereoisomers, isotopically labeled derivatives, and prodrugs thereof. The compounds described herein may be binders and/or modulators (e.g., inhibitors or activators) of Myc (e.g., c-Myc, L-Myc, and/or N-Myc). Also provided are pharmaceutical compositions, kits, methods, and uses including a compound described herein.

Compounds

One aspect of the present disclosure relates to the compounds described herein. The compounds described herein may be Myc modulators (e.g., Myc inhibitors) and/or Myc binders. In certain embodiments, a compound described herein is a compound of Formula (I-a), or a pharmaceutically acceptable salt, solvate, hydrate, polymorph, co-crystal, tautomer, stereoisomer, isotopically labeled derivative, or prodrug thereof. In certain embodiments, a compound described herein is a compound of Formula (I), or a pharmaceutically acceptable salt, solvate, hydrate, polymorph, co-crystal, tautomer, stereoisomer, isotopically labeled derivative, or prodrug thereof. In certain embodiments, a compound described herein is a compound of Formula (I), or a pharmaceutically acceptable salt thereof. In certain embodiments, a compound described herein is a compound of Formula (II), or a pharmaceutically acceptable salt, solvate, hydrate, polymorph, co-crystal, tautomer, stereoisomer, isotopically labeled derivative, or prodrug thereof.

Compounds of Formula (I-a)

In certain embodiments, the compound of Formula (I-a) is of the formula:

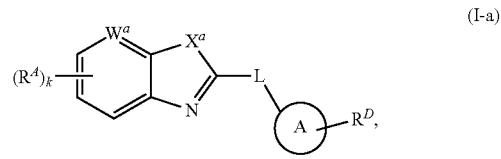

or a pharmaceutically acceptable salt, solvate, hydrate, polymorph, co-crystal, tautomer, stereoisomer, isotopically labeled derivative, or prodrug thereof, wherein:

each instance of $R^A$ is independently hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^a$, —N(R$^a$)$_2$, —SR$^a$, —CN, —SCN, —C(=NR$^a$)R$^a$, —C(=NR$^a$)OR$^a$, —C(=NR$^a$)N(R$^a$)$_2$, —C(=O)R$^a$, —C(=O)OR$^a$, —C(=O)N(R$^a$)$_2$, —NO$_2$, —N(R$^a$)C(=O)R$^a$, —N(R$^a$)C(=O)OR$^a$, —N(R$^a$)C(=O)N(R$^a$)$_2$, —N(R$^a$)S(=O)R$^a$, —N(R$^a$)S(=O)OR$^a$, —N(R$^a$)S(=O)N(R$^a$)$_2$, —N(R$^a$)S(=O)$_2$R$^a$, —N(R$^a$)S(=O)$_2$OR$^a$, —N(R$^a$)S(=O)$_2$N(R$^a$)$_2$, —OC(=O)R$^a$, —OC(=O)OR$^a$, or —OC(=O)N(R$^a$)$_2$, or two instances of $R^A$ are joined to form a substituted or unsubstituted, carbocyclic ring, substituted or unsubstituted, heterocyclic ring, substituted or unsubstituted, aryl ring, or substituted or unsubstituted, heteroaryl ring;

k is 0, 1, 2, or 3;

L is —N—, —O—, —S—, or a bond;

X$^a$ is —NR$^B$—, —O—, or —S—;

W$^a$ is —CR$^A$= or —N=;

R$^B$ is hydrogen, substituted or unsubstituted C$_{1-6}$ alkyl, or a nitrogen protecting group;

R$^D$ is hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^{d1}$, —N(R$^{d1}$)$_2$, —NO$_2$, —NR$^{d1}$C(=O)R$^{d1}$, —NR$^{d1}$C(=O)OR$^{d1}$, —NR$^{d1}$C(=O)N(R$^{d1}$)$_2$, —OC(=O)R$^{d1}$, —OC(=O)OR$^{d1}$, —OC(=O)N(R$^{d1}$)$_2$, —C(=O)R$^{d1}$, —C(=O)OR$^{d1}$, —C(=O)N(R$^{d1}$)$_2$, —CH$_2$N(R$^{d1}$)$_2$, or —CH$_2$OR$^{d1}$;

each instance of $R^a$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of R are joined to form a substituted or unsubstituted carbocyclyl ring, substituted or unsubstituted, heterocyclic ring, substituted or unsubstituted aryl ring, or substituted or unsubstituted, heteroaryl ring;

each instance of $R^{d1}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^{d1}$ are joined to form a substituted or unsubstituted carbocyclyl ring, substituted or unsubstituted, heterocyclic ring, substituted or unsubstituted aryl ring, or substituted or unsubstituted, heteroaryl ring; and Ring A is a substituted or unsubstituted aryl, or substituted or unsubstituted heteroaryl.

Formula (I-a) may include one or more instances of substituent $R^A$. When Formula (I-a) includes two or more instances of $R^A$, any two instances of $R^A$ may be the same or different from each other. In certain embodiments, at least one instance of $R^A$ is halogen (e.g., F, Cl, Br, or I). In certain embodiments, at least one instance of $R^A$ is F. In certain embodiments, at least one instance of $R^A$ is Cl. In certain embodiments, at least one instance of $R^A$ is substituted or unsubstituted alkyl. In certain embodiments, at least one instance of $R^A$ is substituted or unsubstituted $C_{1-6}$alkyl. In certain embodiments, at least one instance of $R^A$ is Me. In certain embodiments, at least one instance of $R^A$ is substituted methyl (e.g., —CF$_3$, —CH$_2$OH, or Bn). In certain embodiments, at least one instance of $R^A$ is Et, substituted ethyl (e.g., perfluoroethyl), Pr (e.g., n-Pr or i-Pr), substituted propyl (e.g., perfluoropropyl), Bu, or substituted butyl (e.g., perfluorobutyl). In certain embodiments, at least one instance of $R^A$ is substituted or unsubstituted alkenyl (e.g., substituted or unsubstituted $C_{2-6}$ alkenyl). In certain embodiments, at least one instance of $R^A$ is substituted or unsubstituted alkynyl (e.g., substituted or unsubstituted $C_{2-6}$ alkynyl). In certain embodiments, at least one instance of $R^A$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, at least one instance of $R^A$ is substituted or unsubstituted cyclopropyl, substituted or unsubstituted cyclobutyl, substituted or unsubstituted cyclopentyl, or substituted or unsubstituted cyclohexyl. In certain embodiments, at least one instance of $R^A$ is substituted or unsubstituted heterocyclyl (e.g., substituted or unsubstituted, 3- to 7-membered, monocyclic heterocyclyl comprising zero, one, or two double bonds in the heterocyclic ring system, wherein one, two, or three atoms in the heterocyclic ring system are independently nitrogen, oxygen, or sulfur). In certain embodiments, at least one instance of $R^A$ is substituted or unsubstituted oxetanyl, substituted or unsubstituted tetrahydrofuranyl, substituted or unsubstituted pyrrolidinyl, substituted or unsubstituted tetrahydropyranyl, substituted or unsubstituted piperidinyl, substituted or unsubstituted morpholinyl, or substituted or unsubstituted piperazinyl. In certain embodiments, at least one instance of $R^A$ is substituted or unsubstituted aryl (e.g., substituted or unsubstituted, 6- to 10-membered aryl). In certain embodiments, at least one instance of $R^A$ is unsubstituted phenyl. In certain embodiments, at least one instance of $R^A$ is substituted phenyl. In certain embodiments, at least one instance of $R^A$ is substituted or unsubstituted naphthyl. In certain embodiments, at least one instance of $R^A$ is substituted or unsubstituted heteroaryl. In certain embodiments, at least one instance of $R^A$ is substituted or unsubstituted, 5- to 6-membered, monocyclic heteroaryl, wherein one, two, three, or four atoms in the heteroaryl ring system are independently nitrogen, oxygen, or sulfur. In certain embodiments, at least one instance of $R^A$ is substituted or unsubstituted, 9- to 10-membered, bicyclic heteroaryl, wherein one, two, three, or four atoms in the heteroaryl ring system are independently nitrogen, oxygen, or sulfur. In certain embodiments, at least one instance of $R^A$ is —OR$^a$ (e.g., —OH, —O(substituted or unsubstituted $C_{1-6}$ alkyl) (e.g., —OMe, —OCF$_3$, —OEt, —OPr, —OBu, or —OBn), or —O(substituted or unsubstituted phenyl) (e.g., —OPh)). In certain embodiments, at least one instance of $R^A$ is —SR$^a$ (e.g., —SH, —S(substituted or unsubstituted $C_{1-6}$ alkyl) (e.g., —SMe, —SEt, —SPr, —SBu, or —SBn), or —S(substituted or unsubstituted phenyl) (e.g., —SPh)). In certain embodiments, at least one instance of $R^A$ is —N(R$^a$)$_2$ (e.g., —NH$_2$, —NH(substituted or unsubstituted $C_1$. alkyl) (e.g., —NHMe), or —N(substituted or unsubstituted $C_{1-6}$ alkyl)-(substituted or unsubstituted $C_{1-6}$ alkyl) (e.g., —NMe$_2$)). In certain embodiments, at least one instance of $R^A$ is —CN or —SCN. In certain embodiments, at least one instance of $R^A$ is —NO$_2$. In certain embodiments, at least one instance of $R^A$ is —C(=NR$^a$)R$^a$, —C(=NR$^a$)OR$^a$, or —C(=NR$^a$)N(R$^a$)$_2$. In certain embodiments, at least one instance of $R^A$ is —C(=O)R$^a$ (e.g., —C(=O)(substituted or unsubstituted alkyl) (e.g., —C(=O)Me) or —C(=O)(substituted or unsubstituted phenyl)). In certain embodiments, at least one instance of $R^A$ is —C(=O)OR$^a$ (e.g., —C(=O)OH, —C(=O)O(substituted or unsubstituted alkyl) (e.g., —C(=O)OMe), or —C(=O)O(substituted or unsubstituted phenyl)). In certain embodiments, at least one instance of $R^A$ is —C(=O)N(R$^a$)$_2$ (e.g., —C(=O)NH$_2$, —C(=O)NH(substituted or unsubstituted alkyl) (e.g., —C(=O)NHMe), —C(=O)NHPh, —C(=O)NH(substituted phenyl), —C(=O)N(substituted or unsubstituted alkyl)-(substituted or unsubstituted alkyl), —C(=O)N(substituted or unsubstituted phenyl)-(substituted or unsubstituted alkyl)). In certain embodiments, at least one instance of $R^A$ is —C(=O)N(R$^a$)$_2$, wherein two instances of R$^a$ are joined to form a substituted or unsubstituted, 3- to 7-membered, monocyclic heterocyclic ring comprising zero, one, or two double bonds in the heterocyclic ring system, wherein one, two, or three atoms in the heterocyclic ring system are independently nitrogen, oxygen, or sulfur. In certain embodiments, at least one instance of $R^A$ is —C(=O)-(1-morpholinyl). In certain embodiments, at least one instance of $R^A$ is —NR$^a$C(=O)R$^a$ (e.g., —NHC(=O)(substituted or unsubstituted $C_{1-6}$ alkyl) (e.g., —NHC(=O)Me), —NHC(=O)Ph, or —NHC(=O)(substituted phenyl)). In certain embodiments, at least one instance of $R^A$ is —NR$^a$C(=O)OR$^a$. In certain embodiments, at least one instance of $R^A$ is —NR$^a$C(=O)N(R$^a$)$_2$ (e.g., —NHC(=O)NH$_2$, —NHC(=O)NH(substituted or unsubstituted $C_{1-6}$ alkyl) (e.g., —NHC(=O)NHMe or —NHC(=O)NH(i-Pr)), —NHC(=O)NHPh, or —NHC(=O)NH(substituted phenyl)). In certain embodiments, at least one instance of $R^A$ is —OC(=O)R$^a$, —OC(=O)OR$^a$, or —OC(=O)N(R$^a$)$_2$. In certain embodiments, at least one instance of $R^A$ is —NR$^a$S(=O)R$^a$ (e.g., —NHS(=O)(substituted or unsubstituted $C_{1-6}$ alkyl) (e.g., —NHS(=O)Me), —NHS(=O)Ph, or —NHS(=O)(substituted phenyl)). In certain embodiments, at least one instance of $R^A$ is —NR$^a$S(=O)OR$^a$. In certain embodiments, at least one instance of $R^A$ is —NR$^a$S(=O)N(R$^a$)$_2$ (e.g., —NHS(=O)NH$_2$, —NHS(=O)NH(substituted or unsubstituted $C_{1-6}$ alkyl) (e.g., —NHS(=O)NHMe), —NHS(=O)NHPh, or —NHS(=O)NH(substituted phenyl)). In certain embodiments, at least one instance of $R^A$ is —NR$^a$S(=O)$_2$R$^a$ (e.g., —NHS(=O)$_2$(substituted or unsubstituted $C_{1-6}$alkyl) (e.g., —NHS(=O)$_2$Me), —NHS(=O)$_2$Ph, or —NHS(=O)$_2$(substituted phenyl)). In certain embodiments, at least one instance of $R^A$ is —NR$^a$S(=O)$_2$OR$^a$. In certain embodiments, at least one instance of $R^A$ is —NR$^a$S(=O)$_2$N(R$^a$)$_2$ (e.g., —NHS(=O)$_2$NH$_2$, —NHS(=O)$_2$NH(substituted or unsubstituted $C_{1-6}$ alkyl) (e.g., —NHS(=O)$_2$NHMe), —NHS(=O)$_2$NHPh, or —NHS(=O)$_2$NH(substituted phenyl)). In certain embodiments, at least one instance of $R^A$ is halogen, —OR$^a$, —N(R$^a$)$_2$, —NO$_2$, —C(=O)R$^a$, —C(=O)OR$^a$, —C(=O)N(R$^a$)$_2$, —N(R$^a$)C(=O)R$^a$, —N(R$^a$)C(=O)N(R$^a$)$_2$, or —N(R$^a$)S(=O)$_2$R$^a$. In certain embodiments, at least one instance of R$^A$ is Cl, —OMe, —OCF$_3$, —NH$_2$, —NHMe, —NMe$_2$, —NO$_2$, —C(=O)Me, —C(=O)OH, —C(=O)OMe, —C(=O)NH$_2$, —C(=O)NHMe, —C(=O)NHPh, —C(=OH)-(1-morpholinyl), —NHC(=O)Me, —NHC(=O)Ph, —NHC(=O)NH(i-Pr), —NHC(=O)NHPh, —NHS(=O)$_2$Me, or —NHS(=O)$_2$Ph. In certain embodiments, at least one instance of R$^A$ is —CF$_3$, —CH$_2$OH, or i-Pr.

When Formula (I-a) include two or more instances of R$^A$, any two instances of R$^A$ may be joined to form a substituted or unsubstituted ring. In certain embodiments, two instances of R$^A$ are joined to form a substituted or unsubstituted, carbocyclic ring (e.g., substituted or unsubstituted, 3- to 7-membered, monocyclic carbocyclic ring comprising zero, one, or two double bonds in the carbocyclic ring system). In certain embodiments, two instances of R$^A$ are joined to form a substituted or unsubstituted, heterocyclic ring (e.g., substituted or unsubstituted, 3- to 7-membered, monocyclic heterocyclic ring comprising zero, one, or two double bonds in the heterocyclic ring system, wherein one, two, or three atoms in the heterocyclic ring system are independently nitrogen, oxygen, or sulfur). In certain embodiments, two instances of R$^A$ are joined to form a substituted or unsubstituted, aryl ring (e.g., substituted or unsubstituted phenyl ring). In certain embodiments, two instances of R$^A$ are joined to form a substituted or unsubstituted, heteroaryl ring (e.g., substituted or unsubstituted, 5- to 6-membered, monocyclic heteroaryl ring, wherein one, two, or three atoms in the heteroaryl ring system are independently nitrogen, oxygen, or sulfur).

In certain embodiments, k is 0. In certain embodiments, k is 1. In certain embodiments, k is 2. In certain embodiments, k is 3.

In certain embodiments, k is 1; and R$^A$ is halogen, —OR$^a$, —N(R$^a$)$_2$, —NO$_2$, —C(=O)R$^a$, —C(=O)OR$^a$, —C(=O)N(R$^a$)$_2$, —N(R$^a$)C(=O)R$^a$, —N(R$^a$)C(=O)N(R$^a$)$_2$, or —N(R$^a$)S(=O)$_2$R$^a$. In certain embodiments, k is 1; and R$^A$ is Cl, —OMe, —OCF$_3$, —NH$_2$, —NHMe, —NMe$_2$, —NO$_2$, —C(=O)Me, —C(=O)OH, —C(=O)OMe, —C(=O)NH$_2$, —C(=O)NHMe, —C(=O)NHPh, —C(=O)-(1-morpholinyl), —NHC(=O)Me, —NHC(=O)Ph, —NHC(=O)NH(i-Pr), —NHC(=O)NHPh, —NHS(=O)$_2$Me, or —NHS(=O)$_2$Ph. In certain embodiments, k is 1; and R$^A$ is halogen. In certain embodiments, k is 1; and R$^A$ is Cl. In certain embodiments, k is 2; and each instance of R$^A$ is independently halogen. In certain embodiments, k is 2; and each instance of R$^A$ is Cl.

Formula (I-a) includes W$^a$ and X$^a$ in a fused bicyclic heterocyclic ring. In certain embodiments, W$^a$ is —CR$^A$= or —N=. In certain embodiments, W$^a$ is —C(R$^A$)=. In certain embodiments, W$^a$ is —CH=. In certain embodiments, W$^a$ is —N=. In certain embodiments, X$^a$ is —NR$^B$—, —O—, or —S—. In certain embodiments, X$^a$ is —NH—. In certain embodiments, W$^a$ is —CH=, and X$^a$ is —NH—. In certain embodiments, W$^a$ is —CH=, and X$^a$ is —S—. In certain embodiments, W$^a$ is —CH=, and X$^a$ is —O—. In certain embodiments, W$^a$ is —N=, and X$^a$ is —NH—.

In certain embodiments, when X$^a$ is N, Formula (I-a) includes substituent R$^B$ on atom X$^a$ of the fused bicyclic heterocyclic ring. In certain embodiments, R$^B$ is hydrogen. In certain embodiments, R$^B$ is substituted or unsubstituted C$_{1-6}$ alkyl. In certain embodiments, R$^B$ is Me. In certain embodiments, R$^B$ is substituted methyl (e.g., —CF$_3$ or Bn). In certain embodiments, R$^B$ is Et, substituted ethyl (e.g., perfluoroethyl), Pr, substituted propyl (e.g., perfluoropropyl or —(CH$_2$)$_3$NH$_2$), Bu, or substituted butyl (e.g., perfluorobutyl). In certain embodiments, R$^B$ is of the formula: —(CH$_2$)$_a$N(R$^{a1}$)$_2$, wherein a may be 1, 2, 3, or 4, and each instance of R$^{a1}$ may be independently H, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl. In certain embodiments, a is 3. In certain embodiments, R$^{a1}$ is hydrogen.

In certain embodiments, R$^B$ is of the formula: —(CH$_2$)$_a$NHC(=O)(CH$_2$)$_b$R$^{b1}$, wherein: each instance of a and b is independently 1, 2, or 3, or 4; R$^{b1}$ is H, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or —N(R$^{b2}$)C(=O)R$^{b3}$; and each instance of R$^{b2}$ and R$^{b3}$ is independently H, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl. In certain embodiments, a is 1. In certain embodiments, a is 2. In certain embodiments, a is 3. In certain embodiments, b is 1. In certain embodiments, b is 2. In certain embodiments, b is 3.

In certain embodiments, R$^{b1}$ is of the formula: —N(R$^{b2}$)C(=O)R$^{b3}$. In certain embodiments, R$^{b2}$ is alkynl (e.g., propyne). In certain embodiments, R$^{b3}$ is acyl.

In certain embodiments, R$^B$ is of the formula:

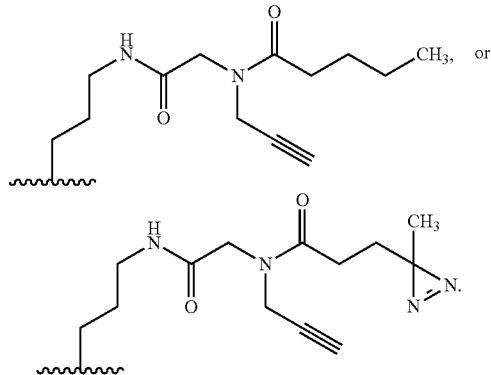

In certain embodiments, R$^{b1}$ is a heterocyclic ring (e.g., substituted or unsubstituted, 5- to 10-membered bicyclic heterocyclic ring, wherein 1, 2, or 3 atoms in the heterocyclic ring are independently nitrogen, oxygen, or sulfur). In certain embodiments, R$^{b1}$ is of the formula:

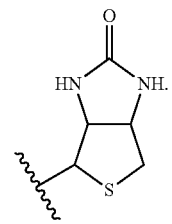 [SMILES: *C1SCC2NC(=O)NC21]

In certain embodiments, $R^B$ is of the formula: —$(CH_2)_aC(=O)NHR^{c1}$, wherein $R^{c1}$ is H, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl. In certain embodiments, $R^{c1}$ is substituted or unsubstituted $C_{1-6}$ alkyl. In certain embodiments, $R^{c1}$ is of the formula: —$(CH_2)_aO(CH_2)_eO(CH_2)_fC(=O)NHR^{e1}$, wherein $R^{e1}$ is independently H, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl; and each instance of d, e, or f is independently 1, 2, 3, 4, 5, or 6. In certain embodiments, all instances of d, e, and f are 2. In certain embodiments, $R^{e1}$ is a heterocyclic ring (e.g., substituted or unsubstituted, 5- to 10-membered monocyclic or bicyclic heterocyclic ring, wherein one or two atoms in the heterocyclic ring are independently nitrogen, oxygen, or sulfur).

In certain embodiments, $R^B$ is of the formula:

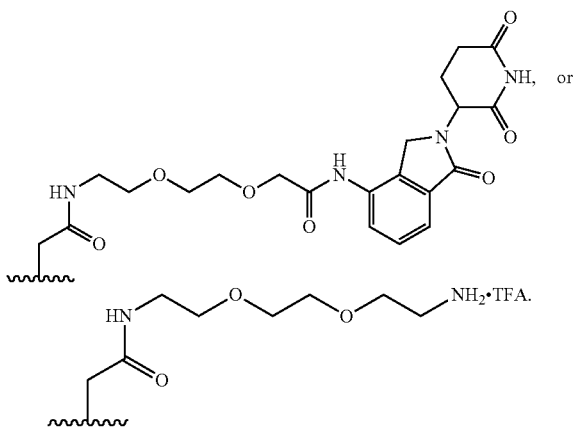

In certain embodiments, $R^B$ is of the formula: —$(CH_2)_aNHC(=O)R^{f1}$, wherein $R^{f1}$ is independently H, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl. In certain embodiments, a is 3. In certain embodiments, $R^{f1}$ is substituted phenyl. In certain embodiments, $R^B$ is of the formula:

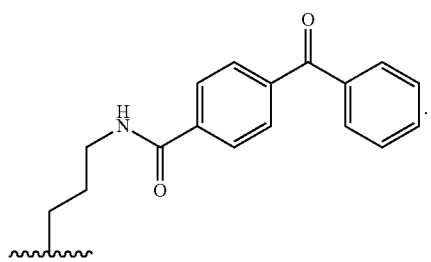 [SMILES: *CCCNC(=O)c1ccc(C(=O)c2ccccc2)cc1]

In certain embodiments, $R^B$ is a nitrogen protecting group (e.g., benzyl (Bn), t-butyl carbonate (BOC or Boc), benzyl carbamate (Cbz), 9-fluorenylmethyl carbonate (Fmoc), trifluoroacetyl, triphenylmethyl, acetyl, or p-toluenesulfonamide (Ts)).

Formula (I-a) includes a linker L connecting the fused bicyclic heterocyclic ring with Ring A. In certain embodiments, L is —N—. In certain embodiments, L is —O—. In certain embodiments, L is —S—. In certain embodiments, L is a bond. In certain embodiments, L is an optionally substituted $C_{1-4}$ hydrocarbon chain.

Formula (I-a) includes Ring A. In certain embodiments, Ring A is substituted or unsubstituted aryl ring (e.g., phenyl). In certain embodiments, Ring A is a heteroaryl ring (e.g., a substituted or unsubstituted, 5- to 6-membered, monocyclic or bicyclic heteroaryl ring, wherein one or two atoms in the heteroaryl ring are independently nitrogen, oxygen, or sulfur). In certain embodiments, Ring A is of the formula:

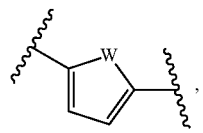

wherein: W is —NH—, —O— or —S—. In certain embodiments, W is —N—. In certain embodiments, W is —O—. In certain embodiments, W is —S—. In certain embodiments, Ring A is of the formula:

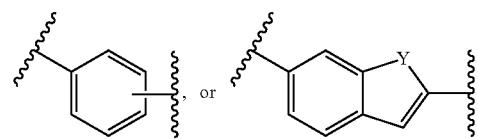

wherein: Y is —O— or —S—. In certain embodiments, Y is —O—. In certain embodiments, Y is —S—. In certain embodiments, Ring A is of the formula:

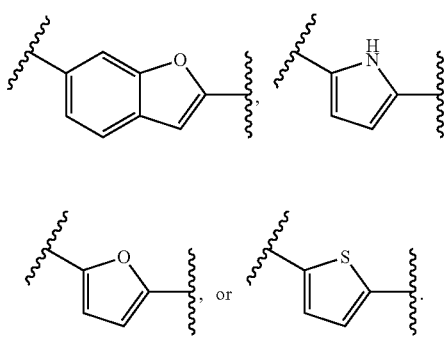

Formula (I-a) includes substituent $R^D$ on Ring A. In certain embodiments, $R^D$ is hydrogen. In certain embodiments, $R^D$ is acyl. In certain embodiments, $R^D$ is substituted or unsubstituted alkyl. In certain embodiments, $R^D$ is substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl. In certain embodiments, $R^D$ is substituted alkenyl. In certain embodiments, $R^D$ is unsubstituted alkenyl. In certain embodiments, $R^D$ is of the formula:

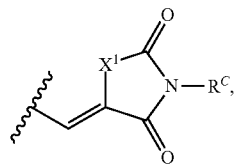

wherein $X^1$ may be —S—, —NR$^C$—, or —CH$_2$—. In certain embodiments, $X^1$ is —S—. In certain embodiments, $X^1$ is —NR$^C$—. In certain embodiments, $X^1$ is —CH$_2$—. In certain embodiments, $R^D$ is of the formula:

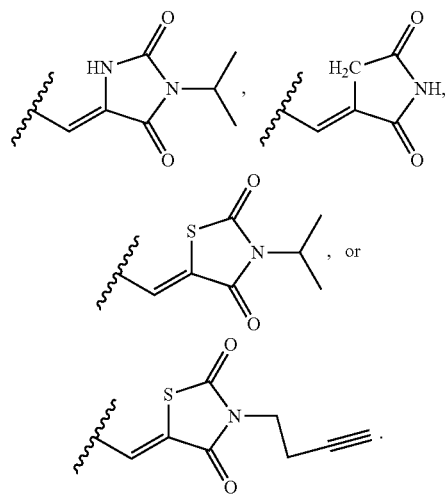

In certain embodiments, $R^D$ may include substituent $R^C$. In certain embodiments, $R^C$ is hydrogen. In certain embodiments, $R^C$ is substituted or unsubstituted alkyl. In certain embodiments, $R^C$ is substituted or unsubstituted $C_{1-6}$ alkyl. In certain embodiments, $R^C$ is Me. In certain embodiments, $R^C$ is substituted methyl. In certain embodiments, $R^C$ is —CF$_3$ or Bn. In certain embodiments, $R^C$ is —C(R$_a$)$_2$—C(=O)OR$^a$, optionally wherein each instance of $R^a$ is independently H, substituted or unsubstituted $C_{1-6}$ alkyl, or substituted or unsubstituted phenyl. In certain embodiments, $R^C$ is —CH$_2$—CO$_2$H, —CH$_2$—CO$_2$Me, —CH$_2$—CO$_2$(t-Bu), —CH(Me)-CO$_2$Me, or —CH(Me)-CO$_2$Et.

In certain embodiments, $R^D$ is of the formula: —OR$^{d1}$, —N(R$^{d1}$)$_2$, —NO$_2$, —NR$^{d1}$C(=O)R$^{d1}$, —NR$^{d1}$C(=O)OR$^{d1}$, —NR$^{d1}$C(=O)N(R$^{d1}$)$_2$, —OC(=O)R$^{d1}$, —OC(=O)OR$^{d1}$, —OC(=O)N(R$^{d1}$)$_2$, —C(=O)R$^{d1}$, —C(=O)OR$^{d1}$, —C(=O)N(R$^{d1}$)$_2$, —CH$_2$N(R$^{d1}$)$_2$, or —CH$_2$OR$^{d1}$. In certain embodiments, $R^D$ is —OR$^{d1}$ (e.g., —OH, —O(substituted or unsubstituted $C_{1-6}$ alkyl)). In certain embodiments, $R^D$ is —N(R$^{d1}$)$_2$ (e.g., —NH$_2$, —NH(substituted or unsubstituted $C_{1-6}$ alkyl) (e.g., —NHMe)). In certain embodiments, $R^D$ is —CH$_2$OR$^{d1}$ (e.g., —CH$_2$OH, —CH$_2$O(substituted or unsubstituted $C_{1-6}$ alkyl)). In certain embodiments, $R^D$ is —CH$_2$N(R$^{d1}$)$_2$ (e.g., —CH$_2$NH(substituted or unsubstituted $C_{1-6}$ alkyl), or —CH$_2$NH(phenyl)). In certain embodiments, $R^D$ is —CH$_2$N(R$^{d1}$)$_2$, wherein two instances of $R^{d1}$ are combined to form a substituted or unsubstituted, 5- to 6-membered, monocyclic or bicyclic heterocyclic ring, wherein one or two atoms in the heterocyclic ring are independently nitrogen, oxygen, or sulfur). In certain embodiments, $R^D$ is —C(=O)OR$^{d1}$ (e.g., —C(=O)OH, —C(=O)O(substituted or unsubstituted $C_{1-4}$ alkyl)). In certain embodiments, $R^D$ is —C(=O)N(R$^{d1}$)$_2$ (e.g., —C(=O)NH(phenyl)), —C(=O)NH(substituted or unsubstituted $C_{1-6}$ alkyl). In certain embodiments, $R^D$ is —C(=O)N(R$^{d1}$)$_2$, wherein two instances of $R^{d1}$ are combined to form a substituted or unsubstituted, 5- to 6-membered, monocyclic or bicyclic heterocyclic ring, wherein one or two atoms in the heterocyclic ring are independently nitrogen, oxygen, or sulfur).

Formula (I-a) may include one or more instances of substituent $R^a$ or substituent $R^{d1}$. When Formula (I-a) includes two or more instances of $R^a$, any two instances of $R^a$ may be the same or different from each other. When Formula (I-a) includes two or more instances of $R^{d1}$, any two instances of $R^{d1}$ may be the same or different from each other. In certain embodiments, at least one instance of $R^a$ or $R^{d1}$ is hydrogen. In certain embodiments, each instance of $R^a$ or $R^{d1}$ is hydrogen. In certain embodiments, at least one instance of $R^a$ or $R^{d1}$ is substituted or unsubstituted alkyl (e.g., substituted or unsubstituted $C_{1-6}$ alkyl). In certain embodiments, at least one instance of $R^a$ or $R^{d1}$ is substituted or unsubstituted acyl, substituted or unsubstituted alkenyl, substituted or unsubstituted alkynyl, substituted or unsubstituted carbocyclyl, substituted or unsubstituted heterocyclyl, substituted or unsubstituted aryl (e.g., substituted or unsubstituted phenyl), substituted or unsubstituted heteroaryl, a nitrogen protecting group (e.g., benzyl (Bn), t-butyl carbonate (BOC or Boc), benzyl carbamate (Cbz), 9-fluorenylmethyl carbonate (Fmoc), trifluoroacetyl, triphenylmethyl, acetyl, or p-toluenesulfonamide (Ts)) when attached to a nitrogen atom, an oxygen protecting group (e.g., silyl, t-butyldiphenylsilyl (TBDPS), t-butyldimethylsilyl (TBDMS), triisopropylsilyl (TIPS), trimethylsilyl (TMS), triethylsilyl (TES), methoxylmethyl (MOM), tetrahydropyranyl (THP), t-Bu, benzyl (Bn), allyl, acetyl, pivaloyl, or benzoyl) when attached to an oxygen atom, or a sulfur protecting group (e.g., acetamidomethyl, t-Bu, 3-nitro-2-pyridine sulfenyl, 2-pyridine-sulfenyl, or triphenylmethyl) when attached to a sulfur atom. In certain embodiments, two instances of $R^a$, or two instances of $R^{d1}$, are joined to form a substituted or unsubstituted carbocyclyl ring, substituted or unsubstituted, heterocyclic ring, substituted or unsubstituted aryl ring, or substituted or unsubstituted, heteroaryl ring.

In certain embodiments, $R^{d1}$ is hydrogen. In certain embodiments, $R^{d1}$ is substituted or unsubstituted alkyl (e.g., substituted or unsubstituted $C_{1-6}$ alkyl). In certain embodiments, $R^{d1}$ is methyl. In certain embodiments, $R^{d1}$ is isopropyl. In certain embodiments, $R^{d1}$ is substituted or unsubstituted alkenyl (e.g., substituted or unsubstituted $C_{2-6}$ alkenyl). In certain embodiments, $R^{d1}$ is substituted or unsubstituted aryl (e.g., substituted or unsubstituted phenyl). In certain embodiments, two instances of $R^{d1}$ are joined to form a heterocyclic ring (e.g., substituted or unsubstituted, 5- to 6-membered monocyclic heterocyclic ring, wherein one or two atoms in the heterocyclic ring are independently nitrogen, oxygen, or sulfur). In certain embodiments, $R^D$ is of the formula:

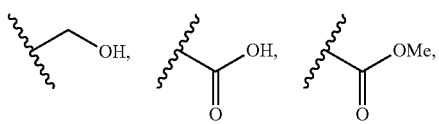

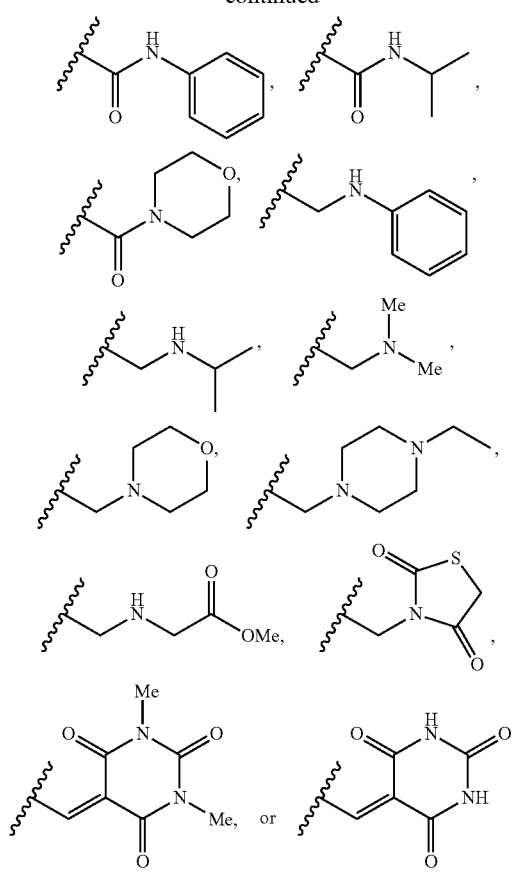
In certain embodiments, the compound of Formula (I-a) is of one of the following formulae:
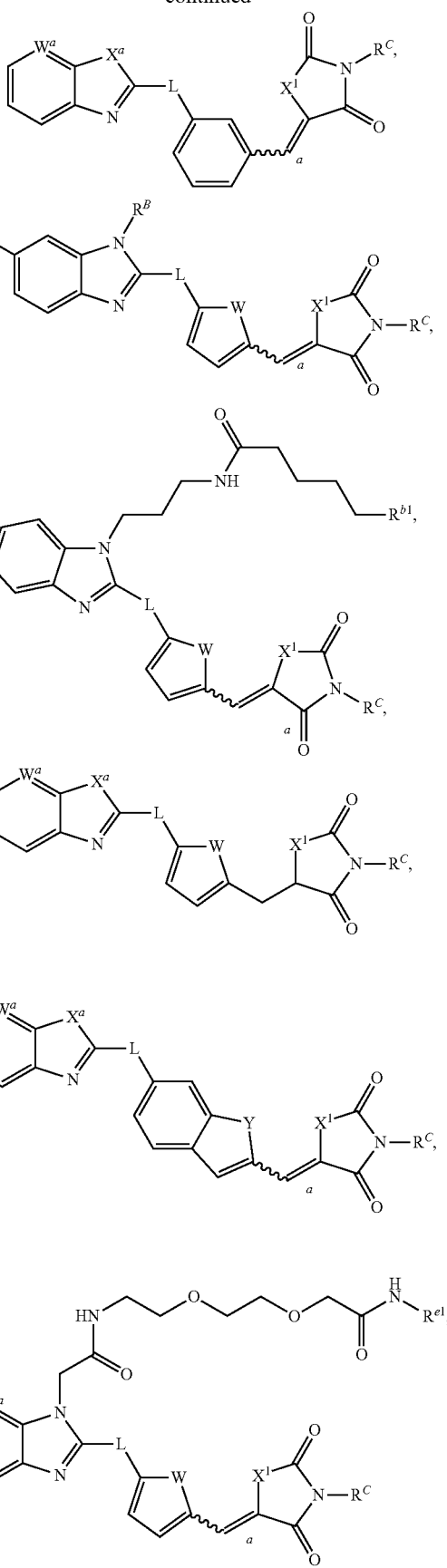

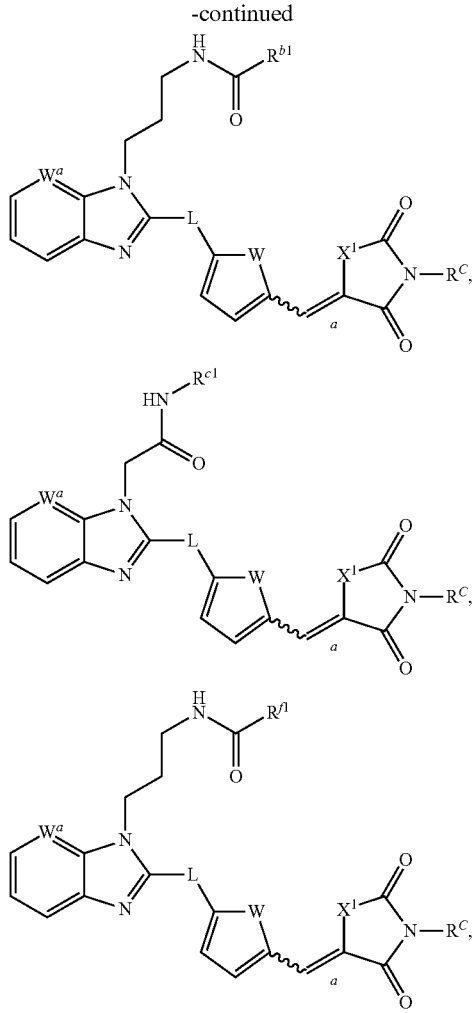
or a pharmaceutically acceptable salt thereof.
In certain embodiments, the compound of Formula (I-a) is of the formula:
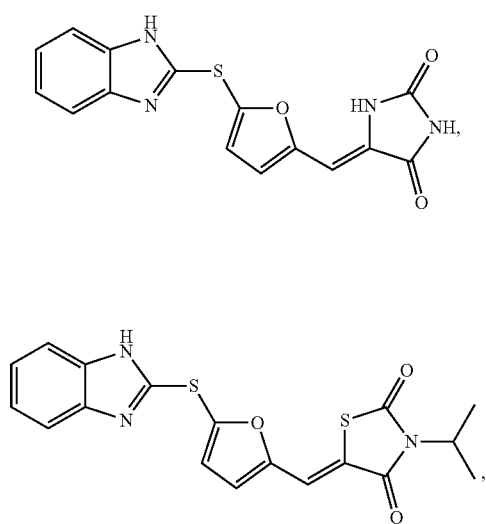
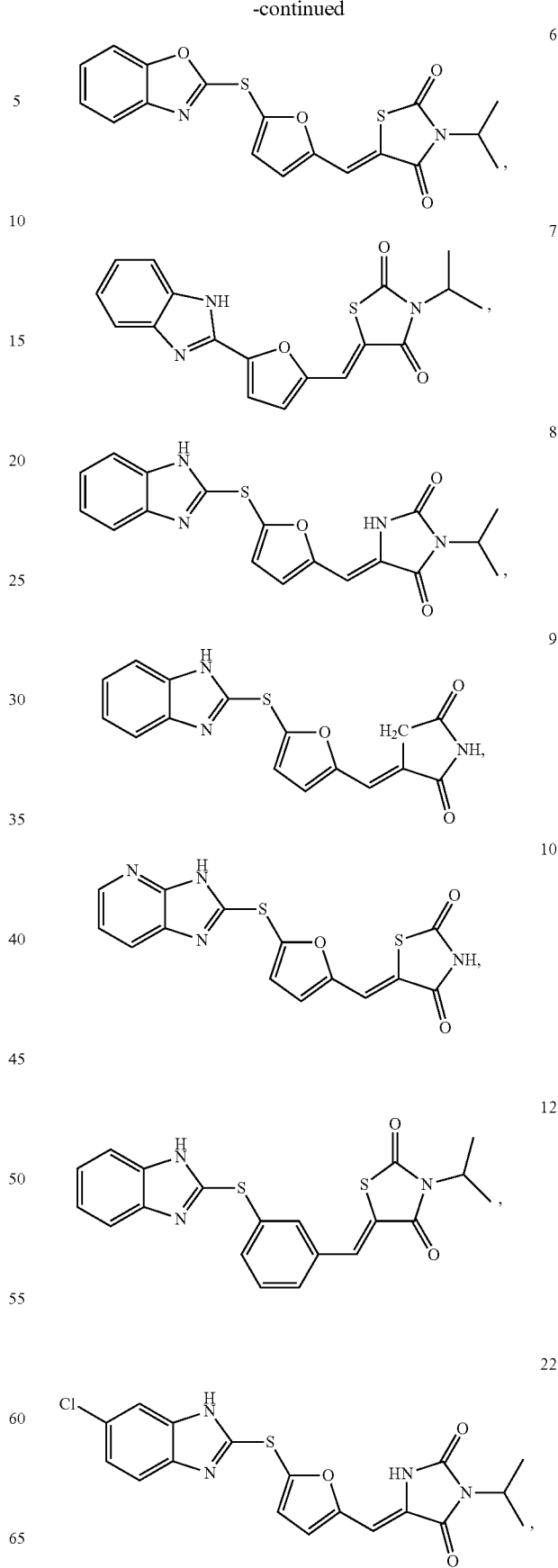

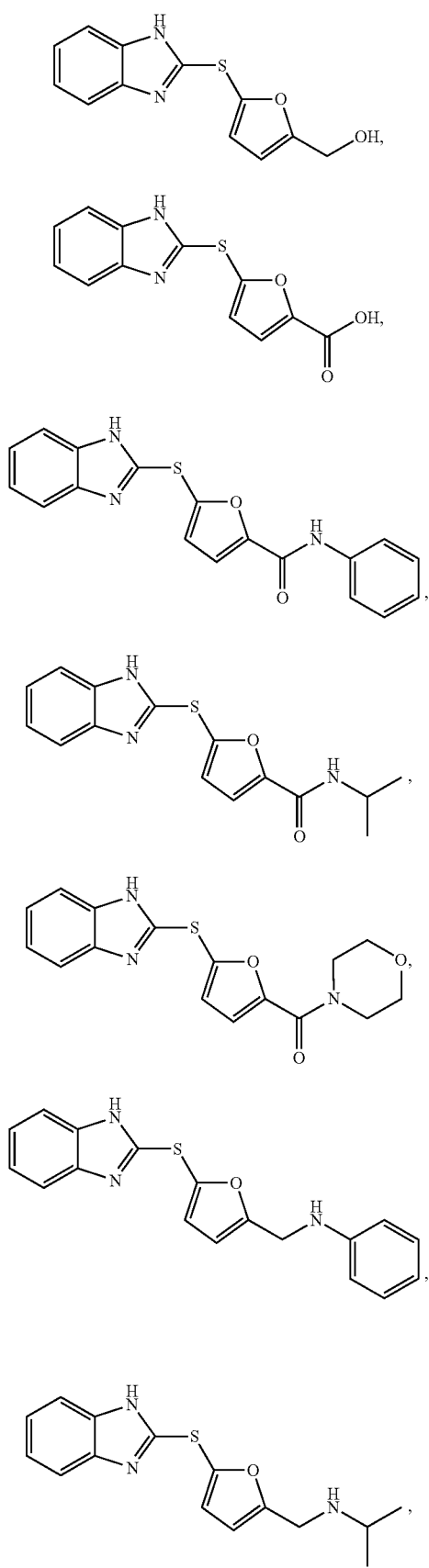
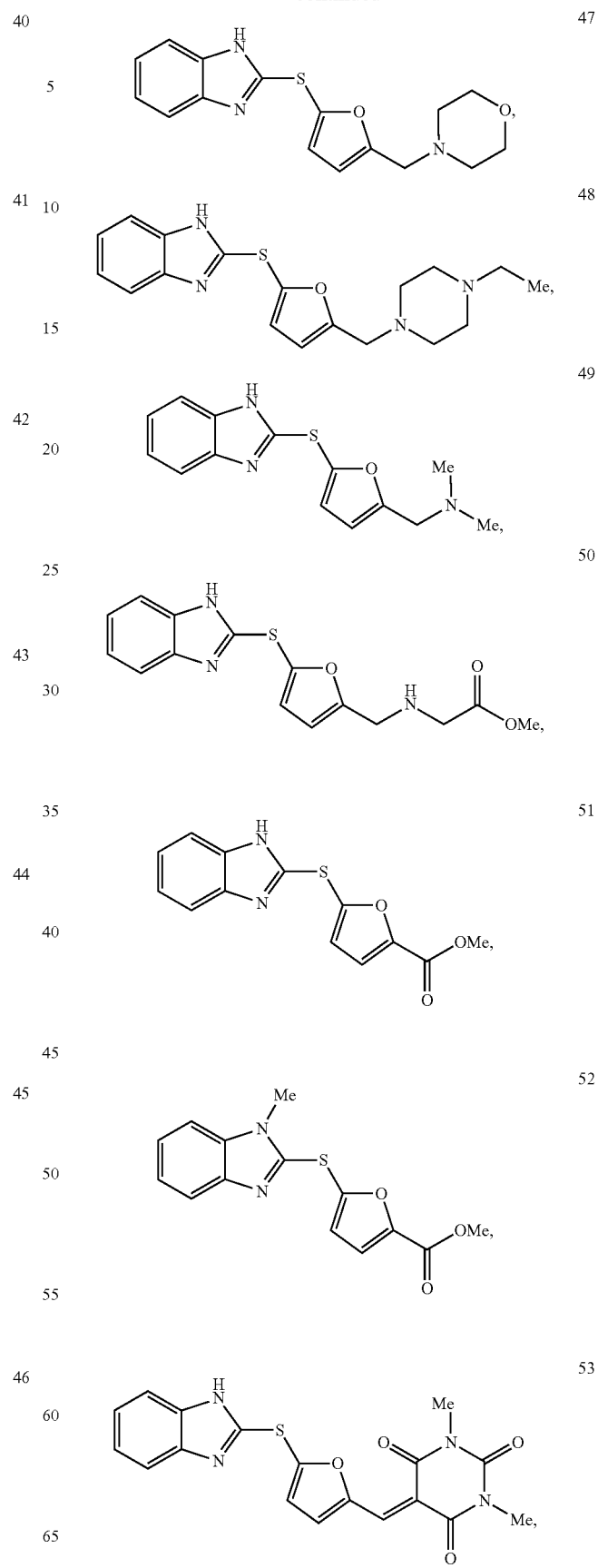

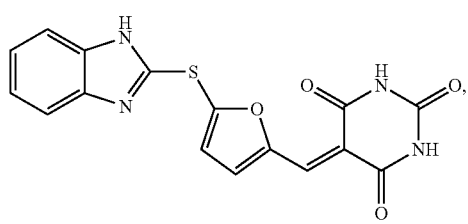
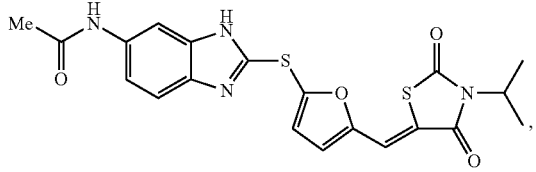
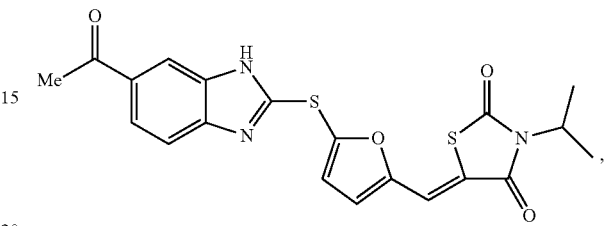
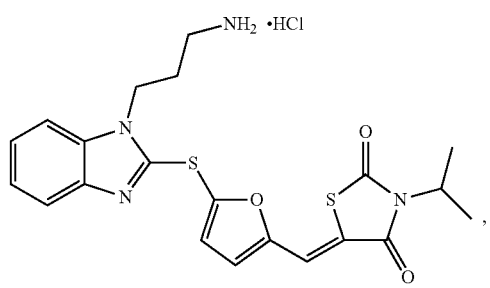
or a pharmaceutically acceptable salt thereof.
In certain embodiments, the compound of Formula (I-a) is of the formula:
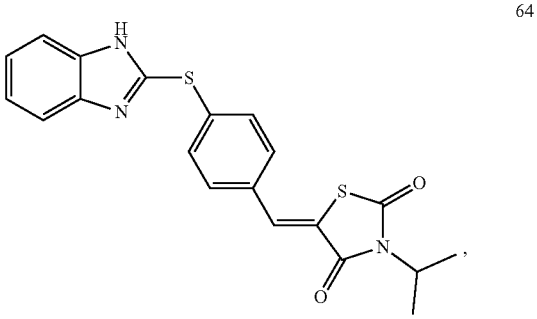
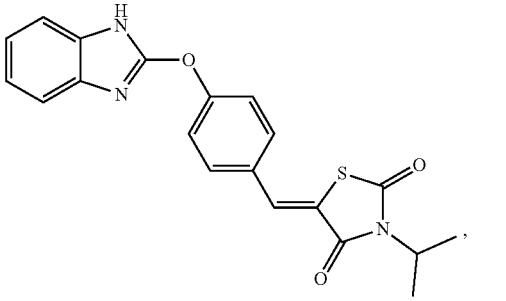
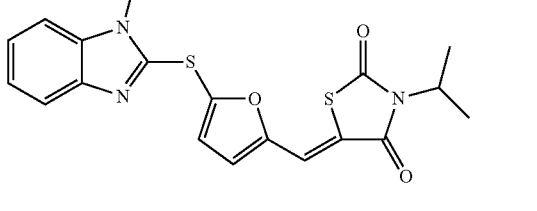
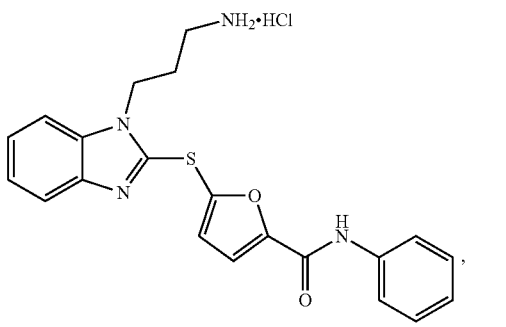
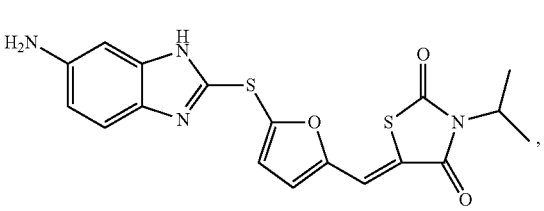
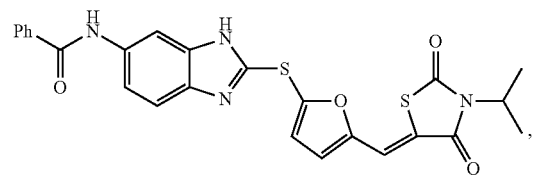
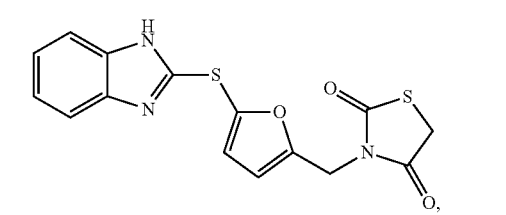

-continued

68
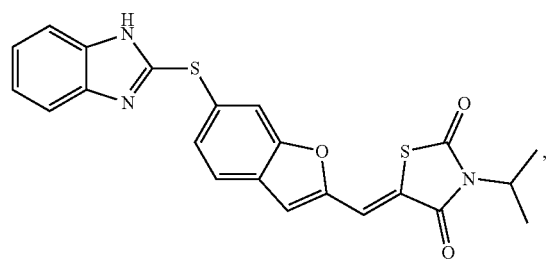

69
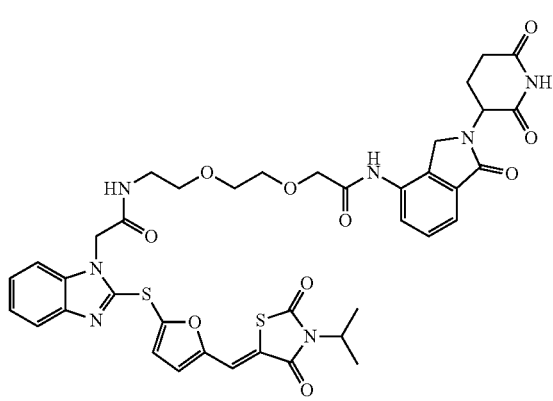

70
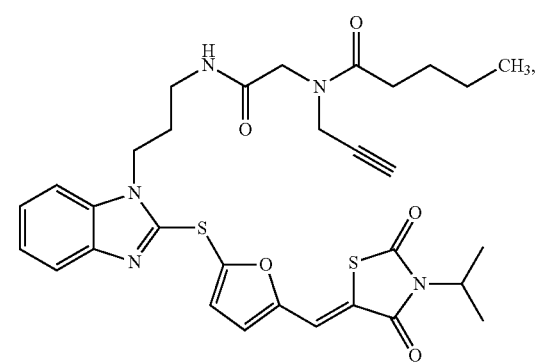

71
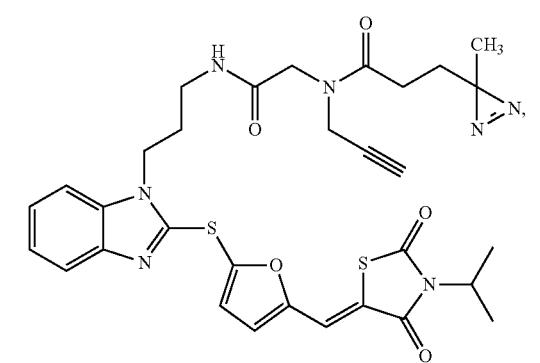

-continued

72
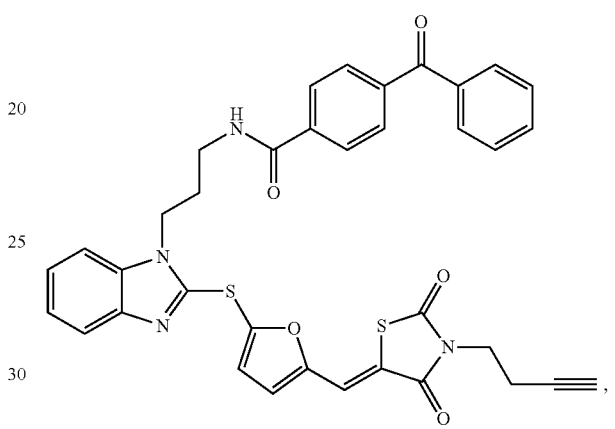

73
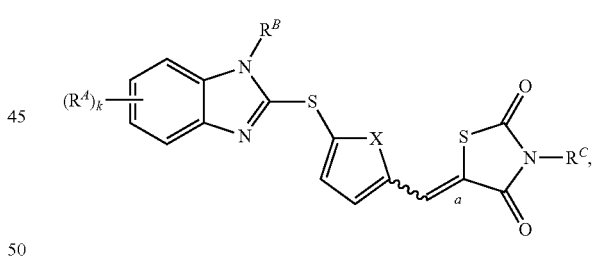

or a pharmaceutically acceptable salt thereof.

Compounds of Formula (I)

In certain embodiments, the compound of Formula (I) is of the formula:

(I)

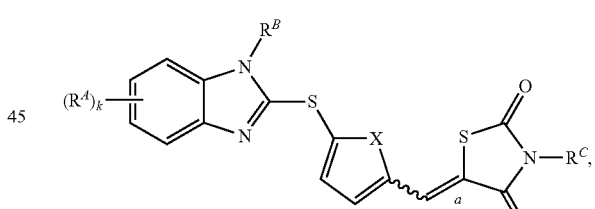

or a pharmaceutically acceptable salt, solvate, hydrate, polymorph, co-crystal, tautomer, stereoisomer, isotopically labeled derivative, or prodrug thereof, wherein:

each instance of $R^A$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^a$, —$N(R^a)_2$, —$SR^a$, —CN, —SCN, —C(=$NR^a$)$R^a$, —C(=$NR^a$)$OR^a$, —C(=$NR^a$)N($R^a$)$_2$, —C(=O)$R^a$, —C(=O)$OR^a$, —C(=O)N($R^a$)$_2$, —$NO_2$, —N($R^a$)C(=O)$R^a$, —N($R^a$)C(=O)$OR^a$, —N($R^a$)C(=O)N($R^a$)$_2$, —N($R^a$)S(=O)$R^a$, —N($R^a$)S(=O)$OR^a$, —N($R^a$)S(=O)N($R^a$)$_2$, —N($R^a$)S(=O)$_2R^a$, —N($R^a$)S(=O)$_2OR^a$, —N($R^a$)S(=O)$_2$N($R^a$)$_2$, —OC(=O)$R^a$, —OC(=O)$OR^a$, or —OC(=O)N($R^a$)$_2$, or two instances of $R^A$ are joined to form a substituted or unsubstituted, carbocyclic ring, substituted or unsubstituted, heterocyclic ring, substituted or unsubstituted, aryl ring, or substituted or unsubstituted, heteroaryl ring;

each instance of $R^a$ is independently H, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^a$ are joined to form a substituted or unsubstituted, heterocyclic ring, or substituted or unsubstituted, heteroaryl ring;

k is 0, 1, 2, 3, or 4;

$R^B$ is H, substituted or unsubstituted $C_{1-6}$ alkyl, or a nitrogen protecting group;

X is —O— or —S—;

the double bond labeled with "a" is in the (E)- or (Z)-configuration; and $R^C$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —C(=O)$R^a$, —C(=O)O$R^a$, —C(=O)N($R^a$)$_2$, or a nitrogen protecting group.

Formula (I) may include one or more instances of substituent $R^A$ on the benzimidazolyl moiety. When Formula (I) includes two or more instances of $R^A$, any two instances of $R^A$ may be the same or different from each other. In certain embodiments, at least one instance of $R^A$ is halogen (e.g., F, Cl, Br, or I). In certain embodiments, at least one instance of $R^A$ is substituted or unsubstituted alkyl. In certain embodiments, at least one instance of $R^A$ is substituted or unsubstituted $C_{1-6}$ alkyl. In certain embodiments, at least one instance of $R^A$ is Me. In certain embodiments, at least one instance of $R^A$ is substituted methyl (e.g., —CF$_3$, —CH$_2$OH, or Bn). In certain embodiments, at least one instance of $R^A$ is Et, substituted ethyl (e.g., perfluoroethyl), Pr (e.g., n-Pr or i-Pr), substituted propyl (e.g., perfluoropropyl), Bu, or substituted butyl (e.g., perfluorobutyl). In certain embodiments, at least one instance of $R^A$ is substituted or unsubstituted alkenyl (e.g., substituted or unsubstituted $C_{2-6}$ alkenyl). In certain embodiments, at least one instance of $R^A$ is substituted or unsubstituted alkynyl (e.g., substituted or unsubstituted $C_{2-6}$ alkynyl). In certain embodiments, at least one instance of $R^A$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, at least one instance of $R^A$ is substituted or unsubstituted cyclopropyl, substituted or unsubstituted cyclobutyl, substituted or unsubstituted cyclopentyl, or substituted or unsubstituted cyclohexyl. In certain embodiments, at least one instance of $R^A$ is substituted or unsubstituted heterocyclyl (e.g., substituted or unsubstituted, 3- to 7-membered, monocyclic heterocyclyl comprising zero, one, or two double bonds in the heterocyclic ring system, wherein one, two, or three atoms in the heterocyclic ring system are independently nitrogen, oxygen, or sulfur). In certain embodiments, at least one instance of $R^A$ is substituted or unsubstituted oxetanyl, substituted or unsubstituted tetrahydrofuranyl, substituted or unsubstituted pyrrolidinyl, substituted or unsubstituted tetrahydropyranyl, substituted or unsubstituted piperidinyl, substituted or unsubstituted morpholinyl, or substituted or unsubstituted piperazinyl. In certain embodiments, at least one instance of $R^A$ is substituted or unsubstituted aryl (e.g., substituted or unsubstituted, 6- to 10-membered aryl). In certain embodiments, at least one instance of $R^A$ is unsubstituted phenyl. In certain embodiments, at least one instance of $R^A$ is substituted phenyl. In certain embodiments, at least one instance of $R^A$ is substituted or unsubstituted naphthyl. In certain embodiments, at least one instance of $R^A$ is substituted or unsubstituted heteroaryl. In certain embodiments, at least one instance of $R^A$ is substituted or unsubstituted, 5- to 6-membered, monocyclic heteroaryl, wherein one, two, three, or four atoms in the heteroaryl ring system are independently nitrogen, oxygen, or sulfur. In certain embodiments, at least one instance of $R^A$ is substituted or unsubstituted, 9- to 10-membered, bicyclic heteroaryl, wherein one, two, three, or four atoms in the heteroaryl ring system are independently nitrogen, oxygen, or sulfur. In certain embodiments, at least one instance of $R^A$ is —O$R^a$ (e.g., —OH, —O(substituted or unsubstituted $C_{1-6}$ alkyl) (e.g., —OMe, —OCF$_3$, —OEt, —OPr, —OBu, or —OBn), or —O(substituted or unsubstituted phenyl) (e.g., —OPh)). In certain embodiments, at least one instance of $R^A$ is —S$R^a$ (e.g., —SH, —S(substituted or unsubstituted $C_{1-6}$alkyl) (e.g., —SMe, —SEt, —SPr, —SBu, or —SBn), or —S(substituted or unsubstituted phenyl) (e.g., —SPh)). In certain embodiments, at least one instance of $R^A$ is —N($R^a$)$_2$ (e.g., —NH$_2$, —NH(substituted or unsubstituted $C_{1-6}$ alkyl) (e.g., —NHMe), or —N(substituted or unsubstituted $C_{1-6}$ alkyl)-(substituted or unsubstituted $C_{1-6}$ alkyl) (e.g., —NMe$_2$)). In certain embodiments, at least one instance of $R^A$ is —CN or —SCN. In certain embodiments, at least one instance of $R^A$ is —NO$_2$. In certain embodiments, at least one instance of $R^A$ is —C(=N$R^a$)$R^a$, —C(=N$R^a$)O$R^a$, or —C(=N$R^a$)N($R^a$)$_2$. In certain embodiments, at least one instance of $R^A$ is —C(=O)R (e.g., —C(=O)(substituted or unsubstituted alkyl) (e.g., —C(=O)Me) or —C(=O)(substituted or unsubstituted phenyl)). In certain embodiments, at least one instance of $R^A$ is —C(=O)OR (e.g., —C(=O)OH, —C(=O)O(substituted or unsubstituted alkyl) (e.g., —C(=O)OMe), or —C(=O)O(substituted or unsubstituted phenyl)). In certain embodiments, at least one instance of $R^A$ is —C(=O)N($R^a$)$_2$ (e.g., —C(=O)NH$_2$, —C(=O)NH(substituted or unsubstituted alkyl) (e.g., —C(=O)NHMe), —C(=O)NHPh, —C(=O)NH(substituted phenyl), —C(=O)N(substituted or unsubstituted alkyl)-(substituted or unsubstituted alkyl), —C(=O)N(substituted or unsubstituted phenyl)-(substituted or unsubstituted alkyl)). In certain embodiments, at least one instance of $R^A$ is —C(=O)N($R^a$)$_2$, wherein two instances of $R^a$ are joined to form a substituted or unsubstituted, 3- to 7-membered, monocyclic heterocyclic ring comprising zero, one, or two double bonds in the heterocyclic ring system, wherein one, two, or three atoms in the heterocyclic ring system are independently nitrogen, oxygen, or sulfur. In certain embodiments, at least one instance of $R^A$ is —C(=O)-(1-morpholinyl). In certain embodiments, at least one instance of $R^A$ is —NR C(=O)R (e.g., —NHC(=O)(substituted or unsubstituted $C_{1-6}$ alkyl) (e.g., —NHC(=O)Me), —NHC(=O)Ph, or —NHC(=O)(substituted phenyl)). In certain embodiments, at least one instance of $R^A$ is —NRC(=O)O$R^a$. In certain embodiments, at least one instance of $R^A$ is —NR$^a$C(=O)N($R^a$)$_2$ (e.g., —NHC(=O)NH$_2$, —NHC(=O)NH(substituted or unsubstituted $C_{1-6}$ alkyl) (e.g., —NHC(=O)NHMe or —NHC(=O)NH(i-Pr)), —NHC(=O)NHPh, or —NHC(=O)NH(substituted phenyl)). In certain embodiments, at least one instance of $R^A$ is —OC(=O)$R^a$, —OC(=O)O$R^a$, or —OC(=O)N($R^a$)$_2$. In certain embodiments, at least one instance of $R^A$ is —N$R^a$S(=O)$R^a$ (e.g., —NHS(=O)(substituted or unsubstituted $C_{1-6}$ alkyl) (e.g., —NHS(=O)Me), —NHS(=O)Ph, or —NHS(=O)(substituted phenyl)). In certain embodiments, at least one instance of $R^A$ is —N$R^a$S(=O)O$R^a$. In certain embodiments, at least one instance of $R^A$ is —N$R^a$S(=O)N($R^a$)$_2$ (e.g., —NHS(=O)NH$_2$, —NHS(=O)NH(substituted or unsubstituted $C_{1-6}$ alkyl) (e.g., —NHS(=O)NHMe), —NHS(=O)NHPh, or —NHS(=O)NH(substituted phenyl)). In certain embodiments, at least one instance of $R^A$ is —N$R^a$S(=O)$_2$$R^a$ (e.g., —NHS(=O)$_2$(substituted or unsubstituted $C_{1-6}$ alkyl) (e.g., —NHS(=O)$_2$Me), —NHS(=O)$_2$Ph, or —NHS(=O)$_2$(substituted phenyl)). In certain embodiments, at least one instance of $R^A$ is —N$R^a$S(=O)$_2$O$R^a$. In certain embodiments, at least one instance of $R^A$ is —N$R^a$S(=O)$_2$N($R^a$)$_2$ (e.g., —NHS(=O)$_2$NH$_2$, —NHS(=O)$_2$NH(substituted or unsubstituted $C_{1-6}$ alkyl) (e.g., —NHS(=O)$_2$NHMe), —NHS(=O)$_2$NHPh, or —NHS(=O)$_2$NH(substituted phenyl)). In certain embodiments, at least one instance of $R^A$ is halogen, —O$R^a$, —N($R^a$)$_2$, —NO$_2$, —C(=O)$R^a$, —C(=O)O$R^a$, —C(=O)N($R^a$)$_2$, —N($R^a$)C(=O)$R^a$, —N($R^a$)C(=O)N($R^a$)$_2$, or —N($R^a$)S(=O)$_2$$R^a$. In certain embodiments, at least one instance of $R^A$ is Cl, —OMe, —OCF$_3$, —NH$_2$, —NHMe, —NMe$_2$, —NO$_2$, —C(=O)Me, —C(=O)OH, —C(=O)OMe, —C(=O)NH$_2$, —C(=O)NHMe, —C(=O)NHPh, —C(=O)-(1-morpholinyl), —NHC(=O)Me, —NHC(=O)Ph, —NHC(=O)NH(i-Pr), —NHC(=O)NHPh, —NHS(=O)$_2$Me, or —NHS(=O)$_2$Ph. In certain embodiments, at least one instance of $R^A$ is —CF$_3$, —CH$_2$OH, or i-Pr.

When Formula (I) include two or more instances of $R^A$, any two instances of $R^A$ may be joined to form a substituted or unsubstituted ring. In certain embodiments, two instances of $R^A$ are joined to form a substituted or unsubstituted, carbocyclic ring (e.g., substituted or unsubstituted, 3- to 7-membered, monocyclic carbocyclic ring comprising zero, one, or two double bonds in the carbocyclic ring system). In certain embodiments, two instances of $R^A$ are joined to form a substituted or unsubstituted, heterocyclic ring (e.g., substituted or unsubstituted, 3- to 7-membered, monocyclic heterocyclic ring comprising zero, one, or two double bonds in the heterocyclic ring system, wherein one, two, or three atoms in the heterocyclic ring system are independently nitrogen, oxygen, or sulfur). In certain embodiments, two instances of $R^A$ are joined to form a substituted or unsubstituted, aryl ring (e.g., substituted or unsubstituted phenyl ring). In certain embodiments, two instances of $R^A$ are joined to form a substituted or unsubstituted, heteroaryl ring (e.g., substituted or unsubstituted, 5- to 6-membered, monocyclic heteroaryl ring, wherein one, two, or three atoms in the heteroaryl ring system are independently nitrogen, oxygen, or sulfur).

Formula (I) may include one or more instances of substituent $R^a$. When Formula (I) includes two or more instances of $R^a$, any two instances of $R^a$ may be the same or different from each other. In certain embodiments, at least one instance of $R^a$ is H. In certain embodiments, each instance of $R^a$ is H. In certain embodiments, at least one instance of $R^a$ is substituted or unsubstituted alkyl (e.g., substituted or unsubstituted $C_{1-6}$ alkyl). In certain embodiments, at least one instance of $R^a$ is substituted or unsubstituted acyl, substituted or unsubstituted alkenyl, substituted or unsubstituted alkynyl, substituted or unsubstituted carbocyclyl, substituted or unsubstituted heterocyclyl, substituted or unsubstituted aryl (e.g., substituted or unsubstituted phenyl), substituted or unsubstituted heteroaryl, a nitrogen protecting group (e.g., Bn, Boc, Cbz, Fmoc, trifluoroacetyl, triphenylmethyl, acetyl, or Ts) when attached to a nitrogen atom, an oxygen protecting group (e.g., silyl, TBDPS, TBDMS, TIPS, TES, TMS, MOM, THP, t-Bu, Bn, allyl, acetyl, pivaloyl, or benzoyl) when attached to an oxygen atom, or a sulfur protecting group (e.g., acetamidomethyl, t-Bu, 3-nitro-2-pyridine sulfenyl, 2-pyridinesulfenyl, or triphenylmethyl) when attached to a sulfur atom. In certain embodiments, two instances of $R^a$ are joined to form a substituted or unsubstituted, heterocyclic ring, or substituted or unsubstituted, heteroaryl ring.

In certain embodiments, k is 0. In certain embodiments, k is 1. In certain embodiments, k is 2. In certain embodiments, k is 3. In certain embodiments, k is 4.

In certain embodiments, k is 1; and $R^A$ is halogen, —O$R^a$, —N($R^a$)$_2$, —NO$_2$, —C(=O)$R^a$, —C(=O)O$R^a$, —C(=O)N($R^a$)$_2$, —N($R^a$)C(=O)$R^a$, —N($R^a$)C(=O)N($R^a$)$_2$, or —N($R^a$)S(=O)$_2$$R^a$. In certain embodiments, k is 1; and $R^A$ is Cl, —OMe, —OCF$_3$, —NH$_2$, —NHMe, —NMe$_2$, —NO$_2$, —C(=O)Me, —C(=O)OH, —C(=O)OMe, —C(=O)NH$_2$, —C(=O)NHMe, —C(=O)NHPh, —C(=O)-(1-morpholinyl), —NHC(=O)Me, —NHC(=O)Ph, —NHC(=O)NH(i-Pr), —NHC(=O)NHPh, —NHS(=O)$_2$Me, or —NHS(=O)$_2$Ph. In certain embodiments, k is 2; and each instance of $R^A$ is independently halogen. In certain embodiments, k is 2; and each instance of $R^A$ is Cl.

Formula (I) includes substituent $R^B$ on a nitrogen atom of the benzimidazolyl moiety. In certain embodiments, $R^B$ is H. In certain embodiments, $R^B$ is substituted or unsubstituted $C_{1-6}$ alkyl. In certain embodiments, $R^B$ is Me. In certain embodiments, $R^B$ is substituted methyl (e.g., —CF$_3$ or Bn). In certain embodiments, $R^B$ is Et, substituted ethyl (e.g., perfluoroethyl), Pr, substituted propyl (e.g., perfluoropropyl or —(CH$_2$)$_3$NH$_2$), Bu, or substituted butyl (e.g., perfluorobutyl). In certain embodiments, $R^B$ is a nitrogen protecting group (e.g., Bn, Boc, Cbz, Fmoc, trifluoroacetyl, triphenylmethyl, acetyl, or Ts).

Formula (I) includes an unsubstituted furanyl ring (when X is —O—) or unsubstituted thienyl ring (when X is —S—).

Formula (I) includes a double bond that is labeled with "a." When the double bond that is labeled with "a" is attached to a substituent through a wavy bond (e.g., ⌇ ), both the (E)- and (Z)-configurations of the double bond are contemplated. When the double bond that is labeled with "a" is not attached to any substituent through a wavy bond, the configuration of the double bond is either the (E)- or (Z)-configuration, as determined by the way in which the double bond and any substituents thereon are drawn.

Formula (I) includes substituent $R^C$ on the thiazolidine-2,4-dione moiety. In certain embodiments, $R^C$ is H. In certain embodiments, $R^C$ is substituted or unsubstituted alkyl. In certain embodiments, $R^C$ is substituted or unsubstituted $C_{1-6}$ alkyl. In certain embodiments, $R^C$ is Me. In certain embodiments, $R^C$ is substituted methyl. In certain embodiments, $R^C$ is —CF$_3$ or Bn. In certain embodiments, $R^C$ is —C($R^a$)$_2$—C(=O)O$R^a$, optionally wherein each instance of $R^a$ is independently H, substituted or unsubstituted $C_{1-6}$alkyl, or substituted or unsubstituted phenyl. In certain embodiments, $R^C$ is —CH$_2$—CO$_2$H, —CH$_2$—CO$_2$Me, —CH$_2$—CO$_2$(t-Bu), —CH(Me)-CO$_2$Me, or —CH(Me)-CO$_2$Et. In certain embodiments, $R^C$ is —C($R^a$)$_2$—C(=O)N($R^a$)$_2$, optionally wherein each instance of $R^a$ is independently H, substituted or unsubstituted $C_{1-6}$ alkyl, or substituted or unsubstituted phenyl, or two instances of $R^a$ on the nitrogen atom are joined to form a substituted or unsubstituted heterocyclic ring or substituted or unsubstituted heteroaryl ring. In certain embodiments, $R^C$ is of the formula:

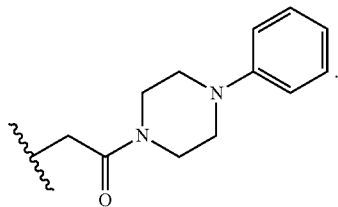 [SMILES: *CC(=O)N1CCN(c2ccccc2)CC1]

In certain embodiments, $R^C$ is Et or substituted ethyl (e.g., perfluoroethyl). In certain embodiments, $R^C$ is n-Pr. In certain embodiments, $R^C$ is i-Pr. In certain embodiments, $R^C$ is substituted propyl (e.g., perfluoropropyl). In certain embodiments, $R^C$ is n-Bu, i-Bu, or t-Bu. In certain embodiments, $R^C$ is sec-Bu. In certain embodiments, $R^C$ is substituted butyl (e.g., perfluorobutyl). In certain embodiments, $R^C$ is —$(CH_2)_n$—$N(R^a)_2$, —$(CH_2)_n$—$N(R^a)C(=O)R^a$, —$(CH_2)_n$—$C(=O)N(R^a)_2$, or —$(CH_2)_n$—$N(R^a)C(=O)N(R^a)_2$, wherein each instance of n is independently 2, 3, 4, 5, or 6 (e.g., 3); and optionally wherein each instance of $R^a$ is independently H, substituted or unsubstituted $C_{1-6}$ alkyl, substituted or unsubstituted phenyl, a nitrogen protecting group when attached to a nitrogen atom, or a small molecule label (e.g., a biotin moiety (e.g., 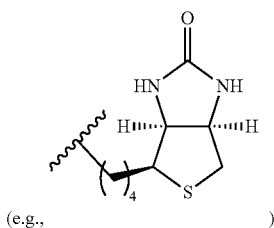 )

or a small molecule fluorophore), or two instances of $R^a$ on the same nitrogen atom are joined to form a substituted or unsubstituted heterocyclic ring or substituted or unsubstituted heteroaryl ring. In certain embodiments, $R^C$ is —$(CH_2)_3$—$NH_2$, —$(CH_2)_3$—$NHC(=O)NHEt$, —$(CH_2)_3$—$NHC(=O)NHPh$, or

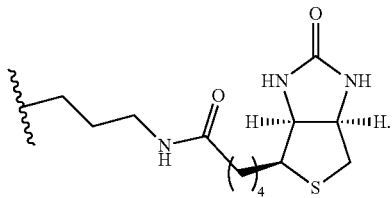

In certain embodiments, $R^C$ is substituted or unsubstituted alkenyl (e.g., substituted or unsubstituted $C_{2-6}$ alkenyl). In certain embodiments, $R^C$ is substituted or unsubstituted alkynyl (e.g., substituted or unsubstituted $C_{2-6}$ alkynyl). In certain embodiments, $R^C$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, $R^C$ is substituted or unsubstituted cyclopropyl, substituted or unsubstituted cyclobutyl, substituted or unsubstituted cyclopentyl, or substituted or unsubstituted cyclohexyl. In certain embodiments, $R^C$ is substituted or unsubstituted heterocyclyl (e.g., substituted or unsubstituted, 3- to 7-membered, monocyclic heterocyclyl comprising zero, one, or two double bonds in the heterocyclic ring system, wherein one, two, or three atoms in the heterocyclic ring system are independently nitrogen, oxygen, or sulfur). In certain embodiments, $R^C$ is substituted or unsubstituted oxetanyl, substituted or unsubstituted tetrahydrofuranyl, substituted or unsubstituted pyrrolidinyl, substituted or unsubstituted tetrahydropyranyl, substituted or unsubstituted piperidinyl, substituted or unsubstituted morpholinyl, or substituted or unsubstituted piperazinyl. In certain embodiments, $R^C$ is substituted or unsubstituted aryl (e.g., substituted or unsubstituted, 6- to 10-membered aryl). In certain embodiments, $R^C$ is unsubstituted phenyl. In certain embodiments, $R^C$ is substituted phenyl. In certain embodiments, $R^C$ is substituted or unsubstituted naphthyl. In certain embodiments, $R^C$ is substituted or unsubstituted heteroaryl. In certain embodiments, $R^C$ is substituted or unsubstituted, 5- to 6-membered, monocyclic heteroaryl, wherein one, two, three, or four atoms in the heteroaryl ring system are independently nitrogen, oxygen, or sulfur. In certain embodiments, $R^C$ is substituted or unsubstituted, 9- to 10-membered, bicyclic heteroaryl, wherein one, two, three, or four atoms in the heteroaryl ring system are independently nitrogen, oxygen, or sulfur. In certain embodiments, $R^C$ is —$C(=O)R^a$ (e.g., —$C(=O)$(substituted or unsubstituted alkyl) (e.g., —$C(=O)Me$) or —$C(=O)$(substituted or unsubstituted phenyl)). In certain embodiments, $R^C$ is —$C(=O)OR^a$ (e.g., —$C(=O)OH$, —$C(=O)O$(substituted or unsubstituted alkyl) (e.g., —$C(=O)OMe$), or —$C(=O)O$(substituted or unsubstituted phenyl)). In certain embodiments, $R^C$ is —$C(=O)N(R^a)_2$ (e.g., —$C(=O)NH_2$, —$C(=O)NH$(substituted or unsubstituted alkyl) (e.g., —$C(=O)NHMe$), —$C(=O)NH$(substituted or unsubstituted phenyl), —$C(=O)N$(substituted or unsubstituted alkyl)-(substituted or unsubstituted alkyl), —$C(=O)N$(substituted or unsubstituted phenyl)-(substituted or unsubstituted alkyl)). In certain embodiments, $R^C$ is —$C(=O)N(R^a)_2$, wherein two instances of $R^a$ are joined to form a substituted or unsubstituted, 3- to 7-membered, monocyclic heterocyclic ring comprising zero, one, or two double bonds in the heterocyclic ring system, wherein one, two, or three atoms in the heterocyclic ring system are independently nitrogen, oxygen, or sulfur. In certain embodiments, $R^C$ is a nitrogen protecting group (e.g., Bn, Boc, Cbz, Fmoc, trifluoroacetyl, triphenylmethyl, acetyl, or Ts).

In certain embodiments, the compound of Formula (I) is of the formula:

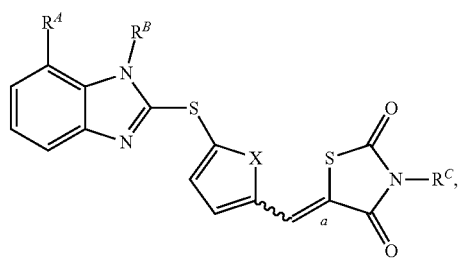

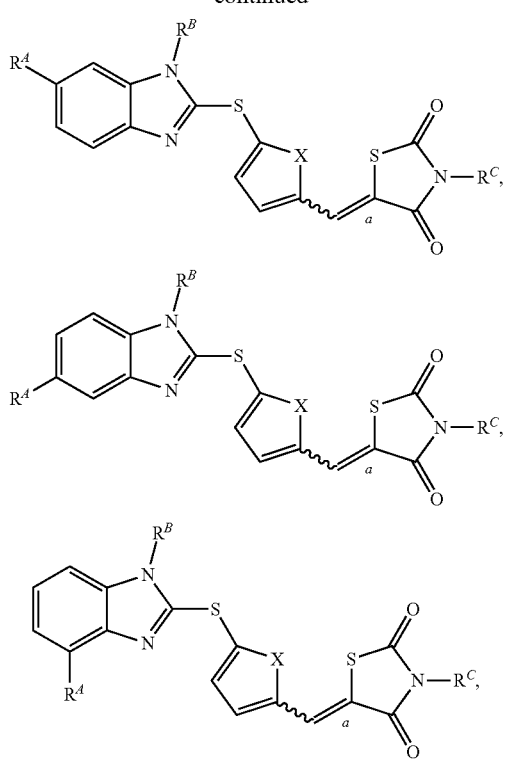
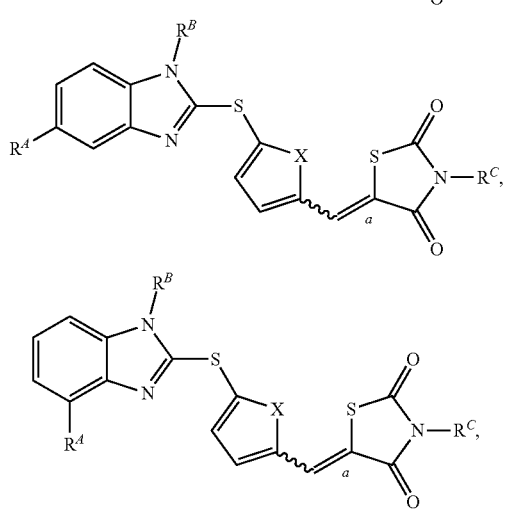
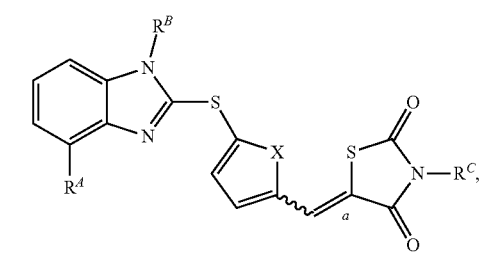

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

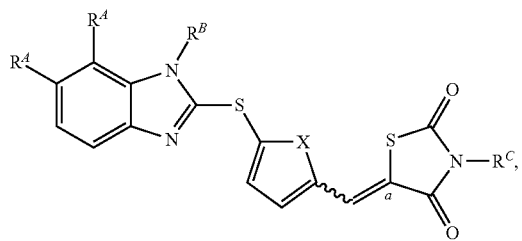
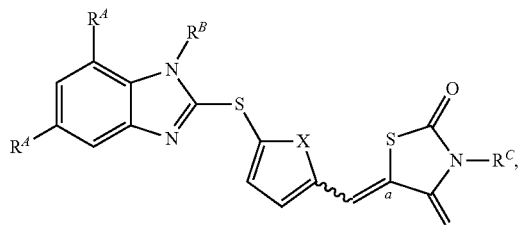
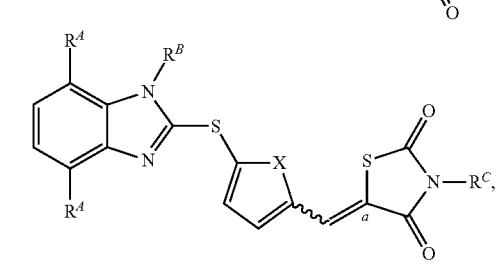

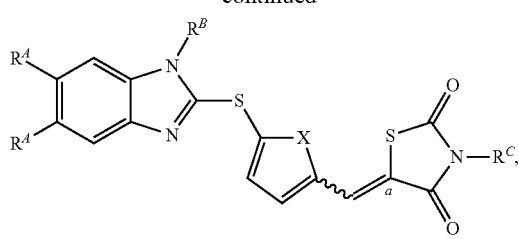
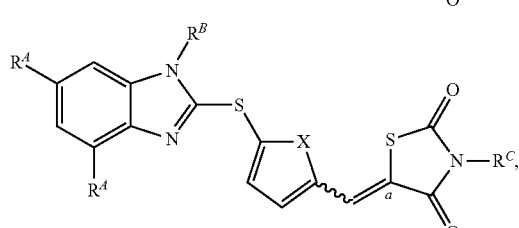
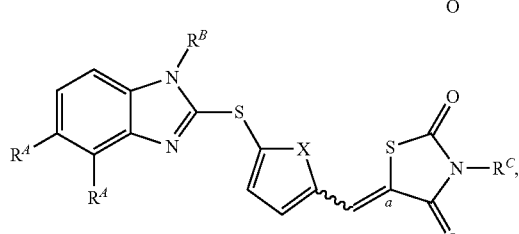

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

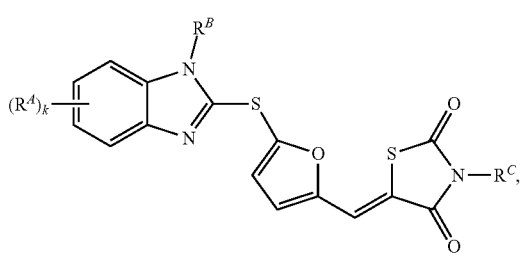

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

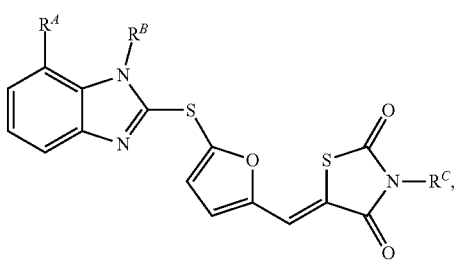

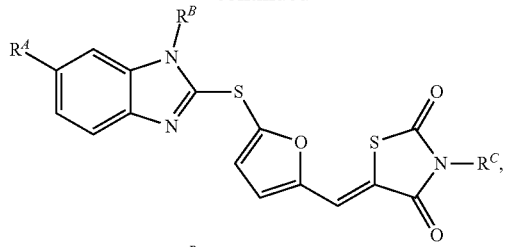

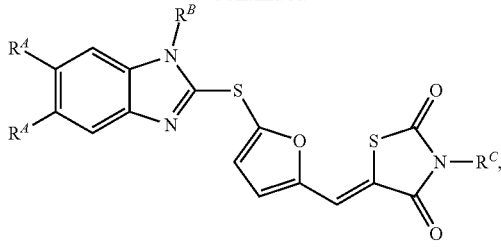

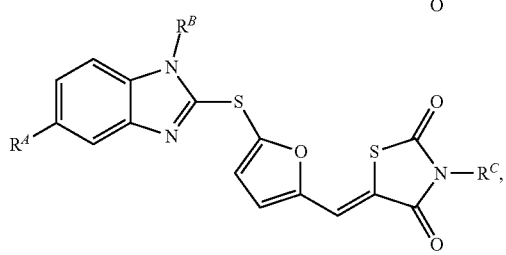

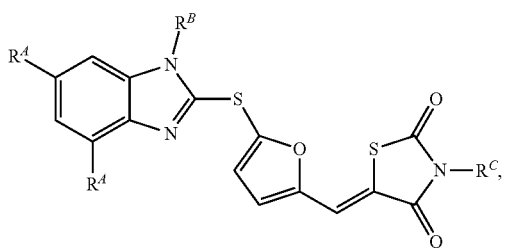

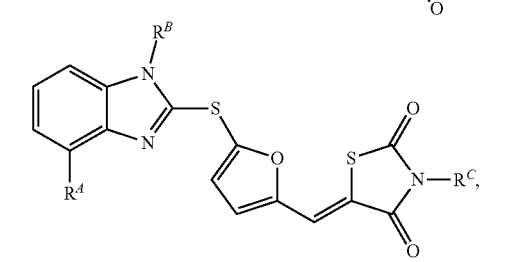

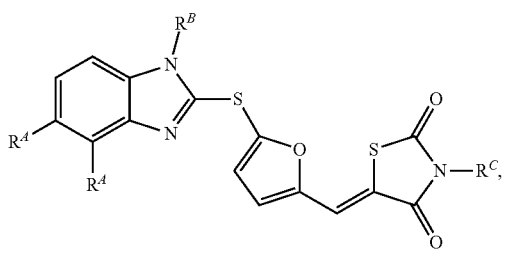

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

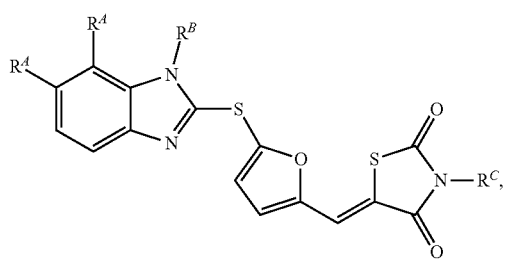

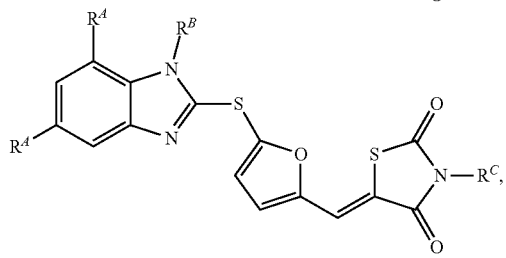

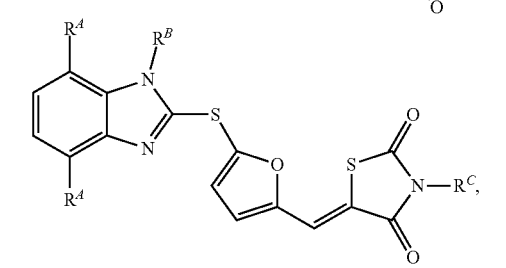

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

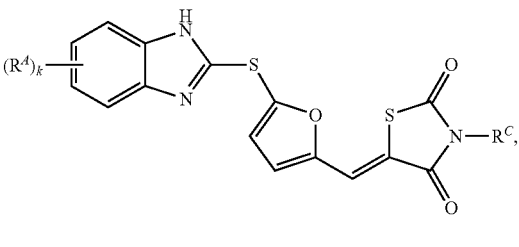

or a pharmaceutically acceptable salt, solvate, hydrate, polymorph, co-crystal, tautomer, stereoisomer, isotopically labeled derivative, or prodrug thereof.

In certain embodiments, when X is —O—, then k is 1, 2, 3, or 4, and no instance of $R^A$ is Me. In certain embodiments, when X is —O—, then k is 1, 2, 3, or 4, and no instance of $R^A$ is unsubstituted $C_{1-6}$ alkyl. In certain embodiments, wherein when X is —O—, and k is 1, then no instance of $R^A$ is Me. In certain embodiments, wherein when X is —O—, and k is 1, then no instance of $R^A$ is unsubstituted $C_{1-6}$ alkyl. In certain embodiments, the compound of Formula (I) is not of the formula:

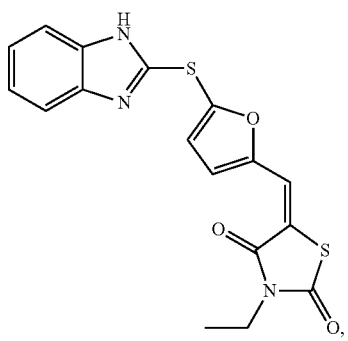
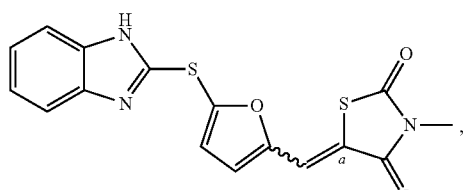
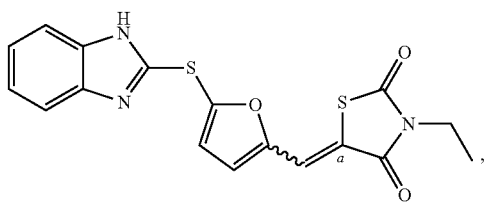
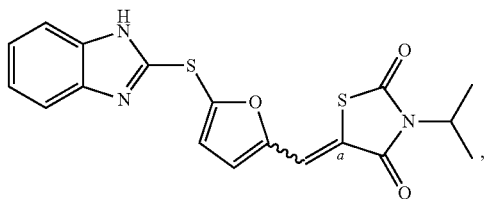
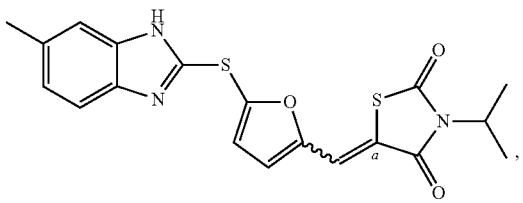
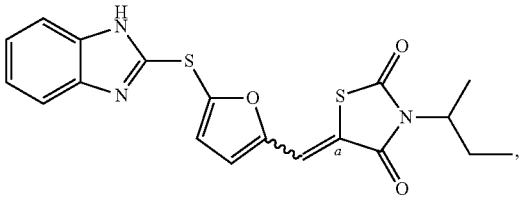
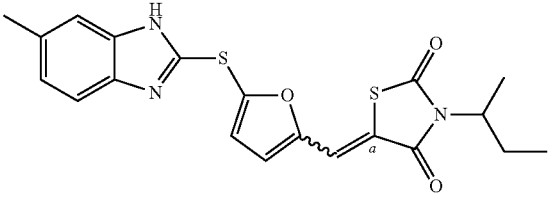
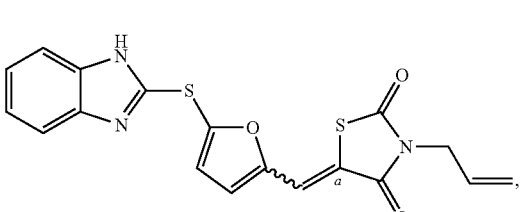
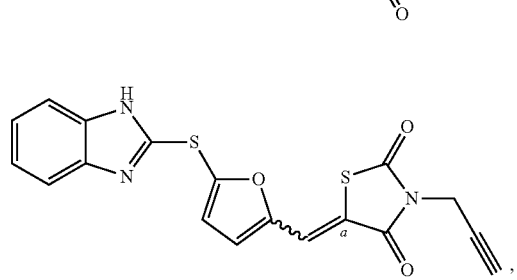
or a pharmaceutically acceptable salt thereof.
In certain embodiments, the compound of Formula (I) is not of the formula:

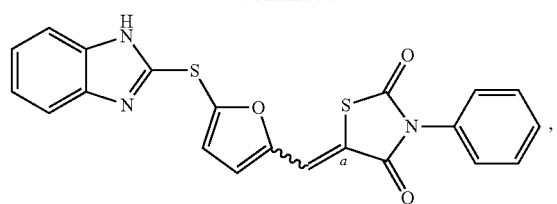
,
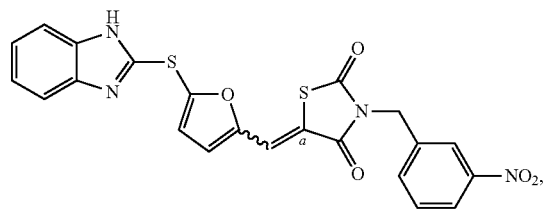
,
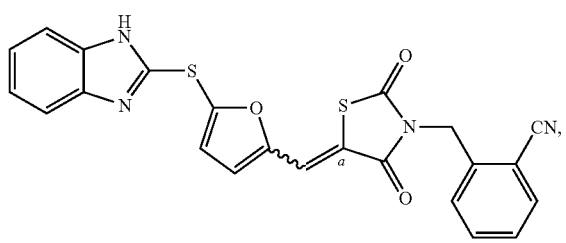
,
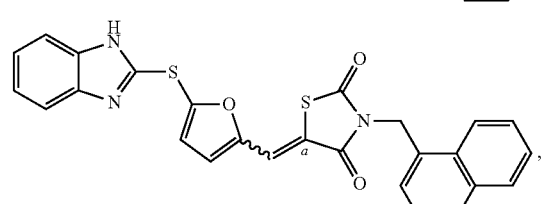
,
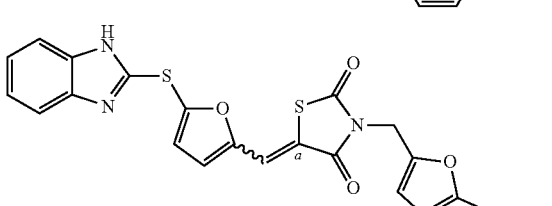
,
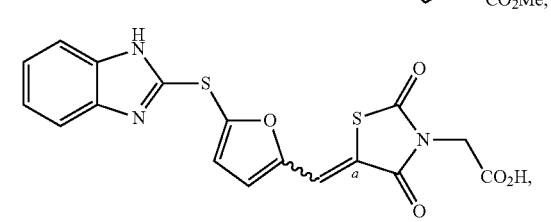
,
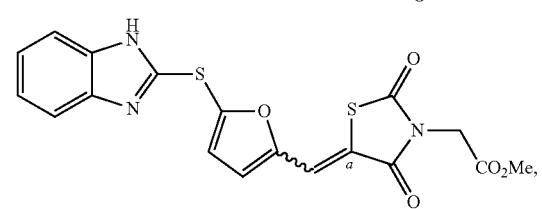
,
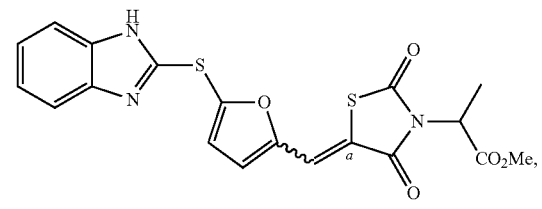
,
Exemplary compounds of Formula (I) include, but are not limited to:
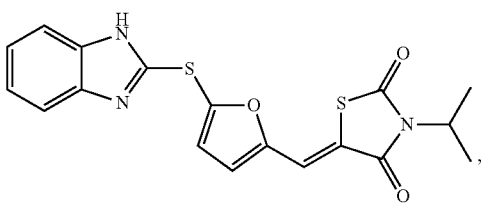
, 13
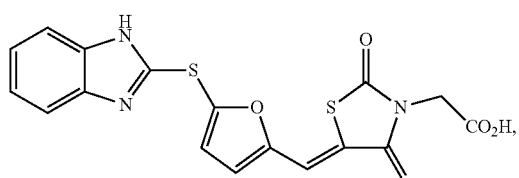
14
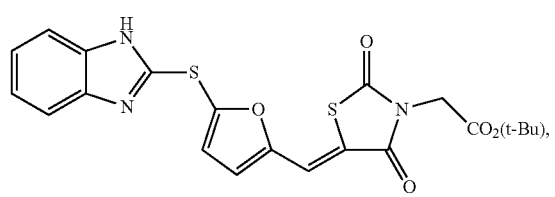
15
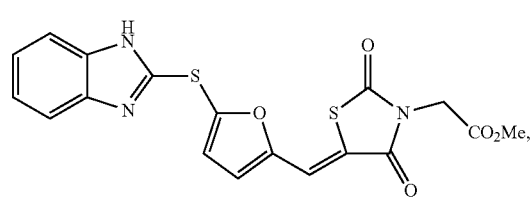
31
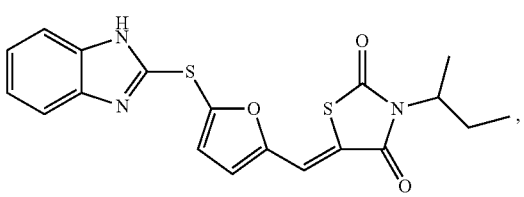
32
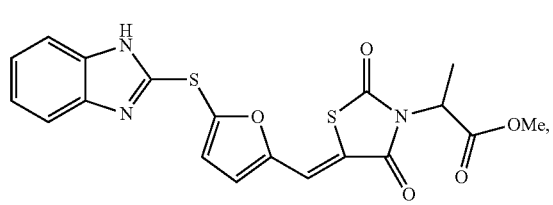
33
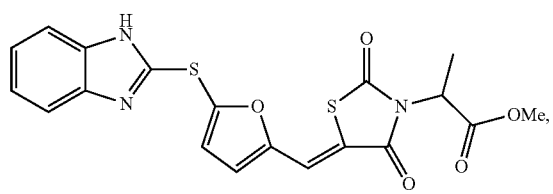
34
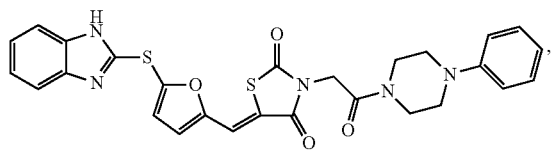
35
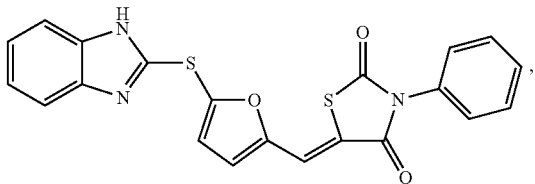
and pharmaceutically acceptable salts, solvates, hydrates, polymorphs, co-crystals, tautomers, stereoisomers, isotopically labeled derivatives, and prodrugs thereof.
Additional exemplary compounds of Formula (I) include, but are not limited to:
4
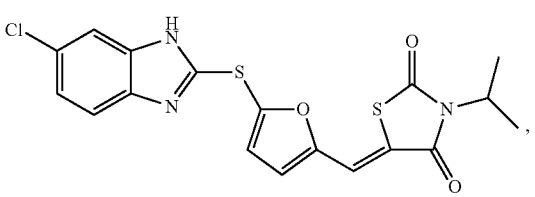
5
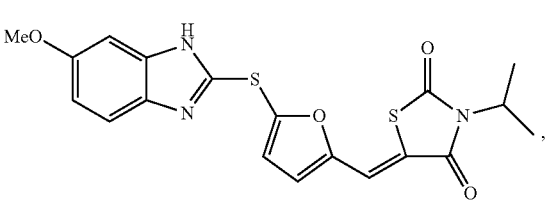
18
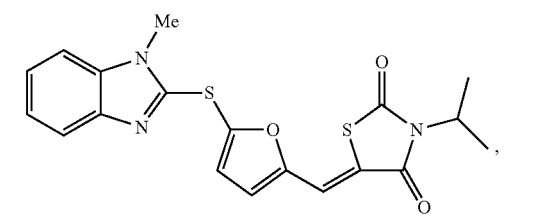
19
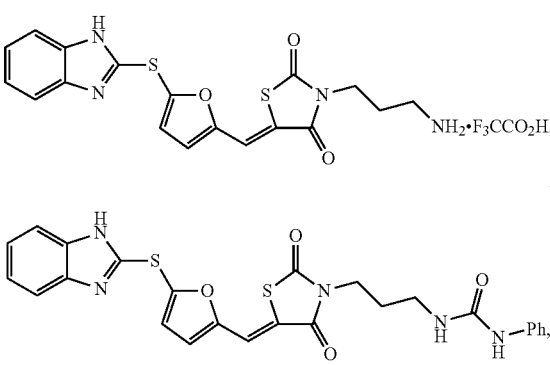
20
21
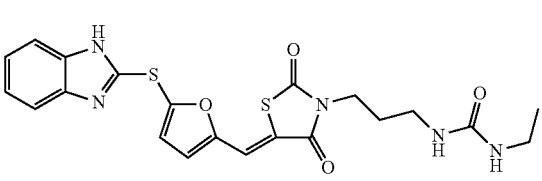

-continued
23
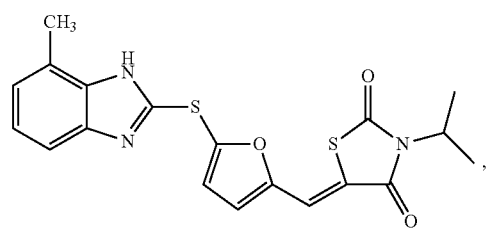
24
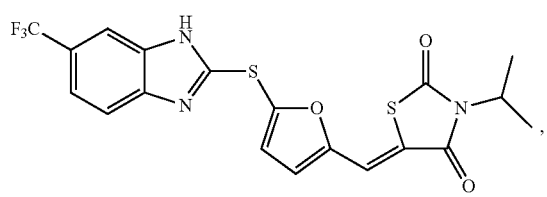
25
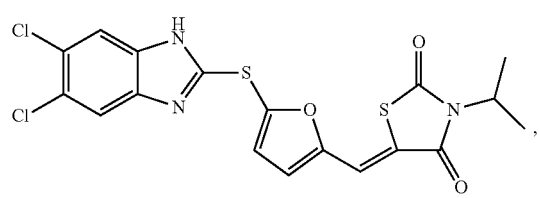
26
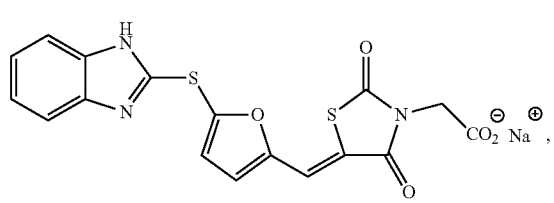
27
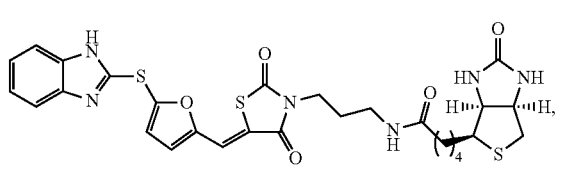
28
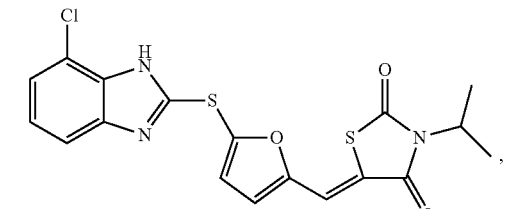
29
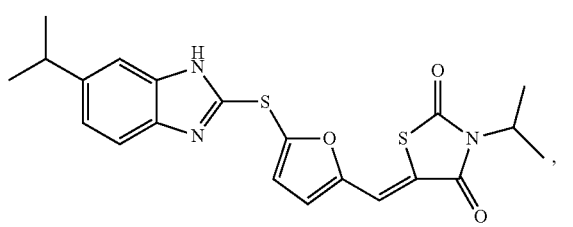
-continued
30
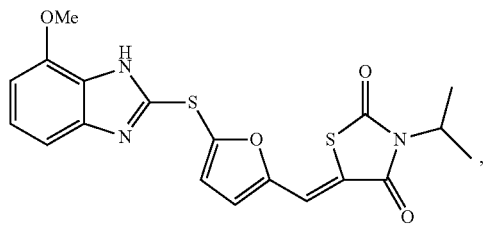
55
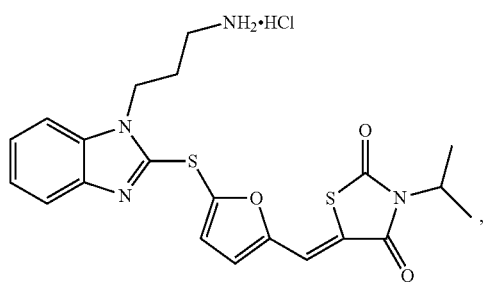
56
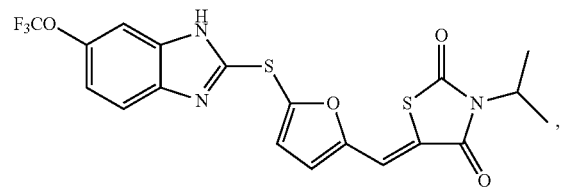
57
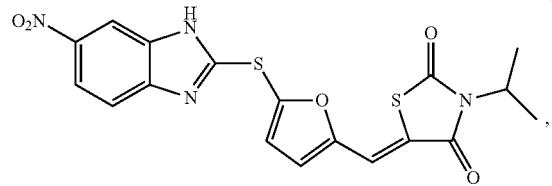
58
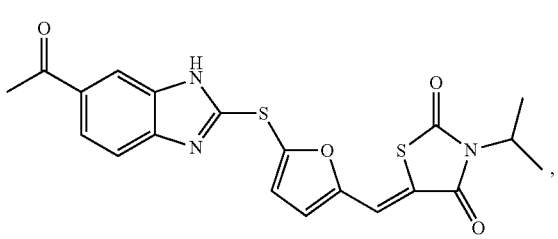
and pharmaceutically acceptable salts, solvates, hydrates, polymorphs, co-crystals, tautomers, stereoisomers, isotopically labeled derivatives, and prodrugs thereof.
Further exemplary compounds of Formula (I) include, but are not limited to:
11
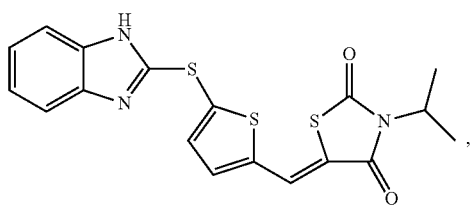

Compounds of Formula (II)

In certain embodiments, the compound of Formula (II) is of the formula:

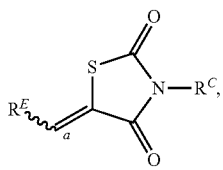

or a pharmaceutically acceptable salt, solvate, hydrate, polymorph, co-crystal, tautomer, stereoisomer, isotopically labeled derivative, or prodrug thereof, wherein:

the double bond labeled with "a" is in the (E)- or (Z)-configuration; and $R^C$ is hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —C(=O)R$^a$, —C(=O)OR$^a$, —C(=O)N(R$^a$)$_2$, or a nitrogen protecting group;

each instance of $R^a$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of R are joined to form a substituted or unsubstituted, heterocyclic ring, or substituted or unsubstituted, heteroaryl ring; and $R^E$ is a substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl.

Formula (II) includes substituent $R^E$. In certain embodiments, $R^E$ is substituted or unsubstituted alkyl (e.g., substituted or unsubstituted $C_{1-6}$ alkyl). In certain embodiments, $R^E$ is substituted or unsubstituted alkenyl (e.g., substituted or unsubstituted $C_{2-6}$ alkenyl). In certain embodiments, $R^E$ is of the formula:

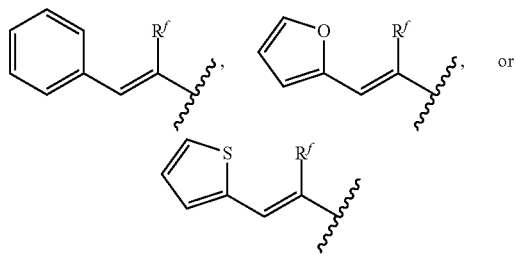

wherein $R^f$ is H, or substituted or unsubstituted alkyl. In certain embodiments $R^f$ is substituted or unsubstituted $C_{1-6}$ alkyl. In certain embodiments $R^f$ is methyl. In certain embodiments, $R^E$ is substituted or unsubstituted aryl (e.g., substituted or unsubstituted phenyl). In certain embodiments, $R^E$ is a heterocyclic ring (e.g., substituted or unsubstituted, 5- to 10-membered monocyclic or bicyclic heterocyclic ring, wherein 1, 2, or 3 atoms in the heterocyclic ring are independently nitrogen, oxygen, or sulfur). In certain embodiments, $R^E$ is substituted or unsubstituted heteroaryl (e.g., substituted or unsubstituted, 5- to 6-membered heteroaryl ring, wherein one or two atoms in the heteroaryl ring are independently nitrogen, oxygen, or sulfur). In certain embodiments, $R^E$ is of the formula:

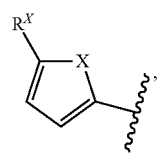

wherein X is —O— or —S—; and $R^X$ is H, substituted or unsubstituted alkyl, substituted or unsubstituted acyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl. In certain embodiments, $R^X$ is substituted or unsubstituted alkyl (e.g., substituted or unsubstituted $C_{1-6}$ alkyl). In certain embodiments, $R^E$ is of the formula:

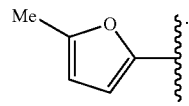

In certain embodiments, $R^E$ is of the formula:

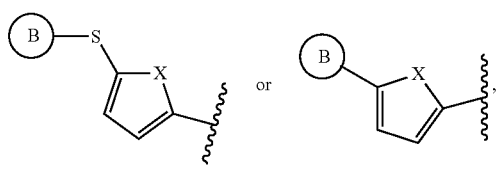

wherein X is —O— or —S—; and Ring B is a substituted or unsubstituted carbocyclyl, substituted or unsubstituted heterocyclyl, substituted or unsubstituted aryl, or substituted or unsubstituted heteroaryl. In certain embodiments Ring B is a heterocyclic ring (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, Ring B is substituted or unsubstituted aryl (e.g., substituted or unsubstituted phenyl). In certain embodiments, Ring B is of the formula:

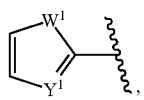

wherein $W^1$ and $Y^1$ are independently —N—, or —NR$^W$—, as valency permits, and R$^W$ is H, substituted or unsubstituted alkyl, substituted or unsubstituted acyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or a nitrogen protecting group. In certain embodiments, Ring B is of the formula:

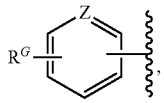

wherein Z is —N—, or —CH—; and R$^G$ is H, or substituted or unsubstituted alkyl. In certain embodiments, R$^G$ is substituted or unsubstituted alkyl (e.g., substituted or unsubstituted $C_{1-6}$ alkyl).

In certain embodiments, Ring B is of the formula:

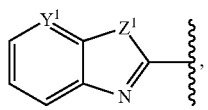

wherein $Y^1$ and $Z^1$ are independently —NR$^g$—, —CH—, or —O—; and R$^g$ is H, or substituted or unsubstituted alkyl.

In certain embodiments, Ring B is of the formula:

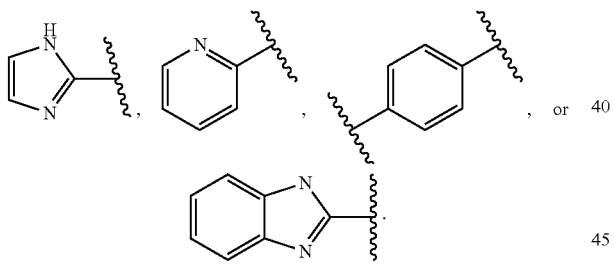

In certain embodiments, the compound of Formula (II) is of one of the following formulae:

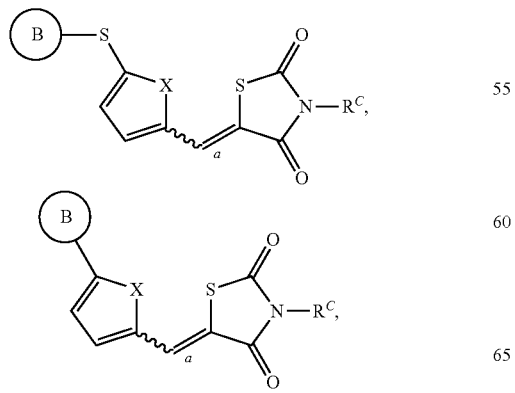

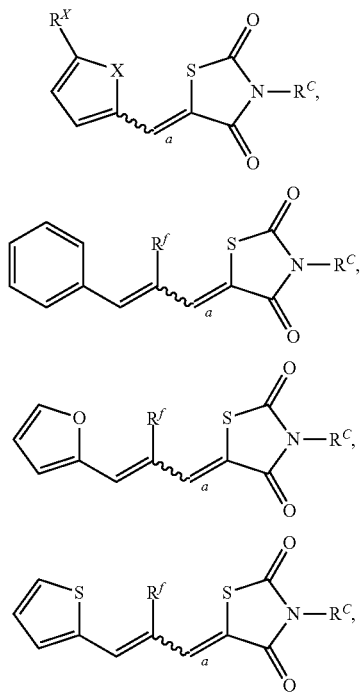

or a pharmaceutically acceptable salt thereof.

In certain embodiments, the compound of Formula (II) is of the formula:

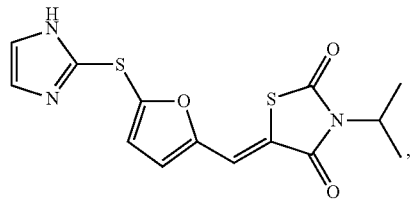

16

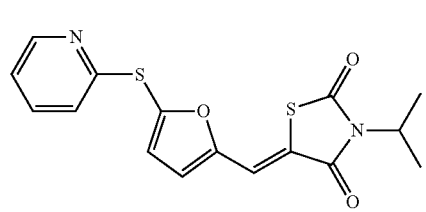

17

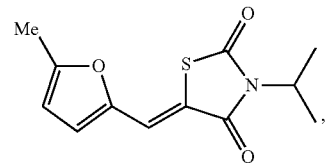

36

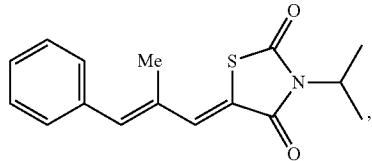

37

-continued

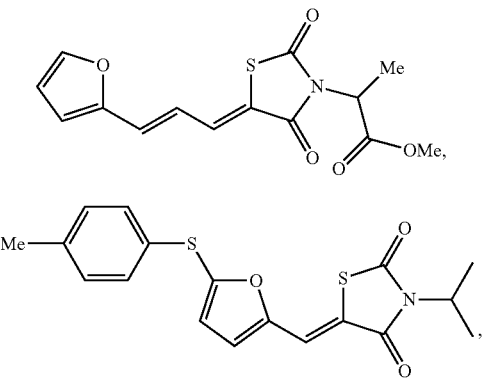

or a pharmaceutically acceptable salt thereof.

The compounds described herein may be capable of binding (e.g., reversibly binding or irreversibly binding, through covalent and/or non-covalent interactions) Myc. The compounds described herein may also be capable of preventing or reducing the interaction or binding of Myc with another molecule (e.g., peptide or protein). The compounds described herein may be useful in modulating (e.g., inhibiting) the activity of Myc in a subject in need thereof, treating diseases associated with Myc (e.g., diseases associated with aberrant activity (e.g., increased activity) of Myc) in a subject in need thereof, treating proliferative diseases in a subject in need thereof, preventing diseases associated with Myc (e.g., diseases associated with aberrant activity (e.g., increased activity) of Myc) in a subject in need thereof, preventing proliferative diseases in a subject in need thereof, and/or inducing apoptosis of a cell in a subject, biological sample, or tissue. The compounds described herein may also be useful as research tools, e.g., for studying Myc (e.g., studying the activity of Myc) in a subject, biological sample, tissue, or cell.

Pharmaceutical Compositions, Kits, and Administration

The present disclosure also provides pharmaceutical compositions comprising a compound described herein and optionally a pharmaceutically acceptable excipient. The pharmaceutical compositions may be useful in modulating (e.g., inhibiting) the activity of Myc in a subject in need thereof, treating diseases associated with Myc (e.g., diseases associated with aberrant activity (e.g., increased activity) of Myc) in a subject in need thereof, treating proliferative diseases in a subject in need thereof, preventing diseases associated with Myc (e.g., diseases associated with aberrant activity (e.g., increased activity) of Myc) in a subject in need thereof, preventing proliferative diseases in a subject in need thereof, and/or inducing apoptosis of a cell in a subject, biological sample, or tissue. The pharmaceutical compositions described herein may also be useful as research tools, e.g., for studying Myc (e.g., studying the activity of Myc) in a subject, biological sample, tissue, or cell.

In certain embodiments, the Myc is c-Myc. In certain embodiments, the Myc is L-Myc or N-Myc.

In certain embodiments, the subject is an animal. The animal may be of either sex and may be at any stage of development. In certain embodiments, the subject described herein is a human. In certain embodiments, the subject is a non-human animal. In certain embodiments, the subject is a mammal. In certain embodiments, the subject is a non-human mammal. In certain embodiments, the subject is a domesticated animal, such as a dog, cat, cow, pig, horse, sheep, or goat. In certain embodiments, the subject is a companion animal, such as a dog or cat. In certain embodiments, the subject is a livestock animal, such as a cow, pig, horse, sheep, or goat. In certain embodiments, the subject is a zoo animal. In another embodiment, the subject is a research animal, such as a rodent (e.g., mouse, rat), dog, pig, or non-human primate. In certain embodiments, the animal is a genetically engineered animal. In certain embodiments, the animal is a transgenic animal (e.g., transgenic mice and transgenic pigs). In certain embodiments, the subject is a fish or reptile.

In certain embodiments, the cell is in vitro. In certain embodiments, the cell is in vivo.

In certain embodiments, the compound described herein is provided in an effective amount in the pharmaceutical composition. In certain embodiments, the effective amount is a therapeutically effective amount. In certain embodiments, the effective amount is a prophylactically effective amount. In certain embodiments, a therapeutically effective amount is an amount effective for modulating (e.g., inhibiting) the activity of Myc. In certain embodiments, a therapeutically effective amount is an amount effective for treating a proliferative disease. In certain embodiments, a therapeutically effective amount is an amount effective for modulating (e.g., inhibiting) the activity of Myc and treating a proliferative disease. In certain embodiments, a therapeutically effective amount is an amount effective for inducing apoptosis of a cell. In certain embodiments, a prophylactically effective amount is an amount effective for modulating (e.g., inhibiting) the activity of Myc. In certain embodiments, a prophylactically effective amount is an amount effective for preventing a proliferative disease. In certain embodiments, a prophylactically effective amount is an amount effective for modulating (e.g., inhibiting) the activity of Myc and preventing a proliferative disease. In certain embodiments, a prophylactically effective amount is an amount effective for inducing apoptosis of a cell.

In certain embodiments, the effective amount is an amount effective for modulating (e.g., inhibiting) the activity of Myc by at least 10%, at least 20%, at least 30%, at least 40%, at least 50%, at least 60%, at least 70%, at least 80%, at least 90%, at least 95%, or at least 98%. In certain embodiments, the effective amount is an amount effective for modulating (e.g., inhibiting) the activity of Myc by not more than 10%, not more than 20%, not more than 30%, not more than 40%, not more than 50%, not more than 60%, not more than 70%, not more than 80%, not more than 90%, not more than 95%, or not more than 98%.

Pharmaceutical compositions described herein can be prepared by any method known in the art of pharmacology. In general, such preparatory methods include bringing the compound described herein (i.e., the "active ingredient") into association with a carrier or excipient, and/or one or more other accessory ingredients, and then, if necessary and/or desirable, shaping, and/or packaging the product into a desired single- or multi-dose unit.

Pharmaceutical compositions can be prepared, packaged, and/or sold in bulk, as a single unit dose, and/or as a plurality of single unit doses. A "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage, such as one-half or one-third of such a dosage.

Relative amounts of the active ingredient, the pharmaceutically acceptable excipient, and/or any additional ingredients in a pharmaceutical composition described herein will vary, depending upon the identity, size, and/or condition of the subject treated and further depending upon the route by which the composition is to be administered. The composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose, and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g., bentonite (aluminum silicate) and Veegum (magnesium aluminum silicate)), long chain amino acid derivatives, high molecular weight alcohols (e.g., stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters (e.g., polyoxyethylene sorbitan monolaurate (Tween® 20), polyoxyethylene sorbitan (Tween® 60), polyoxyethylene sorbitan monooleate (Tween® 80), sorbitan monopalmitate (Span® 40), sorbitan monostearate (Span® 60), sorbitan tristearate (Span® 65), glyceryl monooleate, sorbitan monooleate (Span® 80), polyoxyethylene esters (e.g., polyoxyethylene monostearate (Myrj® 45), polyoxyethylene hydrogenated castor oil, polyethoxylated castor oil, polyoxymethylene stearate, and Solutol®), sucrose fatty acid esters, polyethylene glycol fatty acid esters (e.g., Cremophor®), polyoxyethylene ethers, (e.g., polyoxyethylene lauryl ether (Brij® 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic® F-68, poloxamer P-188, cetrimonium bromide, cetylpyridinium chloride, benzalkonium chloride, docusate sodium, and/or mixtures thereof.

Exemplary binding agents include starch (e.g., cornstarch and starch paste), gelatin, sugars (e.g., sucrose, glucose, dextrose, dextrin, molasses, lactose, lactitol, mannitol, etc.), natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum®), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, antiprotozoan preservatives, alcohol preservatives, acidic preservatives, and other preservatives. In certain embodiments, the preservative is an antioxidant. In other embodiments, the preservative is a chelating agent.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant® Plus, Phenonip®, methylparaben, Germall® 115, Germaben® II, Neolone®, Kathon®, and Euxyl®.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, *eucalyptus*, evening primrose, fish, flaxseed, geraniol, gourd, grape seed, hazel nut, hyssop, isopropyl myristate, jojoba, kukui nut, lavandin, lavender, lemon, *litsea cubeba*, macadamia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates described herein are mixed with solubilizing agents such as Cremophor®, alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension, or emulsion in a nontoxic parenterally acceptable diluent or solvent, for example, as a solution in 1,3-butanediol. Among the acceptable vehicles and solvents that can be employed are water, Ringer's solution, U.S.P., and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form may be accomplished by dissolving or suspending the drug in an oil vehicle.

Compositions for rectal or vaginal administration are typically suppositories which can be prepared by mixing the conjugates described herein with suitable non-irritating excipients or carriers such as cocoa butter, polyethylene glycol, or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may include a buffering agent.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the art of pharmacology. They may optionally comprise opacifying agents and can be of a composition that they release the active ingredient(s) only, or preferentially, in a certain part of the intestinal tract, optionally, in a delayed manner. Examples of encapsulating compositions which can be used include polymeric substances and waxes. Solid compositions of a similar type can be employed as fillers in soft and hard-filled gelatin capsules using such excipients as lactose or milk sugar as well as high molecular weight polyethylene glycols and the like.

The active ingredient can be in a micro-encapsulated form with one or more excipients as noted above. The solid dosage forms of tablets, dragees, capsules, pills, and granules can be prepared with coatings and shells such as enteric coatings, release controlling coatings, and other coatings well known in the pharmaceutical formulating art. In such solid dosage forms the active ingredient can be admixed with at least one inert diluent such as sucrose, lactose, or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of encapsulating agents which can be used include polymeric substances and waxes.

Dosage forms for topical and/or transdermal administration of a compound described herein may include ointments, pastes, creams, lotions, gels, powders, solutions, sprays, inhalants, and/or patches. Generally, the active ingredient is admixed under sterile conditions with a pharmaceutically acceptable carrier or excipient and/or any needed preservatives and/or buffers as can be required. Additionally, the present disclosure contemplates the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Suitable devices for use in delivering intradermal pharmaceutical compositions described herein include short needle devices. Intradermal compositions can be administered by devices which limit the effective penetration length of a needle into the skin. Alternatively or additionally, conventional syringes can be used in the classical mantoux method of intradermal administration. Jet injection devices which deliver liquid formulations to the dermis via a liquid jet injector and/or via a needle which pierces the stratum corneum and produces a jet which reaches the dermis are suitable. Ballistic powder/particle delivery devices which use compressed gas to accelerate the compound in powder form through the outer layers of the skin to the dermis are suitable.

Formulations suitable for topical administration include, but are not limited to, liquid and/or semi-liquid preparations such as liniments, lotions, oil-in-water and/or water-in-oil emulsions such as creams, ointments, and/or pastes, and/or solutions and/or suspensions. Topically administrable formulations may, for example, comprise from about 1% to about 10% (w/w) active ingredient, although the concentration of the active ingredient can be as high as the solubility limit of the active ingredient in the solvent. Formulations for topical administration may further comprise one or more of the additional ingredients described herein.

A pharmaceutical composition described herein can be prepared, packaged, and/or sold in a formulation suitable for pulmonary administration via the buccal cavity. Such a formulation may comprise dry particles which comprise the active ingredient and which have a diameter in the range from about 0.5 to about 7 nanometers, or from about 1 to about 6 nanometers. Such compositions are conveniently in the form of dry powders for administration using a device comprising a dry powder reservoir to which a stream of propellant can be directed to disperse the powder and/or using a self-propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions described herein formulated for pulmonary delivery may provide the active ingredient in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

Formulations described herein as being useful for pulmonary delivery are useful for intranasal delivery of a pharmaceutical composition described herein. Another formulation suitable for intranasal administration is a coarse powder comprising the active ingredient and having an average particle from about 0.2 to 500 micrometers. Such a formulation is administered by rapid inhalation through the nasal passage from a container of the powder held close to the nares.

Formulations for nasal administration may, for example, comprise from about as little as 0.1% (w/w) to as much as 100% (w/w) of the active ingredient, and may comprise one or more of the additional ingredients described herein. A pharmaceutical composition described herein can be prepared, packaged, and/or sold in a formulation for buccal administration. Such formulations may, for example, be in the form of tablets and/or lozenges made using conventional methods, and may contain, for example, 0.1 to 20% (w/w) active ingredient, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

A pharmaceutical composition described herein can be prepared, packaged, and/or sold in a formulation for ophthalmic administration. Such formulations may, for example, be in the form of eye drops including, for example, a 0.1-1.0% (w/w) solution and/or suspension of the active ingredient in an aqueous or oily liquid carrier or excipient. Such drops may further comprise buffering agents, salts, and/or one or more other of the additional ingredients described herein. Other opthalmically-administrable formulations which are useful include those which comprise the active ingredient in microcrystalline form and/or in a liposomal preparation. Ear drops and/or eye drops are also contemplated as being within the scope of this disclosure.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

Compounds provided herein are typically formulated in dosage unit form for ease of administration and uniformity of dosage. It will be understood, however, that the total daily usage of the compositions described herein will be decided by a physician within the scope of sound medical judgment. The specific therapeutically effective dose level for any particular subject or organism will depend upon a variety of factors including the proliferative disease being treated and the severity of the disorder, the activity of the specific active ingredient employed; the specific composition employed; the age, body weight, general health, sex, and diet of the subject; the time of administration, route of administration, and rate of excretion of the specific active ingredient employed; the duration of the treatment; drugs used in combination or coincidental with the specific active ingredient employed; and like factors well known in the medical arts.

The compounds and compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general, the most appropriate route of administration will depend upon a variety of factors including the nature of the agent (e.g., its stability in the environment of the gastrointestinal tract), and/or the condition of the subject (e.g., whether the subject is able to tolerate oral administration). In certain embodiments, the compound or pharmaceutical composition described herein is suitable for topical administration to the eye of a subject.

The exact amount of a compound required to achieve an effective amount will vary from subject to subject, depending, for example, on species, age, and general condition of a subject, severity of the side effects or disorder, identity of the particular compound, mode of administration, and the like. An effective amount may be included in a single dose (e.g., single oral dose) or multiple doses (e.g., multiple oral doses). In certain embodiments, when multiple doses are administered to a subject or applied to a biological sample, tissue, or cell, any two doses of the multiple doses include different or substantially the same amounts of a compound described herein. In certain embodiments, when multiple doses are administered to a subject or applied to a biological sample, tissue, or cell, the frequency of administering the multiple doses to the subject or applying the multiple doses to the biological sample, tissue, or cell is three doses a day, two doses a day, one dose a day, one dose every other day, one dose every third day, one dose every week, one dose every two weeks, one dose every three weeks, or one dose every four weeks. In certain embodiments, the frequency of administering the multiple doses to the subject or applying the multiple doses to the biological sample, tissue, or cell is one dose per day. In certain embodiments, the frequency of administering the multiple doses to the subject or applying the multiple doses to the biological sample, tissue, or cell is two doses per day. In certain embodiments, the frequency of administering the multiple doses to the subject or applying the multiple doses to the biological sample, tissue, or cell is three doses per day. In certain embodiments, when multiple doses are administered to a subject or applied to a biological sample, tissue, or cell, the duration between the first dose and last dose of the multiple doses is one day, two days, four days, one week, two weeks, three weeks, one month, two months, three months, four months, six months, nine months, one year, two years, three years, four years, five years, seven years, ten years, fifteen years, twenty years, or the lifetime of the subject, tissue, or cell. In certain embodiments, the duration between the first dose and last dose of the multiple doses is three months, six months, or one year. In certain embodiments, the duration between the first dose and last dose of the multiple doses is the lifetime of the subject, tissue, or cell. In certain embodiments, a dose (e.g., a single dose, or any dose of multiple doses) described herein includes independently between 0.1 µg and 1 µg, between 0.001 mg and 0.01 mg, between 0.01 mg and 0.1 mg, between 0.1 mg and 1 mg, between 1 mg and 3 mg, between 3 mg and 10 mg, between 10 mg and 30 mg, between 30 mg and 100 mg, between 100 mg and 300 mg, between 300 mg and 1,000 mg, or between 1 g and 10 g, inclusive, of a compound described herein. In certain embodiments, a dose described herein includes independently between 1 mg and 3 mg, inclusive, of a compound described herein. In certain embodiments, a dose described herein includes independently between 3 mg and 10 mg, inclusive, of a compound described herein. In certain embodiments, a dose described herein includes independently between 10 mg and 30 mg, inclusive, of a compound described herein. In certain embodiments, a dose described herein includes independently between 30 mg and 100 mg, inclusive, of a compound described herein.

Dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

A compound or composition, as described herein, can be administered in combination with one or more additional pharmaceutical agents (e.g., therapeutically and/or prophylactically active agents). The compounds or compositions can be administered in combination with additional pharmaceutical agents that improve their activity (e.g., activity (e.g., potency and/or efficacy) in treating a proliferative disease in a subject in need thereof, in preventing a proliferative disease in a subject in need thereof, in modulating (e.g., inhibiting) the activity of Myc in a subject, biological sample, tissue, or cell, or in inducing apoptosis of a cell in a subject, biological sample, or tissue), improve bioavailability, improve safety, reduce drug resistance, reduce and/or modify metabolism, inhibit excretion, and/or modify distribution in a subject, biological sample, tissue, or cell. It will also be appreciated that the therapy employed may achieve a desired effect for the same disorder, and/or it may achieve different effects. In certain embodiments, a pharmaceutical composition described herein including a compound described herein and an additional pharmaceutical agent shows a synergistic effect that is absent in a pharmaceutical composition including one of the compound and the additional pharmaceutical agent, but not both.

The compound or composition can be administered concurrently with, prior to, or subsequent to one or more additional pharmaceutical agents, which may be useful as, e.g., combination therapies. Pharmaceutical agents include therapeutically active agents. Pharmaceutical agents also include prophylactically active agents. Pharmaceutical agents include small organic molecules such as drug compounds (e.g., compounds approved for human or veterinary use by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells. Each additional pharmaceutical agent may be administered at a dose and/or on a time schedule determined for that pharmaceutical agent. The additional pharmaceutical agents may also be administered together with each other and/or with the compound or composition described herein in a single dose or administered separately in different doses. The particular combination to employ in a regimen will take into account compatibility of the compound described herein with the additional pharmaceutical agent(s) and/or the desired therapeutic and/or prophylactic effect to be achieved. In general, it is expected that the additional pharmaceutical agent(s) in combination be utilized at levels that do not exceed the levels at which they are utilized individually. In some embodiments, the levels utilized in combination will be lower than those utilized individually.

The additional pharmaceutical agents include, but are not limited to, anti-proliferative agents, anti-cancer agents, anti-angiogenesis agents, anti-inflammatory agents, immunosuppressants, anti-bacterial agents, anti-viral agents, cardiovascular agents, cholesterol-lowering agents, anti-diabetic agents, anti-allergic agents, contraceptive agents, pain-relieving agents, and a combination thereof. In certain embodiments, the additional pharmaceutical agent is an anti-proliferative agent (e.g., anti-cancer agent). In certain embodiments, the additional pharmaceutical agent is an anti-leukemia agent. In certain embodiments, the additional pharmaceutical agent is ABITREXATE (methotrexate), ADE, Adriamycin RDF (doxorubicin hydrochloride), Ambochlorin (chlorambucil), ARRANON (nelarabine), ARZERRA (ofatumumab), BOSULIF (bosutinib), BUSULFEX (busulfan), CAMPATH (alemtuzumab), CERUBIDINE (daunorubicin hydrochloride), CLAFEN (cyclophosphamide), CLOFAREX (clofarabine), CLOLAR (clofarabine), CVP, CYTOSAR-U (cytarabine), CYTOXAN (cyclophosphamide), ERWINAZE (Asparaginase *Erwinia Chrysanthemi*), FLUDARA (fludarabine phosphate), FOLEX (methotrexate), FOLEX PFS (methotrexate), GAZYVA (obinutuzumab), GLEEVEC (imatinib mesylate), Hyper-CVAD, ICLUSIG (ponatinib hydrochloride), IMBRUVICA (ibrutinib), LEUKERAN (chlorambucil), LINFOLIZIN (chlorambucil), MARQIBO (vincristine sulfate liposome), METHOTREXATE LPF (methorexate), MEXATE (methotrexate), MEXATE-AQ (methotrexate), mitoxantrone hydrochloride, MUSTARGEN (mechlorethamine hydrochloride), MYLERAN (busulfan), NEOSAR (cyclophosphamide), ONCASPAR (Pegaspargase), PURINETHOL (mercaptopurine), PURIXAN (mercaptopurine), Rubidomycin (daunorubicin hydrochloride), SPRYCEL (dasatinib), SYNRIBO (omacetaxine mepesuccinate), TARABINE PFS (cytarabine), TASIGNA (nilotinib), TREANDA (bendamustine hydrochloride), TRISENOX (arsenic trioxide), VINCASAR PFS (vincristine sulfate), ZYDELIG (idelalisib), or a combination thereof. In certain embodiments, the additional pharmaceutical agent is an anti-lymphoma agent. In certain embodiments, the additional pharmaceutical agent is ABITREXATE (methotrexate), ABVD, ABVE, ABVE-PC, ADCETRIS (brentuximab vedotin), ADRIAMYCIN PFS (doxorubicin hydrochloride), ADRIAMYCIN RDF (doxorubicin hydrochloride), AMBOCHLORIN (chlorambucil), AMBOCLORIN (chlorambucil), ARRANON (nelarabine), BEACOPP, BECENUM (carmustine), BELEODAQ (belinostat), BEXXAR (tositumomab and iodine I 131 tositumomab), BICNU (carmustine), BLENOXANE (bleomycin), CARMUBRIS (carmustine), CHOP, CLAFEN (cyclophosphamide), COPP, COPP-ABV, CVP, CYTOXAN (cyclophosphamide), DEPOCYT (liposomal cytarabine), DTIC-DOME (dacarbazine), EPOCH, FOLEX (methotrexate), FOLEX PFS (methotrexate), FOLOTYN (pralatrexate), HYPER-CVAD, ICE, IMBRUVICA (ibrutinib), INTRON A (recombinant interferon alfa-2b), ISTODAX (romidepsin), LEUKERAN (chlorambucil), LINFOLIZIN (chlorambucil), Lomustine, MATULANE (procarbazine hydrochloride), METHOTREXATE LPF (methotrexate), MEXATE (methotrexate), MEXATE-AQ (methotrexate), MOPP, MOZOBIL (plerixafor), MUSTARGEN (mechlorethamine hydrochloride), NEOSAR (cyclophosphamide), OEPA, ONTAK (denileukin diftitox), OPPA, R-CHOP, REVLIMID (lenalidomide), RITUXAN (rituximab), STANFORD V, TREANDA (bendamustine hydrochloride), VAMP, VELBAN (vinblastine sulfate), VELCADE (bortezomib), VELSAR (vinblastine sulfate), VINCASAR PFS (vincristine sulfate), ZEVALIN (ibritumomab tiuxetan), ZOLINZA (vorinostat), ZYDELIG (idelalisib), or a combination thereof. In certain embodiments, the additional pharmaceutical agent is REVLIMID (lenalidomide), DACOGEN (decitabine), VIDAZA (azacitidine), CYTOSAR-U (cytarabine), IDAMYCIN (idarubicin), CERUBIDINE (daunorubicin), LEUKERAN (chlorambucil), NEOSAR (cyclophosphamide), FLUDARA (fludarabine), LEUSTATIN (cladribine), or a combination thereof. In certain embodiments, the additional pharmaceutical agent is ABITREXATE (methotrexate), ABRAXANE (paclitaxel albumin-stabilized nanoparticle formulation), AC, AC-T, ADE, ADRIAMYCIN PFS (doxorubicin hydrochloride), ADRUCIL (fluorouracil), AFINITOR (everolimus), AFINITOR DISPERZ (everolimus), ALDARA (imiquimod), ALIMTA (pemetrexed disodium), AREDIA (pamidronate disodium), ARIMIDEX (anastrozole), AROMASIN (exemestane), AVASTIN (bevacizumab), BECENUM (carmustine), BEP, BICNU (carmustine), BLENOXANE (bleomycin), CAF, CAMPTOSAR (irinotecan hydrochloride), CAPOX, CAPRELSA (vandetanib), CARBOPLATIN-TAXOL, CARMUBRIS (carmustine), CASODEX (bicalutamide), CEENU (lomustine), CERUBIDINE (daunorubicin hydrochloride), CERVARIX (recombinant HPV bivalent vaccine), CLAFEN (cyclophosphamide), CMF, COMETRIQ (cabozantinib-s-malate), COSMEGEN (dactinomycin), CYFOS (ifosfamide), CYRAMZA (ramucirumab), CYTOSAR-U (cytarabine), CYTOXAN (cyclophosphamide), DACOGEN (decitabine), DEGARELIX, DOXIL (doxorubicin hydrochloride liposome), DOXORUBICIN HYDROCHLORIDE, DOX-SL (doxorubicin hydrochloride liposome), DTIC-DOME (dacarbazine), EFUDEX (fluorouracil), ELLENCE (epirubicin hydrochloride), ELOXATIN (oxaliplatin), ERBITUX (cetuximab), ERIVEDGE (vismodegib), ETOPOPHOS (etoposide phosphate), EVACET (doxorubicin hydrochloride liposome), FARESTON (toremifene), FASLODEX (fulvestrant), FEC, FEMARA (letrozole), FLUOROPLEX (fluorouracil), FOLEX (methotrexate), FOLEX PFS (methotrexate), FOLFIRI, FOLFIRI-BEVACIZUMAB, FOLFIRI-CETUXIMAB, FOLFIRINOX, FOLFOX, FU-LV, GARDASIL (recombinant human papillomavirus (HPV) quadrivalent vaccine), GEMCITABINE-CISPLATIN, GEMCITABINE-OXALIPLATIN, GEMZAR (gemcitabine hydrochloride), GILOTRIF (afatinib dimaleate), GLEEVEC (imatinib mesylate), GLIADEL (carmustine implant), GLIADEL WAFER (carmustine implant), HERCEPTIN (trastuzumab), HYCAMTIN (topotecan hydrochloride), IFEX (ifosfamide), IFOSFAMIDUM (ifosfamide), INLYTA (axitinib), INTRON A (recombinant interferon alfa-2b), IRESSA (gefitinib), IXEMPRA (ixabepilone), JAKAFI (ruxolitinib phosphate), JEVTANA (cabazitaxel), KADCYLA (ado-trastuzumab emtansine), KEYTRUDA (pembrolizumab), KYPROLIS (carfilzomib), LIPODOX (doxorubicin hydrochloride liposome), LUPRON (leuprolide acetate), LUPRON DEPOT (leuprolide acetate), LUPRON DEPOT-3 MONTH (leuprolide acetate), LUPRON DEPOT-4 MONTH (leuprolide acetate), LUPRON DEPOT-PED (leuprolide acetate), MEGACE (megestrol acetate), MEKINIST (trametinib), METHAZOLASTONE (temozolomide), METHOTREXATE LPF (methotrexate), MEXATE (methotrexate), MEXATE-AQ (methotrexate), MITOXANTRONE HYDROCHLORIDE, MITOZYTREX (mitomycin c), MOZOBIL (plerixafor), MUSTARGEN (mechlorethamine hydrochloride), MUTAMYCIN (mitomycin c), MYLOSAR (azacitidine), NAVELBINE (vinorelbine tartrate), NEOSAR (cyclophosphamide), NEXAVAR (sorafenib tosylate), NOLVADEX (tamoxifen citrate), NOVALDEX (tamoxifen citrate), OFF, PAD, PARAPLAT (carboplatin), PARAPLATIN (carboplatin), PEG-INTRON (peginterferon alfa-2b), PEMETREXED DISODIUM, PERJETA (pertuzumab), PLATINOL (cisplatin), PLATINOL-AQ (cisplatin), POMALYST (pomalidomide), prednisone, PROLEUKIN (aldesleukin), PROLIA (denosumab), PROVENGE (sipuleucel-t), REVLIMID (lenalidomide), RUBIDOMYCIN (daunorubicin hydrochloride), SPRYCEL (dasatinib), STIVARGA (regorafenib), SUTENT (sunitinib malate), SYLATRON (peginterferon alfa-2b), SYLVANT (siltuximab), SYNOVIR (thalidomide), TAC, TAFINLAR (dabrafenib), TARABINE PFS (cytarabine), TARCEVA (erlotinib hydrochloride), TASIGNA (nilotinib), TAXOL (paclitaxel), TAXOTERE (docetaxel), TEMODAR (temozolomide), THALOMID (thalidomide), TOPOSAR (etoposide), TORISEL (temsirolimus), TPF, TRISENOX (arsenic trioxide), TYKERB (lapatinib ditosylate), VECTIBIX (panitumumab), VEIP, VELBAN (vinblastine sulfate), VELCADE (bortezomib), VELSAR (vinblastine sulfate), VEPESID (etoposide), VIADUR (leuprolide acetate), VIDAZA (azacitidine), VINCASAR PFS (vincristine sulfate), VOTRIENT (pazopanib hydrochloride), WELLCOVORIN (leucovorin calcium), XALKORI (crizotinib), XELODA (capecitabine), XELOX, XGEVA (denosumab), XOFIGO (radium 223 dichloride), XTANDI (enzalutamide), YERVOY (ipilimumab), ZALTRAP (ziv-aflibercept), ZELBORAF (vemurafenib), ZOLADEX (goserelin acetate), ZOMETA (zoledronic acid), ZYKADIA (ceritinib), ZYTIGA (abiraterone acetate), or a combination thereof. In certain embodiments, the additional pharmaceutical agent is a binder or modulator (e.g., inhibitor or activator) of Myc. In certain embodiments, the additional pharmaceutical agent is a protein kinase inhibitor (e.g., tyrosine protein kinase inhibitor). In certain embodiments, the additional pharmaceutical agent is selected from the group consisting of epigenetic or transcriptional modulators (e.g., DNA methyltransferase inhibitors, histone deacetylase inhibitors (HDAC inhibitors), lysine methyltransferase inhibitors), antimitotic drugs (e.g., taxanes and vinca alkaloids), hormone receptor modulators (e.g., estrogen receptor modulators and androgen receptor modulators), cell signaling pathway inhibitors (e.g., tyrosine protein kinase inhibitors), modulators of protein stability (e.g., proteasome inhibitors), Hsp90 inhibitors, glucocorticoids, all-trans retinoic acids, and other agents that promote differentiation. In certain embodiments, the compounds described herein or pharmaceutical compositions can be administered in combination with an anti-cancer therapy including, but not limited to, surgery, radiation therapy, transplantation (e.g., stem cell transplantation, bone marrow transplantation), immunotherapy, and chemotherapy.

Also encompassed by the disclosure are kits (e.g., pharmaceutical packs). The kits provided may comprise a pharmaceutical composition or compound described herein and a container (e.g., a vial, ampule, bottle, syringe, and/or dispenser package, or other suitable container). In some embodiments, provided kits may optionally further include a second container comprising a pharmaceutical excipient for dilution or suspension of a pharmaceutical composition or compound described herein. In some embodiments, the pharmaceutical composition or compound described herein provided in the first container and the second container are combined to form one unit dosage form.

Thus, in one aspect, provided are kits including a first container comprising a compound or pharmaceutical composition described herein. The kits described herein may be useful in modulating (e.g., inhibiting) the activity of Myc in a subject in need thereof, treating diseases associated with Myc (e.g., diseases associated with aberrant activity (e.g., increased activity) of Myc) in a subject in need thereof, treating proliferative diseases in a subject in need thereof, preventing diseases associated with Myc (e.g., diseases associated with aberrant activity (e.g., increased activity) of Myc) in a subject in need thereof, preventing proliferative diseases in a subject in need thereof, and/or inducing apoptosis of a cell in a subject, biological sample, or tissue. The kits described herein may also be useful as research tools, e.g., for studying Myc (e.g., studying the activity of Myc) in a subject, biological sample, tissue, or cell.

In certain embodiments, a kit described herein further includes instructions for using the compound or pharmaceutical composition included in the kit. A kit described herein may also include information as required by a regulatory agency such as the U.S. Food and Drug Administration (FDA). In certain embodiments, the information included in the kits is prescribing information. In certain embodiments, the kits and instructions provide for treating a proliferative disease in a subject in need thereof. In certain embodiments, the kits and instructions provide for preventing a proliferative disease in a subject in need thereof. In certain embodiments, the kits and instructions provide for modulating (e.g., inhibiting) the activity of Myc in a subject, biological sample, tissue, or cell. In certain embodiments, the kits and instructions provide for inducing apoptosis of a cell in a subject, biological sample, or tissue. A kit described herein may include one or more additional pharmaceutical agents described herein as a separate composition.

Methods of Treatment and Uses

Myc is associated with a wide range of proliferative diseases. The compounds described herein may be capable of binding (e.g., reversibly binding or irreversibly binding) Myc and modulating (e.g., inhibiting or increasing) the activity (e.g., aberrant activity, such as increased or decreased activity) of the Myc. In certain embodiments, the aberrant activity of Myc is increased activity of Myc. Modulation of Myc using the compounds described herein may be an effective approach to treat and/or prevent the proliferative disease. Compounds described herein that include a small-molecule label may also be useful in identifying the association of Myc with a proliferative disease. The present disclosure thus provides methods of modulating (e.g., inhibiting or increasing) the activity of Myc in a subject, biological sample, tissue, or cell, methods of treating and/or preventing proliferative diseases in a subject in need thereof, and methods of inducing apoptosis of a cell in a subject, biological sample, or tissue.

In another aspect, the present disclosure provides methods of modulating (e.g., inhibiting) the activity of Myc (e.g., c-Myc, L-Myc, or N-Myc) in a subject in need thereof, the methods comprising administering to the subject an effective amount of a compound or pharmaceutical composition described herein.

In another aspect, the present disclosure provides methods of modulating (e.g., inhibiting) the activity of Myc (e.g., c-Myc, L-Myc, or N-Myc) in a biological sample, tissue, or cell, the methods comprising contacting the biological sample, tissue, or cell with an effective amount of a compound or pharmaceutical composition described herein.

In certain embodiments, the activity of Myc in a subject, biological sample, tissue, or cell is inhibited by a compound, pharmaceutical composition, kit, use, or method described herein by at least 1%, at least 3%, at least 10%, at least 20%, at least 30%, at least 40%, at least 50%, at least 60%, at least 70%, at least 80%, or at least 90%. In certain embodiments, the activity of Myc in a subject, biological sample, tissue, or cell is inhibited by a compound, pharmaceutical composition, kit, use, or method described herein by not more than 1%, not more than 3%, not more than 10%, not more than 20%, not more than 30%, not more than 40%, not more than 50%, not more than 60%, not more than 70%, not more than 80%, or not more than 90%. In some embodiments, the activity of Myc in a subject, biological sample, tissue, or cell is selectively inhibited by the compound, pharmaceutical composition, kit, use, or method. In some embodiments, the activity of Myc in a subject, biological sample, tissue, or cell is selectively inhibited by the compound, pharmaceutical composition, kit, use, or method, compared to a different transcription factor (e.g., SP1, AP-1, C/EBP, heat shock factor, ATF/CREB, Oct-1, NF-1). In some embodiments, the activity of c-Myc in a subject, biological sample, tissue, or cell is selectively inhibited by the compound, pharmaceutical composition, kit, use, or method, compared to a different Myc (e.g., L-Myc, N-Myc) and/or a different transcription factor (e.g., SP1, AP-1, C/EBP, heat shock factor, ATF/CREB, Oct-1, NF-1). In some embodiments, the activity of Myc in a subject, biological sample, tissue, or cell is reversibly inhibited by the compound, pharmaceutical composition, kit, use, or method. In some embodiments, the activity of Myc in a subject, biological sample, tissue, or cell is irreversibly inhibited by the compound, pharmaceutical composition, kit, use, or method. In certain embodiments, the compound, pharmaceutical composition, kit, use, or method inhibits the activity of a mutant (e.g., point mutant) form of Myc (e.g., MYC, MYCL, and/or MYCN). In certain embodiments, the compound, pharmaceutical composition, kit, use, or method modulates (e.g., inhibits) somatic amplification of Myc (e.g., MYC, MYCL, and/or MYCN). In certain embodiments, the compound, pharmaceutical composition, kit, use, or method modulates (e.g., inhibits) chromosomal translocation. In certain embodiments, the compound, pharmaceutical composition, kit, use, or method regulates (e.g., down-regulates) the expression of Myc (e.g., MYC, MYCL, and/or MYCN). In certain embodiments, the compound, pharmaceutical composition, kit, use, or method modulates (e.g., inhibits) translation of Myc (e.g., MYC, MYCL, and/or MYCN). In certain embodiments, the compound, pharmaceutical composition, kit, use, or method modulates (e.g., decreases) the stability of a protein that encodes Myc (e.g., MYC, MYCL, and/or MYCN). In certain embodiments, the compound, pharmaceutical composition, kit, use, or method modulates (e.g., decreases) the stability of Myc.

Another aspect of the present disclosure relates to methods of treating a disease associated with Myc (e.g., a disease associated with aberrant activity (e.g., increased activity) of Myc) in a subject in need thereof, the methods comprising administering to the subject an effective amount (e.g., therapeutically effective amount) of a compound or pharmaceutical composition described herein.

Another aspect of the present disclosure relates to methods of treating a proliferative disease in a subject in need thereof, the methods comprising administering to the subject an effective amount (e.g., therapeutically effective amount) of a compound or pharmaceutical composition described herein.

In certain embodiments, a disease described herein is associated with Myc. In certain embodiments, a disease described herein is associated with aberrant activity (e.g., increased or decreased activity) of Myc. In certain embodiments, a disease described herein is associated with increased activity of Myc. In certain embodiments, a disease described herein is associated with a mutant (e.g., point mutant) form of Myc (e.g., MYC, MYCL, and/or MYCN). In certain embodiments, a disease described herein is associated with aberrant (e.g., increased) somatic amplification of Myc (e.g., MYC, MYCL, and/or MYCN). In certain embodiments, a disease described herein is associated with aberrant chromosomal translocation. In certain embodiments, a disease described herein is associated with overexpression of Myc (e.g., MYC, MYCL, and/or MYCN). In certain embodiments, a disease described herein is associated with aberrant translation of Myc. In certain embodiments, a disease described herein is associated with the increased stability of a protein that encodes Myc (e.g., MYC, MYCL, and/or MYCN). In certain embodiments, a disease described herein is associated with the increased stability of Myc. In certain embodiments, a disease described herein is a proliferative disease. In certain embodiments, a disease described herein is cancer. In certain embodiments, a disease described herein is lung cancer (e.g., bronchogenic carcinoma, small cell lung cancer (SCLC), non-small cell lung cancer (NSCLC), adenocarcinoma of the lung). In certain embodiments, a disease described herein is cervical cancer. In certain embodiments, a disease described herein is breast cancer (e.g., adenocarcinoma of the breast, papillary carcinoma of the breast, mammary cancer, medullary carcinoma of the breast). In certain embodiments, a disease described herein is colorectal cancer (e.g., colon cancer, rectal cancer, colorectal adenocarcinoma). In certain embodiments, a disease described herein is ovarian cancer, pancreatic cancer, gastric cancer, or uterine cancer. In certain embodiments, a disease described herein is hematological malignancy. In certain embodiments, a disease described herein is lymphoma (e.g., Hodgkin lymphoma, non-Hodgkin lymphoma (e.g., Burkitt's lymphoma)). In certain embodiments, a disease described herein is leukemia. In certain embodiments, a disease described herein is a benign neoplasm. In certain embodiments, a disease described herein is pathological angiogenesis.

A method of treating a disease (e.g., a disease associated with Myc or a proliferative disease) may further comprise, prior to the step of administering, steps of identifying the subject in need thereof (e.g., subject in need of treatment of the disease). In certain embodiments, the steps of identifying comprise:

optionally, obtaining a biological sample from a subject; and determining Myc activity of the biological sample; wherein:

if the Myc activity is higher than a control Myc activity, then the subject is identified to be a subject in need thereof; or if the Myc activity is not higher than a control Myc activity, then the subject is identified not to be a subject in need thereof.

In certain embodiments, a control Myc activity described herein is the Myc activity of a biological sample of a normal subject.

Another aspect of the present disclosure relates to methods of preventing a disease associated with Myc (e.g., a disease associated with aberrant activity (e.g., increased activity) of Myc) in a subject in need thereof, the methods comprising administering to the subject an effective amount (e.g., prophylactically effective amount) of a compound or pharmaceutical composition described herein.

In another aspect, the present disclosure provides methods of preventing a proliferative disease described herein in a subject in need thereof, the methods comprising administering to the subject an effective amount (e.g., prophylactically effective amount) of a compound or pharmaceutical composition described herein.

In another aspect, the present disclosure provides methods of inducing apoptosis of a cell in a subject in need thereof, the methods comprising administering to the subject an effective amount (e.g., therapeutically effective amount) of a compound or pharmaceutical composition described herein.

In another aspect, the present disclosure provides methods of inducing apoptosis of a cell in a biological sample, tissue, or cell, the methods comprising contacting the biological sample, tissue, or cell with an effective amount of a compound or pharmaceutical composition described herein.

In another aspect, the present disclosure provides the compounds described herein for use in a method described herein (e.g., a method of modulating (e.g., inhibiting) the activity of Myc, a method of treating a disease associated with Myc (e.g., disease associated with aberrant activity (e.g., increased activity) of Myc), a method of treating a proliferative disease, a method of preventing a disease associated with Myc (e.g., disease associated with aberrant activity (e.g., increased activity) of Myc), a method of preventing a proliferative disease, a method of inducing apoptosis, and/or a method of screening a library of compounds).

In still another aspect, the present disclosure provides the pharmaceutical compositions described herein for use in a method described herein (e.g., a method of modulating (e.g., inhibiting) the activity of Myc, a method of treating a disease associated with Myc (e.g., disease associated with aberrant activity (e.g., increased activity) of Myc), a method of treating a proliferative disease, a method of preventing a disease associated with Myc (e.g., disease associated with aberrant activity (e.g., increased activity) of Myc), a method of preventing a proliferative disease, a method of inducing apoptosis, and/or a method of screening a library of compounds).

Methods of Screening a Library of Compounds

Another aspect of the disclosure relates to methods of screening a library of compounds, and pharmaceutical acceptable salts thereof, to identify a compound, or a pharmaceutical acceptable salt thereof, that is useful in a method described herein. In certain embodiments, the methods of screening a library include obtaining at least two different compounds described herein; and performing at least one assay using the different compounds described herein. In certain embodiments, at least one assay is useful in identifying a compound that is useful in a method described herein.

Typically, the methods of screening a library of compounds involve at least one assay. In certain embodiments, the assay is performed to detect one or more characteristics associated with the treatment and/or prevention of a proliferative disease described herein or with the modulation (e.g., inhibition) of the activity of Myc (e.g., c-Myc, L-Myc, N-Myc). The characteristics may be desired characteristics (e.g., the activity of Myc having been modulated (e.g., inhibited), a disease associated with Myc (e.g., disease associated with aberrant activity (e.g., increased activity) of Myc) having been treated, a proliferative disease having been treated, a disease associated with Myc (e.g., disease associated with aberrant activity (e.g., increased activity) of Myc) having been prevented, a proliferative disease having been prevented, and/or apoptosis having been induced). The characteristics may be undesired characteristics (e.g., the activity of Myc not having been modulated (e.g., inhibited), a disease associated with Myc (e.g., disease associated with aberrant activity (e.g., increased activity) of Myc) not having been treated, a proliferative disease not having been treated, a disease associated with Myc (e.g., disease associated with aberrant activity (e.g., increased activity) of Myc) not having been prevented, a proliferative disease not having been prevented, and/or apoptosis not having been induced). The assay may be an immunoassay, such as a sandwich-type assay, competitive binding assay, one-step direct test, two-step test, or blot assay. The step of performing at least one assay may be performed robotically or manually. In certain embodiments, the assay comprises (a) contacting a library of compounds with Myc; and (b) detecting the binding of the library of compounds to the Myc. In certain embodiments, the assay comprises detecting the specific binding of the library of compounds to the Myc. In certain embodiments, the detected binding of the library of compounds to the Myc is useful in identifying the compound that is useful in a method described herein. In certain embodiments, the step of detecting the binding comprises using differential scanning fluorimetry (DSF), isothermal titration calorimetry (ITC), and/or an amplified luminescence proximity homogeneous assay (ALPHA). The step of performing at least one assay may be performed in a cell in vitro or in vivo.

EXAMPLES

In order that the present disclosure may be more fully understood, the following examples are set forth. The synthetic and biological examples described in this application are offered to illustrate the compounds, pharmaceutical compositions, and methods provided herein and are not to be construed in any way as limiting their scope.

Preparation and Characterization of the Compounds Described Herein

Preparation of the Compounds

The compounds provided herein can be prepared from readily available starting materials using methods known in the art, such as the methods described in Mauger et al., Eur. Pat. Appl., 1746097, 24 Jan. 2007, and the methods described in Nitsche et al., *Journal of Medicinal Chemistry*, 56(21), 8389-8403; 2013. Where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvents used, but such conditions can be determined by those skilled in the art by routine optimization procedures.

Preparation of Substituted 2-Mercaptobenzimidazoles

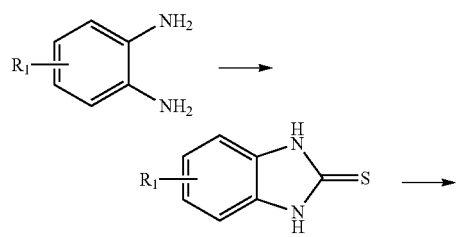

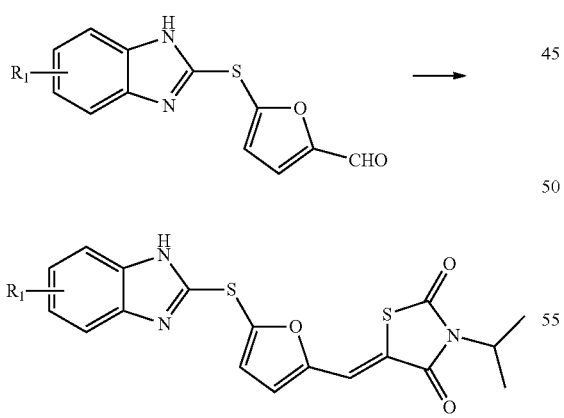

To a solution of aryl 1,2-diamine (1.0 eq) in dry pyridine (0.1M) was added carbon disulfide (1.5 eq) at room temperature. The flask was flushed with argon and stirred at 50° C. overnight under argon atmosphere. The mixture was cooled down, concentrated and purified by column chromatography on silica gel to afford the corresponding 2-mercaptobenzimidazole.

General Procedure A

Example 1. Preparation of (Z)-5-((5-((1H-benzo[d]imidazol-2-yl)thio)furan-2-yl)methylene)-3-isopropylthiazolidine-2,4-dione 1

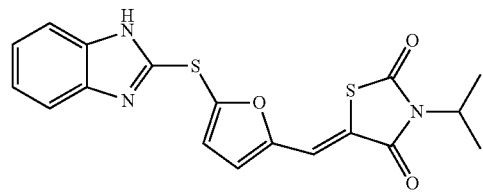 [SMILES: CC(C)N1C(=O)S/C(=C\c2ccc(Sc3nc4ccccc4[nH]3)o2)C1=O]

In a dry flask, 2-mercaptobenzimidazole (4.78 g, 31.82 mmol) was dissolved in dry $CH_3CN:DMF$ (1:1, 0.05M) and cooled to 0° C. under argon atmosphere. NaH (1.40 g, 35.00 mmol) was added portionwise over 2 minutes at 0° C. and kept at this temperature until gas evolution ceased. The mixture was then refluxed for 30 minutes prior to be cooled to room temperature. A solution of 5-nitro-2-furaldehyde (4.71 g, 33.38 mmol) in dry $CH_3CN$ (0.1M) was added dropwise at room temperature and stirred overnight at 70° C. The reacting mixture cooled down and quenched by addition of water, extracted with AcOEt (3×), dried over $MgSO_4$, filtered and concentrated. Purification by chromatography on silica gel or recrystallization from EtOH afforded the corresponding 5-((1H-benzo[d]imidazol-2-yl)thio)furan-2-carbaldehyde (6.3 g, 88% yield).

To a solution of 5-((1H-benzo[d]imidazol-2-yl)thio)furan-2-carbaldehyde (1.0 eq) in EtOH (0.05M) was added 3-isopropylthiazolidine-2,4-dione (1.1 eq) followed by piperidine (1.1 eq) at room temperature. The mixture was stirred overnight at room temperature (heating might be require in some cases). The solution was concentrated and purified by column chromatography on silica gel or by recrystallization from EtOH to afford 1.

General Procedure B

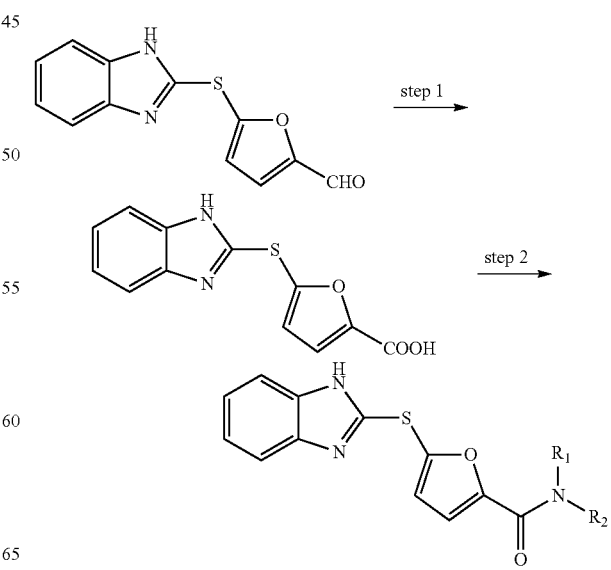

Step 1: To a solution of 5-((1H-benzo[d]imidazol-2-yl)thio)furan-2-carbaldehyde (1 eq) in t-BuOH:Water (2.6:1, 0.05M) was added 2-methyl-2-butene (4.0 eq), NaH₂PO₄ (1.1 eq) and NaClO₂ (3.0 eq) at room temperature and stirred overnight. The reacting mixture was quenched with sat. NaHCO₃ and the aqueous layer washed with AcOEt. 1N HCl was added to the aqueous layer (pH 2), and extracted with AcOEt (3×). The combined organic layers were dried over MgSO₄, filtered and concentrated to provide 5-((1H-benzo[d]imidazol-2-yl)thio)furan-2-carboxylic acid.

Step 2: To a solution of 5-((1H-benzo[d]imidazol-2-yl)thio)furan-2-carboxylic acid (1 eq) in DMF (0.1M) was added the amine (1.3 eq), HATU (1.3 eq) and DIPEA (2.0 eq) at room temperature and stirred overnight. The mixture was concentrated and purified by column chromatography on silica gel.

General Procedure C

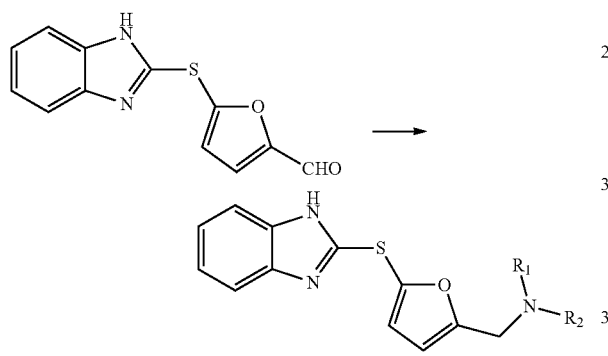

NaBH(OAc)₃ (1.3 eq) was added to a solution of 5-((1H-benzo[d]imidazol-2-yl)thio)furan-2-carbaldehyde (1.0 eq), Amine (1.1 eq), AcOH (1.5 eq) in DCM:THF (1:1, 0.05M) and stirred overnight at room temperature. The reacting mixture was quenched with sat. NaHCO₃, extracted with AcOEt (3×), dried over MgSO₄, filtered and concentrated. Purification by chromatography on silica gel provided the corresponding product.

General Procedure D

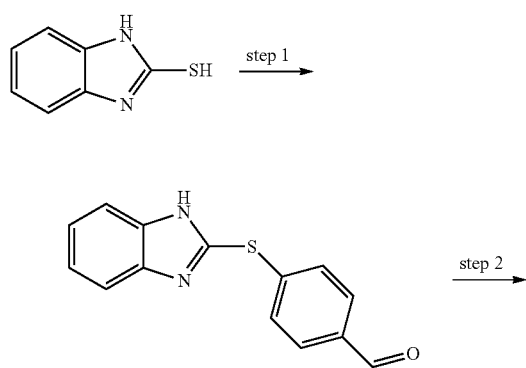

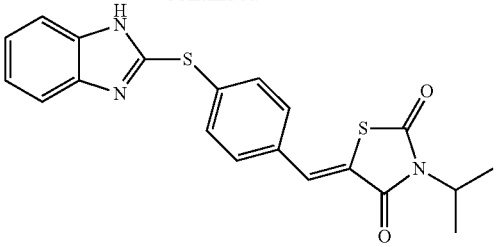

Example 2. Preparation of (Z)-5-(4-((1H-benzo[d]imidazol-2-yl)thio)benzylidene)-3-isopropylthiazolidine-2,4-dione 64

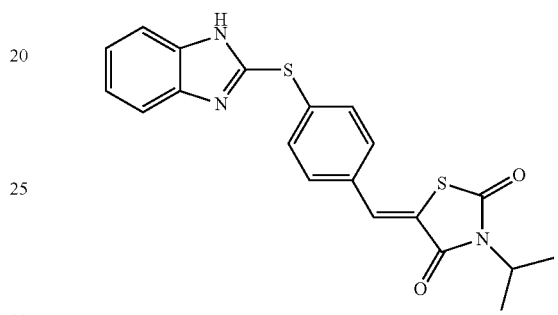

Step 1: CuI (18 mg, 96 μmol), 1,10-Phenanthroline (35 mg, 192 μmol), and K₂CO₃ (0.53 g, 3.84 mmol) were placed in an oven dried sealed flask and purged with argon. Dry DMF (2 ml) was then added followed by 2-mercaptobenzimidazole (288 mg, 1.92 mmol) and 4-iodobenzaldehyde (446 mg, 1.92 mmol). The mixture was stirred at 140° C. for 18 hours. After being cooled down, water was added and the aqueous layer extracted with AcOEt (3×). The combined organic layers were dried over MgSO₄, filtered and concentrated. Purification by column chromatography on silica gel (20 to 75% AcOEt in hexanes) afforded 4-((1H-benzo[d]imidazol-2-yl)thio)benzaldehyde (425 mg, 87% yield).

Step 2: Prepared following general procedure A. ¹H NMR (500 MHz, CDCl₃): δ (ppm)=7.68 (1H, s), 7.57 (2H, dd, J=6.0, 3.0 Hz), 7.50 (2H, d, J=8.5 Hz), 7.35 (2H, d, J=8.5 Hz), 7.28 (2H, dd, J=6.0, 3.0 Hz), 4.67 (1H, sep, J=7.0 Hz), 1.47 (6H, d, J=7.0 Hz).

General Procedure E: Alkylation of 2,4-thiazolidinedione

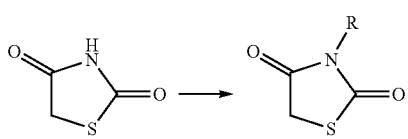

To a solution of 2,4-thiazolidinedione (1 eq) in DMF (0.1M) was successively added K₂CO₃ (2.0 eq) and the alkyl halide (1.05 eq). The reacting mixture was stirred at 70° C. until completion. The reaction was cooled down, water was added and the aqueous layer extracted with AcOEt (3×). The combined organic layers were dried over MgSO₄, filtered and concentrated. Purification by column chromatography on silica gel provided the desired alkylated 2,4-thiazolidinedione.

General Procedure F

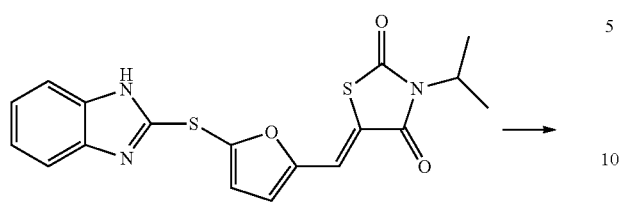

Example 3. Preparation of (Z)-3-isopropyl-5-((5-((1-methyl-1H-benzo[d]imidazol-2-yl)thio)furan-2-yl)methylene)thiazolidine-2, 4-dione 18

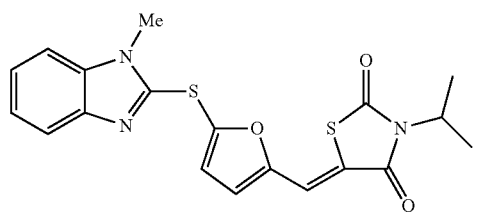 [SMILES: CC(C)N1C(=O)S/C(=C\c2ccc(Sc3nc4ccccc4n3C)o2)C1=O]

MeI (110 mg, 778 μmol) was added to a solution of (Z)-5-((5-((1H-benzo[d]imidazol-2-yl)thio)furan-2-yl)methylene)-3-isopropylthiazolidine-2,4-dione (150 mg, 389 μmol) and K$_2$CO$_3$ (108 mg, 778 μmol) in DMF (2 ml) at room temperature. The mixture was stirred overnight prior to be quenched with water. The aqueous layer was extracted with AcOEt (3×) and the combined organic layers dried over MgSO$_4$, filtered and concentrated. Purification by column chromatography on silica gel (10 to 25% AcOEt in hexanes) afforded 18 (142 mg, 91% yield). $^1$H NMR (500 MHz, CDCl$_3$): δ (ppm)=7.75 (1H, d, J=8.0 Hz), 7.50 (1H, s), 7.27-7.36 (3H, m), 6.91 (1H, d, J=3.5 Hz), 6.75 (1H, d, J=3.5 Hz), 4.62 (1H, sep, J=7.0 Hz), 4.00 (3H, s), 1.44 (6H, d, J=7.0 Hz).

Example 4. (Z)-5-((5-((1H-benzo[d]imidazol-2-yl)thio)furan-2-yl)methylene)imidazolidine-2, 4-dione 2

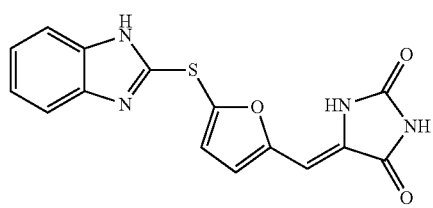 [SMILES: O=C1NC(=O)/C(=C/c2ccc(Sc3nc4ccccc4[nH]3)o2)N1]

Compound 2 was prepared following general procedure A using hydantoin. $^1$H NMR (500 MHz, DMSO-d6): δ (ppm)=11.35 (1H, brs), 10.52 (1H, brs), 7.51 (2H, br), 7.18 (2H, m), 7.16 (H, d, J=3.5 Hz), 7.10 (1H, d, J=3.5 Hz), 6.33 (1H, s).

Example 5. (Z)-5-((5-(benzo[d]thiazol-2-ylthio)furan-2-yl)methylene)-3-isopropylthiazolidine-2,4-dione 3

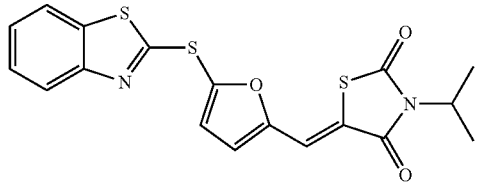 [SMILES: CC(C)N1C(=O)S/C(=C\c2ccc(Sc3nc4ccccc4s3)o2)C1=O]

Compound 3 was prepared following general procedure A using 2-mercaptobenzothiazole. $^1$H NMR (500 MHz, CDCl$_3$): δ (ppm)=7.94 (1H, d, J=8.0 Hz), 7.74 (1H, d, J=8.0 Hz), 7.60 (1H, s), 7.45 (1H, t, J=8.0 Hz), 7.34 (1H, t, J=8.0 Hz), 7.06 (1H, d, J=3.5 Hz), 6.87 (1H, d, J=3.5 Hz).

Example 6. Preparation of (Z)-5-((5-((6-chloro-1H-benzo[d]imidazol-2-yl)thio)furan-2-yl)methylene)-3-isopropylthiazolidine-2,4-dione 4

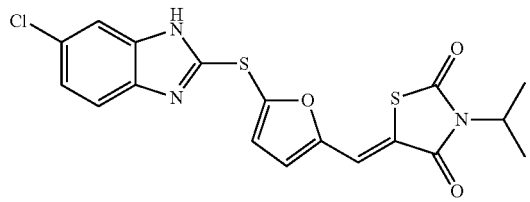 [SMILES: CC(C)N1C(=O)S/C(=C\c2ccc(Sc3nc4ccc(Cl)cc4[nH]3)o2)C1=O]

Compound 4 was prepared following general procedure A using 6-chloro-1H-benzo[d]imidazole-2-thiol. $^1$H NMR (500 MHz, CDCl$_3$): δ (ppm)=7.34-7.38 (3H, m), 7.07 (1H, dd, J=8.5, 2.0 Hz), 6.89 (1H, d, J=3.5 Hz), 6.64 (1H, d, J=3.5 Hz), 4.54 (1H, sep, 7.0 Hz), 1.37 (6H, d, J=7.0 Hz).

Example 7. Preparation of (Z)-3-isopropyl-5-((5-((6-methoxy-1H-benzo[d]imidazol-2-yl)thio)furan-2-yl)methylene)thiazolidine-2, 4-dione 5

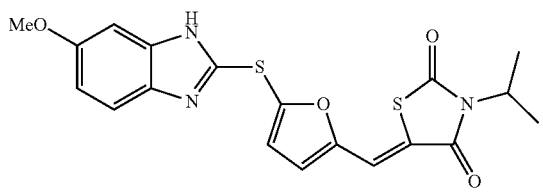 [SMILES: COc1ccc2nc(Sc3ccc(/C=C4\SC(=O)N(C(C)C)C4=O)o3)[nH]c2c1]

Compound 5 was prepared following general procedure A using 6-methoxy-1H-benzo[d]imidazole-2-thiol. $^1$H NMR (500 MHz, CDCl$_3$): δ (ppm)=7.41 (1H, d, J=8.5 Hz), 7.30 (1H, d, J=2.0 Hz), 6.96 (1H, d, J=2.5 Hz), 6.92 (1H, d, J=3.5

Hz), 6.85 (1H, dd, J=8.5, 2.5 Hz), 6.62 (1H, dd, J=3.5, 2.0 Hz), 4.61 (1H, sep, J=7.0 Hz), 3.79 (3H, s), 1.44 (6H, d, J=7.0 Hz).

Example 8. (Z)-5-((5-(benzo[d]oxazol-2-ylthio) furan-2-yl)methylene)-3-isopropylthiazolidine-2, 4-dione 6

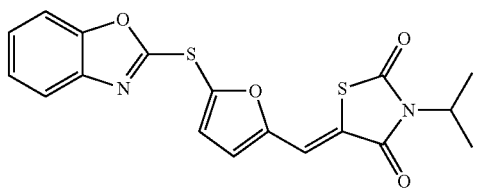 [SMILES: CC(C)N1C(=O)S/C(=C\c2ccc(Sc3nc4ccccc4o3)o2)C1=O]

Compound 5 was prepared following general procedure A using 2-mercaptobenzoxazole. ¹H NMR (500 MHz, CDCl₃): δ (ppm)=7.64 (1H, m), 7.60 (1H, m), 7.46 (1H, m), 7.31 (2H, m), 7.05 (1H, d, J=3.5 Hz), 6.86 (1H, d, J=3.5 Hz), 4.64 (1H, sep, J=7.0 Hz), 1.45 (6H, d, J=7.0 Hz).

Example 9. Preparation of (Z)-5-((5-((6-chloro-1H-benzo[d]imidazol-2-yl)thio)furan-2-yl)methylene)-3-isopropylthiazolidine-2,4-dione 7

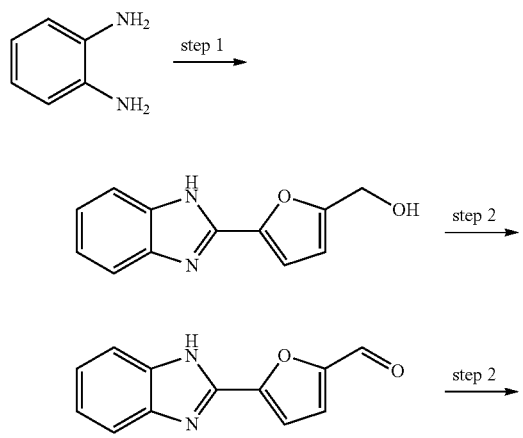

Step 1: A mixture of 1,3-phenyldiamine (1.36 g, 7.51 mmol), 5-(hydroxymethyl)furan-2-carbaldehyde (0.95 g, 7.51 mmol) and DDQ (1.70 g, 7.51 mmol) in ethanol (30 ml) was stirred at reflux overnight under argon. Sat. NaHCO₃ was added and the aqueous layer extracted with AcOEt (3×). The combined organic layers were dried over MgSO₄, filtered and concentrated. Purification by column chromatography on silica gel (30 to 60% acetone in hexane) provided (5-(1H-benzo[d]imidazol-2-yl)furan-2-yl)methanol (700 mg, 44% yield).

Step 2: Dess-Martin Periodinane (1.52 g, 3.60 mmol) was added to a solution of (5-(1H-benzo[d]imidazol-2-yl)furan-2-yl)methanol (700 mg, 3.27 mmol) in DCM (30 ml) at 0° C. After 2 hours, sat. NaHCO₃ was added and the aqueous layer extracted with AcOEt (3×). The combined organic layers were dried over MgSO₄, filtered and concentrated. Purification by column chromatography on silica gel (20 to 60% acetone in hexanes) provided 5-(1H-benzo[d]imidazol-2-yl)furan-2-carbaldehyde (600 mg, 87% yield).

Step 3: Prepared following general procedure A. ¹H NMR (500 MHz, CDCl₃): δ (ppm)=7.65-7.80 (3H, m), 7.34 (1H, d, J=3.5 Hz), 7.36 (2H, m), 6.95 (1H, d, J=3.5 Hz), 4.69 (1H, sep, J=7.0 Hz), 1.50 (6H, d, J=7.0 Hz).

Example 10. Preparation of (Z)-5-((5-((1H-benzo[d]imidazol-2-yl)thio)furan-2-yl)methylene)-3-isopropylimidazolidine-2,4-dione 8

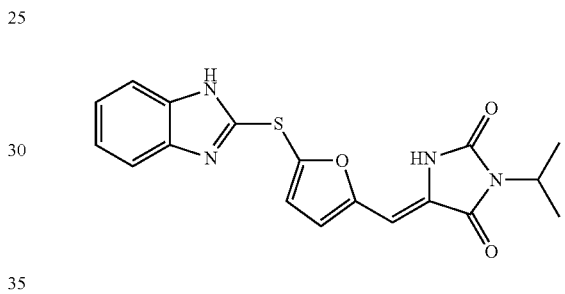

Compound 8 was prepared following general procedure A using 3-isopropylimidazolidine-2,4-dione. ¹H NMR (500 MHz, CDCl₃): δ (ppm)=9.22 (1H, brs), 7.59 (2H, br), 7.22 (2H, m), 6.82 (1H, d, J=3.5 Hz), 6.51 (1H, d, J=3.5 Hz), 6.32 (1H, s), 4.33 (1H, sep, J=7.0 Hz), 1.42 (6H, d, J=7.0 Hz).

Example 11. Preparation of (E)-3-((5-((1H-benzo[d]imidazol-2-yl)thio)furan-2-yl)methylene)pyrrolidine-2,5-dione 9

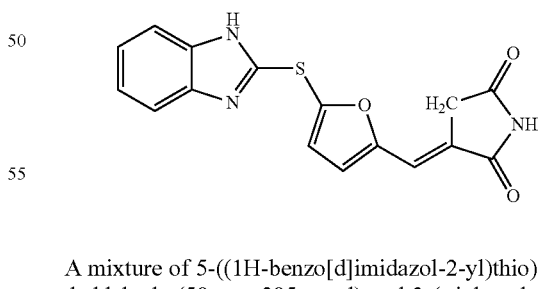

A mixture of 5-((1H-benzo[d]imidazol-2-yl)thio)furan-2-carbaldehyde (50 mg, 205 µmol) and 3-(triphenylphosphoranylidene)pyrrolidine-2,5-dione (74 mg, 205 µmol) in EtOH (5 ml) was stirred at 50° C. overnight. The mixture was concentrated and purified by reverse phase (25 to 75% CH3CN in water) to afford 9 (66 mg, 99% yield). ¹H NMR (500 MHz, DMSO-d6): δ (ppm)=12.72 (1H, brs), 11.44 (1H, brs), 7.64 (1H, m), 7.61 (2H, m), 7.42 (1H, d, J=7.5 Hz), 7.13 (2H, m), 7.09 (1H, d, J=3.5 Hz).

Example 12. Preparation of (Z)-5-((5-((3H-imidazo[4,5-b]pyridin-2-yl)thio)furan-2-yl)methylene)-3-isopropylthiazolidine-2,4-dione 10

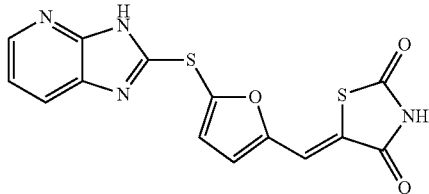 [SMILES: O=C1NC(=O)/C(=C/c2ccc(Sc3nc4cccnc4[nH]3)o2)S1]

Prepared following general procedure A using 3H-imidazo[4,5-b]pyridine-2-thiol. $^1$H NMR (500 MHz, DMSO-d6): δ (ppm)=13.20 (1H, brs), 8.28 (1H, d, J=4.5 Hz), 7.90 (1H, d, J=7.0 Hz), 7.71 (1H, s), 7.27 (1H, d, J=3.5 Hz), 7.24 (1H, d, J=3.5 Hz), 7.21 (1H, dd, J=7.0, 4.5 Hz), 4.47 (1H, sep, J=7.0 Hz), 1.34 (6H, d, J=7.0 Hz).

Example 13. Preparation of (Z)-5-((5-((1H-benzo[d]imidazol-2-yl)thio)thiophen-2-yl)methylene)-3-isopropylthiazolidine-2,4-dione 11

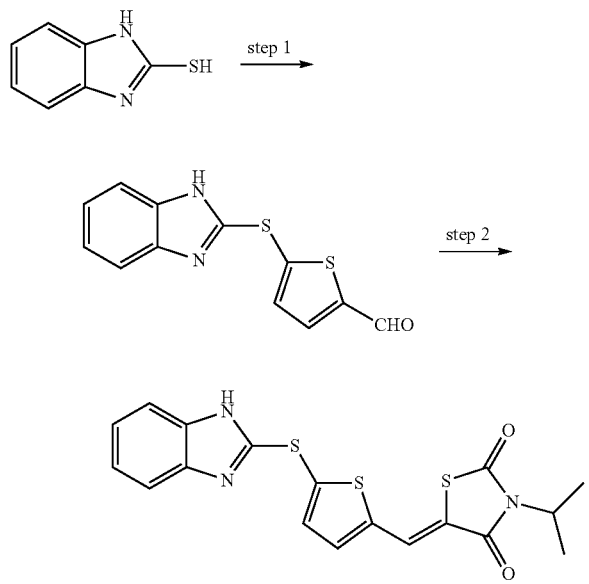

Step 1: To a solution of 2-mercaptobenzimidazole (500 mg, 3.33 mmol) and K$_2$CO$_3$ (506 mg, 3.66 mmol) in DMF (6.5 ml) was added 5-bromothiophene-2-carbaldehyde (636 mg, 3.33 mmol) at room temperature. The mixture was stirred at 120° C. overnight. The reacting mixture was quenched with water, extracted with AcOEt (3×), dried over MgSO$_4$, filtered and concentrated. Purification by chromatography on silica gel (20 to 50% AcOEt in hexanes) provided 5-((1H-benzo[d]imidazol-2-yl)thio)thiophene-2-carbaldehyde (302 mg, 35% yield).

Step 2: Prepared following general procedure A. $^1$H NMR (500 MHz, CDCl$_3$): δ (ppm)=9.60 (1H, brs), 7.82 (1H, s), 7.45 (1H, d, J=4.0 Hz), 7.20-7.27 (5H, m), 4.65 (1H, sep, J=7.0 Hz), 1.47 (6H, d, J=7.0 Hz).

Example 14. Preparation of (Z)-1-(3-(5-((5-((1H-benzo[d]imidazol-2-yl)thio)furan-2-yl)methylene)-2,4-dioxothiazolidin-3-yl)propyl)-3-phenylurea 12

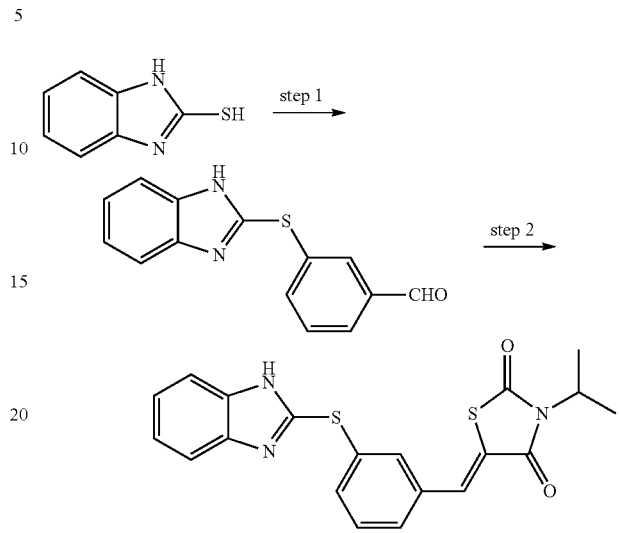

Step 1: Literature precedent was followed, as described in: *Tetrahedron Letters* 2011, 52, 3347-3352.

Step 2: Prepared following general procedure A. $^1$H NMR (500 MHz, DMSO-d6): δ (ppm)=12.94 (1H, brs), 7.85 (1H, s), 7.69 (1H, br), 7.55-7.60 (4H, m), 7.43 (1H, m), 7.20 (2H, m), 4.49 (1H, sep, J=7.0 Hz), 1.37 (6H, d, J=7.0 Hz).

Example 15. Preparation of (Z)-2-(5-((5-((1H-benzo[d]imidazol-2-yl)thio)furan-2-yl)methylene)-2, 4-dioxothiazolidin-3-yl)acetic acid 13

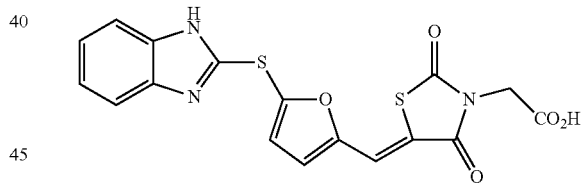

To a solution of 14 (200 mg, 437 μmol) in DCM (2.2 ml) was added TFA (335 μl) at room temperature. Stirred for 4 hours then concentrated to provide 13 (174 mg, 99% yield). LCMS (M+1)=402, >95% purity.

Example 16. Preparation of (Z)-tert-butyl 2-(5-((5-((1H-benzo[d]imidazol-2-yl)thio)furan-2-yl)methylene)-2,4-dioxothiazolidin-3-yl)acetate 14

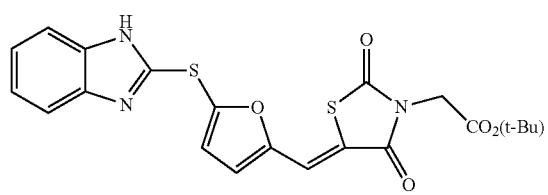

Compound 14 was prepared following general procedure A and E using tert-butyl 2-(2,4-dioxothiazolidin-3-yl)acetate. $^1$H NMR (500 MHz, DMSO-d6): δ (ppm)=12.84 (1H, brs), 7.82 (1H, s), 7.55 (1H, d, J=7.5 Hz), 7.42 (1H, d, J=7.5 Hz), 7.28 (1H, d, J=3.5 Hz), 7.23 (1H, d, J=3.5 Hz), 7.14-7.18 (2H, m), 4.31 (2H, s), 1.39 (9H, s).

Example 17. Preparation of (Z)-methyl 2-(5-((5-((1H-benzo[d]imidazol-2-yl)thio)furan-2-yl)methylene)-2,4-dioxothiazolidin-3-yl)acetate 15

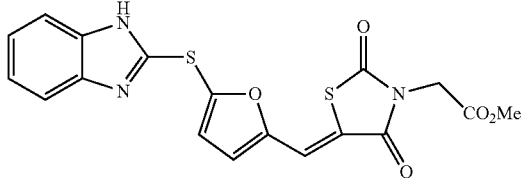 [SMILES: COC(=O)CN1C(=O)S/C(=C\c2ccc(Sc3nc4ccccc4[nH]3)o2)C1=O]

Compound 15 was prepared following general procedure A and E using methyl 2-(2,4-dioxothiazolidin-3-yl)acetate. LCMS (M+1)=416, >95% purity.

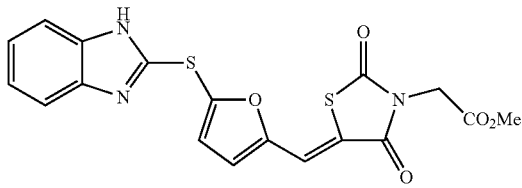 [SMILES: COC(=O)CN1C(=O)S/C(=C\c2ccc(Sc3nc4ccccc4[nH]3)o2)C1=O]

Example 18. Preparation of (Z)-5-((5-((1H-imidazol-2-yl)thio)furan-2-yl)methylene)-3-isopropylthiazolidine-2,4-dione 16

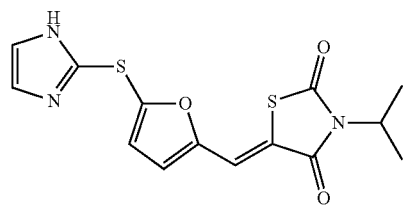 [SMILES: CC(C)N1C(=O)S/C(=C\c2ccc(Sc3ncc[nH]3)o2)C1=O]

Compound 16 was prepared following general procedure A starting from 2-mercaptoimidazole. $^1$H NMR (500 MHz, DMSO-d6): δ (ppm)=12.92 (1H, brs), 7.60 (1H, s), 7.20 (2H, br), 7.12 (1H, d, J=3.5 Hz), 6.87 (1H, d, J=3.5 Hz), 4.47 (1H, sep, J=7.0 Hz), 1.36 (6H, d, J=7.0 Hz).

Example 19. Preparation of (Z)-3-isopropyl-5-((5-(pyridin-2-ylthio)furan-2-yl)methylene)thiazolidine-2, 4-dione 17

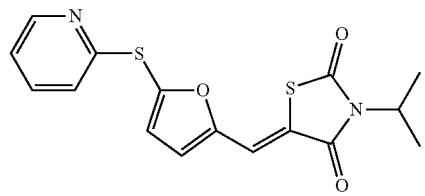 [SMILES: CC(C)N1C(=O)S/C(=C\c2ccc(Sc3ccccn3)o2)C1=O]

Compound 17 was prepared following general procedure A starting from 2-mercaptopyridine. $^1$H NMR (500 MHz, CDCl$_3$): δ (ppm)=8.45 (1H, d, J=4.5 Hz), 7.58 (1H, s), 7.57 (1H, dt, J=8.0, 1.5 Hz), 7.11 (1H, dd, J=5.0, 1.5 Hz), 7.00 (1H, d, J=8.0 Hz), 6.93 (1H, d, J=3.5 Hz), 6.84 (1H, d, J=3.5 Hz), 4.64 (1H, sep, J=7.0 Hz), 1.46 (6H, d, J=7.0 Hz).

Example 20. Preparation of (Z)-5-((5-((1H-benzo[d]imidazol-2-yl)thio)furan-2-yl)methylene)-3-(3-aminopropyl)thiazolidine-2, 4-dione 2, 2,2-trifluoroacetate 19

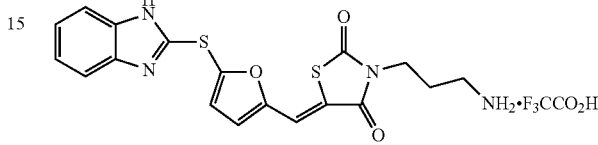

Compound 19 was prepared following general procedure A and E starting from tert-butyl (3-bromopropyl)carbamate to provide (Z)-tert-butyl (3-(5-((5-((1H-benzo[d]imidazol-2-yl)thio)furan-2-yl)methylene)-2,4-dioxothiazolidin-3-yl)propyl)carbamate. Boc deprotection: TFA (177 μl, 2.30 mmol) was added to (Z)-tert-butyl (3-(5-((5-((1H-benzo[d]imidazol-2-yl)thio)furan-2-yl)methylene)-2,4-dioxothiazolidin-3-yl)propyl)carbamate (230 mg, 459 mol) in DCM (2.5 ml) at 0° C. The reacting mixture was stirred at room temperature for 5 hours. Concentration and removal of TFA by azeotropic distillation with toluene provided 19 (182 mg, 99% yield). LCMS (M+1)=401, >90% purity.

Example 21. Preparation of (Z)-1-(3-(5-((5-((1H-benzo[d]imidazol-2-yl)thio)furan-2-yl)methylene)-2, 4-dioxothiazolidin-3-yl)propyl)-3-phenylurea 20

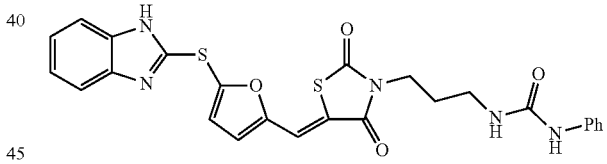

Phenylisocyanate (1.5 eq) was added to a solution of 19 (1 eq) and DIPEA (2.5 eq) in DCM at room temperature. The mixture was stirred overnight, concentrated and purified by column chromatography to afford 20. LCMS (M+1)=520, >95% purity.

Example 22. Preparation of (Z)-1-ethyl-3-(3-(5-((5-((1-methyl-1H-benzo[d]imidazol-2-yl)thio)furan-2-yl)methylene)-2,4-dioxothiazolidin-3-yl)propyl)urea 21

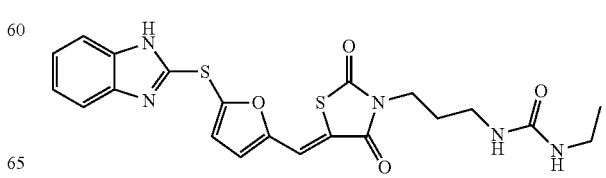

Ethylisocyanate (1.5 eq) was added to a solution of 19 (1 eq) and DIPEA (2.5 eq) in DCM at room temperature. The mixture was stirred overnight, concentrated and purified by column chromatography to afford 21. LCMS (M+1)=472, >90% purity.

Example 23. Preparation of (Z)-5-((5-((6-chloro-1H-benzo[d]imidazol-2-yl)thio)furan-2-yl)methylene)-3-isopropylimidazolidine-2,4-dione 22

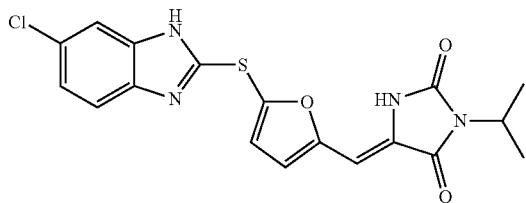 [SMILES: CC(C)N1C(=O)N/C(=C\c2ccc(Sc3nc4ccc(Cl)cc4[nH]3)o2)C1=O]

Compound 22 was prepared following general procedure A using 6-chloro-1H-benzo[d]imidazole-2-thiol and 3-isopropylimidazolidine-2,4-dione. $^1$H NMR (500 MHz, CDCl$_3$): δ (ppm)=9.09 (1H, brs), 7.47 (2H, m), 7.22 (1H, dd, J=8.0, 2.5 Hz), 6.85 (1H, d, J=3.5 Hz), 6.55 (1H, d, J=3.5 Hz), 6.36 (1H, s), 4.44 (1H, sep, J=7.0 Hz), 1.50 (6H, d, J=7.0 Hz).

Example 24. Preparation of (Z)-3-isopropyl-5-((5-((7-methyl-1H-benzo[d]imidazol-2-yl)thio)furan-2-yl)methylene)thiazolidine-2,4-dione 23

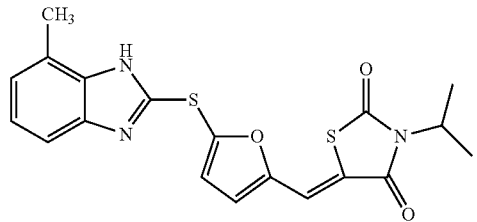 [SMILES: Cc1cccc2nc(Sc3ccc(/C=C4\SC(=O)N(C(C)C)C4=O)o3)[nH]c12]

Compound 23 was prepared following general procedure A using 7-methyl-1H-benzo[d]imidazole-2-thiol. $^1$H NMR (500 MHz, DMSO-d6): δ (ppm)=7.67 (1H, s), 7.26 (1H, br), 7.21 (1H, d, J=3.5 Hz), 7.17 (1H, d, J=3.5 Hz), 7.08 (1H, t, J=7.0 Hz), 6.98 (1H, d, J=7.0 Hz), 4.46 (1H, sep, J=7.0 Hz), 2.49 (3H, s), 1.33 (6H, d, J=7.0 Hz).

Example 25. Preparation of (Z)-3-isopropyl-5-((5-((6-(trifluoromethyl)-1H-benzo[d]imidazol-2-yl)thio)furan-2-yl)methylene)thiazolidine-2, 4-dione 24

Compound 22 was prepared following general procedure A using 6-(trifluoromethyl)-1H-benzo[d]imidazole-2-thiol. $^1$H NMR (500 MHz, DMSO-d6): δ (ppm)=13.23 (1H, brs), 7.93 (1H, br), 7.71 (1H, s), 7.62 (1H, br), 7.51 (1H, br), 7.28 (1H, d, J=3.5 Hz), 7.25 (1H, J=3.5 Hz), 4.45 (1H, sep, J=7.0 Hz), 1.33 (6H, d, J=7.0 Hz).

Example 26. Preparation of (Z)-5-((5-((5, 6-dichloro-1H-benzo[d]imidazol-2-yl)thio)furan-2-yl)methylene)-3-isopropylthiazolidine-2,4-dione 25

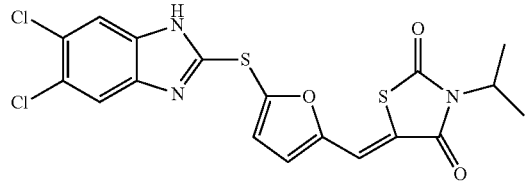 [SMILES: CC(C)N1C(=O)S/C(=C\c2ccc(Sc3nc4cc(Cl)c(Cl)cc4[nH]3)o2)C1=O]

Compound 25 was prepared following general procedure A using 5,6-dichloro-1H-benzo[d]imidazole-2-thiol. $^1$H NMR (500 MHz, CDCl$_3$): δ (ppm)=7.53 (2H, s), 7.00 (1H, d, J=3.5 Hz), 6.61 (1H, d, J=3.5 Hz), 4.63 (1H, sep, J=7.0 Hz), 1.46 (6H, d, J=7.0 Hz).

Example 27. Preparation of N-(3-((Z)-5-((5-((1H-benzo[d]imidazol-2-yl)thio)furan-2-yl)methylene)-2,4-dioxothiazolidin-3-yl)propyl)-5-((3aR,4R,6aS)-2-oxohexahydro-1H-thieno[3,4-d]imidazol-4-yl)pentanamide 27

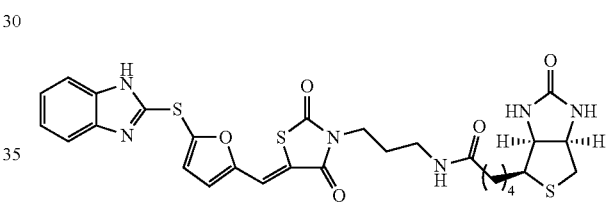

(Z)-5-((5-((1H-benzo[d]imidazol-2-yl)thio)furan-2-yl)methylene)-3-(3-aminopropyl)thiazolidine-2,4-dione 2,2,2-trifluoroacetate (21 mg, 42 μmol) was stirred in 5% TFA in DCM (0.5 ml) for 30 minutes. The mixture was concentrated and diluted in DMF (0.5 ml). Triethylamine (30 μl, 210 μmol) and biotin-NHS (29 mg, 84 μmol) were added at room temperature and stirred overnight. Water was added and the aqueous layer was extracted with DCM (3×). The combined organic layers were dried over MgSO$_4$, filtered and concentrated. Purification by prep TLC on silica gel (12% MeOH in DCM) afforded 27 (20 mg, 76% yield), LCMS (M+1)=627, >95% purity.

Example 28. Preparation of (Z)-5-(5-(((7-chloro-H-benzo[d]imidazol-2-yl)thio)furan-2-yl)methylene)-3-isopropylthiazolidine-2, 4-dione 28

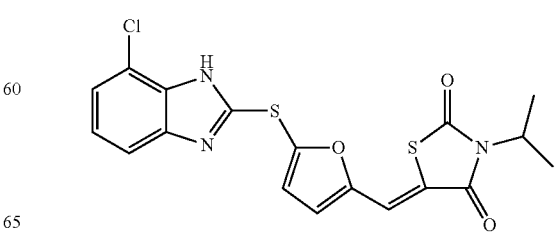

Compound 28 was prepared following general procedure A using 7-chloro-1H-benzo[d]imidazole-2-thiol. ¹H NMR (500 MHz, DMSO-d6): δ (ppm)=7.69 (1H, s), 7.42 (1H, br), 7.25 (3H, m), 7.19 (1H, t, J=8.0 Hz), 4.65 (1H, sep, J=7.0 Hz), 1.34 (6H, d, J=7.0 Hz).

Example 29. Preparation of (Z)-3-isopropyl-5-((5-((6-isopropyl-1H-benzo[d]imidazol-2-yl)thio)furan-2-yl)methylene)thiazolidine-2, 4-dione 29

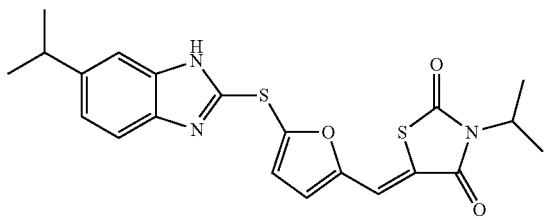

Compound 29 was prepared following general procedure A using 6-isopropyl-1H-benzo[d]imidazole-2-thiol. ¹H NMR (500 MHz, CDCl₃): δ (ppm)=7.50 (1H, d J=8.5 Hz), 7.46 (1H, s), 7.41 (1H, brs), 7.16 (1H, dd, J=8.5, 1.5 Hz), 6.97 (1H, d, J=3.5 Hz), 6.72 (1H, d, J=3.5 Hz), 4.63 (1H, sep, J=7.0 Hz), 3.00 (1H, sep, J=7.0 Hz), 1.45 (6H, d, J=7.0 Hz), 1.27 (6H, d, J=7.0 Hz).

Example 30. Preparation of (Z)-3-isopropyl-5-((5-((7-methoxy-1H-benzo[d]imidazol-2-yl)thio)furan-2-yl)methylene)thiazolidine-2, 4-dione 30

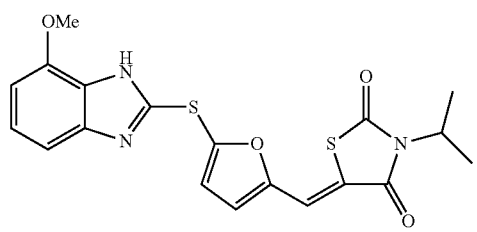 [SMILES: CC(C)N1C(=O)S/C(=C\c2ccc(Sc3nc4cccc(Cl)c4[nH]3)o2)C1=O]

Compound 30 was prepared following general procedure A using 7-methoxy-1H-benzo[d]imidazole-2-thiol. ¹H NMR (500 MHz, DMSO-d6): δ (ppm)=7.67 (1H, s), 7.21 (1H, m), 7.17 (1H, m), 7.11 (1H, m), 6.72 (1H, brs), 4.46 (1H, sep, J=7.0 Hz), 3.89 (3H, s), 1.33 (6H, d, J=7.0 Hz).

Example 31. Preparation of (5-((1H-benzo[d]imidazol-2-yl)thio)furan-2-yl)methanol 40

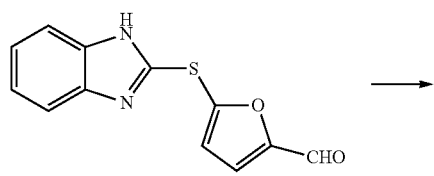

→

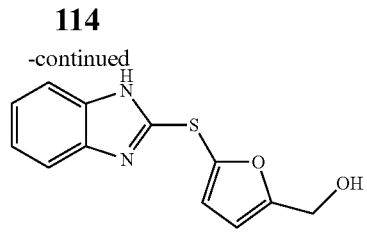

To a solution of 5-((1H-benzo[d]imidazol-2-yl)thio)furan-2-carbaldehyde (115 mg, 0.471 mmol) in MeOH (5 ml) was added NaBH₄ (18 mg, 0.471 mmol) at 0° C. and stirred at room temperature for 2 hours. The reacting mixture was quenched with water, extracted with AcOEt (3×), dried over MgSO₄, filtered and concentrated. Purification by chromatography on silica gel (50 to 100% AcOEt in hexanes) provided 40 (112 mg, 96% yield).

Example 32. Preparation of 5-((1H-benzo[d]imidazol-2-yl)thio)furan-2-carboxylic acid 41

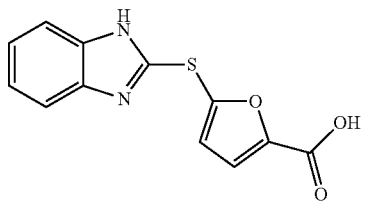 [SMILES: O=C(O)c1ccc(Sc2nc3ccccc3[nH]2)o1]

Compound 41 was prepared following general procedure B. ¹H NMR (500 MHz, DMSO-d6): δ (ppm)=13.24 (1H, brs), 7.48 (2H, br), 7.35 (1H, s), 7.18 (3H, m).

Example 33. Preparation of 5-((1H-benzo[d]imidazol-2-yl)thio)-N-phenylfuran-2-carboxamide 42

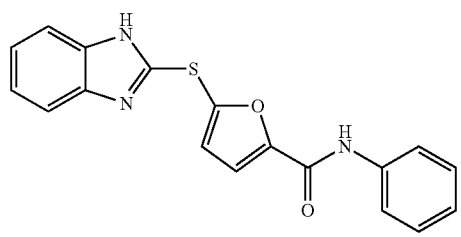 [SMILES: O=C(Nc1ccccc1)c1ccc(Sc2nc3ccccc3[nH]2)o1]

Compound 42 was prepared following general procedure B. ¹H NMR (500 MHz, DMSO-d6): δ (ppm)=12.66 (1H, brs), 10.32 (1H, brs), 7.72 (2H, d, J=8.5 Hz), 7.54 (1H, d, J=8.0 Hz), 7.49 (1H, d, J=3.5 Hz), 7.41 (1H, d, J=7.0 Hz), 7.35 (2H, t, J=8.5 Hz), 7.25 (1H, d, J=3.5 Hz), 7.09-7.20 (3H, m).

Example 34. Preparation of 5-((1H-benzo[d]imidazol-2-yl)thio)-N-isopropylfuran-2-carboxamide 43

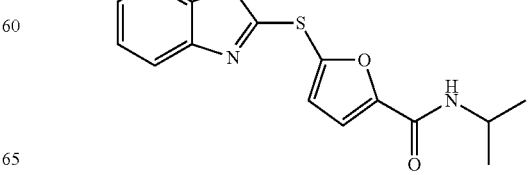

Compound 43 was prepared following general procedure B. ¹H NMR (500 MHz, DMSO-d6): δ (ppm)=12.60 (1H, brs), 8.30 (1H, d, J=8.5 Hz), 7.52 (1H, d, J=7.0 Hz), 7.40 (1H, d, J=7.0 Hz), 7.24 (1H, d, J=3.5 Hz), 7.14-7.18 (2H, m), 4.06 (1H, sep, J=7.5 Hz), 1.12 (6H, d, J=7.5 Hz).

Example 35. Preparation of (5-((1H-benzo[d]imidazol-2-yl)thio)furan-2-yl)(morpholino)methanone 44

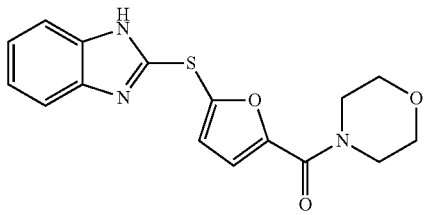 [SMILES: O=C(c1ccc(Sc2nc3ccccc3[nH]2)o1)N1CCOCC1]

Compound 44 was prepared Prepared following general procedure B. ¹H NMR (500 MHz, DMSO-d6): δ (ppm)=12.74 (1H, brs), 7.52 (1H, d, J=7.5 Hz), 7.42 (1H, d, J=7.5 Hz), 7.13-7.18 (4H, m), 3.56-3.62 (8H, m).

Example 36. Preparation of N-((5-((1H-benzo[d]imidazol-2-yl)thio)furan-2-yl)methyl)aniline 45

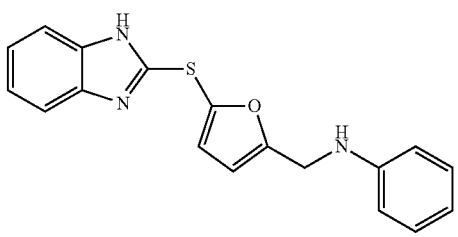 [SMILES: c1ccc(NCc2ccc(Sc3nc4ccccc4[nH]3)o2)cc1]

Compound 45 was prepared following general procedure C. ¹H NMR (500 MHz, CDCl₃): δ (ppm)=7.45 (2H, m), 7.20 (4H, m), 6.81 (2H, m), 6.68 (2H, m), 6.30 (1H, m), 4.32 (2H, m).

Example 37. Preparation of 4-((5-((1H-benzo[d]imidazol-2-yl)thio)furan-2-yl)methyl)morpholine 47

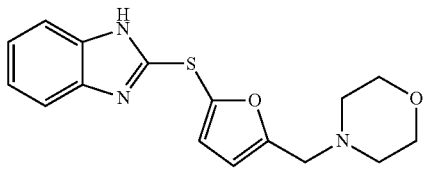 [SMILES: c1ccc2[nH]c(Sc3ccc(CN4CCOCC4)o3)nc2c1]

Compound 47 was prepared following general procedure C. ¹H NMR (500 MHz, CDCl₃): δ (ppm)=7.49 (2H, br), 7.19 (2H, m), 6.77 (1H, d, J=3.0 Hz), 6.27 (1H, d, J=3.0 Hz), 3.73 (4H, m), 3.46 (2H, s), 2.50 (4H, m).

Example 38. Preparation of 2-((5-((4-ethylpiperazin-1-yl)methyl)furan-2-yl)thio)-1H-benzo[d]imidazole 48

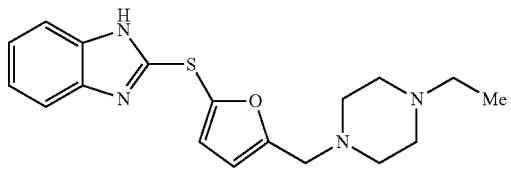 [SMILES: CCN1CCN(Cc2ccc(Sc3nc4ccccc4[nH]3)o2)CC1]

Compound 48 was prepared following general procedure C. ¹H NMR (500 MHz, CDCl₃): δ (ppm)=10.43 (1H, brs), 7.64 (1H, m), 7.31 (1H, m), 7.19 (2H, m), 6.79 (1H, d, J=3.0 Hz), 6.29 (1H, d, J=3.0 Hz), 3.53 (2H, s), 2.53-2.70 (8H, m), 2.44 (2H, q, J=7.5 Hz), 1.09 (3H, t, J=7.5 Hz).

Example 39. Preparation of 1-(5-((1H-benzo[d]imidazol-2-yl)thio)furan-2-yl)-N,N-dimethylmethanamine 49

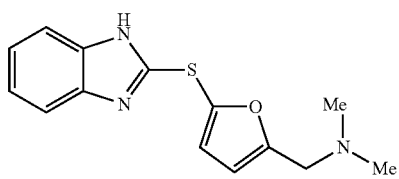 [SMILES: CN(C)Cc1ccc(Sc2nc3ccccc3[nH]2)o1]

Compound 49 was prepared following general procedure C. ¹H NMR (500 MHz, CDCl₃): δ (ppm)=7.46-7.50 (2H, m), 7.20 (2H, m), 6.81 (1H, d, J=3.5 Hz), 6.33 (1H, d, J=3.5 Hz), 3.52 (2H, s), 2.33 (6H, s), Example 40. Preparation of Methyl 2-(((5-((1H-benzo[d]imidazol-2-yl)thio)furan-2-yl)methyl)amino)acetate 50

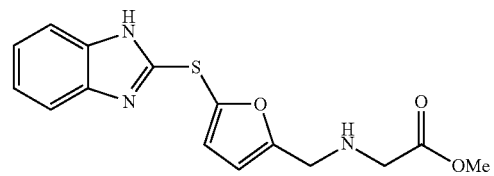 [SMILES: COC(=O)CNCc1ccc(Sc2nc3ccccc3[nH]2)o1]

Compound 50 was prepared following general procedure C. ¹H NMR (500 MHz, CDCl₃): δ (ppm)=7.50 (2H, br), 7.18 (2H, m), 6.76 (1H, d, J=3.5 Hz), 6.29 (1H, d, J=3.5 Hz), 3.85 (2H, s), 3.71 (1H, brs), 3.62 (3H, s), 3.49 (2H, s).

Example 41. Preparation of Methyl 5-((1H-benzo[d]imidazol-2-yl)thio)furan-2-carboxylate 51

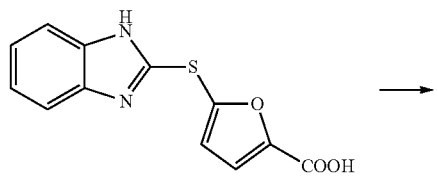

-continued

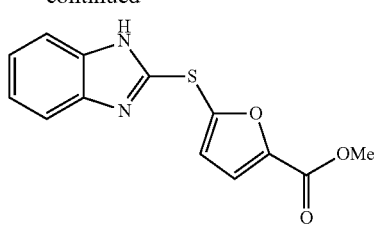

To a solution of 5-((1H-benzo[d]imidazol-2-yl)thio)furan-2-carboxylic acid (26 mg, 0.10 mmol) and K₂CO₃ (18 mg, 0.13 mmol) in DMF (1 ml) was added MeI (7 µl, 0.11 mmol) at room temperature and stirred for 24 hours at this temperature. The mixture was concentrated and purified by reverse phase (5 to 80% CH₃CN in water) to afford 51 (11 mg). LCMS (M+1)=275, >95% purity.

Example 42. Preparation of Methyl 5-((1-methyl-1H-benzo[d]imidazol-2-yl)thio)furan-2-carboxylate 52

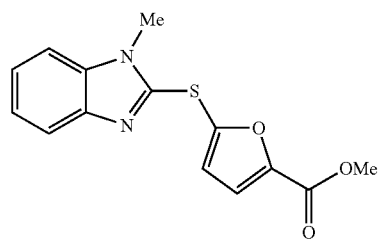 [SMILES: COC(=O)c1ccc(Sc2nc3ccccc3n2C)o1]

Followed procedure F. ¹H NMR (500 MHz, DMSO-d6): δ (ppm)=7.60 (2H, m), 7.41 (1H, d, J=3.5 Hz), 7.31 (1H, m), 7.22 (1H, m), 7.19 (1H, d, J=3.5 Hz), 3.87 (3H, s), 3.80 (3H, s).

Example 43. Preparation of 5-((5-((1H-benzo[d]imidazol-2-yl)thio)furan-2-yl)methylene)-1,3-dimethylpyrimidine-2,4,6(1H,3H,5H)-trione 53

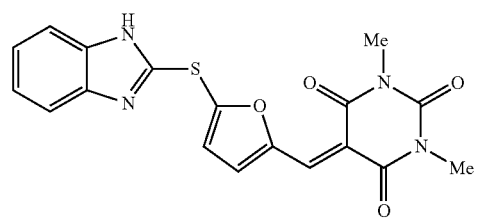 [SMILES: CN1C(=O)C(=Cc2ccc(Sc3nc4ccccc4[nH]3)o2)C(=O)N(C)C1=O]

Compound 53 was prepared Prepared following general procedure A using 1,3-dimethylbarbituric acid. ¹H NMR (500 MHz, DMSO-d6): δ (ppm)=13.0 (1H, brs), 8.51 (1H, d, J=4.0 Hz), 8.02 (1H, s), 7.52 (2H, br), 7.26 (1H, d, J=4.0 Hz), 7.21 (2H, m), 3.22 (6H, s).

Example 44. Preparation of 5-((5-((1H-benzo[d]imidazol-2-yl)thio)furan-2-yl)methylene)pyrimidine-2,4,6(1H,3H,5H)-trione 54

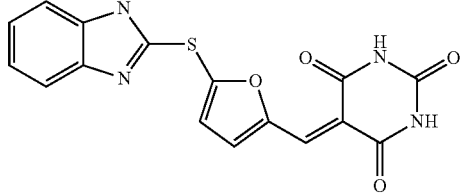

Compound 54 was prepared following general procedure A using barbituric acid. ¹H NMR (500 MHz, DMSO-d6): δ (ppm)=11.41 (1H, brs), 11.34 (1H, brs), 8.47 (1H, 4.0 Hz), 7.93 (1H, s), 7.50-7.55 (2H, br) 7.26 (1H, d, J=4.0 Hz), 7.19 (2H, m).

Example 45. Preparation of 5-((5-((1-(3-aminopropyl)-1H-benzo[d]imidazo-2-yl)thio)furan-2-yl)methylene)-3-isopropylthiazolidine-2,4-dione hydrochloride 55

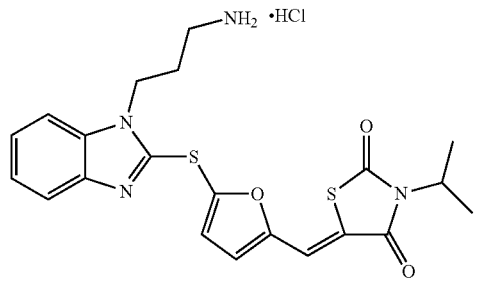 [SMILES: Cl ; CC(C)N1C(=O)S/C(=C\c2ccc(Sc3nc4ccccc4n3CCCN)o2)C1=O]

Compound 55 was prepared following general procedure F using tert-butyl (3-bromopropyl)carbamate. Boc deprotection: The Boc protected amine (70 mg) was dissolved in THF (1 ml) and a 4N HCl in dioxane solution (1 ml) was added at room temperature. The mixture was stirred overnight and concentrated. Diethyl ether (5 ml) was added and the resulting suspension filtered affording 55. LCMS (M+1)=443, >90% purity.

Example 46. Preparation of (Z)-3-isopropyl-5-((5-((6-(trifluoromethoxy)-1H-benzo[d]imidazol-2-yl)thio)furan-2-yl)methylene)thiazolidine-2, 4-dione 56

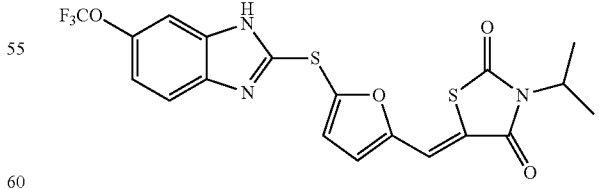

Compound 56 was prepared following general procedure A using 6-(trifluoromethoxy)-1H-benzo[d]imidazole-2-thiol. ¹H NMR (500 MHz, CDCl₃): δ (ppm)=7.56 (1H, d, J=9.0 Hz), 7.46 (2H, s), 7.16 (1H, d, J=9.0 Hz), 7.04 (1H, d, J=3.5 Hz), 6.75 (1H, d, J=3.5 Hz), 4.62 (1H, sep, J=7.0 Hz), 1.44 (6H, d, J=8.0 Hz).

Example 47. Preparation of (Z)-3-isopropyl-5-((5-((6-nitro-1H-benzo[d]imidazol-2-yl)thio)furan-2-yl)methylene)thiazolidine-2, 4-dione 57

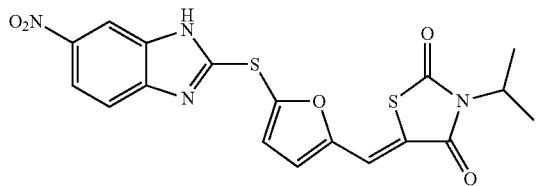 [SMILES: CC(C)N1C(=O)S/C(=C\c2ccc(Sc3nc4ccc([N+](=O)[O-])cc4[nH]3)o2)C1=O]

Compound 57 was prepared following general procedure A using 6-nitro-1H-benzo[d]imidazole-2-thiol. ¹H NMR (500 MHz, DMSO-d6): δ (ppm)=8.38 (1H, brs), 8.09 (1H, d, J=8.5 Hz), 7.27 (1H, s), 7.66 (1H, d, J=8.5 Hz), 7.33 (1H, d, J=3.5 Hz), 7.27 (1H, d, J=3.5 Hz), 4.47 (1H, sep, J=7.0 Hz), 1.34 (6H, d, J=7.0 Hz).

Example 48. Preparation of (Z)-5-((5-((6-acetyl-H-benzo[d]imidazol-2-yl)thio)furan-2-yl)methylene)-3-isopropylthiazolidine-2,4-dione 58

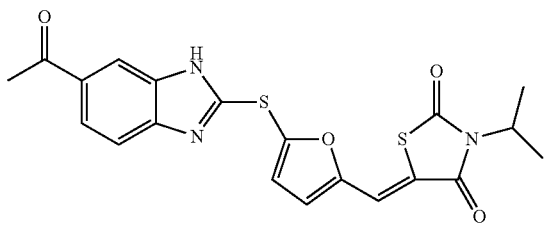 [SMILES: CC(=O)c1ccc2nc(Sc3ccc(/C=C4\SC(=O)N(C(C)C)C4=O)o3)[nH]c2c1]

Compound 58 was prepared following general procedure A using 1-(2-mercapto-1H-benzo[d]imidazol-6-yl)ethanone. ¹H NMR (500 MHz, CDCl₃): δ (ppm)=7.68 (1H, s), 7.39 (1H, d, J=8.5 Hz), 7.12 (1H, s), 7.07 (1H, d, J=8.5 Hz), 6.60 (1H, d, J=3.5 Hz), 6.49 (1H, d, J=3.5 Hz), 4.12 (1H, sep, J=7.0 Hz), 2.18 (3H, s), 0.97 (6H, d, J=7.0 Hz).

Example 49. Preparation of N-(3-(2-((5-((Z)-(3-isopropyl-2,4-dioxothiazolidin-5-ylidene)methyl)furan-2-yl)thio)-1H-benzo[d]imidazol-1-yl)propyl)-5-((3aR,4R,6aS)-2-oxohexahydro-1H-thieno[3, 4-d]imidazol-4-yl)pentanamide 59

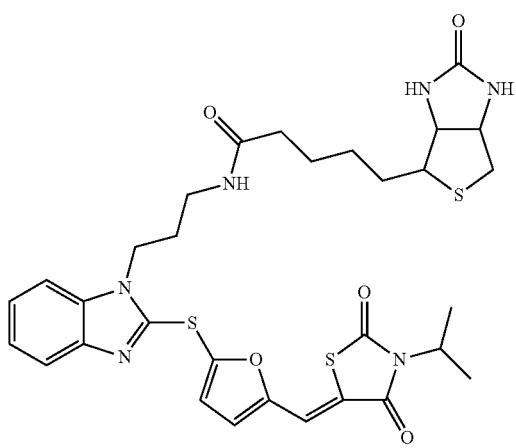 [SMILES: CC(C)N1C(=O)S/C(=C\c2ccc(Sc3nc4ccccc4n3CCCNC(=O)CCCCC3SCC4NC(=O)NC43)o2)C1=O]

Triethylamine (16 μl, 113 μmol) and biotin-NHS (20 mg, 56 μmol) were added to 55 (18 mg, 38 μmol) at room temperature and stirred overnight. The mixture was concentrated and purified by column chromatography on silica gel (0 to 15% MeOH in DCM) to afford 59 (21 mg), LCMS (M+1)=669, >95% purity.

Example 50. Preparation of (Z)-5-((5-((6-amino-1H-benzo[d]imidazol-2-yl)thio)furan-2-yl)methylene)-3-isopropylthiazolidine-2,4-dione 60

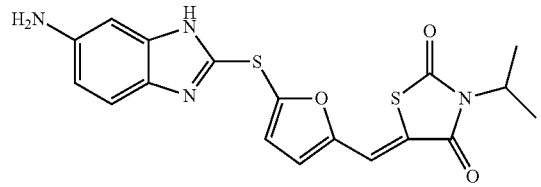

A mixture of 57 (350 mg, 813 μmol) and tin chloride dehydrate (0.55 mg, 2.44 mmol) in EtOH (20 ml) was stirred at reflux overnight. The mixture was cooled down, partioned between DCM and water, and the aqueous layer extracted with DCM (3×). The combined organic layer was dried on MgSO₄, filtered and concentrated. Purification by column chromatography on silica gel (0 to 15% MeOH in DCM) afforded 60 (256 mg), LCMS (M+1)=401, >95% purity.

Example 51. Preparation of (Z)—N-(2-((5-((3-isopropyl-2, 4-dioxothiazolidin-5-ylidene)methyl)furan-2-yl)thio)-1H-benzo[d]imidazol-6-yl)benzamide 61

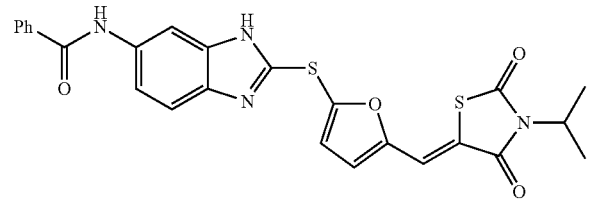 [SMILES: CC(C)N1C(=O)S/C(=C\c2ccc(Sc3nc4ccc(NC(=O)c5ccccc5)cc4[nH]3)o2)C1=O]

Benzoyl chloride was added to a solution of 60 (5 Id, 41 μmol) and DIPEA (10 μl, 56 μmol) in DCM (2 ml) at room temperature. After 2 hours, the mixture was concentrated and purified by isco (0 to 10% MeOH in DCM) affording 61 (7 mg) LCMS (M+1)=505, >90% purity.

Example 52. Preparation of (Z)—N-(2-((5-((3-isopropyl-2, 4-dioxothiazolidin-5-ylidene)methyl)furan-2-yl)thio)-1H-benzo[d]imidazol-6-yl)acetamide 62

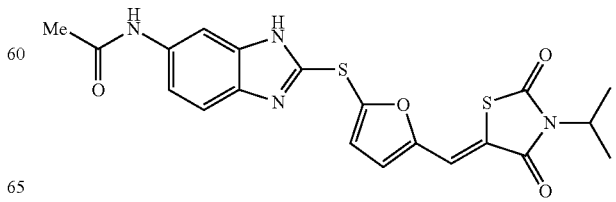

Compound 63 was prepared according to the preparation of 61, using acetyl chloride. $^1$H NMR (500 MHz, CDCl$_3$): δ (ppm)=7.74-7.79 (2H, m), 7.45 (1H, m), 7.34 (1H, m), 7.28 (1H, m), 7.13 (1H, m), 6.94 (1H, m), 6.65 (1H, m), 4.62 (1H, sep, J=7.0 Hz), 2.21 (3H, s), 1.46 (6H, d, J=7.0 Hz).

Example 53. Preparation of (Z)-methyl 2-((5-((3-isopropyl-2,4-dioxothiazolidin-5-ylidene)methyl)furan-2-yl)thio)-1H-benzo[d]imidazole-6-carboxylate 63

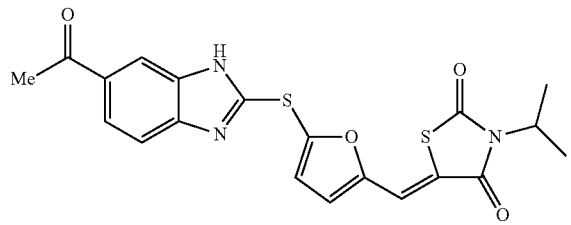 [SMILES: CC(=O)c1ccc2nc(Sc3ccc(/C=C4\SC(=O)N(C(C)C)C4=O)o3)[nH]c2c1]

Compound 63 was prepared following general procedure A using methyl 2-mercapto-1H-benzo[d]imidazole-6-carboxylate. $^1$H NMR (500 MHz, CDCl$_3$): δ (ppm)=8.21 (1H, br), 7.93 (1H, d, J=9.0 Hz), 7.52 (1H, br), 7.37 (1H, m), 7.00 (1H, d, J=3.5 Hz), 6.68 (1H, m), 4.62 (1H, sep, J=7.0 Hz), 3.92 (3H, s), 1.46 (6H, d, J=7.0 Hz).

Example 54. Preparation of (Z)-5-(3-((1H-benzo[d]imidazol-2-yl)oxy)benzylidene)-3-isopropylthiazolidine-2, 4-dione 65

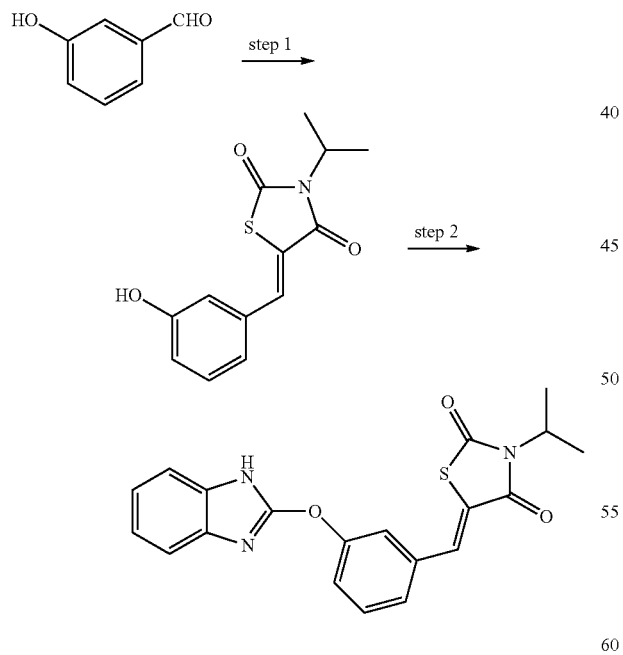

Step 1: Prepared following general procedure A.
Step 2: A mixture of 2-(methylsulfonyl)-1H-benzo[d]imidazole (101 mg, 517 μmol), (Z)-5-(3-hydroxybenzylidene)-3-isopropylthiazolidine-2,4-dione (680 mg, 2.58 mmol) and triethylamine (0.35 ml, 2.58 mmol) was stirred at 120° C. overnight. The reacting mixture was cooled down, concentrated and purified by column chromatography on silica gel (10 to 40% AcOEt in hexanes) to afford 65 (78 mg). $^1$H NMR (500 MHz, CDCl$_3$): δ (ppm)=7.77 (1H, s), 7.46-7.51 (4H, m), 7.35 (2H, m), 7.22 (2H, m), 4.67 (1H, sep, J=7.0 Hz), 1.48 (6H, d, J=7.0 Hz).

Example 55. Preparation of 5-((1-(3-aminopropyl)-1H-benzo[d]imidazol-2-yl)thio)-N-phenylfuran-2-carboxamide hydrochloride 66

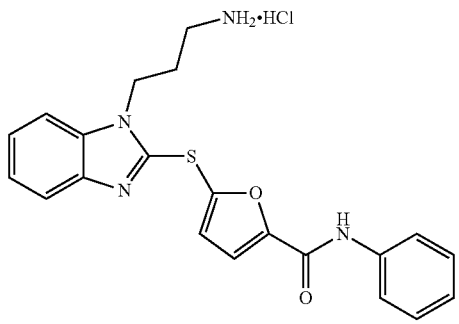

Compound 66 was prepared following general procedure F using tert-butyl (3-bromopropyl)carbamate. Boc deprotection: followed conditions described for 55. LCMS (M+1)=393, >90% purity.

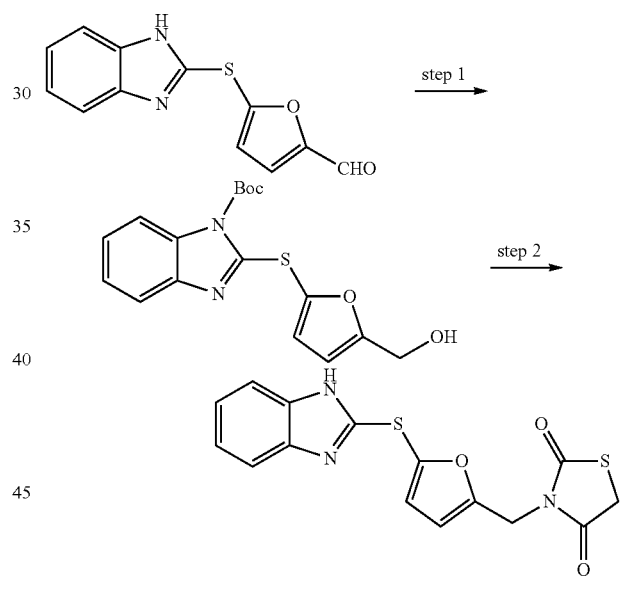

Example 56. Preparation of 3-((5-((1H-benzo[d]imidazol-2-yl)thio)furan-2-yl)methyl)thiazolidine-2, 4-dione 67

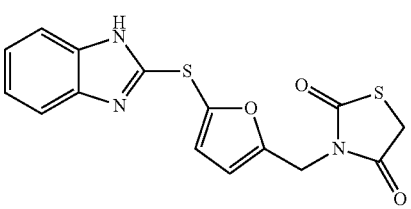 [SMILES: O=C1CSC(=O)N1Cc1ccc(Sc2nc3ccccc3[nH]2)o1]

Step 1: A solution of Boc$_2$O (2.0 eq), DMAP (0.1 eq) and triethylamine (3.0 eq) in DCM (0.05M) was stirred at room temperature overnight. Water was added and the aqueous layer extracted with DCM (3×). The combined organic layers were dried over MgSO₄, filtered and concentrated. Purification by column chromatography on silica gel (10 to 40% AcOEt in hexanes) afforded tert-butyl 2-((5-formyl-furan-2-yl)thio)-1H-benzo[d]imidazole-1-carboxylate.

To a solution of tert-butyl 2-((5-formylfuran-2-yl)thio)-1H-benzo[d]imidazole-1-carboxylate (1 eq) in MeOH (0.05 M) was added NaBH₄ (1.3 eq) at 0° C. The reacting mixture was stirred for 2 hours at room temperature prior to be quenched by addition of water. The aqueous layer was extracted with DCM (3×), and the combined organic layers dried over MgSO₄, filtered and concentrated.

Step 2: Diisopropyl azodicarboxylate (87 μl, 417 μmol) was added dropwise at 0° C. to a solution of tert-butyl 2-((5-(hydroxymethyl)furan-2-yl)thio)-1H-benzo[d]imidazole-1-carboxylate (125 mg, 361 μmol), thiazolidine-2,4-dione (46 mg, 370 μmol) and triphenylphosphine (109 mg, 415 μmol) in dry THF (0.025M) under argon. The reacting mixture was stirred at 60° C. for 3 hours. Water was added and the aqueous layer extracted with AcOEt (3×). The combined organic layers were dried over MgSO₄, filtered and concentrated. Purification by column chromatography on silica gel (20 to 40% AcOEt in hexanes) afforded tert-butyl 2-((5-((2,4-dioxothiazolidin-3-yl)methyl)furan-2-yl)thio)-1H-benzo[d]imidazole-1-carboxylate (140 mg). The resulting product (70 mg) was dissolved in THF (3 ml) and a solution of 4N HCl in dioxane (3 ml) was added at 0° C. The reacting mixture was stirred at room temperature overnight. Sat. NaHCO₃ was added (pH8) and the aqueous layer extracted with AcOEt (3×). The combined organic layers were dried over MgSO₄, filtered and concentrated. Purification by column chromatography on silica gel (30 to 75% AcOEt in hexanes) afforded 67. ¹H NMR (500 MHz, CDCl₃): δ (ppm)=7.55 (2H, m), 7.21 (2H, m), 6.73 (1H, d, J=3.5 Hz), 3.38 (1H, d, J=3.5 Hz), 4.76 (2H, s), 3.98 (2H, s).

Example 57. Preparation of (Z)-5-((6-((1H-benzo[d]imidazol-2-yl)thio)benzofuran-2-yl)methylene)-3-isopropylthiazolidine-2,4-dione 68

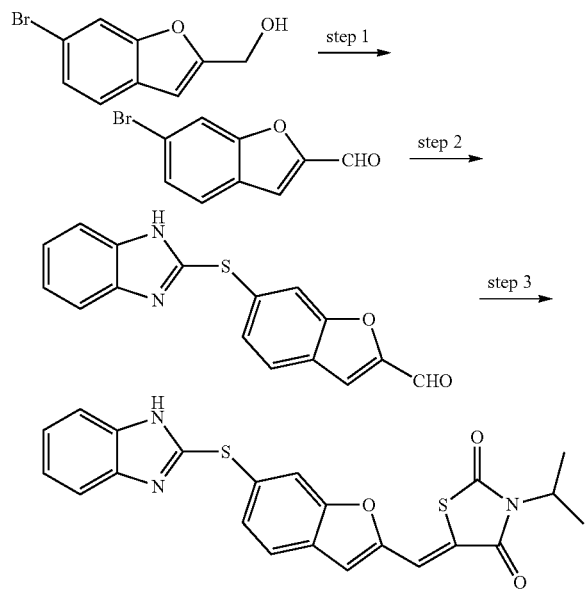

Step 1: PCC (1.3 eq) was added to a solution of (6-bromobenzofuran-2-yl)methanol (1 eq) in DCM (0.05 M) at 0° C. After 5 hours, the mixture was filtered over celite, concentrated and purified by column chromatography on silica gel (0 to 30% AcOEt in hexanes) to afford 6-bromobenzofuran-2-carbaldehyde.

Step 2: Prepared following general procedure D.

Step 3: Prepared following general procedure A. ¹H NMR (500 MHz, DMSO-d6): δ (ppm)=12.74 (1H, brs), 7.94 (1H, m), 7.88 (1H, s), 7.80 (1H, d, J=8.5 Hz), 7.56-7.58 (2H, m), 7.44 (1H, dd, J=8.0, 1.5 Hz), 7.40 (1H, d, J=7.0 Hz), 7.15-7.21 (2H, m), 4.51 (1H, sep, J=7.0 Hz), 1.38 (6H, d, J=7.0 Hz).

Example 58. Preparation of (Z)—N-(2-(2, 6-dioxopiperidin-3-yl)-1-oxoisoindolin-4-yl)-2-(2-(2-(2-(2-((5-((3-isopropyl-2, 4-dioxothiazolidin-5-ylidene)methyl)furan-2-yl)thio)-1H-benzo[d]imidazol-1-yl)acetamido)ethoxy)acetamide 69

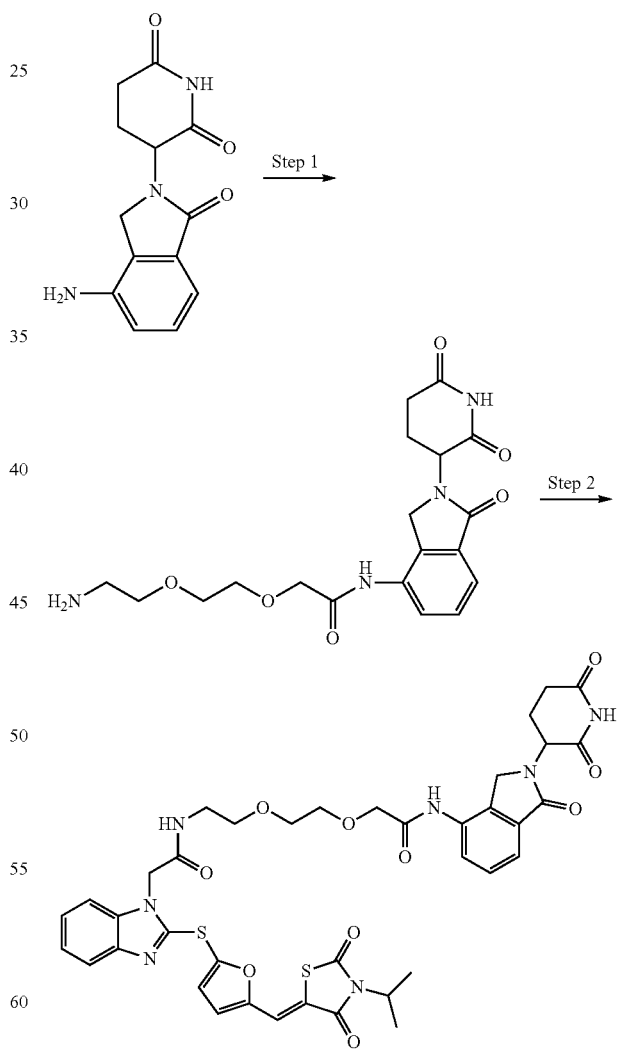

Step 1: HATU (303 mg, 797 mol) and DIPEA (214 μl, 1227 μmol) were added to a solution of Lenalidomide (159 mg, 613 μmol) and 2,2-dimethyl-4-oxo-3,8,11-trioxa-5-azatridecan-13-oic acid (242 mg, 920 μmol) in DMF (0.1 M) at room temperature. The mixture was stirred overnight prior to be quenched with sat. NaHCO₃. The aqueous layer was extracted with AcOEt (3×), dried over MgSO₄, filtered and concentrated. The crude was purified by short plug on silica gel (50 to 75% Acetone in hexane to afford tert-butyl (2-(2-(2-((2-(2,6-dioxopiperidin-3-yl)-1-oxoisoindolin-4-yl)amino)-2-oxoethoxy)ethoxy)ethyl)carbamate. The resulting product was dissolved in THF (5 ml) and a 4N HCl solution in dioxane (5 ml) was added. The resulting mixture was stirred overnight and concentrated to furnish the corresponding Boc deprotected amine HCl salt.

Step 2: HATU (14 mg, 35 μmol) and DIPEA (10 μl, 55 μmol) were added to a solution of 2-(2-(2-aminoethoxy)ethoxy)-N-(2-(2,6-dioxopiperidin-3-yl)-1-oxoisoindolin-4-yl)acetamide (10 mg, 23 μmol) and (Z)-2-(2-((5-((3-isopropyl-2,4-dioxothiazolidin-5-ylidene)methyl)furan-2-yl)thio)-1H-benzo[d]imidazol-1-yl)acetic acid (12 mg, 27 μmol) in DMF (0.5 ml) at room temperature. The mixture was stirred overnight, concentrated and purified by prep TLC (5% MeOH in DCM) to afford 69 (14 mg). LCMS (M+1)=831, >95% purity.

Example 59. Preparation of (Z)—N-(2-((3-(2-((5-((3-isopropyl-2,4-dioxothiazolidin-5-ylidene)methyl)furan-2-yl)thio)-1H-benzo[d]imidazol-1-yl)propyl)amino)-2-oxoethyl)-3-(3-methyl-3H-diazirin-3-yl)-N-(prop-2-yn-1-yl)propanamide 71

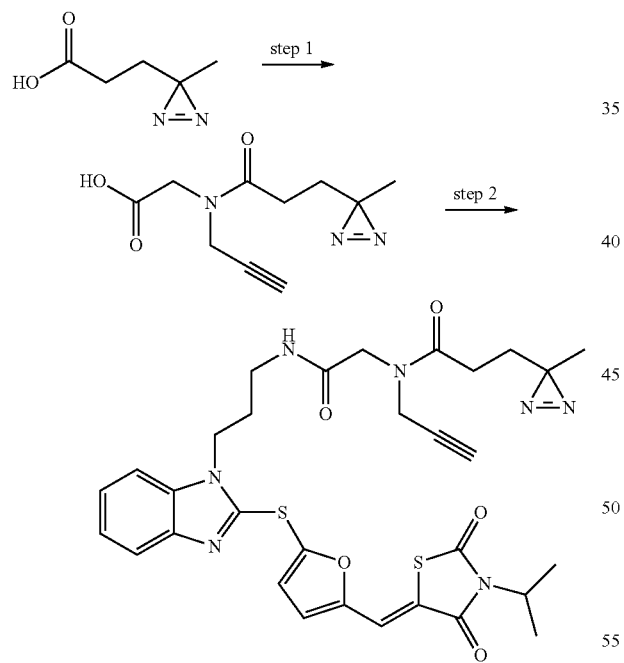

Step 1: PyBOP (2.95 g, 5.66 mmol) and DIPEA (1.97 ml, 11.32 mmol) were added to 3-(3-methyl-3H-diazirin-3-yl)propanoic acid (0.87 g, 6.70 mmol, prepared following Org. Lett. 2013, 15, 5060-5063) and ethyl 2-(prop-2-yn-1-ylamino)acetate (0.80 g, 5.66 mmol, prepared following Synthesis 2009, 3, 488-494) in DMF (10 ml) at room temperature. The reacting mixture was stirred overnight, concentrated and purified by column chromatography on silica gel (25% AcOEt in hexanes) to provide ethyl 2-(3-(3-methyl-3H-diazirin-3-yl)-N-(prop-2-yn-1-yl)propanamido)acetate (1.04 g). The resulting product was dissolved in MeOH (15 ml) and a solution of NaOH (389 mg, 2 eq) in water (3 ml) was added at 0° C. The reacting mixture was stirred overnight at room temperature, then partioned between water and DCM and brought to pH2 with 6N HCl. The aqueous layer was extracted with DCM (3×), the combined organic layers dried over MgSO₄, filtered and concentrated providing 2-(3-(3-methyl-3H-diazirin-3-yl)-N-(prop-2-yn-1-yl)propanamido)acetic acid (880 mg).

Step 2: HATU (20 mg, 53 μmol) and DIPEA (16 μl, 88 μmol) were added to 55 (21 mg, 44 μmol) and 2-(3-(3-methyl-3H-diazirin-3-yl)-N-(prop-2-yn-1-yl)propanamido)acetic acid (11 mg, 48 μmol) in DMF (0.5 ml) at room temperature. The mixture was stirred overnight, then concentrated and purified by reverse phase (5 to 80% CH₃CN in water) providing 71. LCMS (M+1)=648, >90% purity.

Example 60. Preparation of (Z)—N-(2-((3-(2-((5-((3-isopropyl-2,4-dioxothiazolidin-5-ylidene)methyl)furan-2-yl)thio)-1H-benzo[d]imidazol-1-yl)propyl)amino)-2-oxoethyl)-N-(prop-2-yn-1-yl)pentanamide 70

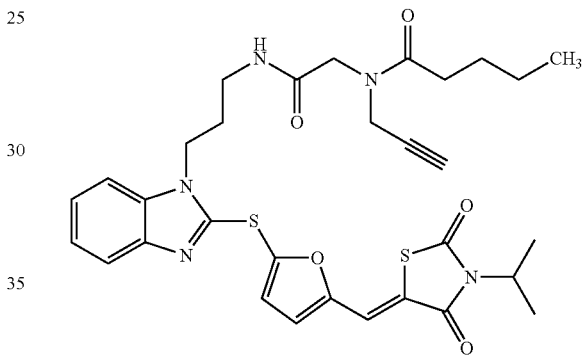

Compound 70 was prepared according to the synthesis of 71 above, starting from valeric acid. LCMS (M+1)=622.

Example 61. Preparation of (Z)—N-(2-(2-(2-aminoethoxy)ethoxy)ethyl)-2-(2-((5-((3-isopropyl-2,4-dioxothiazolidin-5-ylidene)methyl)furan-2-yl)thio)-1H-benzo[d]imidazol-1-yl)acetamide 72

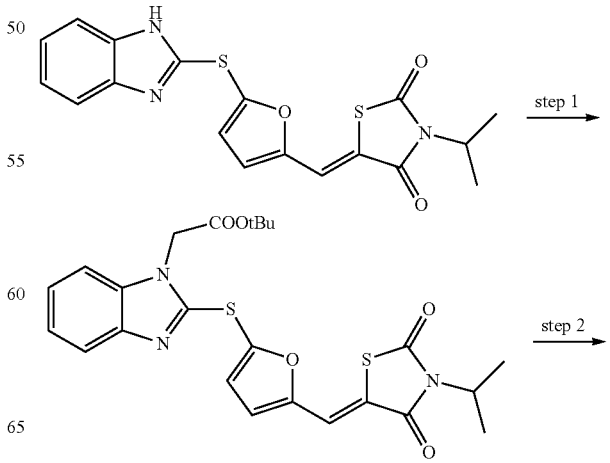

-continued

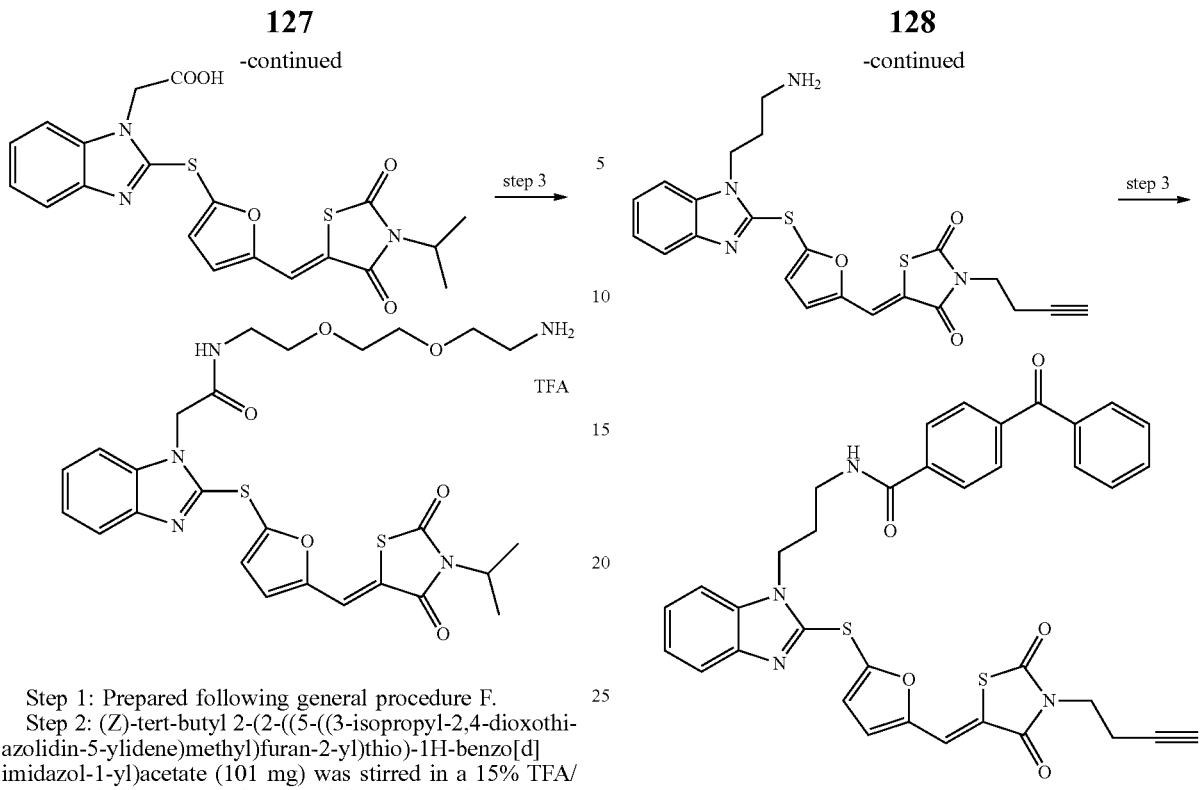

Step 1: Prepared following general procedure F.

Step 2: (Z)-tert-butyl 2-(2-((5-((3-isopropyl-2,4-dioxothiazolidin-5-ylidene)methyl)furan-2-yl)thio)-1H-benzo[d]imidazol-1-yl)acetate (101 mg) was stirred in a 15% TFA/DCM solution (10 ml) overnight. The mixture was concentrated and used as is.

Step 3: HATU (33 mg, 88 µmol) and DIPEA (24 µl, 135 µmol) were added to a solution of (Z)-2-(2-((5-((3-isopropyl-2,4-dioxothiazolidin-5-ylidene)methyl)furan-2-yl)thio)-1H-benzo[d]imidazol-1-yl)acetic acid (30 mg, 68 µmol) and tert-butyl (2-(2-(2-aminoethoxy)ethoxy)ethyl)carbamate (30 mg, 101 µmol) in DMF (1 ml). The reacting mixture was stirred overnight at room temperature, concentrated and purified by column chromatography on silica gel (25 to 75% Acetone in hexanes) to afford (Z)-tert-butyl (2-(2-(2-(2-((5-((3-isopropyl-2,4-dioxothiazolidin-5-ylidene)methyl)furan-2-yl)thio)-1H-benzo[d]imidazol-1-yl)acetamido)ethoxy)ethoxy)ethyl)carbamate. The resulting product (33 mg) was stirred in 10% TFA/DCM (0.5 ml) for 3 hours and concentrated providing 72. LCMS (M+1)=574, >95% purity.

Example 62. Preparation of (Z)-4-benzoyl-N-(3-(2-((5-((3-(but-3-yn-1-yl)-2, 4-dioxothiazolidin-5-ylidene)methyl)furan-2-yl)thio)-1H-benzo[d]imidazol-1-yl)propyl)benzamide 73

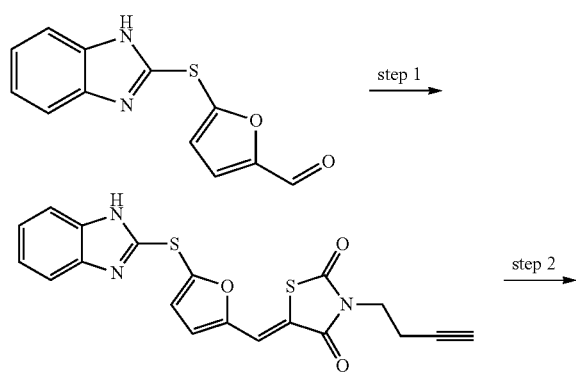

Step 1: Prepared according to general procedure A and E.
Step 2: Prepared according to the synthesis of 55.
Step 3: Prepared according to the synthesis of 71, using 4-benzoylbenzoic acid. LCMS (M+1)=661, >95% purity.

Characterization of the Compounds

Example 1. Solubility and Half-Life of Compound 1

Exemplary solubility and half-life of compound 1 are shown in Table 1.

TABLE 1

Solubility and half-life of compound 1

|  | Solubility at 37° C. (µM) | Half-life (minute) |
|---|---|---|
| Aqueous solubility (simulated intestinal fluid) | 80.2 |  |
| Aqueous solubility (PBS, pH 7.4) | <1 |  |
| Aqueous solubility (simulated gastric fluid) | 62.7 |  |
| Intrinsic clearance (liver microsomes, human) |  | 22 |

More than 40,000 compounds were screened by combining unbiased Small Molecule Microarray (SMMs) binding assays involving c-Myc with a cell-based transcriptional readout. SMMs have been proven to be a general, robust, and scalable screening platform for discovering protein-small molecule interactions that lead to modulators of protein function [10]. Purified 6×His-tagged c-Myc was incubated with SMMs containing the compounds. Binding was detected using an Alexa647-labeled antibody against the 6×His-tag. Z-scores were computed for each compound using fluorescence intensities across three replicates as described previously [10]. 313 compounds scored as selective assay positives.

Biological Assays of the Compounds Described Herein

Example 1. c-Myc Reporter Gene Assay of Exemplary Compounds Described Herein

Figure 1B:
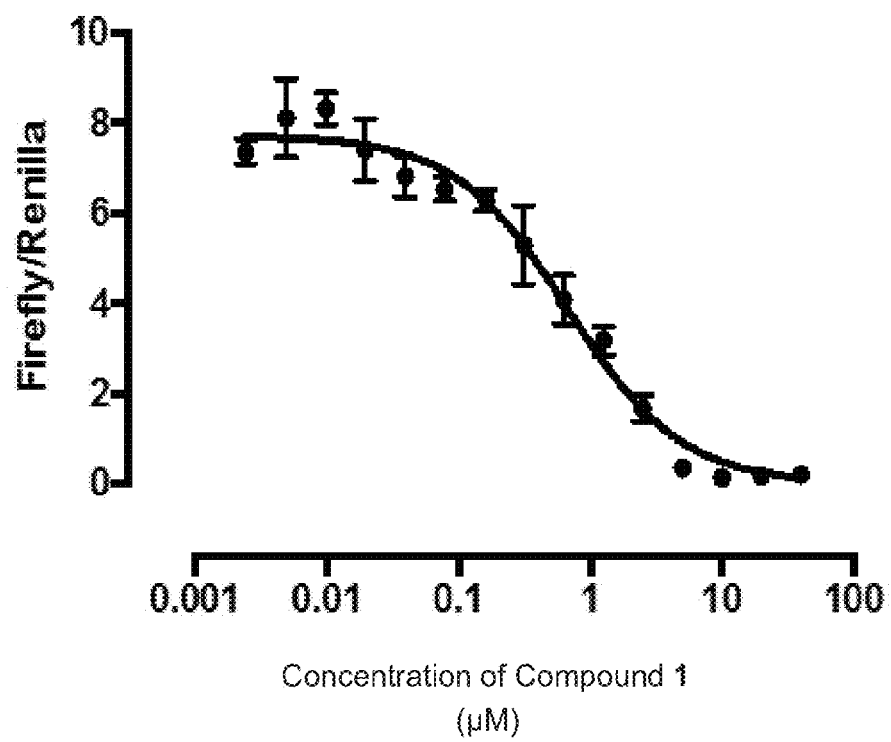
FIG. 1B shows exemplary results of compound 1 in an initial reporter assay. Compound 1's activity against Myc was measured as a Firefly/Renilla ratio, using the Myc reporter assay (Qiagen) in HEK293T cells after treatment with compound 1 for 16 hours. Results are expressed as a mean+/−SD (n=3). SD: standard deviation.
Figure 2A:
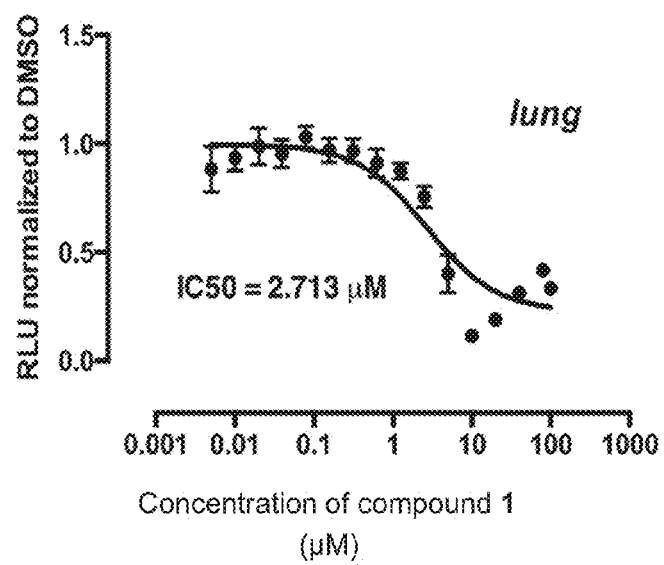
FIGS. 2A to 2E show exemplary results of cell viability assay of compound 1. Compound 1 affected cell viability after treatment with compound 1 for 3 days, as measured using CELL TITER GLO (Promega) in 5 different cancer cell lines: NCIH1975 (lung.
Figure 2B:
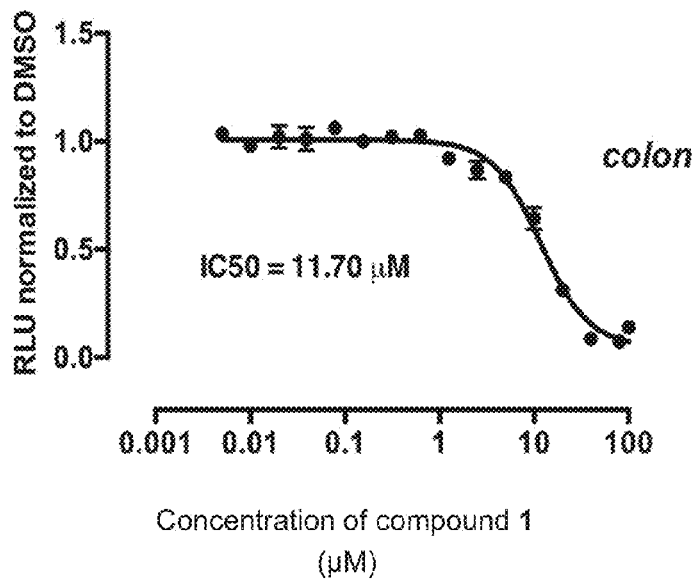
Figure 2C:
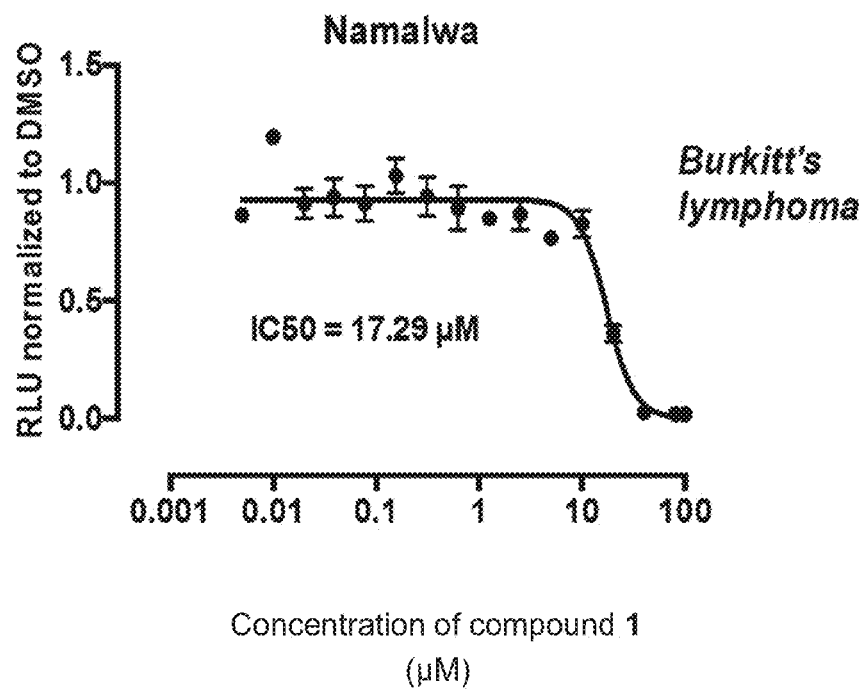
Figure 2D:
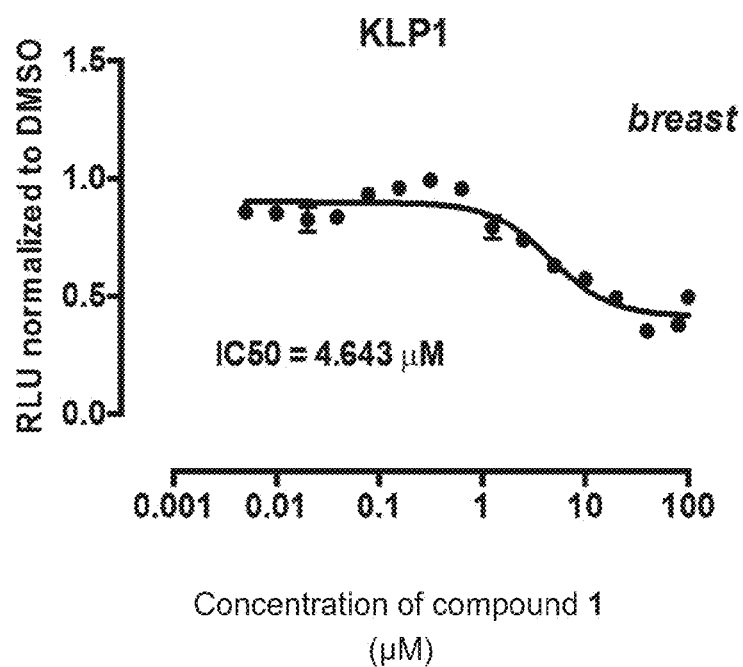
Figure 2E:
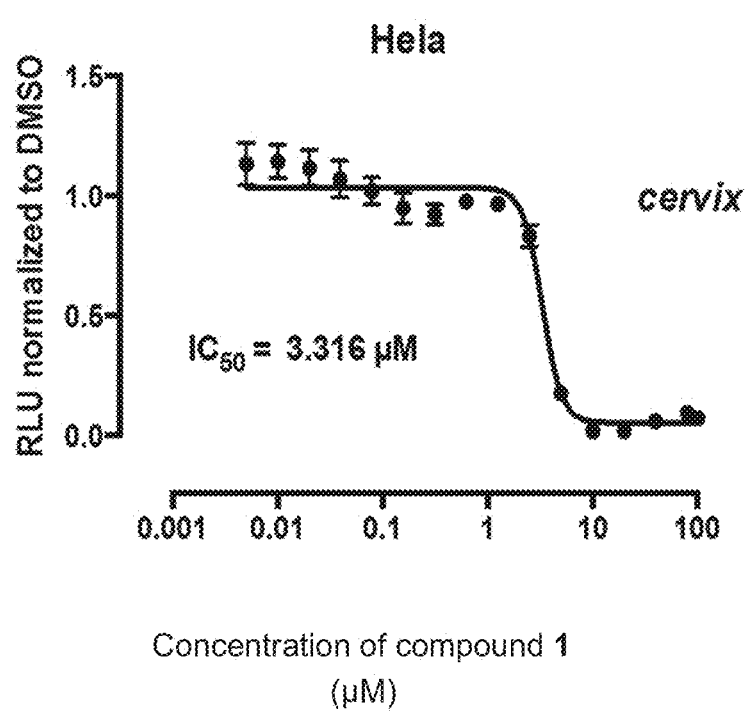

Select compounds described herein that were SMM assay positives were evaluated in several versions of a c-Myc reporter gene assay, including a commercial assay from Qiagen. The compounds' activities against c-Myc were measured as a Firefly/Renilla ratio, using the Myc reporter assay (Qiagen) in HEK293T cells after treatment with the compounds for 16 hours. Exemplary results are shown in Table 2. Compound 1 was a potent inhibitor with an $IC_{50}$ value of 0.67 µM (FIG. 1B and Table 2).

TABLE 2

$IC_{50}$ values of exemplary compounds described herein in the c-Myc reporter assay and viability data in select cell lines. Viability was assessed by CELL TITER GLO assay (Promega). Results expressed as a mean +/− SEM (n = 3).

| Compound # | c-Myc reporter assay $IC_{50}$ (µM) | $IC_{50}$ standard (µM) | Viability in Namalwa cells (µM) | Viability in NCIH1975 cells (µM) | Viability in Eu-Myc Arf −/− cells (µM) | cLogP |
|---|---|---|---|---|---|---|
| 1 | 0.67 | — | 21.14 | 24.91 | 10.2 | 5.2 |
| 2 | 7.5 | 0.74 | >50 | >50 | >50 | 2.5 |
| 3 | 5.72 | 0.74 | 31.12 | >50 | >50 | 5.7 |
| 4 | 0.79 | 0.74 | 12.44 | 17.32 | 11.01 | 6 |
| 5 | 1.19 | 0.74 | 42.15 | 34.53 | >50 | 5.5 |
| 6 | 9.39 | 0.74 | 37.23 | >50 | >50 | 5.1 |
| 7 | >40 | 0.74 | 20.06 | 45.31 | >50 | 4.6 |
| 8 | 0.83 | 0.74 | >50 | >50 | 11.79 | 3.8 |
| 9 | 9.02 | 0.74 | >50 | >50 | >50 | 2.4 |
| 10 | 5.6 | 0.74 | >50 | >50 | 33.13 | 4.4 |
| 11 | 1.62 | 0.84 | — | — | — | 5.7 |
| 13 | inactive | 0.84 | — | — | — | 3.6 |
| 14 | 1.96 | 0.84 | — | — | — | 5.2 |
| 15 | 3.26 | 0.84 | — | — | — | 3.9 |
| 16 | 20.8 | 0.84 | — | — | — | 3.6 |
| 17 | 7.67 | 0.84 | — | — | — | 4.3 |
| 18 | 1.67 | 0.84 | — | — | — | 5.2 |
| 19 | 6.52 | 0.84 | — | — | — | 3.8 |
| 20 | 1.22 | 0.84 | — | — | — | 5.6 |
| 21 | 6.77 | 0.84 | — | — | — | 4.5 |
| 22 | 1.05 | 0.74 | 16.54 | 45.27 | 6.09 | 4.57 |
| 23 | 1.5 | 0.74 | 33.93 | 28.18 | 10.49 | 5.71 |
| 24 | 0.64 | 0.74 | 7.94 | 12.47 | 11.21 | 6.23 |
| 25 | 0.63 | 0.74 | 3.95 | 7.88 | 5.51 | 6.62 |
| 26 | 33.65 | 0.74 | >50 | >50 | >50 | 3.31 |
| 27 | 2.28 | 0.74 | 12.17 | >50 | 26.04 | 1.61 |
| 28 | 0.98 | 0.74 | 9.41 | 15.58 | 5.36 | 6 |
| 29 | 0.64 | 0.74 | 15.27 | 19.95 | 13.05 | 6.64 |
| 30 | 1.63 | 0.74 | 72.03 | 56.3 | 11.14 | 5.51 |
| 31 | 2.22 | 3.00 | — | — | — | 5.74 |
| 32 | 6.24 | 3.00 | — | — | — | 4.24 |
| 33 | 2.77 | 3.00 | — | — | — | 4.77 |
| 34 | 7.01 | 3.00 | — | — | — | 5.52 |
| 35 | 11.9 | 3.00 | — | — | — | 6.28 |
| 36 | >100 | 3.00 | — | — | — | 3.37 |
| 37 | >100 | 3.00 | — | — | — | 4.7 |
| 38 | >100 | 3.00 | — | — | — | 2.5 |
| 39 | >100 | 3.00 | — | — | — | 5.71 |
| 40 | >40 | 0.74 | >50 | >50 | 14.11 | 2.62 |
| 41 | non active | 2.09 | — | — | — | 3.42 |
| 42 | 3.32 | 2.09 | — | — | — | 4.19 |
| 43 | 7.9 | 2.09 | — | — | — | 3.23 |
| 44 | non active | 2.09 | — | — | — | 2.32 |
| 45 | 4.66 | 2.09 | — | — | — | 4.61 |
| 46 | 57.47 | 2.09 | — | — | — | 3.87 |
| 47 | 32.9 | 2.09 | — | — | — | 3.41 |
| 48 | 10.23 | 2.09 | — | — | — | 4.5 |
| 49 | 59.37 | 2.09 | — | — | — | 3.5 |
| 50 | 75.9 | 2.09 | — | — | — | 2.99 |
| 51 | non active | 2.09 | — | — | — | 3.66 |
| 52 | not tested | 2.09 | — | — | — | 3.68 |
| 53 | 26.81 | 2.09 | — | — | — | 3.8 |
| 54 | non active | 2.09 | — | — | — | 2.31 |
| 55 | not tested | — | — | — | — | |
| 56 | 0.44 | 0.26 | — | — | — | 6.6 |
| 57 | 0.36 | 0.26 | — | — | — | 5.1 |
| 58 | 0.26 | 0.26 | — | — | — | 4.9 |
| 59 | not tested | — | not tested | not tested | not tested | |
| 60 | 4.56 | 0.68 | not tested | not tested | not tested | 4.7 |

TABLE 2-continued

IC$_{50}$ values of exemplary compounds described herein in the
c-Myc reporter assay and viability data in select cell lines.
Viability was assessed by CELL TITER GLO assay (Promega).
Results expressed as a mean +/− SEM (n = 3).

| Compound # | c-Myc reporter assay IC$_{50}$ (µM) | IC$_{50}$ standard (µM) | Viability in Namalwa cells (µM) | Viability in NCIH1975 cells (µM) | Viability in Eu-Myc Arf −/− cells (µM) | cLogP |
|---|---|---|---|---|---|---|
| 61 | 0.4 | 0.68 | not tested | not tested | not tested | 6.3 |
| 62 | 0.93 | 0.68 | not tested | not tested | not tested | 4.8 |
| 63 | 1.49 | 0.68 | not tested | not tested | not tested | 5.3 |
| 64 | 1.82 | 0.68 | not tested | not tested | not tested | 6.1 |
| 65 | 0.99 | 0.68 | not tested | not tested | not tested | 5.2 |
| 66 | not tested | — | not tested | not tested | not tested | 3.77 |
| 67 | 29.97 | 0.68 | not tested | not tested | not tested | 3.4 |
| 68 | 0.54 | 0.68 | not tested | not tested | not tested | 6.6 |
| 69 | not tested | — | not tested | not tested | not tested | 3.9 |
| 70 | not tested | — | not tested | not tested | not tested | — |
| 71 | not tested | — | not tested | not tested | not tested | — |
| 72 | not tested | — | not tested | not tested | not tested | — |
| 73 | not tested | — | not tested | not tested | not tested | — |

Example 2. Cell Viability Assay of Exemplary Compounds Described Herein

Figure 3A:
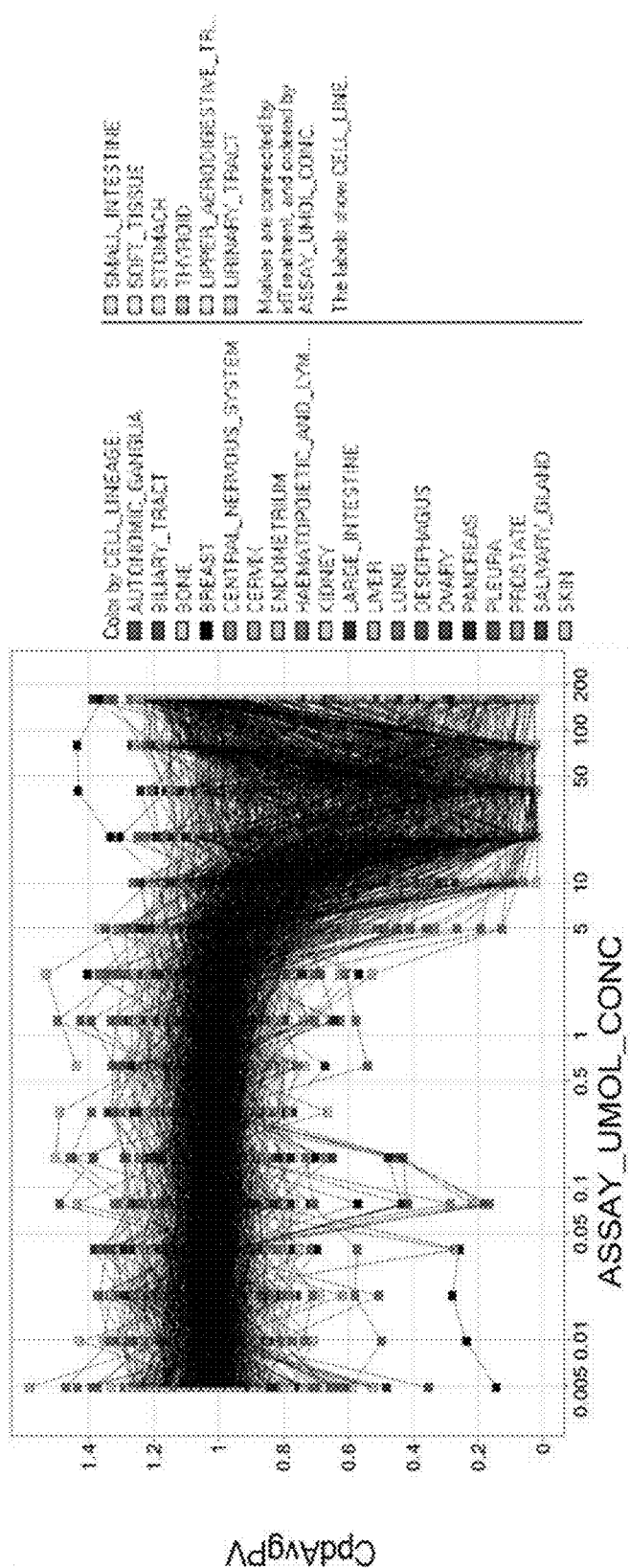

The effect of compound 1 on cell viability in several cancer cell lines were determined. The cancer cell lines employed in the assay included those corresponding to hematopoietic and solid tumors. Exemplary results are shown in FIGS. 2A to 2E, where viability was assessed by CELL TITER GLO assay (Promega). Compound 1 was also submitted in a blinded fashion to the National Cancer Institute's CTD cancer cell line profiling pipeline, which enabled sensitivity profiling in about 800 cancer cell lines with annotation of specific genomic lesions that impart on human cancers (FIGS. 3A to 3B). Compound 1 demonstrated an effect in cell viability in a variety of cancer cell lines, consistent with the notion that Myc is a key oncoprotein in a broad range of cancers. The effects of other compounds described herein on cell viability in several cancer cell lines were also determined, and exemplary results are shown in Table 2, where viability was assessed by CELL TITER GLO assay (Promega).

Figure 4:
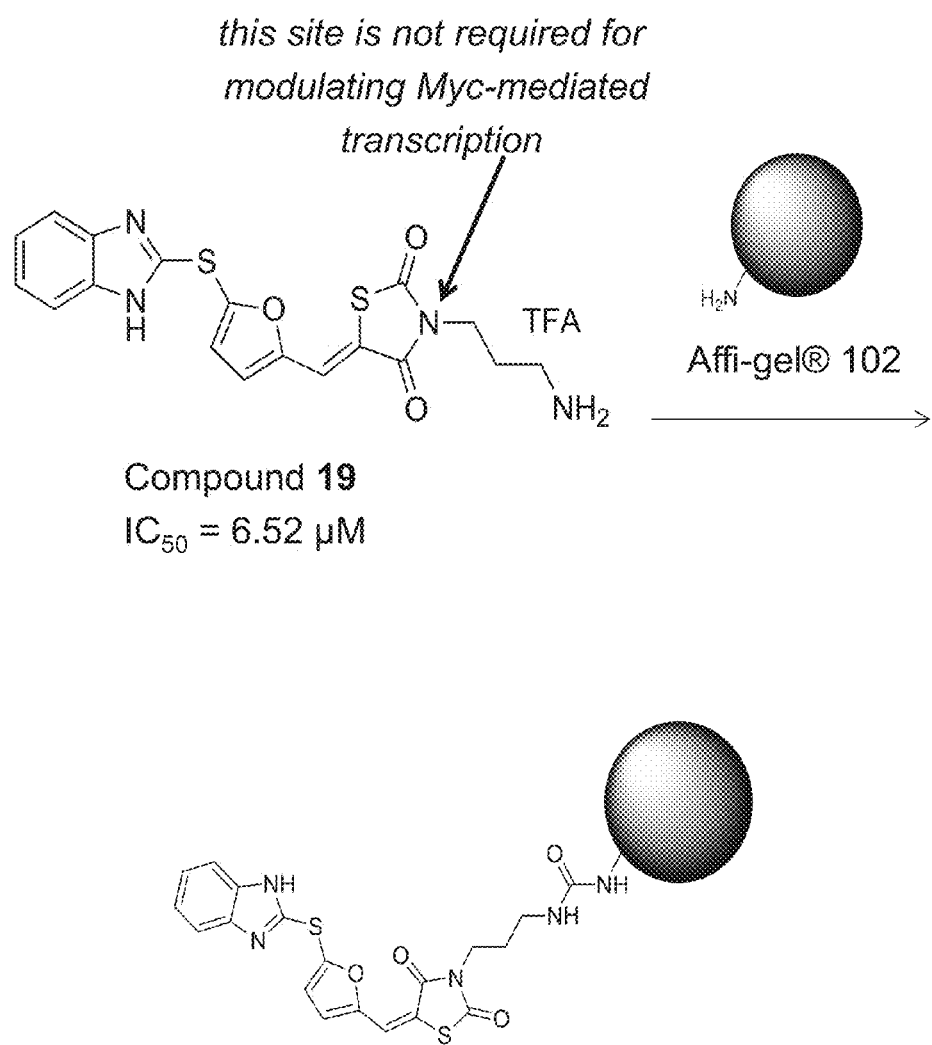
FIG. 4 shows exemplary reagents to enable experiments for demonstrating engagement of Myc in a cellular setting and evaluating the selectivity of the compounds described herein for other proteins in a cellular setting.

Example 3. Target Identification Experiments of Exemplary Compounds Described Herein In order to explore the mechanism of action of compound 1, preliminary target identification experiments involving affinity-based pull downs were carried out. Compound 1 was modified to append a short linker off of the thiazolidine-2,4-dione moiety, which had been shown to be tolerated during an evaluation of select compounds (Table 2). Compound 19 contains a short linker off of the thiazolidine-2,4-dione moiety and was found to have an IC$_{50}$ value of 7.3 µM in Myc reporter assay. The structure of compound 19 allowed for linking compound 1 to beads (AFFI-GEL 102, Bio-Rad) (FIG. 4). Incubating the loaded beads with nuclear lysate, and 1 and 5 µM of compound 1, which was unbound to the beads and acted a soluble competitor, followed by a pull down of the beads and subsequent analysis by Western blot of c-Myc levels, it was observed that there was less c-Myc pulled down in the presence of 5 µM of compound 1 as a soluble competitor (Figure SA), suggesting that compound 1 is capable of binding to Myc-associated complexes in cell lysates.

Figure 5A:
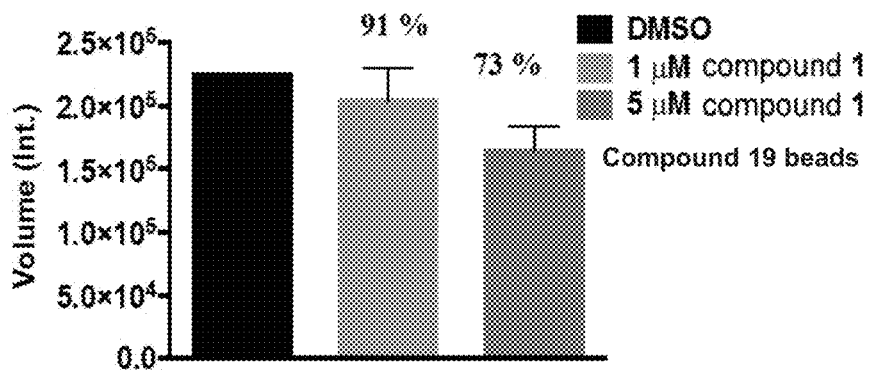
FIGS. 5A and 5B shows exemplary Western blotting results of compound 1-mediated pull downs of Myc where free compound 1 is used as a soluble competitor. Compound 19 beads (Figure SA) and compound 55 beads (FIG. 5B) were used. Results are expressed as a mean+/−SEM (n=3). Compound 55 beads were formed by a method analogous to the method shown in FIG. 4, where beads were linked to the —NH$_2$ moiety of compound 55 by forming a urea moiety.
Figure 5B:
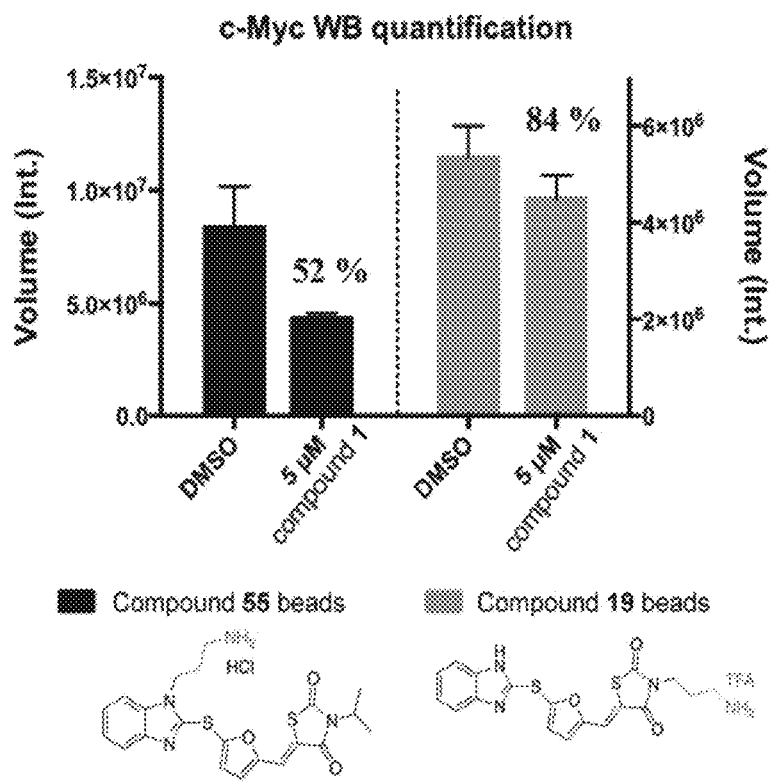

A similar approach that linked the beads onto the right part (e.g., a nitrogen atom of the benzimidazolyl moiety) of the compounds also showed decreased levels of c-Myc when compound 1 was added as a soluble competitor (FIG. 5B). The linkage site to the bead via the nitrogen atom of the benzimidazolyl moiety was the original site of attachment to the small-molecule microarray and represented the orientation in the original screen. This orientation was shown to be superior to the one that corresponds to the linkage site to the bead via the nitrogen atom of the thiazolidine-2,4-dione moiety, from the perspective of pulling down Myc.

REFERENCES

1. Vita et al., *Semin. Cancer Biol.,* 16, 318-330, (2006).
2. Dang, *Mol. Cell Biol.,* 19, 1-11 (1999).
3. Eilers et al., *Genes Dev.,* 22, 2755-2766 (2008).
4. van Riggelen et al., *Nat. Rev. Cancer,* 10, 301-309 (2010).
5. Dang et al., *Semin. Cancer Biol.,* 16, 253-264 (2006).
6. Boxer et al., *Oncogene,* 20, 5595-5610 (2002).
7. Frost et al., *Am. J. Clin. Pathol.,* 121, 384-392 (2004).
8. Felsher et al., *Mol. Cell,* 4, 199-207 (1999).
9. Soucek et al., *Genes Dev.,* 5, 504-513 (2013).
10. Frye, *Nat. Chem. Biol.,* 6, 159-161 (2010).
11. Leskov, *Oncogene,* 32, 1066-1072 (2013).

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A compound of Formula (I-a):

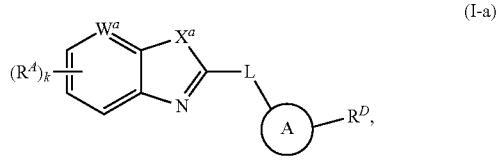

or a pharmaceutically acceptable salt thereof, wherein:
each instance of $R^A$ is independently hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^a$, —$N(R^a)_2$, —$SR^a$, —CN, —SCN, —$C(=NR^a)R^a$, —$C(=NR^a)OR^a$, —$C(=NR^a)N(R^a)_2$, —$C(=O)R^a$, —$C(=O)OR^a$, —$C(=O)N(R^a)_2$, —$NO_2$, —$N(R^a)C(=O)R^a$, —$N(R^a)C(=O)OR^a$, —$N(R^a)C(=O)N(R^a)_2$, —$N(R^a)S(=O)R^a$, —$N(R^a)S(=O)OR^a$, —$N(R^a)S(=O)N(R^a)_2$, —$N(R^a)S(=O)_2R^a$, —$N(R^a)S(=O)_2OR^a$, —$N(R^a)S(=O)_2N(R^a)_2$, —$OC(=O)R^a$, —$OC(=O)OR^a$, or —$OC(=O)N(R^a)_2$, or two instances of $R^A$ are joined to form a substituted or unsubstituted carbocyclic ring, substituted or unsubstituted heterocyclic ring, substituted or unsubstituted aryl ring, or substituted or unsubstituted heteroaryl ring;
k is 0, 1, 2, or 3;
L is —NH—, —O—, or —S—;
$X^a$ is —$NR^B$—, —O—, or —S—;
$W^a$ is —$C(R^A)$=, or —N=;
$R^B$ is hydrogen, substituted or unsubstituted $C_{1-6}$ alkyl, or a nitrogen protecting group;
$R^D$ is of the formula:

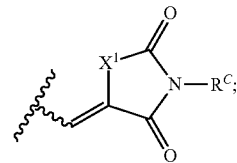

$X^1$ is —S—, —$NR^C$—, or —$CH_2$—;
each instance of $R^C$ is independently substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$C(=O)R^a$, —$C(=O)OR^a$, —$C(=O)N(R^a)_2$, or a nitrogen protecting group;
each instance of $R^a$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^a$ are joined to form a substituted or unsubstituted carbocyclyl ring, substituted or unsubstituted heterocyclic ring, substituted or unsubstituted aryl ring, or substituted or unsubstituted heteroaryl ring; and
Ring A is substituted or unsubstituted aryl, or substituted or unsubstituted heteroaryl; provided that the compound is not of the formula:

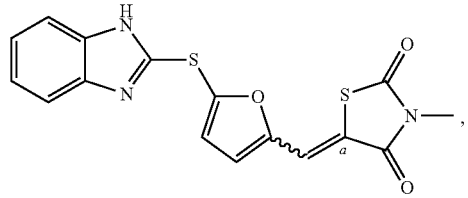

135
-continued
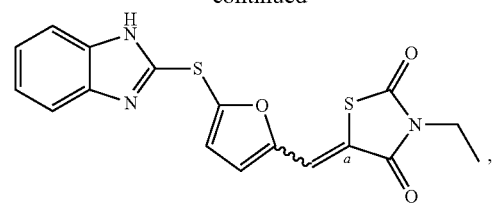,
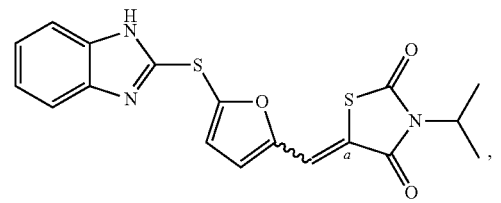,
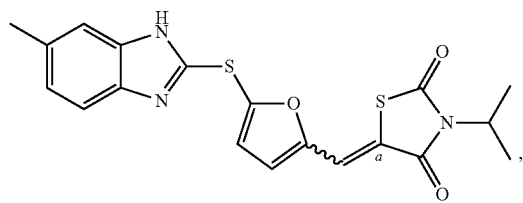,
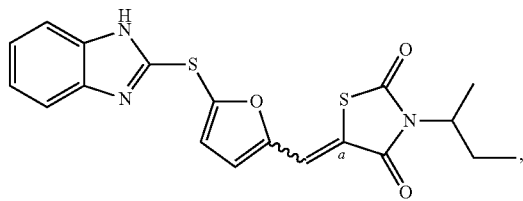,
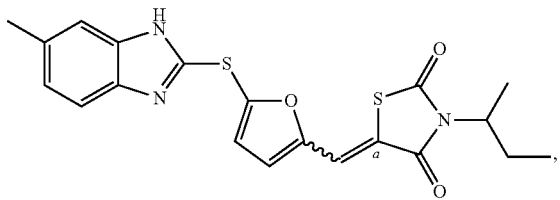,
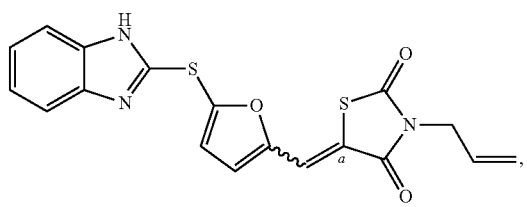,
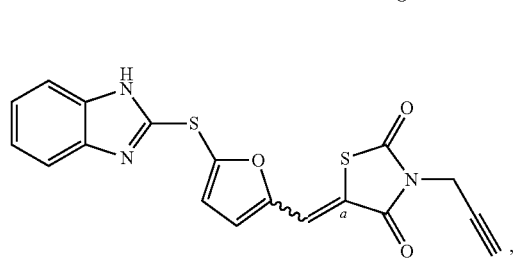,
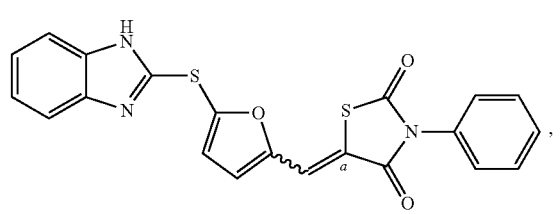,
136
-continued
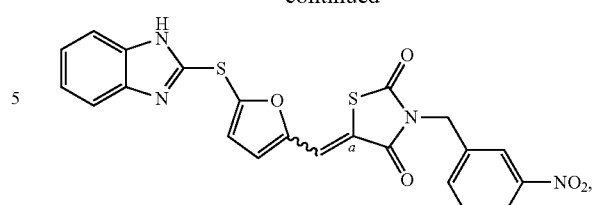,
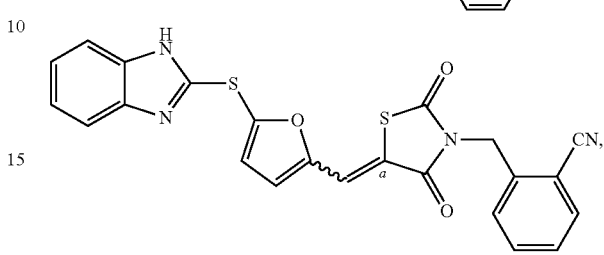,
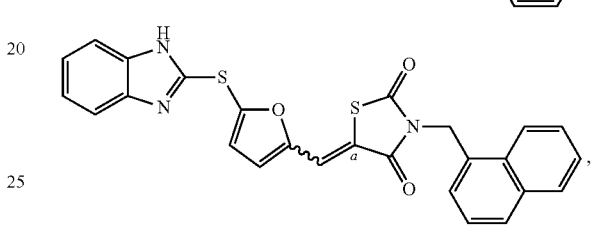,
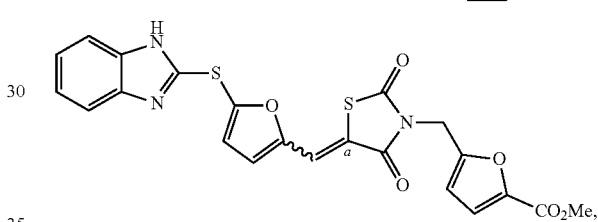,
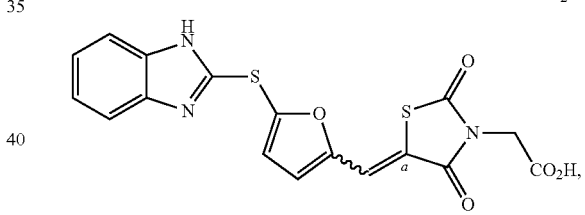,
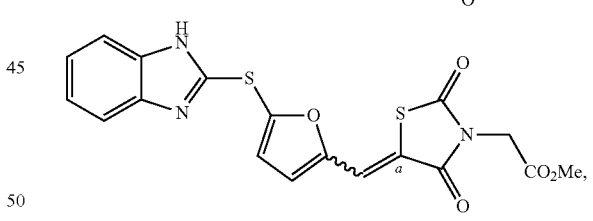,
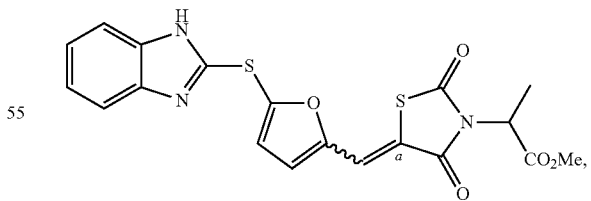,
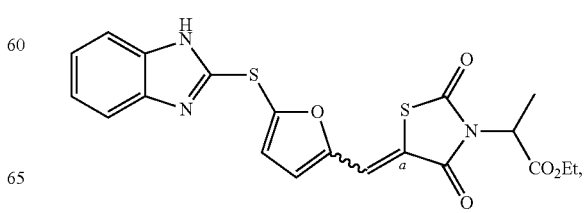, -continued

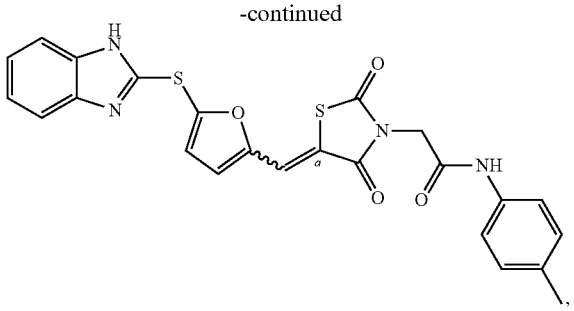

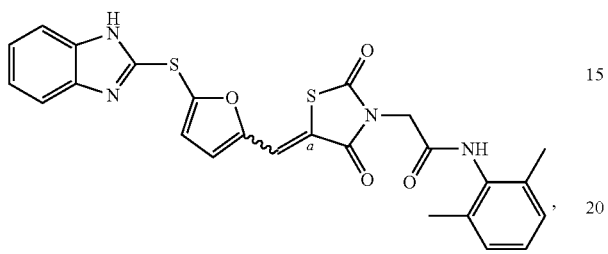

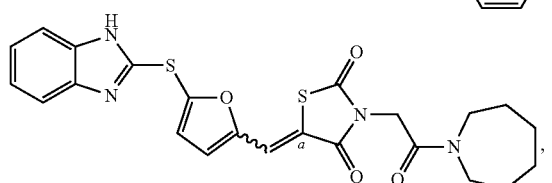

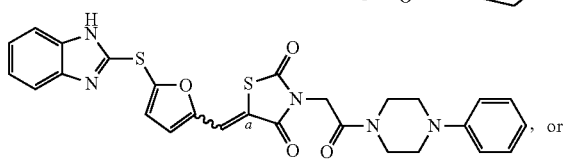

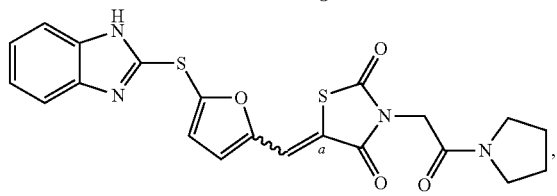

wherein the double bond labeled with "a" is in the (E)- or (Z)-configuration.

2. A compound of Formula (I):

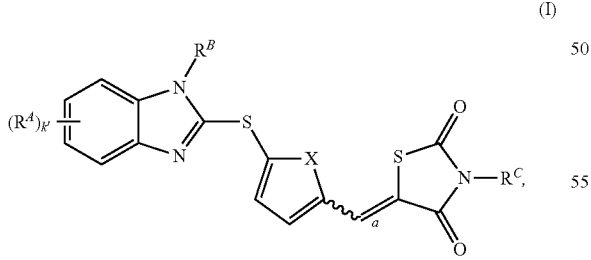

or a pharmaceutically acceptable salt thereof, wherein:
each instance of $R^A$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^a$, —$N(R^a)_2$, —$SR^a$, —CN, —SCN, —C(=$NR^a$)$R^a$, —C(=$NR^a$)$OR^a$, —C(=$NR^a$)$N(R^a)_2$, —C(=O)$R^a$, —C(=O)$OR^a$, —C(=O)$N(R^a)_2$, —$NO_2$, —$N(R^a)$C(=O)$R^a$, —$N(R^a)$C(=O)$OR^a$, —$N(R^a)$C(=O)$N(R^a)_2$, —$N(R^a)$S(=O)$R^a$, —$N(R^a)$S(=O)$OR^a$, —$N(R^a)$S(=O)$N(R^a)_2$, —$N(R^a)$S(=O)$_2R^a$, $N(R^a)$S(=O)$_2OR^a$, —$N(R^a)$S(=O)$_2N(R^a)_2$, —OC(=O)$R^a$, —OC(=O)$OR^a$, or —OC(=O)$N(R^a)_2$, or two instances of $R^A$ are joined to form a substituted or unsubstituted carbocyclic ring, substituted or unsubstituted heterocyclic ring, substituted or unsubstituted aryl ring, or substituted or unsubstituted heteroaryl ring;

each instance of $R^a$ is independently H, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^a$ are joined to form a substituted or unsubstituted heterocyclic ring, or substituted or unsubstituted heteroaryl ring;

k' is 0, 1, 2, 3, or 4;

$R^B$ is hydrogen, substituted or unsubstituted $C_{1-6}$ alkyl, or a nitrogen protecting group;

X is —O— or —S—;

each double bond labeled with "a" is independently in the (E)- or (Z)-configuration; and $R^C$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —C(=O)$R^a$, —C(=O)$OR^a$, —C(=O)$N(R^a)_2$, or a nitrogen protecting group;

provided that the compound is not of the formula:

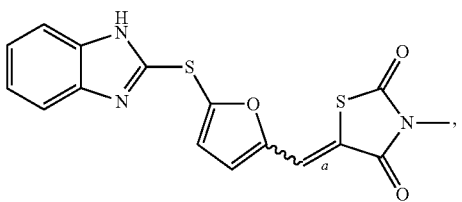

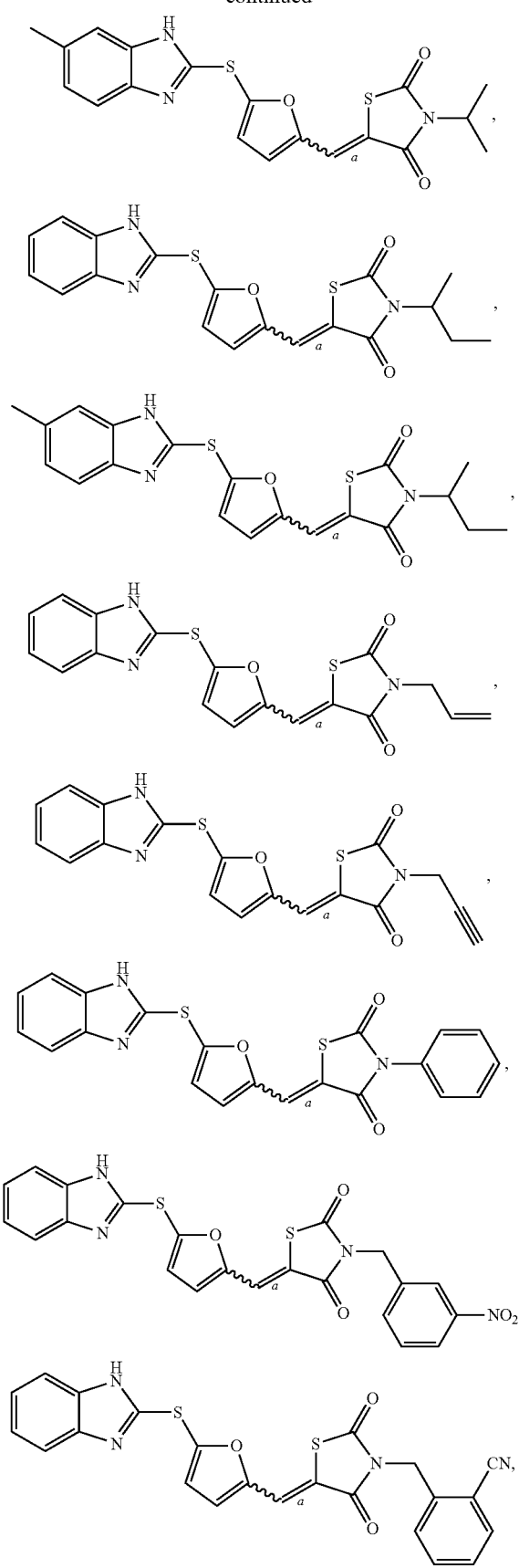
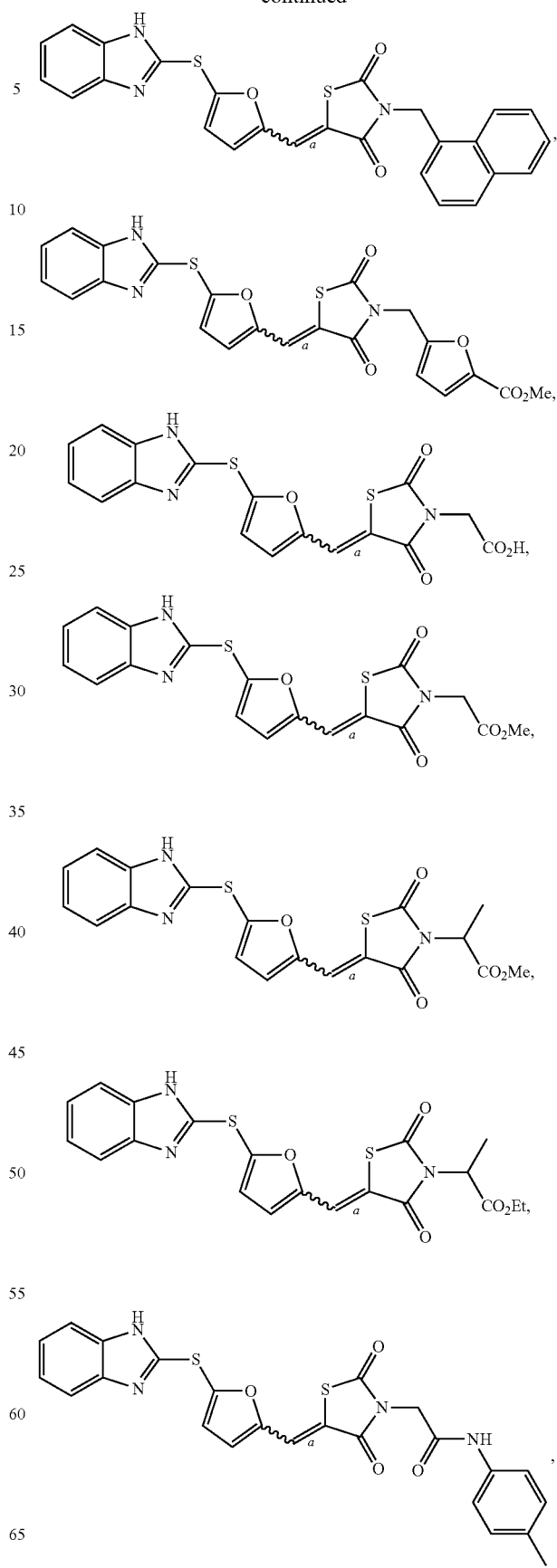

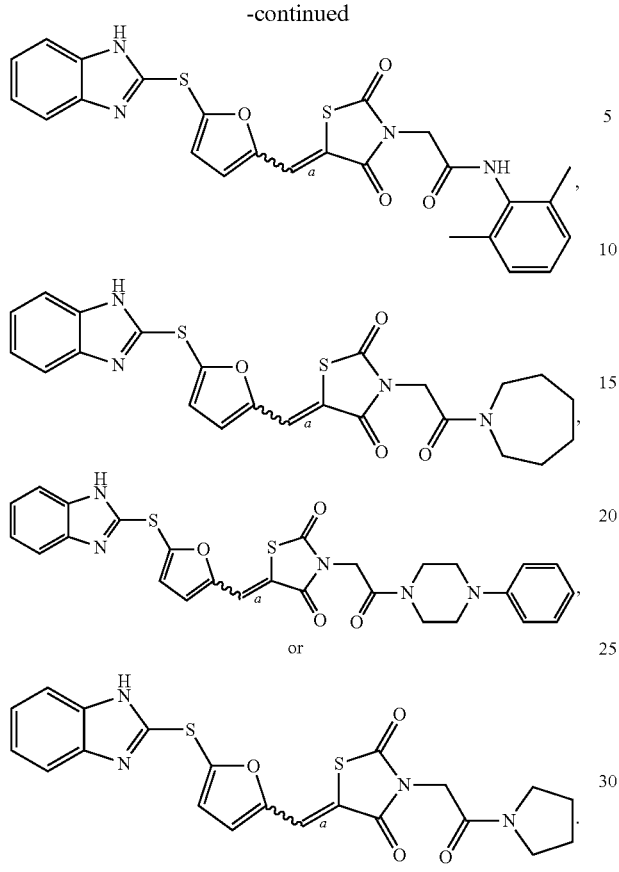
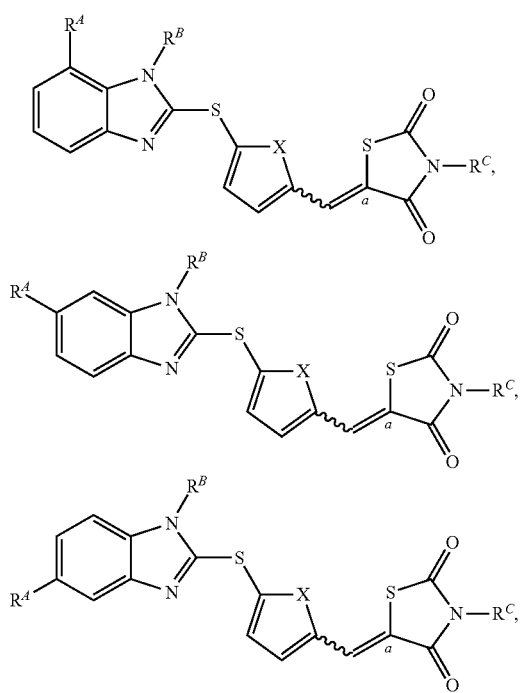
3. The compound of claim 1, or a pharmaceutically acceptable salt thereof, wherein $W^a$ is —N=.
4. The compound of claim 2, wherein the compound is of the formula:
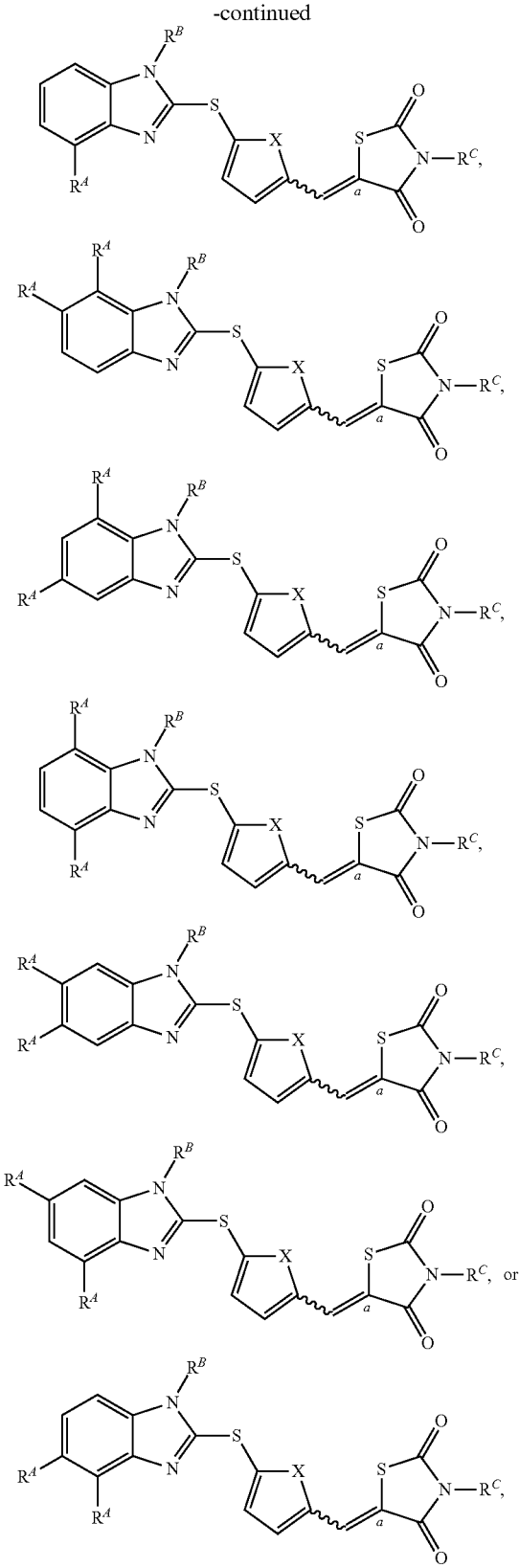
or a pharmaceutically acceptable salt thereof.
5. The compound of claim 2, wherein the compound is of the formula:

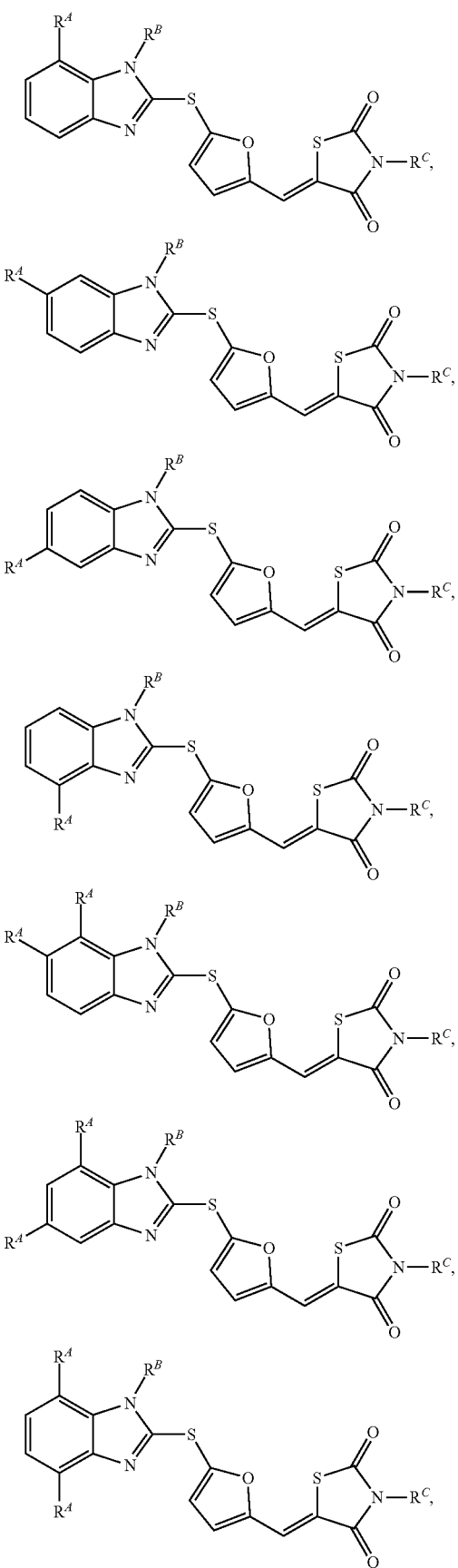

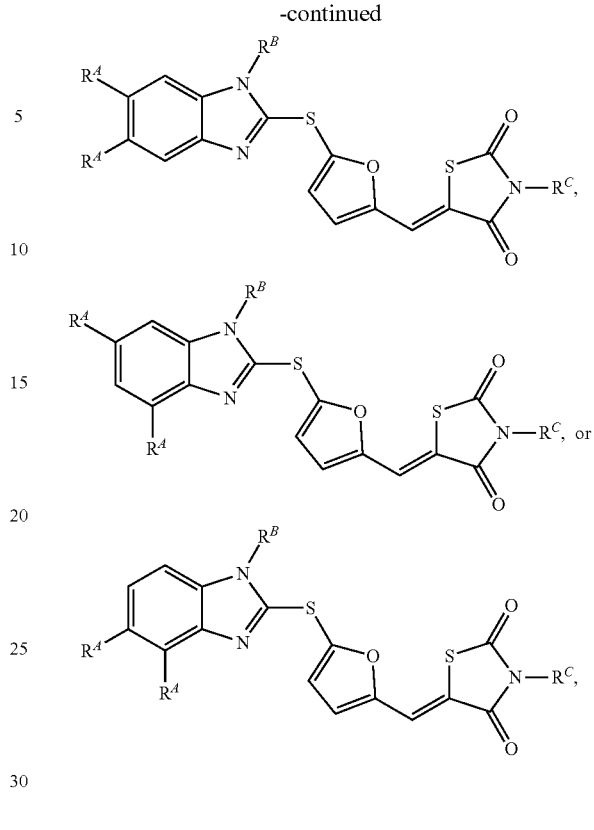

or a pharmaceutically acceptable salt thereof.

6. The compound of claim 1, or a pharmaceutically acceptable salt thereof, wherein at least one instance of $R^A$ is substituted or unsubstituted alkyl, halogen, —$OR^a$, —$N(R^a)_2$, —$NO_2$, —$C(=O)R^a$, —$C(=O)OR^a$, —$C(=O)N(R^a)_2$, —$N(R^a)C(=O)R^a$, —$N(R^a)C(=O)N(R^a)_2$, or —$N(R^a)S(=O)_2R^a$.

7. The compound of claim 1, or a pharmaceutically acceptable salt thereof, wherein k is 0.

8. The compound of claim 1, or a pharmaceutically acceptable salt thereof, wherein $X^a$ is —$NR^B$—, and $R^B$ is hydrogen or substituted or unsubstituted $C_{1-6}$ alkyl.

9. The compound of claim 1, or a pharmaceutically acceptable salt thereof, wherein $X^a$ is —O— or —S—.

10. The compound of claim 2, or a pharmaceutically acceptable salt thereof, wherein $R^C$ is substituted or unsubstituted $C_{1-6}$ alkyl or substituted or unsubstituted phenyl.

11. The compound of claim 1, or a pharmaceutically acceptable salt thereof, wherein Ring A is of the formula:

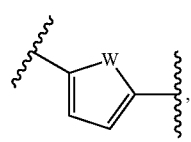

wherein:

W is —NH—, —O— or —S—.

12. The compound of claim 1, or a pharmaceutically acceptable salt thereof, wherein Ring A is of the formula:

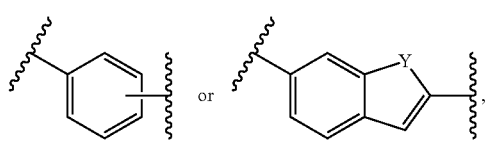
wherein:
Y is —O— or —S—.
13. A compound of the formula:
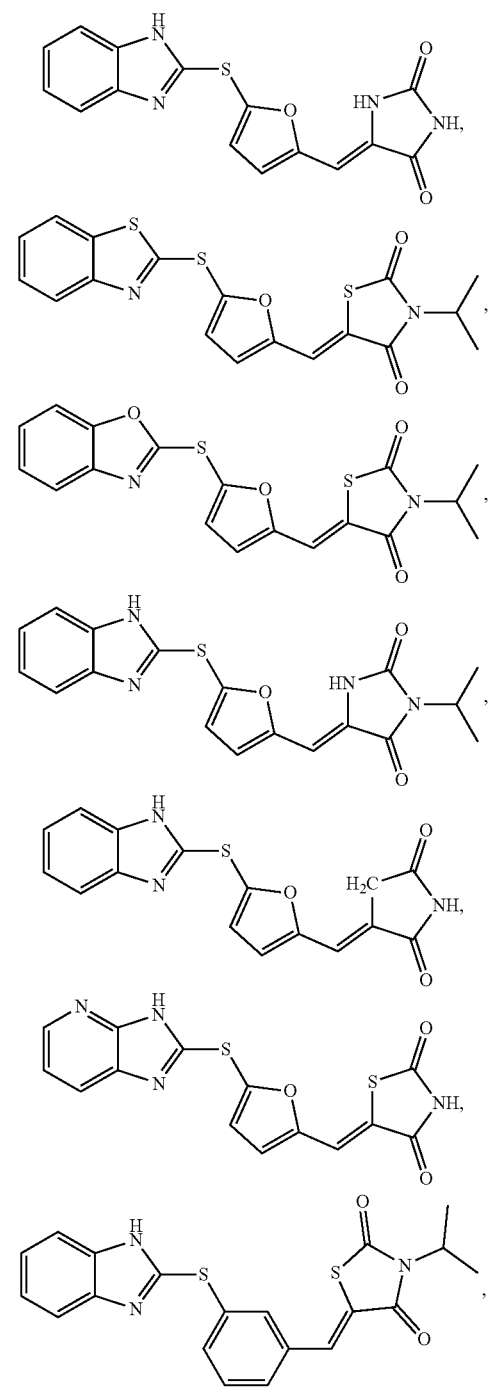
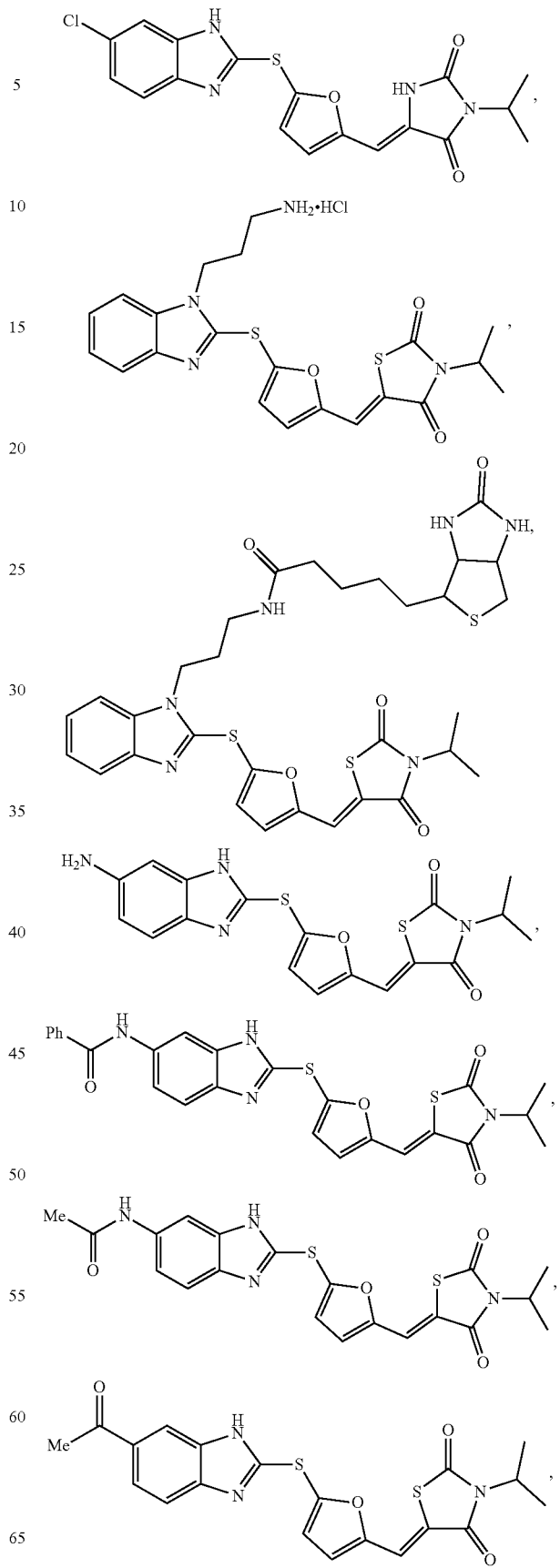

147
-continued

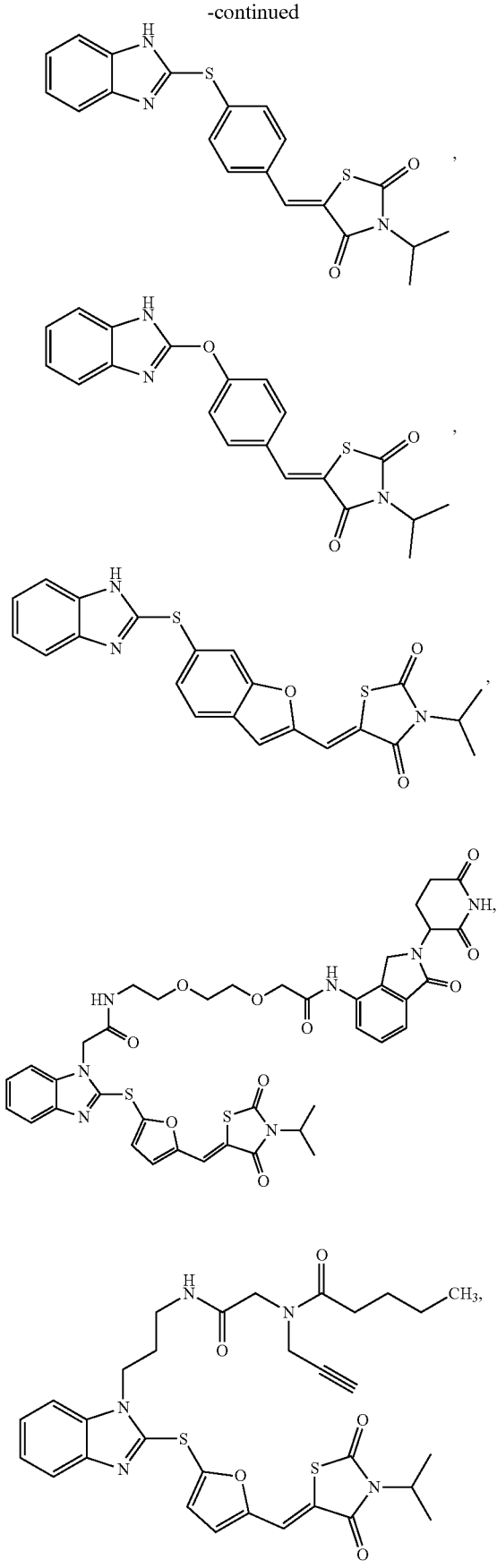

148
-continued

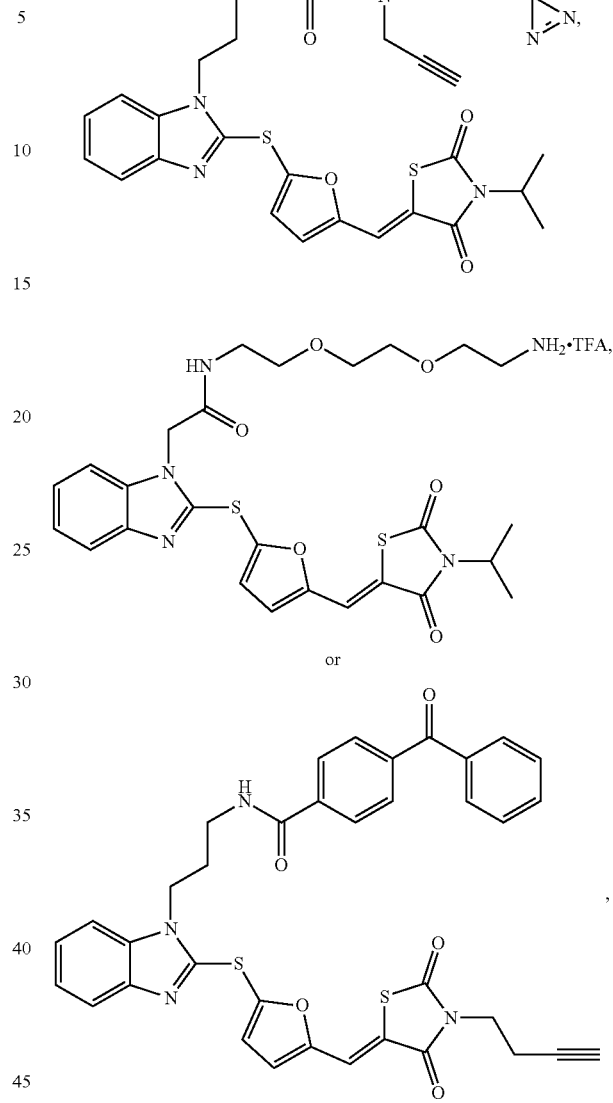

or a pharmaceutically acceptable salt thereof.

14. A pharmaceutical composition comprising a compound of claim 1, or a pharmaceutically acceptable salt thereof, and optionally a pharmaceutically acceptable excipient.

15. The compound of claim 1, or a pharmaceutically acceptable salt thereof, wherein $X^a$ is $-NR^B-$.

16. The compound of claim 1, or a pharmaceutically acceptable salt thereof, wherein $W^a$ is $-C(R^A)=$.

17. The compound of claim 1, or a pharmaceutically acceptable salt thereof, wherein L is $-S-$.

18. The compound of claim 1, or a pharmaceutically acceptable salt thereof, wherein $X^1$ is $-S-$.

19. The compound of claim 2, wherein the compound is of the formula:

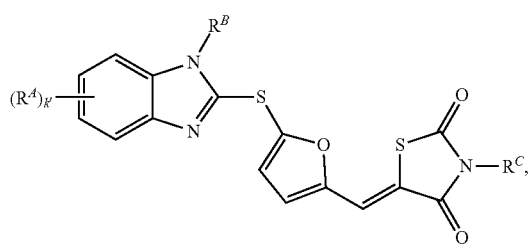
or a pharmaceutically acceptable salt thereof.
20. The compound of claim 2, wherein the compound is of the formula:
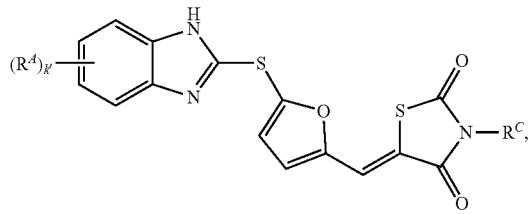
or a pharmaceutically acceptable salt thereof.
21. The compound of claim 2, wherein the compound is of the formula:
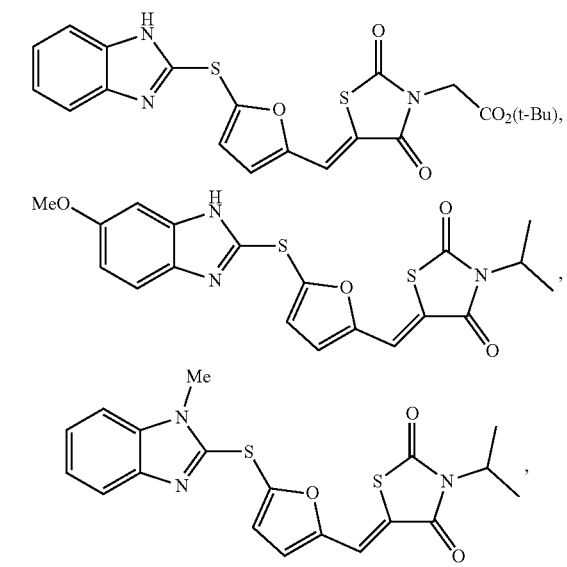
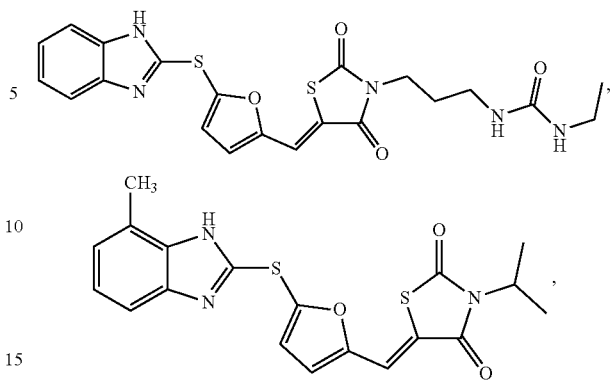
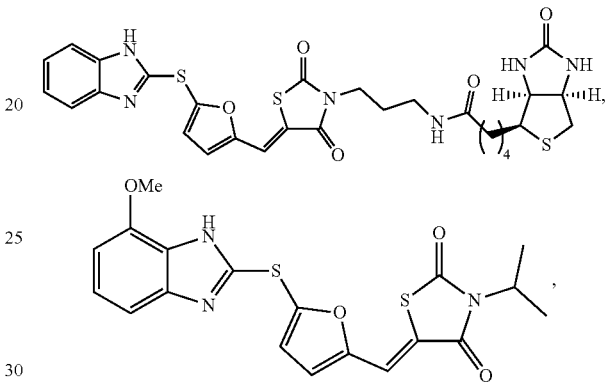
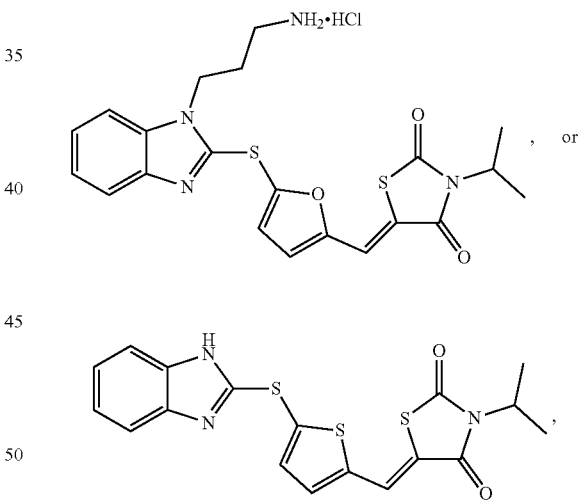
or a pharmaceutically acceptable salt thereof.
22. The compound of claim 2, wherein the compound is of the formula:
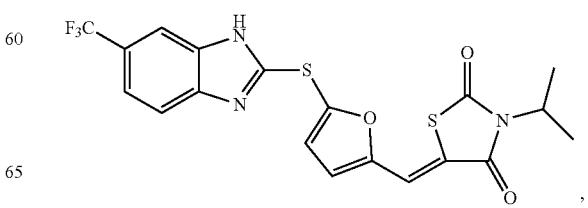

-continued

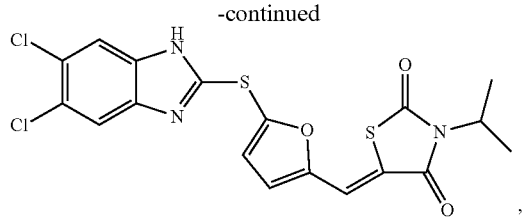

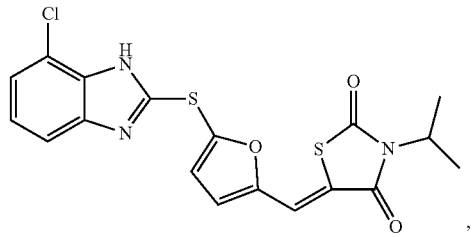

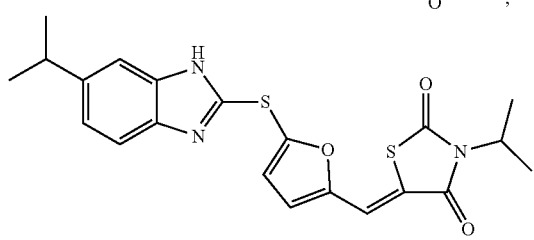

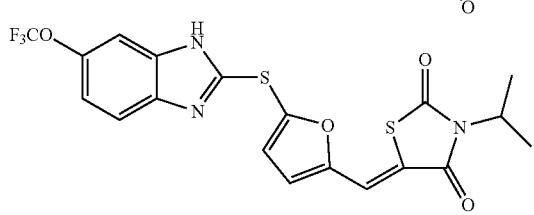

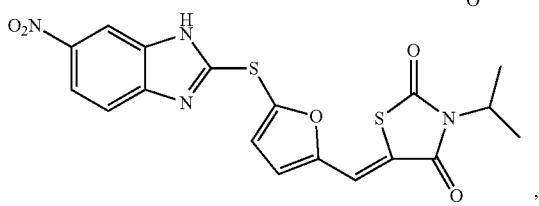, or

-continued

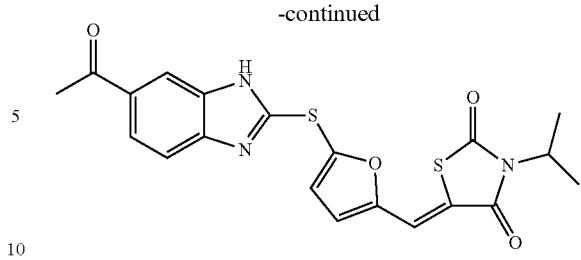

or a pharmaceutically acceptable salt thereof.

23. The compound of claim 2, wherein the compound is of the formula:

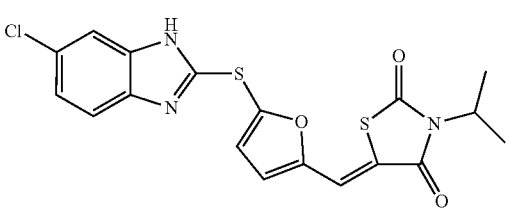

or a pharmaceutically acceptable salt thereof.

24. The compound of claim 2, or a pharmaceutically acceptable salt thereof, wherein $R^B$ is hydrogen.

25. The compound of claim 2, or a pharmaceutically acceptable salt thereof, wherein $R^B$ is substituted or unsubstituted $C_{1-6}$ alkyl.

26. The compound of claim 2, or a pharmaceutically acceptable salt thereof, wherein $R^C$ is hydrogen.

27. The compound of claim 2, or a pharmaceutically acceptable salt thereof, wherein X is —O—.

\* \* \* \* \*